(12) United States Patent
Kawamura et al.

(10) Patent No.: US 10,186,665 B2
(45) Date of Patent: Jan. 22, 2019

(54) ORGANIC ELECTROLUMINESCENT ELEMENT

(71) Applicant: Idemitsu Kosan Co., Ltd., Tokyo (JP)

(72) Inventors: Masahiro Kawamura, Sodegaura (JP);
Yumiko Mizuki, Sodegaura (JP);
Toshinari Ogiwara, Sodegaura (JP);
Hitoshi Kuma, Sodegaura (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 219 days.

(21) Appl. No.: 14/758,118

(22) PCT Filed: Dec. 27, 2013

(86) PCT No.: PCT/JP2013/085151
§ 371 (c)(1),
(2) Date: Jun. 26, 2015

(87) PCT Pub. No.: WO2014/104315
PCT Pub. Date: Jul. 3, 2014

(65) Prior Publication Data
US 2015/0340623 A1    Nov. 26, 2015

(30) Foreign Application Priority Data
Dec. 28, 2012   (JP) ................. 2012-288983

(51) Int. Cl.
*H01L 51/50*    (2006.01)
*H01L 51/00*    (2006.01)
(Continued)

(52) U.S. Cl.
CPC ........ *H01L 51/0067* (2013.01); *C07D 219/06* (2013.01); *C07D 403/10* (2013.01);
(Continued)

(58) Field of Classification Search
None
See application file for complete search history.

(56) References Cited

U.S. PATENT DOCUMENTS

2012/0138915 A1   6/2012   Nishimura et al.
2012/0217869 A1   8/2012   Adachi et al.
(Continued)

FOREIGN PATENT DOCUMENTS

CN    101611298 A    12/2009
CN    101728416 A    6/2010
(Continued)

OTHER PUBLICATIONS

Combined Chinese Office Action and Search Report dated Sep. 1, 2016 in Patent Application No. 201380067794.7 (with partial English translation and English translation of categories of cited documents).
(Continued)

*Primary Examiner* — Gregory D Clark
(74) *Attorney, Agent, or Firm* — Oblon, McClelland, Maier & Neustadt, L.L.P.

(57) ABSTRACT

An organic electroluminescence device includes an anode, a cathode and an emitting layer, in which the emitting layer includes a first compound and a second compound and each of the first compound and the second compound is a compound emitting thermally activated delayed fluorescence.

32 Claims, 4 Drawing Sheets

(51) Int. Cl.
| | |
|---|---|
| C07D 219/06 | (2006.01) |
| C07D 403/10 | (2006.01) |
| C07D 413/10 | (2006.01) |
| C07D 491/048 | (2006.01) |
| C09K 11/06 | (2006.01) |
| C09B 19/00 | (2006.01) |
| C09B 21/00 | (2006.01) |
| C09B 57/00 | (2006.01) |
| C09B 69/00 | (2006.01) |
| H01L 51/52 | (2006.01) |

(52) U.S. Cl.
CPC ....... *C07D 413/10* (2013.01); *C07D 491/048* (2013.01); *C09B 19/00* (2013.01); *C09B 21/00* (2013.01); *C09B 57/00* (2013.01); *C09B 69/008* (2013.01); *C09K 11/06* (2013.01); *H01L 51/0071* (2013.01); *H01L 51/0072* (2013.01); *H01L 51/0073* (2013.01); *H01L 51/0074* (2013.01); *H01L 51/0094* (2013.01); *C09K 2211/1011* (2013.01); *C09K 2211/1029* (2013.01); *C09K 2211/1033* (2013.01); *C09K 2211/1037* (2013.01); *C09K 2211/1044* (2013.01); *C09K 2211/1059* (2013.01); *C09K 2211/1092* (2013.01); *H01L 51/5012* (2013.01); *H01L 51/5024* (2013.01); *H01L 51/5206* (2013.01); *H01L 51/5221* (2013.01); *H01L 2251/5384* (2013.01); *H01L 2251/562* (2013.01)

(56) References Cited

U.S. PATENT DOCUMENTS

| | | | |
|---|---|---|---|
| 2012/0241732 A1 | 9/2012 | Endo et al. | |
| 2012/0248968 A1 | 10/2012 | Ogiwara et al. | |
| 2014/0145151 A1* | 5/2014 | Xia | H01L 51/0069 257/40 |

FOREIGN PATENT DOCUMENTS

| | | |
|---|---|---|
| CN | 101728417 A | 6/2010 |
| CN | 102074656 A | 5/2011 |
| CN | 102648268 A | 8/2012 |
| JP | 2004-241374 A | 8/2004 |
| JP | 2011-213643 A | 10/2011 |
| JP | 2012-028634 A | 2/2012 |
| JP | 2013-258402 A | 12/2013 |
| WO | WO-2011/070963 A1 | 6/2011 |
| WO | WO-2012/124412 A1 | 9/2012 |
| WO | WO-2012/133188 A1 | 10/2012 |
| WO | WO 2014/050904 A1 | 4/2014 |

OTHER PUBLICATIONS

Office Action dated Feb. 7, 2017 in Japanese Patent Application No. 2014-554602 (with English translation).
Translation of the International Preliminary Report on Patentability and the Written Opinion of the International Searching Authority corresponding to Application No. PCT/JP2013/085228, dated Jun. 30, 2015, 8 pages.
Adachi et al., "Expression of Highly-Efficient Thermally-Activated Delayed-Fluorescence and Application Thereof to OLED," Organic EL Symposium, proceeding for the tenth meeting held on Jun. 17-18, 2010, S2-5, pp. 11-12.
Adachi, C., Device Physics of Organic Semiconductors, Kodansha Company Ltd., pp. 261-268.
International Search Report dated Apr. 1, 2014 issued in Application No. PCT/JP2013/085151.
Lee, S.Y. et al., "High-efficiency organic light-emitting diodes utilizing thermally activated delayed fluorescence from triazine-based donor-acceptor hybrid molecules," Applied Physics Letters, 2012, vol. 101, pp. 093306-1/093306-4.
Tanaka et al., "Efficient green thermally activated delayed fluorescence (TADF) from a phenoxazine-triphenyltriazine (PXZ-TRZ) derivative ,"Chem. Commun., 2012, vol. 48, No. 93. pp. 11392-11394.
Tokumaru, K., Organic Photochemical Reaction Theory, Tokyo Kagaku Dojin Co., Ltd., 1973, pp. 79-82.
Translation of the International Preliminary Report on Patentability and the Written Opinion of the International Searching Authority corresponding to Application No. PCT/JP2013/085151, dated Jun. 30, 2015, 5 pages.

* cited by examiner

ORGANIC ELECTROLUMINESCENT ELEMENT

CROSS REFERENCE TO RELATED APPLICATIONS

This application is the National Phase of PCT/JP2013/085151, filed Dec. 27, 2013, which claims priority to Japanese Application No. 2012-288983, filed Dec. 28, 2012.

TECHNICAL FIELD

The present invention relates to an organic electroluminescence device.

BACKGROUND ART

When a voltage is applied to an organic electroluminescence device (hereinafter, occasionally referred to as an organic EL device), holes are injected from an anode into an emitting layer and electrons are injected from a cathode into the emitting layer. The injected electrons and holes are recombined in an emitting layer to form excitons. Here, according to the electron spin statistics theory, singlet excitons and triplet excitons are generated at a ratio of 25%:75%. In the classification according to the emission principle, in a fluorescent EL device which uses emission caused by singlet excitons, the limited value of an internal quantum efficiency of the organic EL device is believed to be 25%. On the other hand, in a phosphorescent EL device which uses emission caused by triplet excitons, it has been known that the internal quantum efficiency can be improved up to 100% when intersystem crossing efficiently occurs from the singlet excitons.

A technology for extending a lifetime of a fluorescent organic EL device has recently been improved and applied to a full-color display of a mobile phone, TV and the like. However, an efficiency of a fluorescent EL device is required to be improved.

Based on such a background, a highly efficient fluorescent organic EL device using delayed fluorescence has been proposed and developed. For instance, an organic EL device using TTF (Triplet-Triplet Fusion) mechanism that is one of mechanisms for delayed fluorescence has been proposed. The TTF mechanism utilizes a phenomenon in which singlet excitons are generated by collision between two triplet excitons.

By using delayed fluorescence by the TTF mechanism, it is considered that an internal quantum efficiency can be theoretically raised up to 40% even in fluorescent emission. However, as compared with phosphorescent emission, the fluorescent emission is still problematic on improving efficiency. Accordingly, in order to enhance the internal quantum efficiency, an organic EL device using another delayed fluorescence mechanism has been studied.

For instance, TADF (Thermally Activated Delayed Fluorescence) mechanism is used. The TADF mechanism utilizes a phenomenon in which inverse intersystem crossing from triplet excitons to singlet excitons is generated by using a material having a small energy gap ($\Delta ST$) between the singlet energy level and the triplet energy level. Thermally activated delayed fluorescence is described in, for instance, "Device Physics of Organic Semiconductor" Chihaya Adachi, pages 261-262, Mar. 22, 2012, published by Kodansha Company Ltd.

An organic EL device using the TADF mechanism is disclosed in, for instance, non-Patent Literature 1.

Non-Patent Literature 1 describes that green emission by the TADF mechanism can be efficiently obtained by using as a luminescent material a compound (hereinafter, occasionally abbreviated as PXZ-TRZ) having phenoxazine as an electron donating unit and 2,4,6-triphenyl-1,3,5-triazine as an electron acceptor unit. Non-Patent Literature 1 also describes that an organic EL device including an emitting layer in which PXZ-TRZ (luminescent material) is doped in CBP (4,4'-Bis(N-carbazolyl)-1,1'-biphenyl)(host material) emits light at an external quantum efficiency (EQE) of up to 12.5%.

CITATION LIST

Non-Patent Literature

Non-Patent Literature 1: Chihaya Adachi et al. "Efficient green thermally activated delayed fluorescence (TADF) from a phenoxazine-triphenylazine (PXZ-TRZ) derivative", Chemical Communications, in 2012, 48, p. 11392-11394

SUMMARY OF THE INVENTION

Problems to be Solved by the Invention

However, voltage reduction in driving the device and a longer lifetime are required for practical use of the organic EL device.

An object of the invention is to provide an organic electroluminescence device requiring a low drive voltage and exhibiting a longer lifetime.

Means for Solving the Problems

According to an aspect of the invention, an organic electroluminescence device includes an anode, a cathode and an emitting layer, in which the emitting layer includes a first compound and a second compound, and each of the first compound and the second compound is a compound emitting thermally activated delayed fluorescence (hereinafter, also referred to as a thermally activated delayed fluorescence compound).

According to the above aspect of the invention, an organic electroluminescence device requiring a low drive voltage and exhibiting a long lifetime can be provided.

DESCRIPTION OF EMBODIMENT(S)

Figure 1:
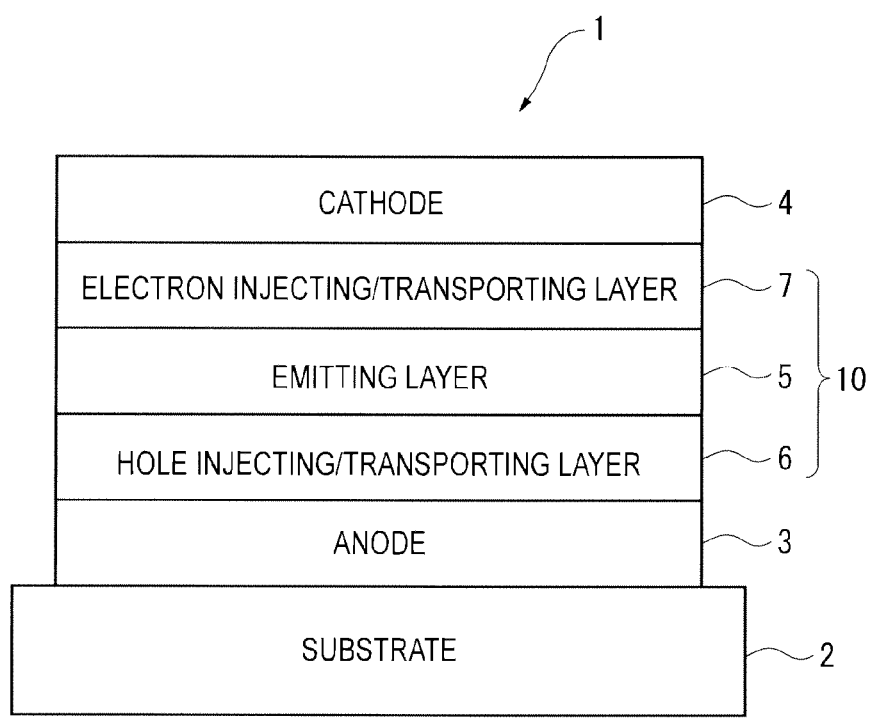
FIG. 1 schematically shows an exemplary arrangement of an organic electroluminescence device according to a first exemplary embodiment of the invention.

An organic EL device according to an exemplary embodiment of the invention will be described below.

First Exemplary Embodiment

Arrangement(s) of Organic EL Device

An organic EL device according to a first exemplary embodiment of the invention will be described below.

The organic EL device in the first exemplary embodiment includes a pair of electrodes and an organic layer between the pair of electrodes. The organic layer includes at least one layer formed of an organic compound. The organic layer may further include an inorganic compound.

In the organic EL device in the exemplary embodiment, at least one layer of the organic layer(s) is the emitting layer. Accordingly, the organic layer may be provided by a single emitting layer. Alternatively, the organic layer may be provided by layers employed in an organic EL device such as a hole injecting layer, a hole transporting layer, an electron injecting layer, an electron transporting layer, a hole blocking layer, and an electron blocking layer.

The following are representative structure examples of an organic EL device:
(a) anode/emitting layer/cathode;
(b) anode/hole injecting•transporting layer/emitting layer/cathode;
(c) anode/emitting layer/electron injecting•transporting layer/cathode;
(d) anode/hole injecting•transporting layer/emitting layer/electron injecting•transporting layer/cathode;
(e) anode/hole injecting•transporting layer/first emitting layer/second emitting layer/electron injecting•transporting layer/cathode; and
(f) anode/hole injecting•transporting layer/emitting layer/blocking layer/electron injecting•transporting layer/cathode.

While the arrangement (d) is preferably used among the above arrangements, the arrangement of the invention is not limited to the above arrangements.

The "hole injecting/transporting layer (or hole injecting•transporting layer)" means "at least one of a hole injecting layer and a hole transporting layer" while the "electron injecting/transporting layer (or electron injecting•transporting layer)" means "at least one of an electron injecting layer and an electron transporting layer." Herein, when the hole injecting layer and the hole transporting layer are provided, the hole injecting layer is preferably adjacent to the anode. When the electron injecting layer and the electron transporting layer are provided, the electron injecting layer is preferably adjacent to the cathode. Moreover, each of the hole injecting layer, hole transporting layer, electron transporting layer and electron injecting layer may be provided by a single layer or a plurality of layers.

In the exemplary embodiment, the electron transporting layer means an organic layer having the highest electron mobility among organic layer(s) providing an electron transporting zone existing between the emitting layer and the cathode. When the electron transporting zone is provided by a single layer, the single layer is the electron transporting layer. Moreover, a blocking layer having an electron mobility that is not always high may be provided as shown in the arrangement (f) between the emitting layer and the electron transporting layer in order to prevent diffusion of excitation energy generated in the emitting layer. Thus, the organic layer adjacent to the emitting layer is not always an electron transporting layer.

FIG. 1 schematically shows an arrangement of an organic EL device according to the exemplary embodiment.

An organic EL device 1 includes a light-transmissive substrate 2, an anode 3, a cathode 4 and an organic layer 10 disposed between the anode 3 and the cathode 4.

The organic layer 10 includes an emitting layer 5 containing a first compound and a second compound. The organic layer 10 also includes a hole injecting/transporting layer 6 between the emitting layer 5 and the anode 3. The organic layer 10 further includes an electron injecting/transporting layer 7 between the emitting layer 5 and the cathode 4.

Emitting Layer

In the organic EL device 1 in the first exemplary embodiment, the first and second compounds used in the emitting layer 5 are compounds emitting delayed fluorescence (hereinafter, also referred to as a "delayed fluorescence compound"). The first compound and the second compound contained in the emitting layer 5 have mutually different molecular structures. The emitting layer 5 preferably has no phosphorescent metal complex. The organic EL device in the first exemplary embodiment emits thermally activated delayed fluorescence. The organic EL device emitting thermally activated delayed fluorescence is advantageous that a luminous efficiency similar to a luminous efficiency of a phosphorescent organic EL device can be probably achieved without using an expensive transition metal complex. Accordingly, a transition metal complex observed to emit phosphorescence is preferably not used in the first exemplary embodiment. However, use of a metal complex is not necessarily prohibited. For instance, there has been known an inexpensive metal complex exhibiting thermally activated delayed fluorescence with use of a copper complex (JP-A-2011-213643). The use of a metal complex exhibiting thermally activated delayed fluorescence is not prohibited. In other words, an organic metal complex is provided by not only a phosphorescent complex but also a metal complex exhibiting thermally activated delayed fluorescence. In the first exemplary embodiment, an organic EL device with use of an organic material exhibiting thermally activated delayed fluorescence is provided. A material exhibiting thermally activated delayed fluorescence is exemplified by a compound described in "Device Physics of Organic Semiconductor" Chihaya Adachi, pages 261-262, Mar. 22, 2012, published by Kodansha Company Ltd.

In the first exemplary embodiment, it is preferable that a difference between singlet energy EgS(M1) of the first compound and singlet energy EgS(M2) of the second compound is 0.3 eV or less. In other words, it is preferable to satisfy a relationship of $|EgS(M1)-EgS(M2)| \leq 0.3$ eV. It is more preferable to satisfy a relationship of $|EgS(M1)-EgS(M2)| \leq 0.2$ eV.

In the first exemplary embodiment, it is preferable that a difference between energy gap $Eg_{77K}(M1)$ at 77K of the first compound and energy gap $Eg_{77K}(M2)$ at 77K of the second compound is 0.3 eV or less. In other words, it is preferable to satisfy a relationship of $|Eg_{77K}(M1)-Eg_{77K}(M2)| \leq 0.3$ eV. It is more preferable to satisfy a relationship of $|Eg_{77K}(M1)-Eg_{77K}(M2)| \leq 0.2$ eV.

In the first exemplary embodiment, at least one of a plurality of the thermally activated delayed fluorescence compounds contained in the emitting layer 5 is preferably a compound in which a difference $\Delta ST$ between singlet energy EgS and energy gap $Eg_{77K}$ at 77K preferably satisfies a relationship represented by a numerical formula (1) (Numerical Formula 1) below, more preferably has $\Delta ST$ of less than 0.2 eV.

$$\Delta ST = EgS - Eg_{77K} < 0.3 \text{ (eV)} \quad \text{(Numerical Formula 1)}$$

In the first exemplary embodiment, the first compound and the second compound which are thermally activated delayed fluorescence compounds are contained in the emitting layer 5. Accordingly, the first compound is preferably a compound in which a difference ΔST(M1) between the singlet energy EgS(M1) and the energy gap $Eg_{77K}$(M1) at 77K satisfies a relationship represented by a numerical formula (1-1) below, more preferably a compound in which ΔST(M1) is less than 0.2 eV.

$$\Delta ST(M1)=EgS(M1)-Eg_{77K}(M1)<0.3 \text{ eV}$$ (Numerical Formula 1-1)

The second compound is preferably a compound in which a difference ΔST(M2) between the singlet energy EgS(M2) and the energy gap $Eg_{77K}$(M2) at 77K satisfies a relationship represented by a numerical formula (1-2) below, more preferably a compound in which ΔST(M2) is less than 0.2 eV.

$$\Delta ST(M2)=EgS(M2)-Eg_{77K}(M2)<0.3 \text{ eV}$$ (Numerical Formula 1-2)

It is further preferable that the first compound satisfies the relationship of the numerical formula (1-1) and the second compound satisfies the relationship of the numerical formula (1-2).

From quantum chemical viewpoint, decrease in the energy difference (ΔST) between the singlet energy EgS and the triplet energy EgT can be achieved by a small exchange interaction therebetween. Physical details of the relationship between ΔST and the exchange interaction are exemplarily described in Reference Documents 1 and 2 below:

Reference Document 1: Organic EL Symposium, proceeding for the tenth meeting edited by Chihaya Adachi et al., S2-5, p 11-12; and Reference Document 2: Organic Photochemical Reaction Theory edited by Katsumi Tokumaru, Tokyo Kagaku Dojin Co., Ltd. (1973).

Such a material can be synthesized according to molecular design based on quantum calculation. Specifically, the material is a compound in which a LUMO electron orbit and a HOMO electron orbit are localized to avoid overlapping.

Examples of the compound having a small ΔST are compounds in which a donor element is bonded to an acceptor element in a molecule and ΔST is in a range of 0 eV or more and less than 0.3 eV in terms of electrochemical stability (oxidation-reduction stability).

A more preferable compound is such a compound that dipoles formed in the excited state of a molecule interact with each other to form an aggregate having a reduced exchange interaction energy. According to analysis by the inventors, the dipoles are oriented substantially in the same direction in the compound, so that ΔST can be further reduced by the interaction of the molecules. In such a case, ΔST can be extremely small in a range of 0 eV to 0.2 eV.

Relationship Between EgT and $Eg_{77K}$

Triplet energy EgT is measured as follows. A compound (measurement target) was deposited on a quartz substrate to prepare a sample encapsulated in an NMR tube. A sample was prepared under the following conditions.

quartz substrate/TH-2: measurement target compound (100 nm of thickness, 12 mass % of concentration of the measurement target compound)

[Formula 1]

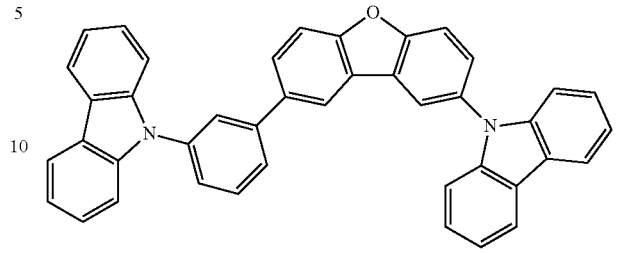

TH-2

A phosphorescent spectrum (ordinate axis: phosphorescent luminous intensity, abscissa axis: wavelength) of each of the samples was measured at a low temperature (77K). A tangent was drawn to the rise of the phosphorescent spectrum on the short-wavelength side. An energy amount was calculated as the energy gap $Eg_{77K}$ at 77K according to a conversion equation 2 below based on a wavelength value $\lambda_{edge}$ (nm) at an intersection of the tangent and the abscissa axis.

$$Eg_{77K} \text{ (eV)}=1239.85/\lambda_{edge}$$ Conversion Equation 2:

For phosphorescence measurement, a spectrophotofluorometer body F-4500 (manufactured by Hitachi High-Technologies Corporation) was used.

The tangent to the rise of the phosphorescence spectrum on the short-wavelength side is drawn as follows. While moving on a curve of the phosphorescence spectrum from the short-wavelength side to the maximum spectral value closest to the short-wavelength side among the maximum spectral values, a tangent is checked at each point on the curve toward the long-wavelength of the phosphorescence spectrum. An inclination of the tangent is increased as the curve rises (i.e., a value of the ordinate axis is increased). A tangent drawn at a point of the maximum inclination (i.e., a tangent at an inflection point) is defined as the tangent to the rise of the phosphorescence spectrum on the short-wavelength side.

The maximum with peak intensity being 15% or less of the maximum peak intensity of the spectrum is not included in the above-mentioned maximum closest to the short-wavelength side of the spectrum. The tangent drawn at a point of the maximum spectral value being closest to the short-wavelength side and having the maximum inclination is defined as a tangent to the rise of the phosphorescence spectrum on the short-wavelength side.

The material used in the first exemplary embodiment is preferably a compound having a small ΔST. When ΔST is small, intersystem crossing and inverse intersystem crossing are likely to occur even at a low temperature (77K), so that the singlet state and the triplet state coexist. As a result, the spectrum to be measured in the same manner as the above includes emission from both the singlet state and the triplet state. Although it is difficult to distinguish emission from the singlet state from emission from the triplet state, the value of the triplet energy is basically considered dominant.

Accordingly, in the exemplary embodiment, the spectrum is measured by the same method as that for measuring a typical triplet energy, but an energy value of the spectrum measured in the aforementioned manner is referred to as an energy gap $Eg_{77K}$ in order to differentiate the measured energy from a typical triplet energy in a strict meaning.

Singlet Energy EgS

Singlet Energy EgS was obtained by the following method.

Each of the compounds was used for forming a 100 nm thick film on a quartz substrate by vacuum deposition to prepare a sample for measurement. Emission spectrum of each sample was measured at a room temperature (300K). The emission spectrum was expressed in coordinates of which ordinate axis indicated the luminous intensity and of which abscissa axis indicated the wavelength. A tangent was drawn to the rise of the emission spectrum on the short-wavelength side, and a wavelength value λedge (nm) at an intersection of the tangent and the abscissa axis was obtained. The wavelength value was converted to an energy value by the following conversion equation. The energy value was defined as EgS.

$EgS$ (eV)=1239.85/λedge        Conversion Equation:

For the emission spectrum measurement, a spectrophotofluorometer body F-7000 (manufactured by Hitachi High-Technologies Corporation) was used.

The tangent to the rise of the emission spectrum on the short-wavelength side was drawn as follows. While moving on a curve of the emission spectrum from the short-wavelength side to the maximum spectral value closest to the short-wavelength side among the maximum spectral values, a tangent is checked at each point on the curve toward the long-wavelength of the phosphorescence spectrum. An inclination of the tangent is increased as the curve rises (i.e., a value of the ordinate axis is increased). A tangent drawn at a point of the maximum inclination was defined as the tangent to the rise of the phosphorescence spectrum on the short-wavelength side.

The maximum with peak intensity being 10% or less of the maximum peak intensity of the spectrum is not included in the above-mentioned maximum closest to the short-wavelength side of the spectrum. The tangent drawn at a point of the maximum spectral value being closest to the short-wavelength side and having the maximum inclination is defined as a tangent to the rise of the emission spectrum on the short-wavelength side.

The calculation of the singlet energy EgS and the energy gap $Eg_{77K}$ will be described in detail later.

TADF Mechanism

As described above, when ΔST of the organic material is small, inverse intersystem crossing from the triplet energy level of the organic material to the singlet energy level thereof is easily caused by heat energy given from the outside. An energy state conversion mechanism to perform spin exchange from the triplet state of electrically excited excitons within the organic EL device to the singlet state by inverse intersystem crossing is referred to as TADF Mechanism.

Each of the first and second compounds used in the first exemplary embodiment is preferably a compound having a small ΔST. Inverse intersystem crossing from the triplet energy level of the compound to the singlet energy level thereof is easily caused by heat energy given from the outside.

Delayed Fluorescence

Thermally activated delayed fluorescence is described in "Device Physics of Organic Semiconductor" Chihaya Adachi, pages 261 to 268, published by Kodansha Company Ltd. This document describes that, when an energy gap $\Delta E_{13}$ between a singlet state and a triplet state of a fluorescent material can be decreased, in spite of a typical low transition probability, inverse energy transfer from the triplet state to the singlet state occurs at a high efficiency to express thermally stimulated delayed fluorescence (TADF). Further, a generating mechanism of delayed fluorescence is described in FIG. 10.38 in this document. The compound emitting delayed fluorescence in the first exemplary embodiment is a compound emitting thermally activated delayed fluorescence to be generated by such a mechanism.

Delayed fluorescence can be observed by measuring transitional PL.

Figure 2:
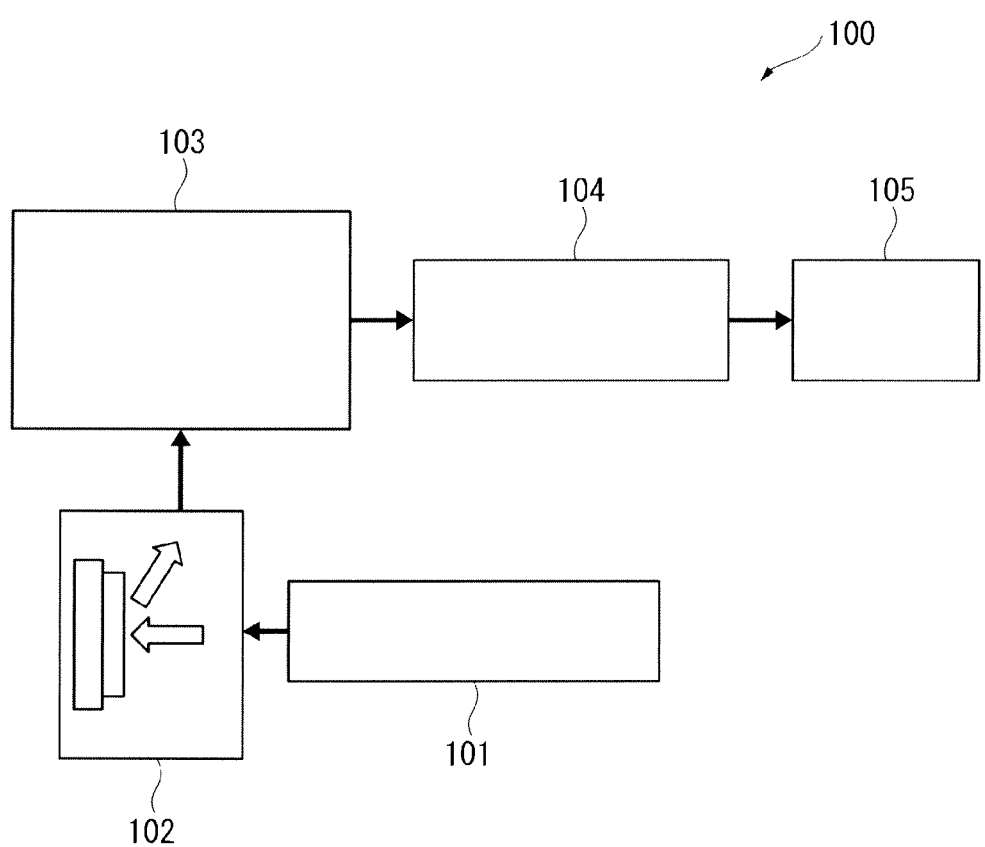
FIG. 2 is a schematic illustration of a measuring device of transitional PL.

FIG. 2 is a schematic illustration of an exemplary device for measuring the transitional PL.

In the first exemplary embodiment, a transitional PL measuring device 100 includes: a pulse laser 101 capable of irradiating light having a predetermined wavelength; a sample chamber 102 that houses a measurement sample; a spectrometer 103 that disperses light irradiated from the measurement sample; a streak camera 104 for forming a two-dimensional image; and a personal computer 105 that scans and analyzes the two-dimensional image. A device usable for the measurement of the transitional PL is not limited to the device described in the first exemplary embodiment.

The sample housed in the sample chamber 102 is obtained by forming a thin film, in which a doping material is doped to a matrix material at a concentration of 12 mass %, on the quartz substrate.

The thin film sample housed in the sample chamber 102 is irradiated with pulse laser from the pulse laser 101 to be excited. Emission is extracted at 90 degrees angle relative to the excited light. The extracted emission is dispersed with the spectrometer 103 to form a two-dimensional image in the streak camera 104. As a result, the two-dimensional image expressed in coordinates of which ordinate axis indicates time and of which abscissa axis indicates a wavelength, in which a luminous point indicates a luminous intensity, can be obtained. If the two-dimensional image is cut out along a predetermined time axis, emission spectrum expressed in coordinates of which ordinate axis indicates a luminous intensity and of which abscissa axis indicates the wavelength can be obtained. If the two-dimensional image is cut out along a wavelength axis, a decay curve (transitional PL) expressed in coordinates of which ordinate axis indicates a logarithm of the luminous intensity and of which abscissa axis indicates time can be obtained.

For instance, using a reference compound H1 below as the matrix material and a reference compound D1 as the doping material, a thin film sample A was prepared as described above and the transitional PL was measured.

[Formula 2]

Reference Compound H1

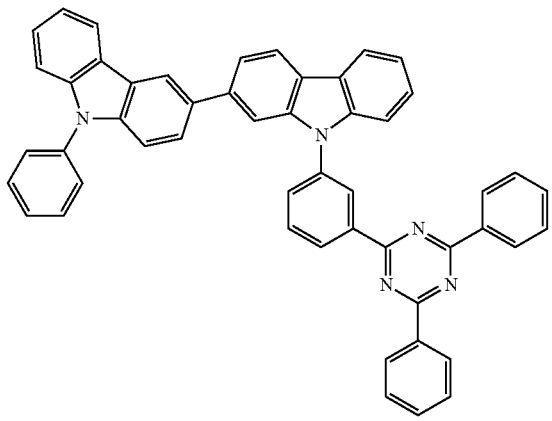

Compound D1

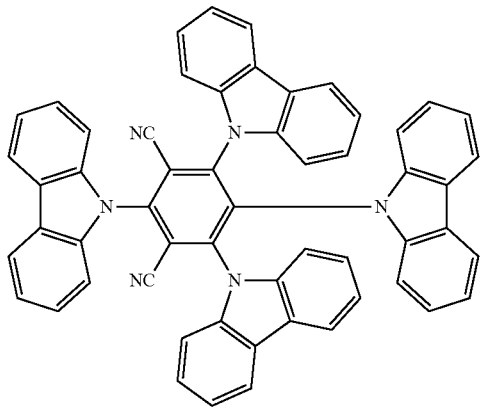

Behavior of delayed fluorescence can also be analyzed based on the decay curve obtained by measuring the transitional PL. The transitional PL measurement is a method for measuring reduction behavior (transitional property) of PL emission obtained after irradiating pulse laser on a sample to excite the sample and stopping irradiating the pulse laser. PL emission in a TADF material is divided into a luminescence component from singlet excitons to be initially generated in PL excitation and a luminescence component from singlet excitons to be generated through triplet excitons. Lifetime of the singlet excitons initially generated in the PL excitation is very short at a nano-second order. Accordingly, the emission from the singlet excitons is rapidly reduced after pulse laser radiation.

On the other hand, since delayed fluorescence provides emission from singlet excitons generated through long-life triplet excitons, emission is gradually reduced. Thus, there is a large difference in time between the emission from the singlet excitons initially generated in the PL excitation and the emission from the singlet excitons derived from the triplet excitons. Accordingly, a luminous intensity derived from delayed fluorescence is obtainable.

Herein, the decay curve was analyzed using the above-described thin film sample A and a thin film sample B. The thin film sample B was prepared as described above, using a reference compound H2 below as the matrix material and the reference compound D1 as the doping material.

Figure 3:
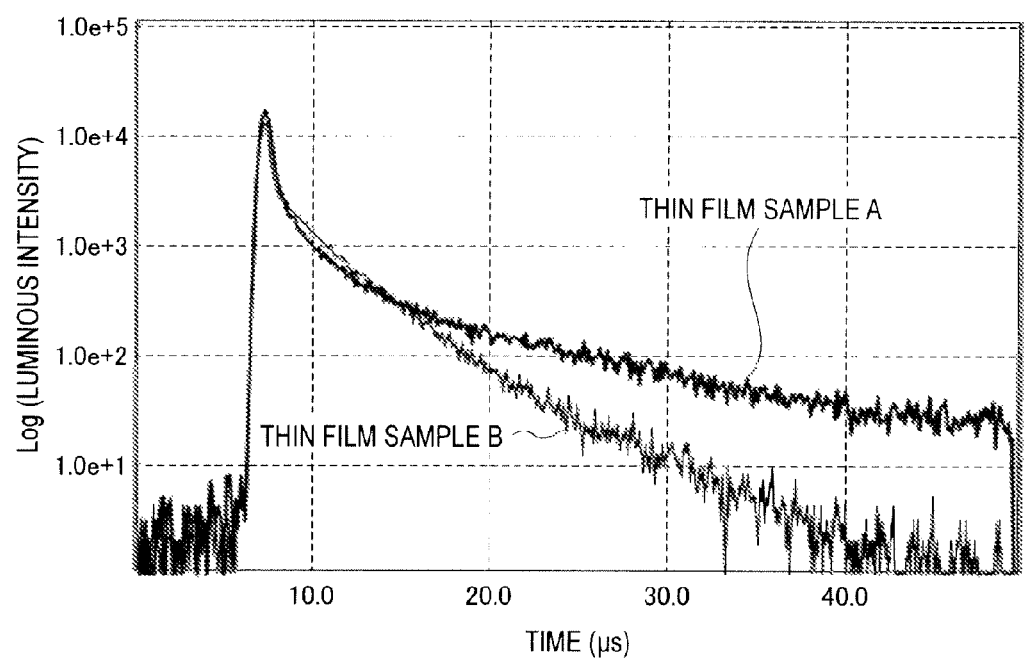
FIG. 3 shows an example of a decay curve of the transitional PL.

FIG. 3 shows a decay curve obtained from the measured transitional PL of the thin film sample A and the thin film sample B.

[Formula 3]

Reference Compound H2

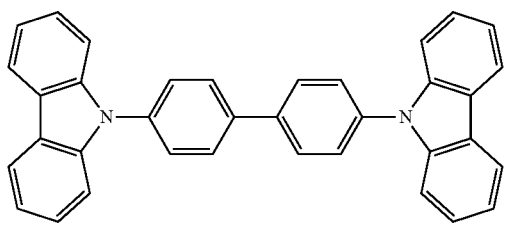

An emission decay curve expressed in coordinates of which ordinate axis indicates a luminous intensity and of which abscissa axis indicates time can be obtained by measuring the transitional PL as described above. Based on the emission decay curve, a fluorescence intensity ratio between fluorescence in the single state generated by light excitation and the delayed fluorescence in the singlet state generated by the inverse energy transfer through the triplet state can be estimated. In the delayed fluorescence material, a ratio of the delayed fluorescence intensity to be gradually reduced is larger to some extent than a ratio of the fluorescence intensity to be rapidly reduced.

In the first exemplary embodiment, an amount of the delayed fluorescence can be calculated using the device of FIG. 2. In the delayed fluorescence compound after excited with pulse light (light irradiated from the pulse laser) having a wavelength to be absorbed in the delayed fluorescence compound, Prompt Emission that is immediately observed in the excited state and Delay Emission that is not observed immediately after the excitation but is later observed are present. In the first exemplary embodiment, an amount of Delay Emission is preferably 5% or more based on an amount of Prompt Emission.

The amount of Prompt Emission and the amount of Delay Emission can be obtained according to the same method as a method described in "Nature 492, 234-238, 2012." The device used for calculating the amounts of Prompt Emission and Delay Emission is not limited to a device described in the above document.

A sample usable for measuring delayed fluorescence is obtained, for instance, by co-depositing a measurement target compound and a compound TH-2 described later on a quartz substrate so that a ratio of the measurement target compound is 12 mass %, thereby forming a 100 nm thin film.

[Formula 4]

TH-2

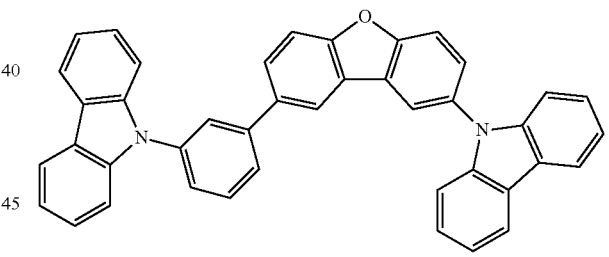

Combination of Thermally Activated Delayed Fluorescence Materials

As a typical arrangement of an organic EL device, an emitting layer contains a fluorescent material and/or a phosphorescent material (a dopant material) and a compound having larger singlet energy or triplet energy than those of the dopant material (a host material). Recombination of holes and electrons in the emitting layer are roughly classified into two types. A first type of recombination is conducted on a host and a second type of recombination is conducted on a dopant (guest).

For the recombination on the host, the host is required to mainly transport carriers and generate excitons on the host. The host is further required to disperse the guest in the film and trap excited energy so as not to disperse the excited energy in adjacent layers.

On the other hand, in the recombination on the guest (dopant), the guest transports carriers and generates excitons. In this recombination, the host is required to mainly disperse the guest in the film of the emitting layer and trap excited energy so as not to disperse the excited energy in adjacent layers.

Thus, a typical host is commonly required to disperse the guest in the film and trap excited energy so as not to disperse the excited energy in adjacent layers.

A fluorescent material and a phosphorescent material which are typically used in the organic EL device cause concentration quenching when contained at a high concentration in the emitting layer. For instance, in a typical fluorescent organic EL device, when a concentration of the guest (dopant) is 10 mass % or more, a significant decrease in the luminous efficiency is caused by a phenomenon called concentration quenching. For this reason, it is required to disperse the guest (dopant) in the film of the emitting layer using the host as described above. Also in a phosphorescent organic EL device, when a concentration of the guest (dopant) is high, a decrease in the luminous efficiency is caused although the decrease is more gradual than in the fluorescent organic EL device.

The inventors found that a significant decrease in the luminous efficiency is not caused even when a concentration of the thermally activated delayed fluorescence material is high (e.g., 50 mass % or more) in the emitting layer. Accordingly, the inventors noted a possible organic EL device in which the host mainly dispersing the guest in the film as described in prior art is not necessarily contained in the emitting layer. Consequently, the inventors confirmed based on the findings that a drive voltage of the organic EL device can be reduced and a emission lifetime thereof can be prolonged by including the thermally activated delayed fluorescence material as the first and second compounds in the emitting layer instead of the host material having a large triplet energy.

In a typical organic EL device, a compound having singlet energy larger than singlet energy of a luminescent material and a compound having triplet energy larger than triplet energy of the luminescent material are contained as the host in the emitting layer. Particularly, in the emitting layer including a blue emitting material, a compound having a particularly large singlet energy or triplet energy is used. However, in such a typical organic EL device, injection and transportation of carriers into the emitting layer are blocked due to a high singlet energy or triplet energy of the host, so that the drive voltage is high and the emission lifetime is short.

In the organic EL device of the first exemplary embodiment, by including the first compound and the second compound (both of which are materials emitting thermally activated delayed fluorescence) in the emitting layer, for instance, even when excited energy is dispersed from the first compound, the second compound absorbs the excited energy to allow thermally activated delayed fluorescence. Moreover, in the organic EL device in the first exemplary embodiment, an energy gap between the first and second compounds is preferably small for the emitting layer to exhibit blue emission. Accordingly, it is preferable that the first and second compounds satisfy at least one of the above relationships of $|EgS(M1)-EgS(M2)| \leq 0.3$ eV and $|Eg_{77K}(M1)-Eg_{77K}(M2)| \leq 0.3$ eV. It is more preferable that the first and second compounds satisfy at least one of the above relationships of $|EgS(M1)-EgS(M2)| \leq 0.2$ eV and $|Eg_{77K}(M1)-Eg_{77K}(M2)| \leq 0.2$ eV.

In the first exemplary embodiment, in case of a blue-emitting organic EL device, it is further preferable that the first and second compounds satisfy at least one of the above relationships of $|EgS(M1)-EgS(M2)| \leq 0.2$ eV and $|Eg_{77K}(M1)-Eg_{77K}(M2)| \leq 0.2$ eV. In case of an organic EL device exhibiting emission in colors (e.g., green, yellow and red) having a longer wavelength than that of blue emission, the energy relationships of the first and second compounds are not limited to the above.

Note that, in the exemplary embodiment, inclusion of the above typical hosts in the emitting layer is not prohibited. A typical host may be included in the emitting layer as long as the first and second compounds according to the exemplary embodiment are present in the emitting layer. However, the emitting layer is preferably formed of the thermally activated delayed fluorescence material.

In the first exemplary embodiment, at least one of the first compound and the second compound preferably has a main peak wavelength of 500 nm or less, more preferably 480 nm or less. The main peak wavelength means a peak wavelength of luminescence spectrum exhibiting a maximum luminous intensity among luminous spectra measured in a toluene solution in which a compound is dissolved at a concentration from $10^{-5}$ mol/l to $10^{-6}$ mol/l.

In the first exemplary embodiment, at least one of the first compound and the second compound preferably emits thermally activated delayed fluorescence in blue.

Content Ratio of Materials in Emitting Layer

In the first exemplary embodiment, it is preferable that a concentration of the first compound in the emitting layer 5 is 20 mass % or more and a concentration of the second compound in the emitting layer 5 is 20 mass % or more. It is more preferable that the concentration of the first compound is 30 mass % or more and the concentration of the second compound is 30 mass % or more. A total concentration of the first compound and the second compound in the emitting layer is 100 mass % or less.

In the first exemplary embodiment, at least one of a plurality of the thermally activated delayed fluorescence compounds contained in the emitting layer 5 is preferably a compound represented by a formula (1) below. For instance, both of the first compound and the second compound may be the compound represented by the formula (1) below. However, in this arrangement, the first compound and the second compound have mutually different molecular structures. Alternatively, for instance, one of the first compound and the second compound may be the compound represented by the formula (1) below and the other of the first compound and the second compound may be a thermally activated delayed fluorescence compound having a different structure.

[Formula 5]

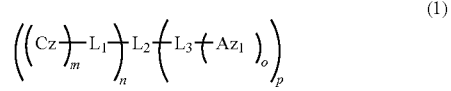

(1)

In the formula (1), Cz is a group derived from a structure represented by a formula (10) below.

[Formula 6]

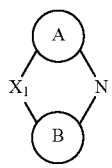

(10)

In the formula (10), $X_1$ represents a single bond, an oxygen atom, a sulfur atom, a carbonyl group, $NR_1$, $CR_2R_3$, $SiR_4R_5$ or $GeR_6R_7$. In other words, a cyclic structure represented by the formula (10) is selected from the group consisting of cyclic structures represented by formulae (10b) to (10i).

[Formula 7]

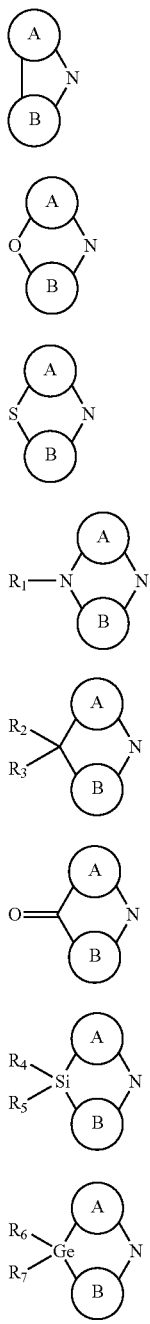

(10b)

(10c)

(10d)

(10e)

(10f)

(10g)

(10h)

(10i)

In the formulae (10), (10b) to (10i), A and B each independently represent a substituted or unsubstituted cyclic structure. When at least one of the cyclic structure A and the cyclic structure B has a plurality of substituents, adjacent substituents may form a ring. The ring to be formed may be a saturated or unsaturated ring. The substituent of the cyclic structures A and B is preferably an electron donating substituent. Moreover, adjacent substituents preferably further form an electron donating ring.

In the formulae (10), (10b) to (10i), when at least one of the cyclic structure A and the cyclic structure B has a substituted or unsubstituted heterocyclic structure, the heterocyclic structure has a partial structure represented by a formula (11) below.

[Formula 8]

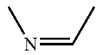

(11)

The group derived from the structure represented by the formula (10) is preferably a group represented by formula (10-1) below.

[Formula 9]

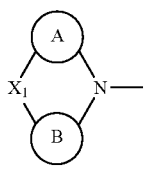

(10-1)

In the formula (10-1), $X_1$ represents the same as $X_1$ in the formula (10). In other words, the group represented by the formula (10-1) is selected from the group consisting of groups represented by formulae (10b-1) to (10i-1) below.

[Formula 10]

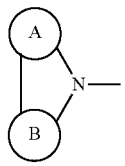

(10b-1)

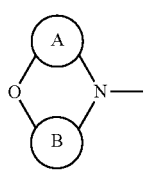

(10c-1)

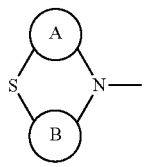

(10d-1)

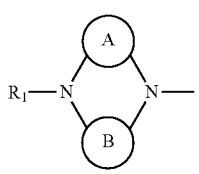

(10e-1)

-continued

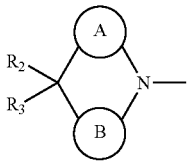
(10f-1)

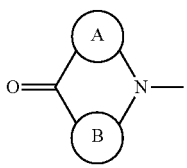
(10g-1)

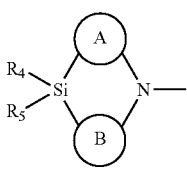
(10h-1)

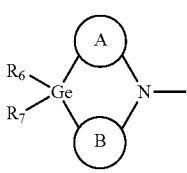
(10i-1)

In the formulae (10b-1) to (10i-1), the cyclic structure A and the cyclic structure B each independently represent the same as the cyclic structure A and the cyclic structure B in the formulae (10) and (10b) to (10i).

In the formula (1), $L_1$ represents a single bond, a substituted or unsubstituted (m+1)-valent aromatic hydrocarbon group or a substituted or unsubstituted (m+1)-valent heterocyclic group.

$L_2$ represents a single bond, a substituted or unsubstituted (n+p)-valent aromatic hydrocarbon group or a substituted or unsubstituted (n+p)-valent heterocyclic group.

$L_3$ represents a single bond, a substituted or unsubstituted (o+1)-valent aromatic hydrocarbon group or a substituted or unsubstituted (o+1)-valent heterocyclic group.

In the formula (1): m is an integer of 1 to 6; n and p are each independently an integer of 1 to 6; and o is an integer of 1 to 6. m, n, o and p are each independently preferably an integer of 1 to 3, more preferably 1 or 2.

In the first exemplary embodiment, $L_1$ is a linking group of which valence is determined depending on a value of m. When m is 1, $L_1$ is a divalent linking group. $L_2$ is a linking group of which valence is determined depending on values of n and p. When both of n and p are 1, $L_2$ is a divalent linking group. The same applies to the later-described linking groups (e.g., $L_3$).

In the formula (1), $Az_1$ is represented by a formula (12) below.

[Formula 11]

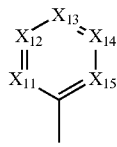
(12)

In the formula (12), $X_{11}$ to $X_{15}$ each independently represent $CR_8$ or a nitrogen atom, in which at least one of $X_{11}$ to $X_{15}$ is a nitrogen atom. In the formula (12), one to three of $X_{11}$ to $X_{15}$ are preferably nitrogen atoms. In the formula (12), adjacent ones of $R_8$ may form a ring.

When a single nitrogen atom is provided, $X_{11}$ or $X_{15}$ is preferably a nitrogen atom. When two nitrogen atoms are provided, $X_{11}$ and $X_{15}$ are preferably nitrogen atoms. When three nitrogen atoms are provided, $X_{11}$, $X_{13}$ and $X_{15}$ are preferably nitrogen atoms. Among the above arrangements, a triazine ring in which $X_{11}$, $X_{13}$ and $X_{15}$ are nitrogen atoms is more preferable in the formula (12).

In the formulae (1), (10), (10b) to (10i) and (10b-1) to (10i-1), $R_1$ to $R_7$ each independently represent a hydrogen atom or a substituent. The substituent in $R_1$ to $R_7$ is selected from the group consisting of a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted alkoxy group having 1 to 30 carbon atoms, a substituted or unsubstituted aryloxy group having 6 to 30 ring carbon atoms, a substituted or unsubstituted alkylamino group having 2 to 30 carbon atoms, a substituted or unsubstituted arylamino group having 6 to 60 ring carbon atoms, a substituted or unsubstituted alkylthio group having 1 to 30 carbon atoms, and a substituted or unsubstituted arylthio group having 6 to 30 ring carbon atoms.

In the formula (12), $R_8$ each independently represents a hydrogen atom or a substituent. The substituent in $R_8$ is selected from the group consisting of a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted alkoxy group having 1 to 30 carbon atoms, a substituted or unsubstituted aryloxy group having 6 to 30 ring carbon atoms, a substituted or unsubstituted alkylamino group having 2 to 30 carbon atoms, a substituted or unsubstituted arylamino group having 6 to 60 ring carbon atoms, a substituted or unsubstituted alkylthio group having 1 to 30 carbon atoms, and a substituted or unsubstituted arylthio group having 6 to 30 ring carbon atoms.

In the first exemplary embodiment, the compound represented by the formula (1) is preferably a compound represented by a formula (13) below.

[Formula 12]

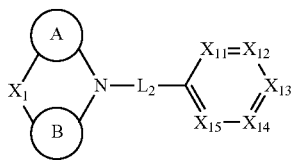

(13)

In the formula (13), $X_1$, a cyclic structure A and a cyclic structure B respectively represent the same as $X_1$, the cyclic structure A and the cyclic structure B in the formula (10).

In the formula (13), $L_2$ represents the same as $L_2$ of the formula (1).

In the formula (13), $X_{11}$ to $X_{15}$ each independently represent the same as $X_{11}$ to $X_{15}$ of the formula (12).

The compound represented by the formula (13) is preferably compounds represented by formulae (13a) to (13c) below, among which a compound represented by the formula (13c) is more preferable.

[Formula 13]

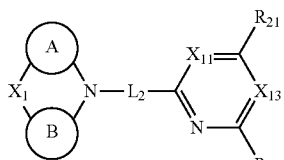

(13a)

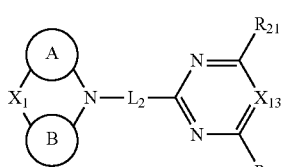

(13b)

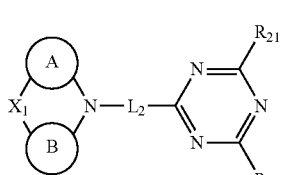

(13c)

In the formulae (13a) to (13c), $X_1$, a cyclic structure A and a cyclic structure B respectively represent the same as $X_1$, the cyclic structure A and the cyclic structure B in the formula (10).

In the formulae (13a) to (13c), $L_2$ represents the same as $L_2$ of the formula (1).

In the formula (13a), $X_{11}$ and $X_{13}$ each independently represent the same as $X_{11}$ to $X_{15}$ of the formula (12).

In the formulae (13a) to (13c), $R_{21}$ and $R_{22}$ each independently represent the same as $R_8$ described above.

In the compounds represented by the formulae (1), (13) and (13a) to (13c) or the groups represented by the formulae (10) and (10b) to (10g), the cyclic structure A and the cyclic structure B are exemplified by a saturated or unsaturated five-membered ring and a saturated or unsaturated six-membered ring. Among the cyclic structures, an aromatic hydrocarbon ring or a heterocyclic ring are preferable, among which a benzene ring and an azine ring are more preferable and a benzene ring is further preferable.

Moreover, in the first exemplary embodiment, both of the cyclic structure A and the cyclic structure B are preferably substituted or unsubstituted benzene rings, in which at least one of the benzene rings more preferably has a substituent. As the substituent of the benzene ring, a substituted or unsubstituted aryl group having 6 to 30 ring carbon atoms and a substituted or unsubstituted heterocyclic group having 5 to 30 ring atoms are preferable. Further, at least one of the cyclic structure A and the cyclic structure B preferably has a substituent. The substituent herein is preferably an electron donating substituent.

In the first exemplary embodiment, Cz of the formula (1) is preferably represented by the formula (10b) and both of the cyclic structure A and the cyclic structure B are preferably substituted or unsubstituted benzene rings. The substituent of the cyclic structures A and B is the same as described above.

In the formula (10b), when one of the cyclic structure A and the cyclic structure B is a heterocycle, the one of the cyclic structure A and the cyclic structure B preferably has the partial structure represented by the formula (11). It is preferable that the cyclic structure A and the cyclic structure B in the formula (10b) are each a six-membered heterocycle having the partial structure represented by the formula (11).

In the first exemplary embodiment, the compound represented by the formula (1) is preferably a compound represented by a formula (14) below.

[Formula 14]

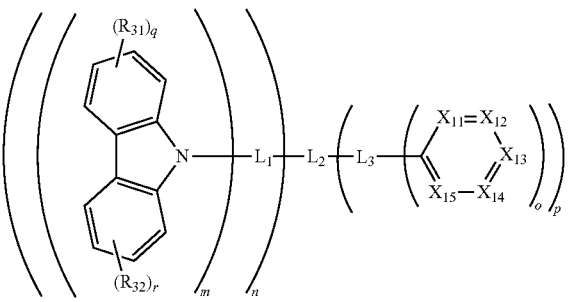

(14)

In the formula (14), $L_1$, $L_2$, $L_3$, m, n, o and p respectively represent the same as $L_1$, $L_2$, $L_3$, m, n, o and p of the formula (1).

In the formula (14), $X_{11}$ to $X_{15}$ each independently represent the same as $X_{11}$ to $X_{15}$ of the formula (12).

In the formula (14), $R_{31}$ and $R_{32}$ each independently represent the same as $R_8$ described above. Adjacent ones of $R_{31}$ may form a ring. Adjacent ones of $R_{32}$ may form a ring.

In the formula (14), q and r are 4.

In the first exemplary embodiment, the compound represented by the formula (1) is preferably a compound represented by a formula (16) below. In other words, in the compound represented by the formula (14), it is preferable that $L_1$ and $L_3$ are each a single bond and n, o and p are 1.

[Formula 15]

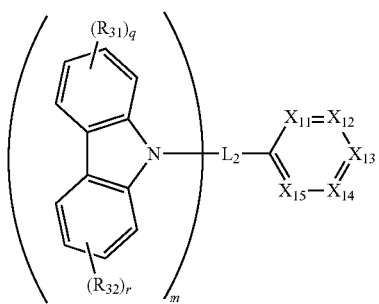

(16)

In the formula (16), $L_2$ and m respectively represent the same as $L_2$ and m of the formula (1).

In the formula (16), $X_{11}$ to $X_{15}$ each independently represent the same as $X_{11}$ to $X_{15}$ of the formula (12).

In the formula (16), $R_{31}$ and $R_{32}$ each independently represent the same as $R_8$ described above. Adjacent ones of $R_{31}$ may form a ring. Adjacent ones of $R_{32}$ may form a ring.

In the formula (16), q and r are 4.

In the first exemplary embodiment, the compound represented by the formula (16) is preferably a compound represented by a formula (17) below. In other words, in the compound represented by the formula (16), it is preferable that m is 1 and one of four $R_{32}$ is a carbazolyl group.

[Formula 16]

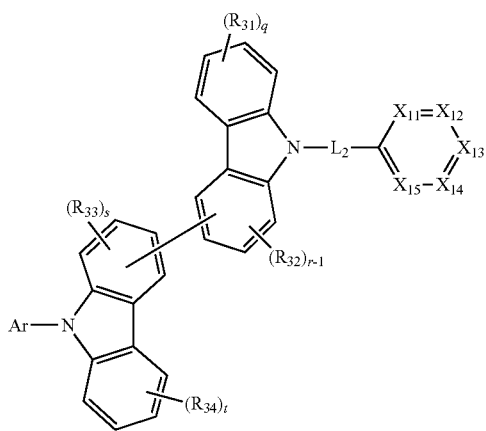

(17)

In the formula (17), $L_2$ represents the same as $L_2$ of the formula (1).

In the formula (17), $X_{11}$ to $X_{15}$ each independently represent the same as $X_{11}$ to $X_{15}$ of the formula (12).

In the formula (17), $R_{31}$ to $R_{34}$ each independently represent the same as $R_8$ described above. Adjacent ones of $R_{31}$ may form a ring. Adjacent ones of $R_{32}$ may form a ring. Adjacent ones of $R_{33}$ may form a ring. Adjacent ones of $R_{34}$ may form a ring.

In the formula (17): q and r are 4; s is 3; and t is 4.

In the formula (17), Ar represents a substituted or unsubstituted aryl group having 6 to 30 ring carbon atoms, or a substituted or unsubstituted heterocyclic group having 5 to 30 ring atoms. Note that Ar may be bonded to a nitrogen atom of a carbazole skeleton through a linking group without being directly bonded thereto. The linking group that links Ar with the nitrogen atom of the carbazole skeleton represents the same as $L_1$ described above. Ar is a substituted or unsubstituted aryl group having 6 to 30 ring carbon atoms. Ar is preferably a phenyl group, biphenyl group, terphenyl group, naphthyl group, phenanthryl group, triphenylyl group, dibenzofuranyl group, dibenzothiophenyl group, carbazolyl group and the like. When Ar is a substituted or unsubstituted aryl group having 6 to 30 ring carbon atoms, Ar is preferably directly bonded to the nitrogen atom of the carbazole skeleton without the linking group.

In the thermally activated delayed fluorescence compound usable in the first exemplary embodiment, as represented by the formula (17), the electron accepting moiety represented by the formula (10) preferably has a biscarbazole structure. When the moiety represented by the formula (10) has a mono-carbazole structure consisting of a single carbazole skeleton, it is speculated that an electron donating performance of the mono-carbazole structure is less than that of the amine structure. In a compound in which an azine ring is bonded to the mono-carbazole structure directly or via a linking group, it is speculated that an electron accepting performance of the azine ring cannot be canceled by the electron donating performance of the mono-carbazole structure. Accordingly, such a compound in which the azine ring is bonded to the mono-carbazole structure directly or via a linking group is an electron accepting compound. On the other hand, in a compound in which a substituent is bonded to the carbazole skeleton, it is considered that the electron donating performance is improved. The above biscarbazole structure is preferable since the electron donating performance is improvable. In the compound represented by the formula (17) in which the azine ring is bonded to the biscarbazole structure via the linking group, it is speculated that the electron accepting performance of the azine ring and the electron donating performance of the biscarbazole structure are balanced with each other, thereby decreasing $\Delta ST$.

In the first exemplary embodiment, the compound represented by the formula (17) is preferably a compound represented by a formula (18) below.

[Formula 17]

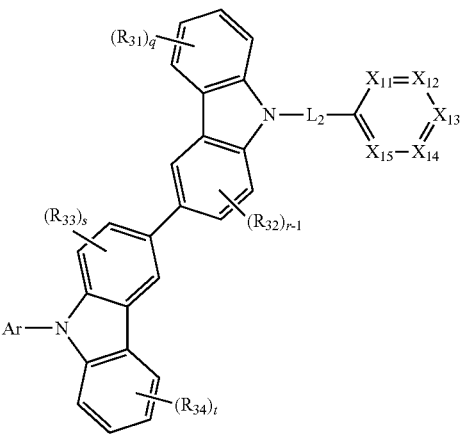

(18)

In the formula (18), $L_2$ represents the same as $L_2$ of the formula (1).

In the formula (18), $X_{11}$ to $X_{15}$ each independently represent the same as $X_{11}$ to $X_{15}$ of the formula (12).

In the formula (18), $R_{31}$ to $R_{34}$ each independently represent the same as $R_8$ described above. Adjacent ones of $R_{31}$ may form a ring. Adjacent ones of $R_{32}$ may form a ring. Adjacent ones of $R_{33}$ may form a ring. Adjacent ones of $R_{34}$ may form a ring.

In the formula (18), q, r, s and t respectively represent the same as q, r, s and t of the formula (17).

In the formula (18), Ar represents the same as Ar of the formula (17).

In the first exemplary embodiment, the compound represented by the formula (17) is preferably a compound represented by a formula (19) below.

[Formula 18]

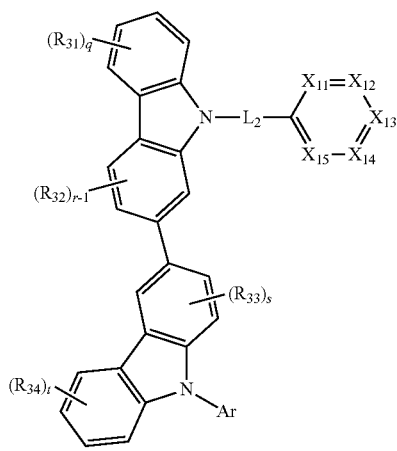

(19)

In the formula (19), $L_2$ represents the same as $L_2$ of the formula (1).

In the formula (19), $X_{11}$ to $X_{15}$ each independently represent the same as $X_{11}$ to $X_{15}$ of the formula (12).

In the formula (19), $R_{31}$ to $R_{34}$ each independently represent the same as $R_8$ described above. Adjacent ones of $R_{31}$ may form a ring. Adjacent ones of $R_{32}$ may form a ring. Adjacent ones of $R_{33}$ may form a ring. Adjacent ones of $R_{34}$ may form a ring.

In the formula (19), q, r, s and t respectively represent the same as q, r, s and t of the formula (17).

In the formula (19), Ar represents the same as Ar of the formula (17).

In the first exemplary embodiment, in the group represented by the formula (10), it is preferable that the cyclic structure A is a substituted or unsubstituted benzene ring and the cyclic structure B is a cyclic structure in which any ones of a plurality of five-membered rings and six-membered rings are mutually fused. In this arrangement, any one of the cyclic structures may have a substituent. In the first exemplary embodiment, the compound represented by the formula (1) is preferably a compound represented by a formula (31) below.

[Formula 19]

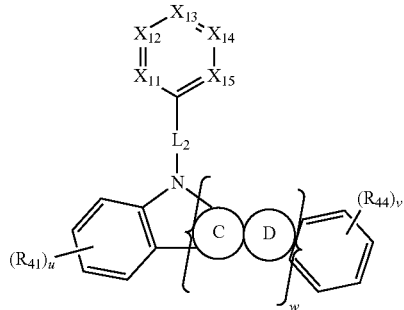

(31)

In the formula (31), $L_2$ represents the same as $L_2$ of the formula (1).

In the formula (31), $X_{11}$ to $X_{15}$ each independently represent the same as $X_{11}$ to $X_{15}$ of the formula (12).

In the formula (31), $R_{41}$ and $R_{44}$ each independently represent the same as $R_8$ described above. Adjacent ones of $R_{41}$ may form a ring. Adjacent ones of $R_{44}$ may form a ring.

In the formula (31), u and v are 4.

In the formula (31), C represents a cyclic structure represented by a formula (32) below and D represents a cyclic structure represented by a formula (33) below. Each of the cyclic structure C and the cyclic structure D is fused to an adjacent cyclic structure at any position.

In the formula (31), w is an integer of 1 to 4. w is a repeating unit of a linking cyclic structure in which the cyclic structure C and the cyclic structure D are fused.

[Formula 20]

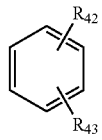

(32)

[Formula 21]

(33)

In the formula (32), $R_{42}$ and $R_{43}$ each independently represent the same as $R_8$ of the formula (1). When $R_{42}$ and $R_{43}$ are substituents at adjacent positions, $R_{42}$ and $R_{43}$ may form a ring.

In the formula (33), $Y_1$ represents $CR_{45}R_{46}$, $NR_{47}$, a sulfur atom, or an oxygen atom. $R_{45}$ to $R_{47}$ each independently represent the same as $R_8$ in the formula (1).

In the thermally activated delayed fluorescence compound usable in the first exemplary embodiment, as represented by the formula (31), the electron accepting moiety represented by the formula (10) is an indolocarbazole skeleton or a skeleton in which an indole ring is further fused to an indolocarbazole ring. Since the electron accepting moiety represented by the formula (10) is provided by such an electron donating moiety, the electron donating performance of the host material in this arrangement can be improved more than that of the above mono-carbazole structure. In the compound represented by the formula (31), it is speculated that the electron accepting performance of the azine ring and the electron donating performance of the electron donating moiety of the indolocarbazole skeleton and the like are balanced with each other, thereby decreasing ΔST.

In the formula (31), w is preferably 1. In this arrangement, the compound represented by the formula (31) is represented by a formula (31a) below.

[Formula 22]

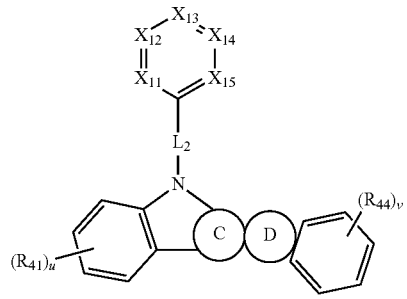

(31a)

In the formula (31a), $L_2$ represents the same as $L_2$ of the formula (1).

In the formula (31a), $X_{11}$ to $X_{15}$ each independently represent the same as $X_{11}$ to $X_{15}$ of the formula (12).

In the formula (31a), $R_{41}$ and $R_{44}$ each independently represent the same as $R_8$ described above. Adjacent ones of $R_{41}$ may form a ring. Adjacent ones of $R_{44}$ may form a ring.

In the formula (31a), u and v are 4.

In the formula (31a), C represents a cyclic structure represented by the formula (32) and D represents a cyclic structure represented by the formula (33). Each of the cyclic structure C and the cyclic structure D is fused to an adjacent cyclic structure at any position.

In the first exemplary embodiment, Cz represented by the formula (1) is preferably a group selected from the group consisting of groups represented by formulae (110) to (115) below.

[Formula 23]

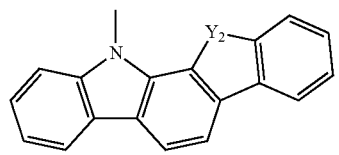
(110)

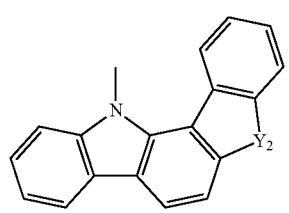
(111)

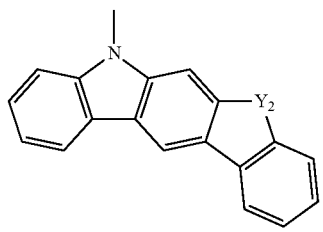
(112)

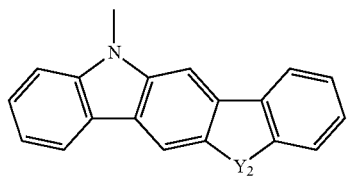
(113)

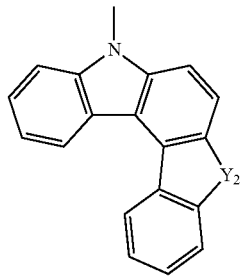
(114)

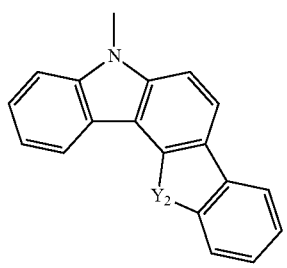
(115)

In the formulae (110) to (115), $Y_2$ represents $CR_{48}R_{49}$, $NR_{50}$, a sulfur atom, or an oxygen atom. $R_{48}$ to $R_{50}$ each independently represent the same as $R_1$ to $R_7$ in the formula (1). The groups represented by the formulae (110) to (115) may further have a substituent.

In the formulae (110) to (115), $Y_2$ is preferably an oxygen atom.

The compounds including the groups represented by the formulae (110) to (115) are preferably compounds represented by the formulae (31b) to (31g).

[Formula 24]

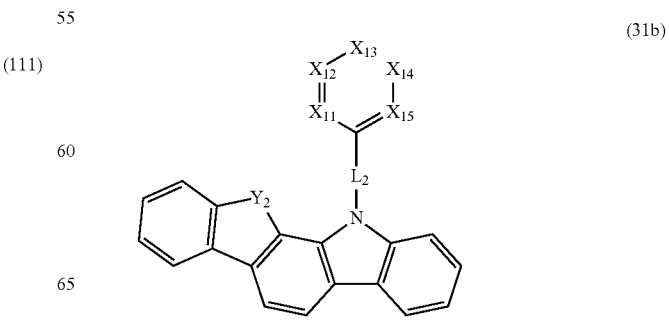
(31b)

(31c)
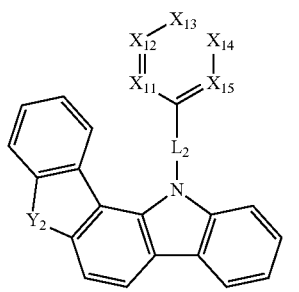

(31d)
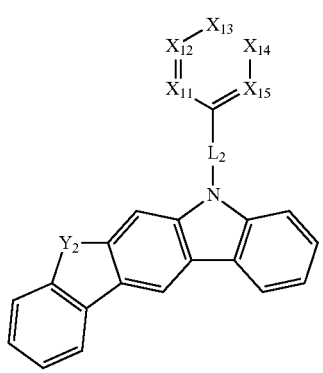

(31e)
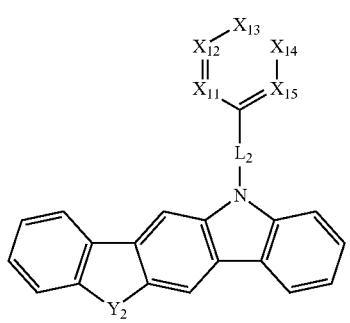

(31f)
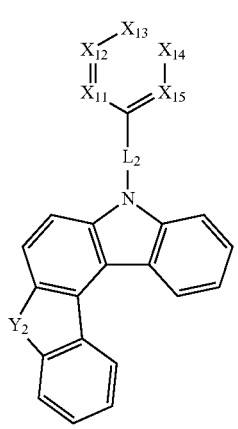

(31g)
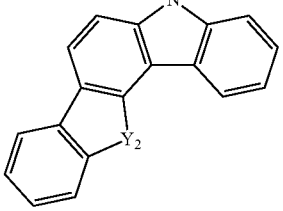

In the formulae (31b) to (31g), $L_2$ represents the same as $L_2$ of the formula (1).

In the formulae (31b) to (31g), $X_{11}$ to $X_{15}$ each independently represent the same as $X_{11}$ to $X_{15}$ of the formula (12).

In the formulae (31b) to (31g), $Y_2$ represents $CR_{48}R_{49}$, $NR_{50}$, a sulfur atom, or an oxygen atom. $R_{48}$ to $R_{50}$ each independently represent the same as $R_1$ to $R_7$ in the formula (1).

In the formulae (31b) to (31g), $Y_2$ is preferably an oxygen atom.

In the organic electroluminescence device in the first exemplary embodiment, Cz of the formula (1) may be a group selected from the group consisting of groups derived from structures represented by formulae (116) to (119) below.

[Formula 25]

(116)
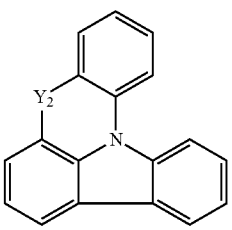

(117)
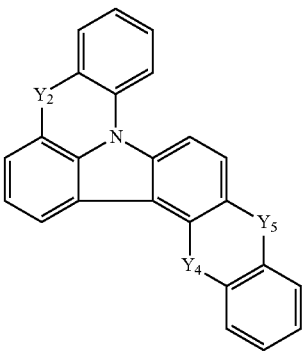

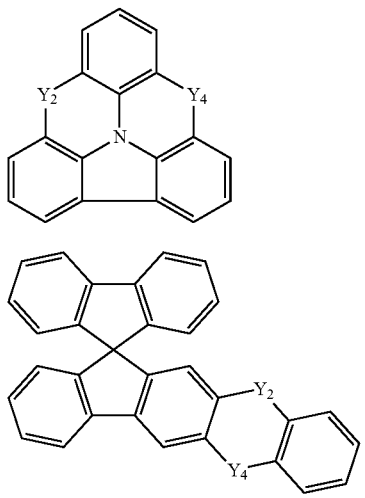

(118)

(119)

In the formulae (116) to (119), $Y_2$, $Y_4$ and $Y_5$ each independently represent $CR_{48}R_{49}$, $NR_{50}$, a sulfur atom, or an oxygen atom. $R_{48}$ to $R_{50}$ each independently represent the same as $R_1$ to $R_{16}$ in the formula (1). The group derived from the structure represented by the formulae (116) to (119) has a hand(s) at any positions and is bonded to $L_2$ in the formula (1). The groups derived from the structures represented by the formulae (116) to (119) may further have a substituent.

In the exemplary embodiment, when $L_2$ is a divalent linking group, $L_2$ is preferably a substituted or unsubstituted divalent aromatic hydrocarbon group.

Moreover, in the exemplary embodiment, when $L_2$ is a divalent linking group, $L_2$ preferably has a divalent six-membered ring structure, more preferably a divalent six-membered ring structure represented by a formula (3), (3a) or (3b) below, further preferably a divalent six-membered ring structure represented by the formula (3) below.

[Formula 26]

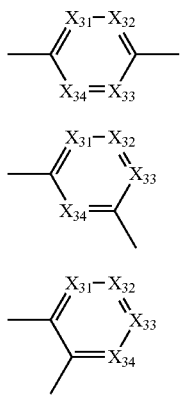

(3)

(3a)

(3b)

In the formulae (3), (3a) and (3b), $X_{31}$ to $X_{34}$ each independently represent $CR_{51}$ or a nitrogen atom. $R_{51}$ each independently represents the same as $R_8$ in the formula (1). In the exemplary embodiment, $X_{31}$ to $X_{34}$ are each independently preferably $CR_{51}$, in which $R_{51}$ is more preferably a hydrogen atom, alkyl group, alkoxy group, aryloxy group, cyano group, halogen atom and silyl group.

In the first exemplary embodiment, the compound represented by the formula (1) is preferably a compound represented by a formula (40) below.

[Formula 27]

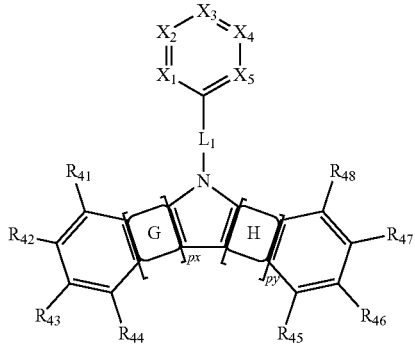

(40)

In the formula (40), $X_1$ to $X_5$ each independently represent $CR_1$ or a nitrogen atom and at least one of $X_1$ to $X_5$ is a nitrogen atom.

In the formula (40), one to three of $X_1$ to $X_5$ are preferably nitrogen atoms. In the formula (40), adjacent ones of $R_1$ as the substituents for carbon atoms may be bonded to each other to form a cyclic structure.

When a single nitrogen atom is provided, $X_1$ or $X_5$ is preferably a nitrogen atom. When two nitrogen atoms are provided, $X_1$ and $X_5$ are preferably nitrogen atoms. When three nitrogen atoms are provided, $X_1$, $X_3$ and $X_5$ are preferably nitrogen atoms. Among the above arrangements, a triazine ring in which $X_1$, $X_3$ and $X_5$ are nitrogen atoms is preferable in the formula (40).

In the formula (40), $L_1$ represents a substituted or unsubstituted divalent aromatic hydrocarbon group.

In the formula (40), $R_1$ and $R_{41}$ to $R_{48}$ each independently represents a hydrogen atom or a substituent. The substituent in $R_1$ and $R_{41}$ to $R_{48}$ is selected from the group consisting of a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted alkoxy group having 1 to 30 carbon atoms, a substituted or unsubstituted aryloxy group having 6 to 30 ring carbon atoms, a substituted or unsubstituted alkylamino group having 2 to 30 carbon atoms, a substituted or unsubstituted arylamino group having 6 to 60 ring carbon atoms, a substituted or unsubstituted alkylthio group having 1 to 30 carbon atoms, and a substituted or unsubstituted arylthio group having 6 to 30 ring carbon atoms.

Each of pairs of $R_{41}$ and $R_{42}$, $R_{42}$ and $R_{43}$, $R_{43}$ and $R_{44}$, $R_{45}$ and $R_{46}$, $R_{46}$ and $R_{47}$, and $R_{47}$ and $R_{48}$ may be mutually bonded to form a cyclic structure.

In the formula (40), G and H each independently represent a cyclic structure represented by a formula (3g) below or a cyclic structure represented by a formula (3h) below. Each of the cyclic structure G and the cyclic structure H is fused to an adjacent cyclic structure at any position.

px and py are each independently an integer of 0 to 4 and respectively represent the number of the cyclic structure G and the number of the cyclic structure H. When px is an integer of 2 to 4, a plurality of cyclic structures G may be mutually the same or different. When py is an integer of 2 to 4, a plurality of cyclic structures H may be mutually the same or different. Accordingly, for instance, when px is 2, the cyclic structures G may be either two cyclic structures represented by the formula (3g) below or two cyclic structures represented by the formula (3h), or alternatively, the cyclic structures G may be a combination of one cyclic structure represented by the formula (3g) and one cyclic structure represented by the formula (3h).

[Formula 28]

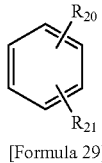
(3g)

[Formula 29]

(3h)

In the formula (3g), $R_{20}$ and $R_{21}$ each independently represent the same as $R_1$ described above and may be mutually bonded to form a cyclic structure. $R_{20}$ and $R_{21}$ are respectively bonded to carbon atoms forming the six-membered ring of the formula (3g).

In the formula (3h), $Z_8$ represents $CR_{22}R_{23}$, $NR_{24}$, a sulfur atom, or an oxygen atom. $R_{22}$ to $R_{24}$ each independently represent a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted alkoxy group having 1 to 30 carbon atoms, a substituted or unsubstituted aryloxy group having 6 to 30 ring carbon atoms, a substituted or unsubstituted alkylamino group having 2 to 30 carbon atoms, a substituted or unsubstituted arylamino group having 6 to 60 ring carbon atoms, a substituted or unsubstituted alkylthio group having 1 to 30 carbon atoms; or a substituted or unsubstituted arylthio group having 6 to 30 ring carbon atoms. $R_{22}$ and $R_{23}$ are each independently preferably a substituted or unsubstituted alkyl group having 1 to 30 carbon atoms or a substituted or unsubstituted aryl group having 6 to 30 ring carbon atoms. Specific examples of $R_{22}$ and $R_{23}$ include a methyl group, ethyl group, n-propyl group, phenyl group, biphenyl group, and terphenyl group. $R_{24}$ is preferably a substituted or unsubstituted aryl group having 6 to 30 ring carbon atoms or a substituted or unsubstituted heterocyclic group having 5 to 30 ring atoms. Specific examples of $R_{24}$ include a phenyl group, biphenyl group, terphenyl group, naphthyl group, phenanthryl group, triphenylyl group, dibenzofuranyl group, dibenzothiophenyl group, and carbazolyl group. $R_{24}$ is more preferably a substituted or unsubstituted aryl group having 6 to 30 ring carbon atoms. Specific examples of $R_{24}$ include a phenyl group, biphenyl group, terphenyl group, naphthyl group, phenanthryl group and triphenylyl group.

In the formula (40), at least one of combinations of substituents selected from $R_{41}$ to $R_{48}$ and $R_{20}$ to $R_{24}$ may be mutually bonded to form a cyclic structure.

$L_1$ of the formula (40) preferably has a divalent six-membered ring structure, more preferably a divalent six-membered ring structure represented by a formula (4), (4a) or (4b) below, further preferably a divalent six-membered ring structure represented by the formula (4) below.

[Formula 30]

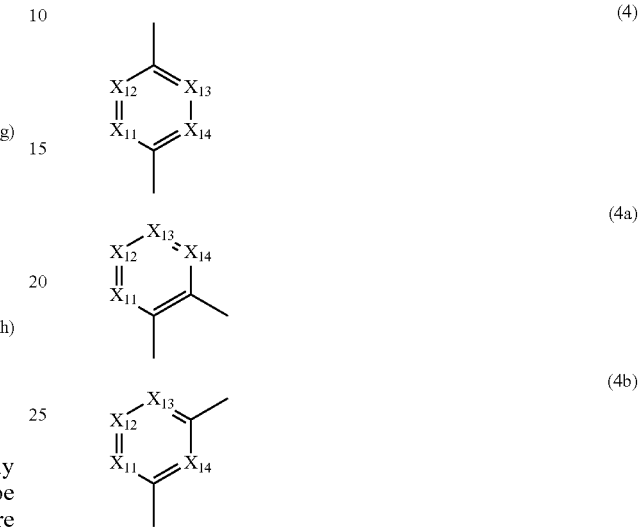

In the formulae (4), (4a) and (4b), $X_{11}$ to $X_{14}$ each independently represent $CR_{11}$ or a nitrogen atom, in which $R_{11}$ each independently represents a hydrogen atom or a substituent. The substituent in $R_{11}$ in the formulae (4), (4a) and (4b) is selected from the group consisting of a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted alkoxy group having 1 to 30 carbon atoms, a substituted or unsubstituted aryloxy group having 6 to 30 ring carbon atoms, a substituted or unsubstituted alkylamino group having 2 to 30 carbon atoms, a substituted or unsubstituted arylamino group having 6 to 60 ring carbon atoms, a substituted or unsubstituted alkylthio group having 1 to 30 carbon atoms, and a substituted or unsubstituted arylthio group having 6 to 30 ring carbon atoms.

$X_{11}$ to $X_{14}$ of the formulae (4), (4a) and (4b) are each independently preferably $CR_{11}$, in which $R_{11}$ is more preferably a hydrogen atom, alkyl group, alkoxy group, aryloxy group, cyano group, halogen atom and silyl group.

Particularly preferably, $L_1$ is represented by the formula (4); $X_{11}$ to $X_{14}$ are each independently $CR_{11}$; $X_1$, $X_3$ and $X_5$ of the formula (40) are nitrogen atoms; and $X_2$ and $X_4$ are $CR_1$. In other words, the compound represented by the formula (1) is preferably provided by a compound in which an electron accepting moiety is a substituted or unsubstituted triazine ring and the triazine ring is connected to an electron donating moiety by a substituted or unsubstituted p-phenylene group. The compound in this arrangement is represented by a formula (41) below.

[Formula 31]

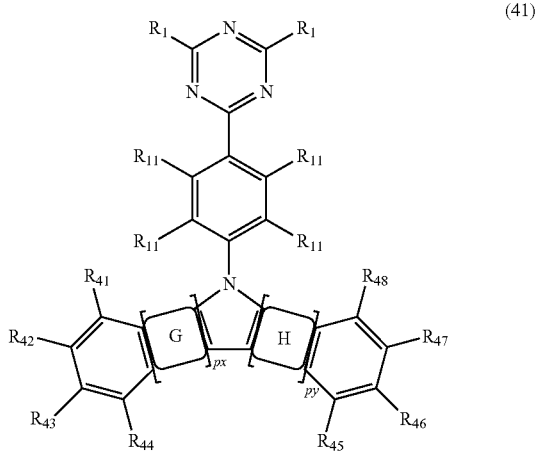

(41)

In the formula (41), $R_1$, $R_{11}$, $R_{41}$ to $R_{48}$, the cyclic structure G, the cyclic structure H, px and py respectively represent the same as $R_1$, $R_{11}$, $R_{41}$ to $R_{48}$, the cyclic structure G, the cyclic structure H, px and py described in the formulae (4) and (40).

In the third exemplary embodiment, px and py are preferably the same integer, among which px and py are preferably 2. In this arrangement, the formula (40) is represented by a formula (42) below.

[Formula 32]

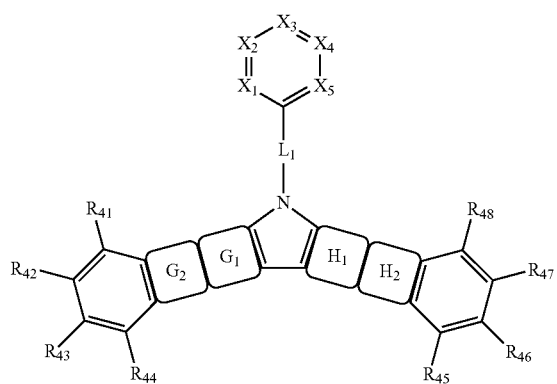

(42)

In the formula (42), $X_1$ to $X_5$, $R_{41}$ to $R_{48}$ and $L_1$ respectively independently represent the same as $X_1$ to $X_5$, $R_{41}$ to $R_{48}$ and $L_1$ of the formula (40).

The cyclic structure $G_1$ and the cyclic structure $G_2$ each independently represent the same as the cyclic structure G described above. The cyclic structure $H_1$ and the cyclic structure $H_2$ each independently represent the same as the cyclic structure H described above.

In the formula (42), the cyclic structure $G_1$ and the cyclic structure $H_1$ are each independently the cyclic structure represented by the formula (3g). The cyclic structure $G_2$ and the cyclic structure $H_2$ are each independently the cyclic structure represented by the formula (3h).

In the exemplary embodiment, it is also preferable that one of px and py is 0 while the other of px and py is 4. For instance, when px is 4 and py is 0, the formula (40) is represented by a formula (43) below.

[Formula 33]

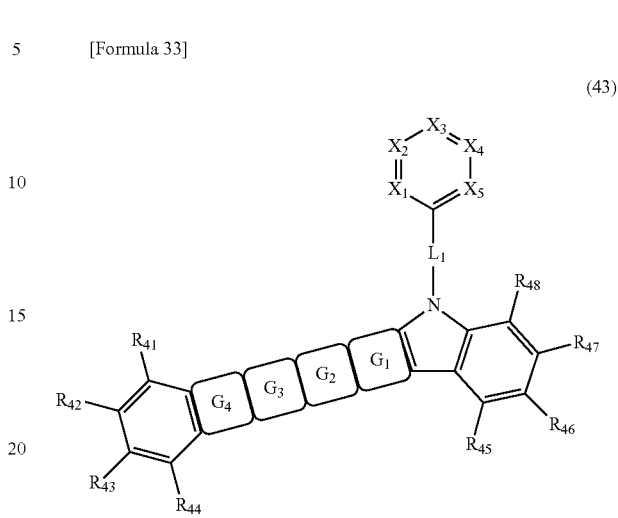

(43)

In the formula (43), $X_1$ to $X_5$, $R_{41}$ to $R_{48}$ and $L_1$ respectively independently represent the same as $X_1$ to $X_5$, $R_{41}$ to $R_{48}$ and $L_1$ of the formula (40).

The cyclic structure $G_1$, the cyclic structure $G_2$, a cyclic structure $G_3$, and a cyclic structure $G_4$ each independently represent the same as the cyclic structure G.

In the formula (43), the cyclic structure $G_1$ and the cyclic structure $G_3$ are each independently the cyclic structure represented by the formula (3g). The cyclic structure $G_2$ and the cyclic structure $G_4$ are each independently the cyclic structure represented by the formula (3h).

In the formulae (42) and (43), $X_1$ to $X_5$ and $L_1$ are preferably the above preferable examples of $X_1$ to $X_5$ and $L_1$.

Herein, the number of carbon atoms forming a ring (also referred to as ring carbon atoms) means the number of carbon atoms included in atoms forming the ring itself of a compound in which the atoms are bonded to form the ring (e.g., a monocyclic compound, a fused ring compound, a cross-linked compound, a carbocyclic compound, and a heterocyclic compound). When the ring is substituted by a substituent, carbon atom(s) included in the substituent is not counted as the ring carbon atoms. The same applies to the "ring carbon atoms" described below, unless particularly noted. For instance, a benzene ring has 6 ring carbon atoms, a naphthalene ring has 10 ring carbon atoms, a pyridinyl group has 5 ring carbon atoms, and a furanyl group has 4 ring carbon atoms. When a benzene ring or a naphthalene ring is substituted, for instance, by an alkyl group, the carbon atoms of the alkyl group are not counted as the ring carbon atoms. For instance, when a fluorene ring (inclusive of a spirofluorene ring) is bonded as a substituent to a fluorene ring, the carbon atoms of the fluorene ring as a substituent are not counted as the ring carbon atoms.

Herein, the number of atoms forming a ring (also referred to as ring atoms) means the number of atoms forming the ring itself of a compound in which the atoms are bonded to form the ring (e.g., a monocyclic compound, a fused ring compound, a cross-linked compound, a carbocyclic compound, and a heterocyclic compound). Atom(s) not forming the ring (e.g., hydrogen atom(s) for saturating the valence of the atom which forms the ring) and atom(s) in a substituent by which the ring is substituted are not counted as the ring atoms. The same applies to the "ring atoms" described below, unless particularly noted. For instance, a pyridine ring has 6 ring atoms, a quinazoline ring has 10 ring atoms, and a furan ring has 5 ring atoms. Hydrogen atoms respectively bonded to carbon atoms of the pyridine ring or the quinazoline ring and atoms forming a substituent are not counted as the ring atoms. For instance, when a fluorene ring (inclusive of a spirofluorene ring) is bonded as a substituent to a fluorene ring, the atoms of the fluorene ring as a substituent are not included in the ring atoms.

Examples of the aryl group having 6 to 30 ring carbon atoms in the exemplary embodiment are a phenyl group, biphenyl group, terphenyl group, naphthyl group, anthryl group, phenanthryl group, fluorenyl group, pyrenyl group, chrysenyl group, fluoranthenyl group, benz[a]anthryl group, benzo[c]phenanthryl group, triphenylenyl group, benzo[k]fluoranthenyl group, benzo[g]chrysenyl group, benzo[b]triphenylenyl group, picenyl group, and perylenyl group.

The aryl group in the exemplary embodiment preferably has 6 to 20 ring carbon atoms, more preferably 6 to 12 ring carbon atoms. Among the aryl group, a phenyl group, biphenyl group, naphthyl group, phenanthryl group, terphenyl group and fluorenyl group are particularly preferable. In a 1-fluorenyl group, 2-fluorenyl group, 3-fluorenyl group and 4-fluorenyl group, a carbon atom at a position 9 is preferably substituted by the substituted or unsubstituted alkyl group having 1 to 30 carbon atoms in a later-described exemplary embodiment.

Examples of the heterocyclic group having 5 to 30 ring atoms in the exemplary embodiment are a pyridyl group, pyrimidinyl group, pyrazinyl group, pyridazynyl group, triazinyl group, quinolyl group, isoquinolinyl group, naphthyridinyl group, phthalazinyl group, quinoxalinyl group, quinazolinyl group, phenanthridinyl group, acridinyl group, phenanthrolinyl group, pyrrolyl group, imidazolyl group, pyrazolyl group, triazolyl group, tetrazolyl group, indolyl group, benzimidazolyl group, indazolyl group, imidazopyridinyl group, benzotriazolyl group, carbazolyl group, furyl group, thienyl group, oxazolyl group, thiazolyl group, isoxazolyl group, isothiazolyl group, oxadiazolyl group, thiadiazolyl group, benzofuranyl group, benzothiophenyl group, benzoxazolyl group, benzothiazolyl group, benzisoxazolyl group, benzisothiazolyl group, benzoxadiazolyl group, benzothiadiazolyl group, dibenzofuranyl group, dibenzothiophenyl group, piperidinyl group, pyrrolidinyl group, piperazinyl group, morpholyl group, phenazinyl group, phenothiazinyl group, and phenoxazinyl group.

The heterocyclic group in the exemplary embodiment preferably has 5 to 20 ring atoms, more preferably 5 to 14 ring atoms. Among the above, a 1-dibenzofuranyl group, 2-dibenzofuranyl group, 3-dibenzofuranyl group, 4-dibenzofuranyl group, 1-dibenzothiophenyl group, 2-dibenzothiophenyl group, 3-dibenzothiophenyl group, 4-dibenzothiophenyl group, 1-carbazolyl group, 2-carbazolyl group, 3-carbazolyl group, 4-carbazolyl group, and 9-carbazolyl group are particularly preferable. A nitrogen atom at a position 9 of each of 1-carbazolyl group, 2-carbazolyl group, 3-carbazolyl group and 4-carbazolyl group is preferably substituted by a substituted or unsubstituted aryl group having 6 to 30 ring carbon atoms or a substituted or unsubstituted heterocyclic group having 5 to 30 ring atoms in the exemplary embodiment.

The alkyl group having 1 to 30 carbon atoms in the exemplary embodiment may be linear, branched or cyclic. Examples of the linear or branched alkyl group are a methyl group, ethyl group, propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neo-pentyl group, amyl group, isoamyl group, 1-methylpentyl group, 2-methylpentyl group, 1-pentylhexyl group, 1-butylpentyl group, 1-heptyloctyl group and 3-methylpentyl group.

The linear or branched alkyl group in the exemplary embodiment preferably has 1 to 10 carbon atoms, more preferably 1 to 6 carbon atoms. Among the linear or branched alkyl group, a methyl group, ethyl group, propyl group, isopropyl group, n-butyl group, s-butyl group, isobutyl group, t-butyl group, n-pentyl group, n-hexyl group, amyl group, isoamyl group and neopentyl group are particularly preferable.

Examples of the cycloalkyl group in the exemplary embodiment are a cyclopropyl group, cyclobutyl group, cyclopentyl group, cyclohexyl group, 4-metylcyclohexyl group, adamantyl group and norbornyl group. The cycloalkyl group preferably has 3 to 10 ring carbon atoms, more preferably 5 to 8 ring carbon atoms. Among the cycloalkyl group, a cyclopentyl group and a cyclohexyl group are particularly preferable.

A halogenated alkyl group provided by substituting an alkyl group with a halogen atom is exemplified by one provided by substituting an alkyl group having 1 to 30 carbon atoms with one or more halogen groups. Specific examples of the above halogenated alkyl group are a fluoromethyl group, difluoromethyl group, trifluoromethyl group, fluoroethyl group, trifluoromethylmethyl group, trifluoroethyl group and pentafluoroethyl group.

The alkylsilyl group having 3 to 30 carbon atoms in the exemplary embodiment is exemplified by a trialkylsilyl group having the above examples of the alkyl group having 1 to 30 carbon atoms. Specific examples of the alkylsilyl group are a trimethylsilyl group, triethylsilyl group, tri-n-butylsilyl group, tri-n-octylsilyl group, triisobutylsilyl group, dimethylethylsilyl group, dimethylisopropylsilyl group, dimethyl-n-propylsilyl group, dimethyl-n-butylsilyl group, dimethyl-t-butylsilyl group, diethylisopropylsilyl group, vinyl dimethylsilyl group, propyldimethylsilyl group, and triisopropylsilyl group. Three alkyl groups in the trialkylsilyl group may be the same or different.

Examples of the arylsilyl group having 6 to 30 ring carbon atoms in the exemplary embodiment are a dialkylarylsilyl group, alkyldiarylsilyl group and triarylsilyl group.

The dialkylarylsilyl group is exemplified by a dialkylarylsilyl group including two of the alkyl group listed as the examples of the alkyl group having 1 to 30 carbon atoms and one of the aryl group listed as the examples of the aryl group having 6 to 30 ring carbon atoms. The dialkylarylsilyl group preferably has 8 to 30 carbon atoms.

The alkyldiarylsilyl group is exemplified by an alkyldiarylsilyl group including one of the alkyl group listed as the examples of the alkyl group having 1 to 30 carbon atoms and two of the aryl group listed as the examples of the aryl group having 6 to 30 ring carbon atoms. The alkyldiarylsilyl group preferably has 13 to 30 carbon atoms.

The triarylsilyl group is exemplified by a triarylsilyl group including three of the aryl group listed as the examples of the aryl group having 6 to 30 ring carbon atoms. The triarylsilyl group preferably has 18 to 30 carbon atoms.

The alkoxy group having 1 to 30 carbon atoms in the exemplary embodiment is represented by $-OZ_1$. $Z_1$ is exemplified by the above alkyl group having 1 to 30 carbon atoms. Examples of the alkoxy group are a methoxy group, ethoxy group, propoxy group, butoxy group, pentyloxy group and hexyloxy group.

A halogenated alkoxy group provided by substituting an alkoxy group with a halogen atom is exemplified by one provided by substituting an alkoxy group having 1 to 30 carbon atoms with one or more halogen groups.

The aryloxy group having 6 to 30 ring carbon atoms in the exemplary embodiment is represented by —$OZ_2$. $Z_2$ is exemplified by the aryl group having 6 to 30 ring carbon atoms or a monocyclic group and a fused cyclic group described below. The aryloxy group is exemplified by a phenoxy group.

The alkylamino group having 2 to 30 carbon atoms is represented by —$NHR_V$ or —$N(R_V)_2$. $R_V$ is exemplified by the alkyl group having 1 to 30 carbon atoms.

The arylamino group having 6 to 60 ring carbon atoms is represented by —$NHR_V$ or —$N(R_V)_2$. $R_V$ is exemplified by the above aryl group having 6 to 30 ring carbon atoms.

The alkylthio group having 1 to 30 carbon atoms is represented by —$SR_V$. $R_V$ is exemplified by the alkyl group having 1 to 30 carbon atoms.

The arylthio group having 6 to 30 ring carbon atoms is represented by —$SR_V$. $R_V$ is exemplified by the above aryl group having 6 to 30 ring carbon atoms.

In the invention, "carbon atoms forming a ring (ring carbon atoms)" mean carbon atoms forming a saturated ring, an unsaturated ring, or an aromatic ring. "Atoms forming a ring (ring atoms)" mean carbon atoms and hetero atoms forming a hetero ring including a saturated ring, unsaturated ring, or aromatic ring.

In the invention, a hydrogen atom includes isotope having different numbers of neutrons, specifically, protium, deuterium and tritium.

In the exemplary embodiment, examples of the substituent meant by "substituted or unsubstituted" and the substituent in the cyclic structures A, B, C, D, G and H are an alkenyl group, alkynyl group, aralkyl group, halogen atom, cyano group, hydroxyl group, nitro group and carboxy group, in addition to the above-described aryl group, heterocyclic group, alkyl group (linear or branched alkyl group, cycloalkyl group and haloalkyl group), alkylsilyl group, arylsilyl group, alkoxy group, aryloxy group, alkylamino group, arylamino group, alkylthio group, and arylthio group.

Among the above substituents, an aryl group, heterocyclic group, alkyl group, halogen atom, alkylsilyl group, arylsilyl group and cyano group are preferable. More preferable substituents are one listed as the preferable substituents described for each substituent.

In the exemplary embodiment, the aromatic hydrocarbon group is preferably an aryl group having 6 to 30 ring atoms and the heterocyclic group is preferably a heterocyclic group having 5 to 30 ring atoms.

The alkenyl group is preferably an alkenyl group having 2 to 30 carbon atoms, which may be linear, branched or cyclic. Examples of the alkenyl group include a vinyl group, propenyl group, butenyl group, oleyl group, eicosapentaenyl group, docosahexaenyl group, styryl group, 2,2-diphenylvinyl group, 1,2,2-triphenylvinyl group, 2-phenyl-2-propenyl group, cyclopentadienyl group, cyclopentenyl group, cyclohexenyl group, and cyclohexadienyl group.

The alkynyl group is preferably an alkynyl group having 2 to 30 carbon atoms, which may be linear, branched or cyclic. Examples of the alkynyl group include ethynyl, propynyl, and 2-phenylethynyl.

The aralkyl group is preferably an aralkyl group having 6 to 30 ring carbon atoms and is represented by —$Z_3$-$Z_4$. $Z_3$ is exemplified by an alkylene group corresponding to the above alkyl group having 1 to 30 carbon atoms. $Z_4$ is exemplified by the above aryl group having 6 to 30 ring carbon atoms. The aralkyl group is preferably an aralkyl group having 7 to 30 carbon atoms, in which an aryl portion has 6 to 30 carbon atoms, preferably 6 to 20 carbon atoms, more preferably 6 to 12 carbon atoms, and an alkyl portion has 1 to 30 carbon atoms, preferably 1 to 20 carbon atoms, more preferably 1 to 10 carbon atoms, further preferably 1 to 6 carbon atoms. Examples of the aralkyl group are a benzyl group, 2-phenylpropane-2-yl group, 1-phenylethyl group, 2-phenylethyl group, 1-phenylisopropyl group, 2-phenylisopropyl group, phenyl-t-butyl group, α-naphthylmethyl group, 1-α-naphthylethyl group, 2-α-naphthylethyl group, 1-α-naphthylisopropyl group, 2-α-naphthylisopropyl group, β-naphthylmethyl group, 1-β-naphthylethyl group, 2-β-naphthylethyl group, 1-β-naphthylisopropyl group, and 2-β-naphthylisopropyl group.

Examples of the halogen atom are fluorine, chlorine, bromine and iodine, among which a fluorine atom is preferable.

"Unsubstituted" in "substituted or unsubstituted" means that a group is not substituted by the above-described substituents but bonded with a hydrogen atom.

Herein, "XX to YY carbon atoms" in the description of "substituted or unsubstituted ZZ group having XX to YY carbon atoms" represent carbon atoms of an unsubstituted ZZ group and do not include carbon atoms of a substituent(s) of a substituted ZZ group. "YY" is larger than "XX" and each of "XX" and "YY" represents an integer of 1 or more.

Herein, "XX to YY atoms" in the description of "substituted or unsubstituted ZZ group having XX to YY atoms" represent atoms of an unsubstituted ZZ group and does not include atoms of a substituent(s) of a substituted ZZ group. "YY" is larger than "XX" and each of "XX" and "YY" represents an integer of 1 or more.

The same description as the above applies to "substituted or unsubstituted" in the following compound or a partial structure thereof.

Specific examples of the compound represented by the formula (1) are shown below, but the compound represented by the formula (4) is not limited thereto.

[Formula 34]

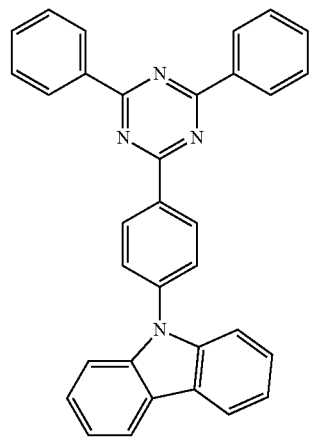

37
-continued
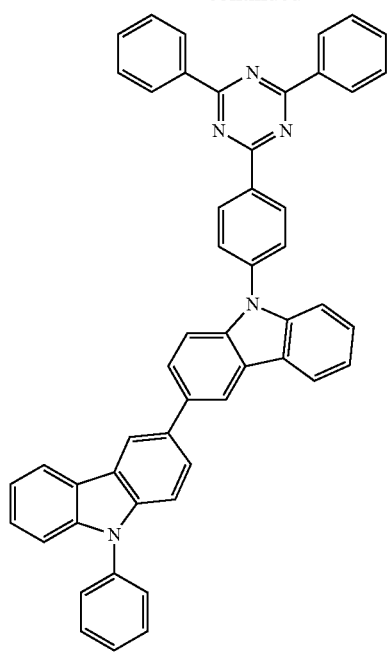
38
-continued
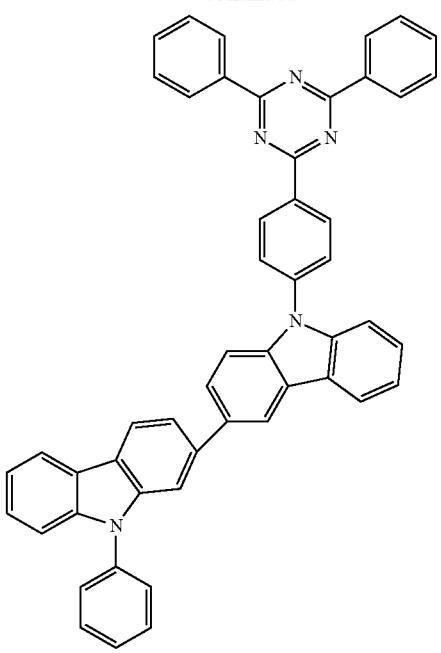
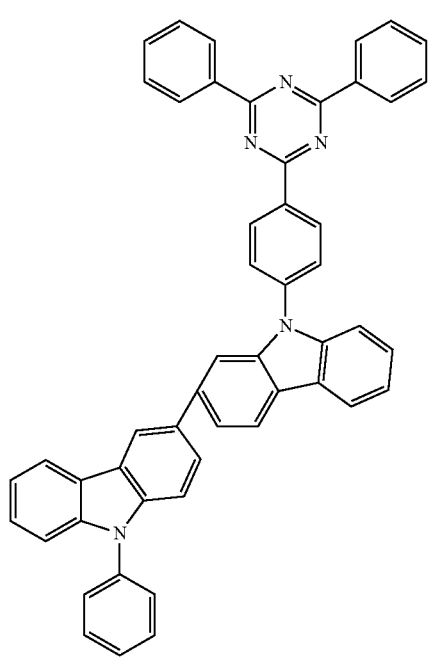
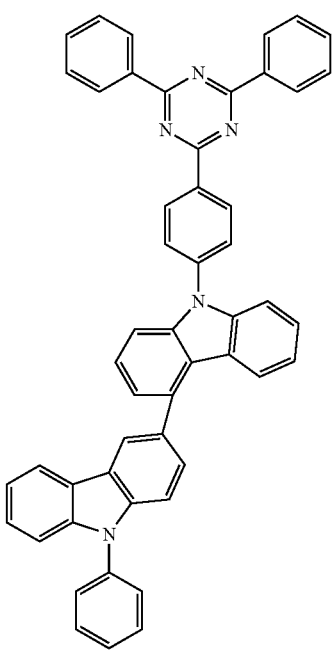

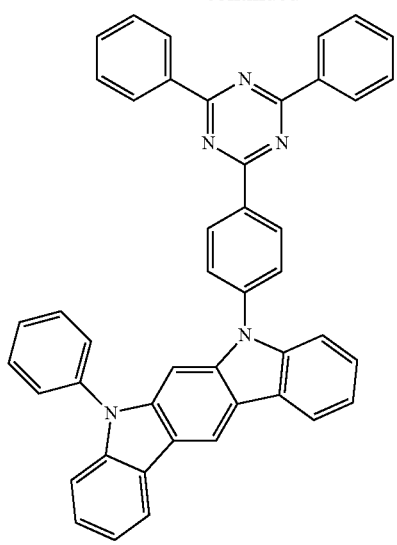
[Formula 35]
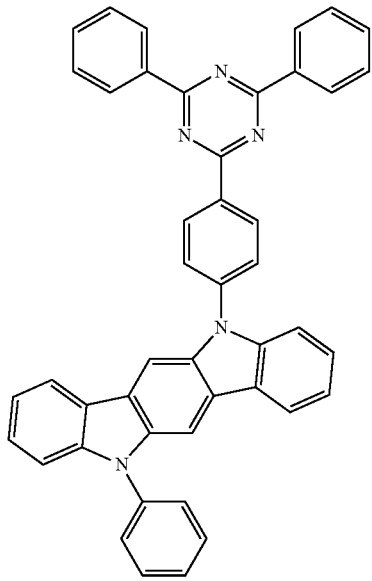
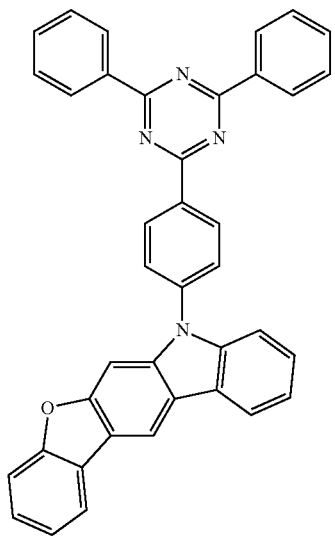
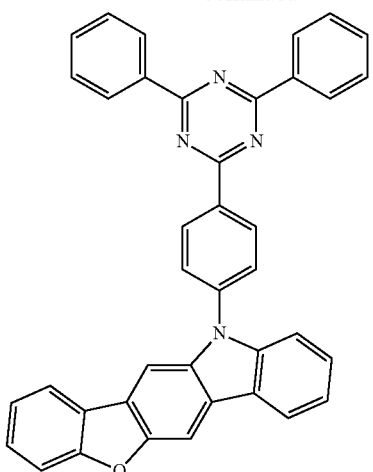
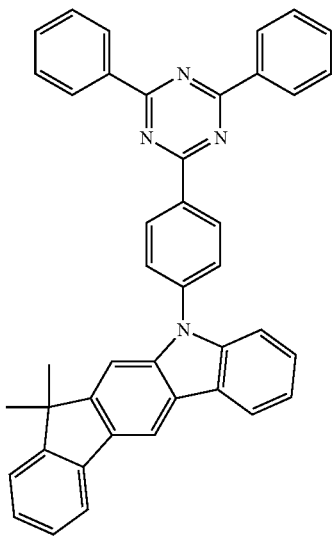
[Formula 36]
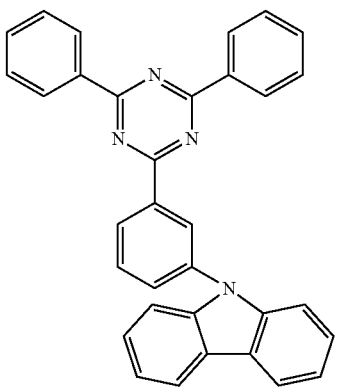

41
-continued
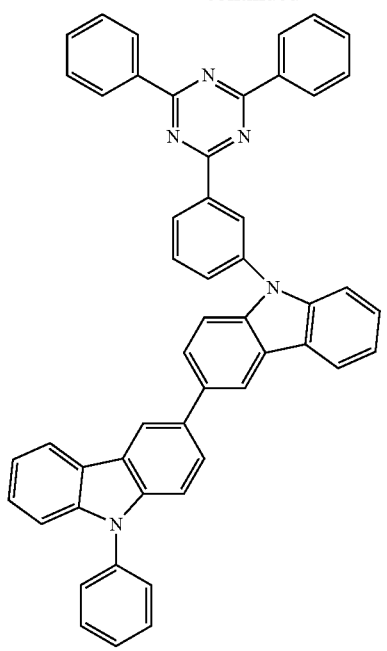
42
-continued
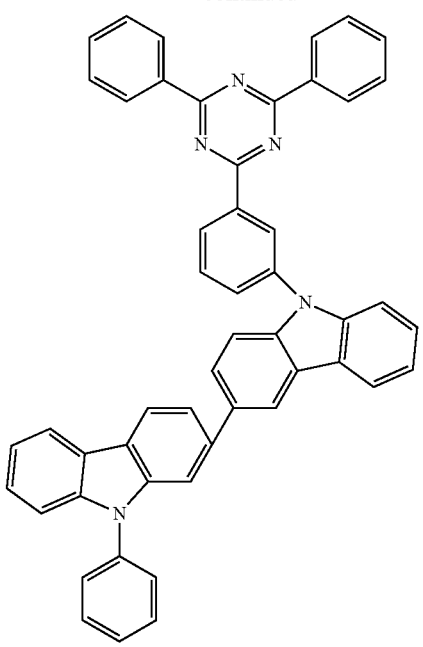
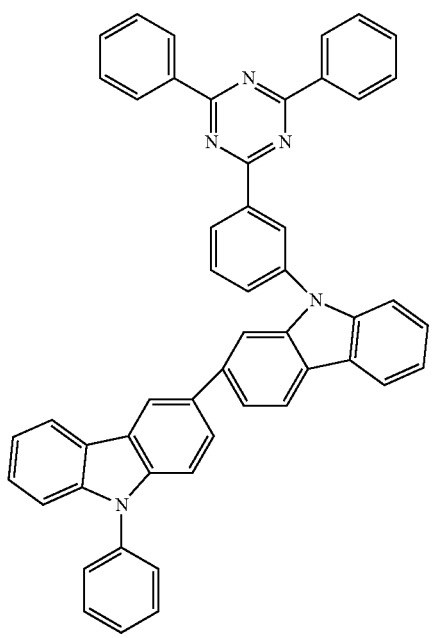
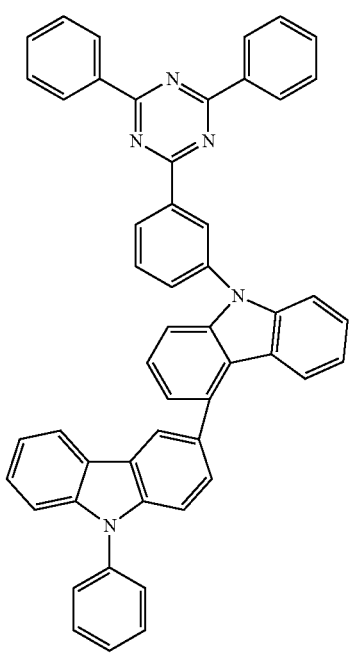

-continued
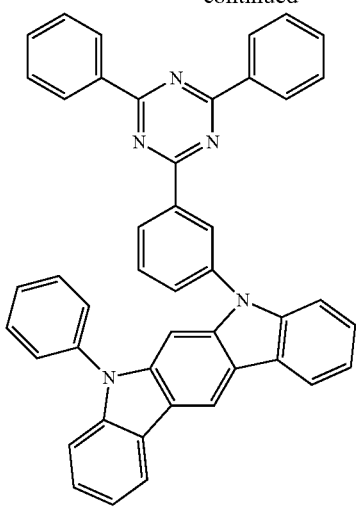
[Formula 37]
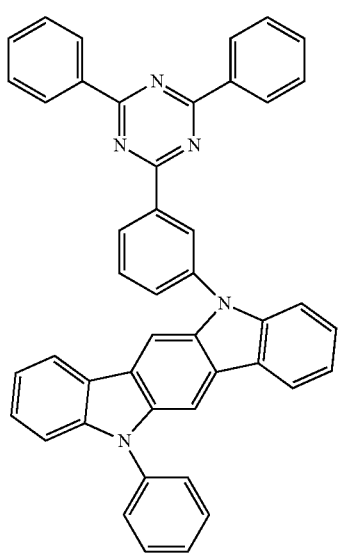
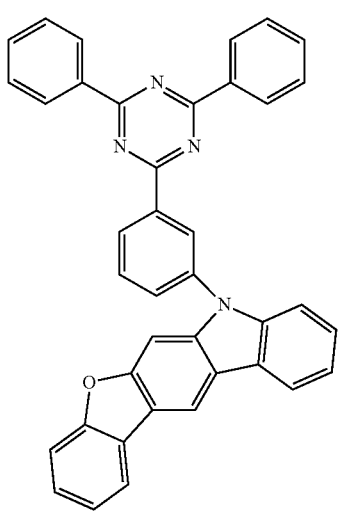
-continued
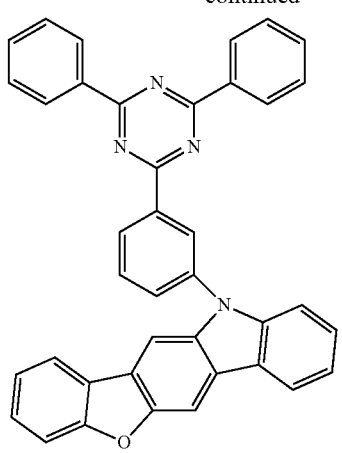
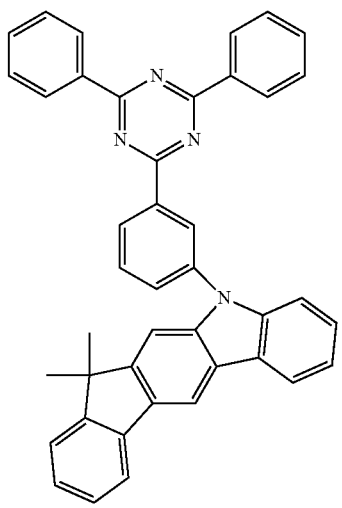
[Formula 38]
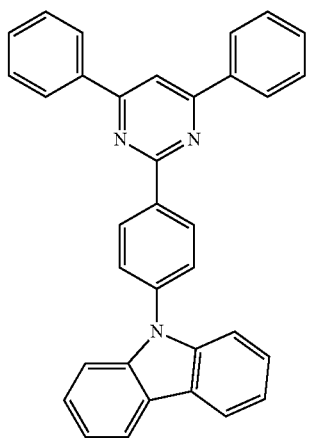

45
-continued
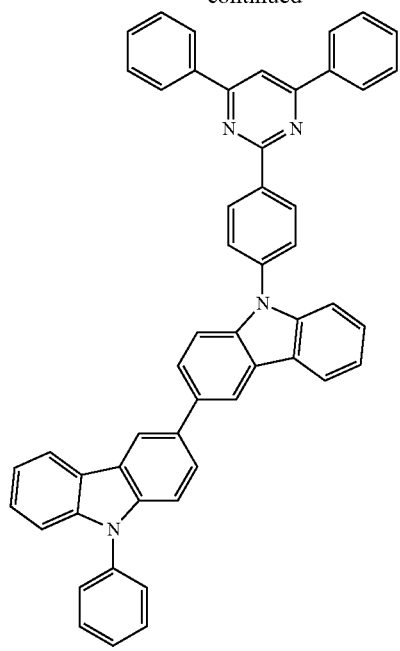
46
-continued
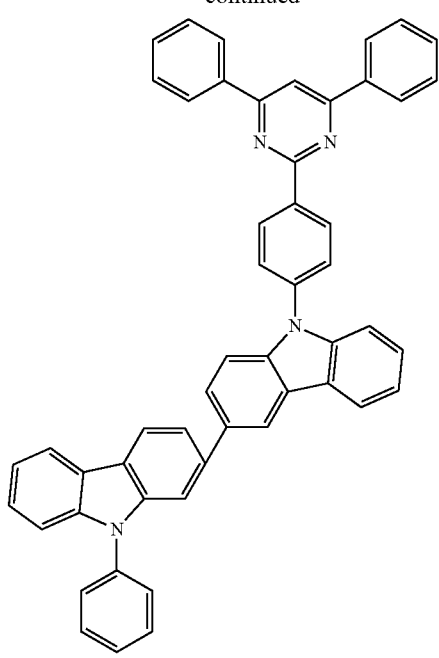
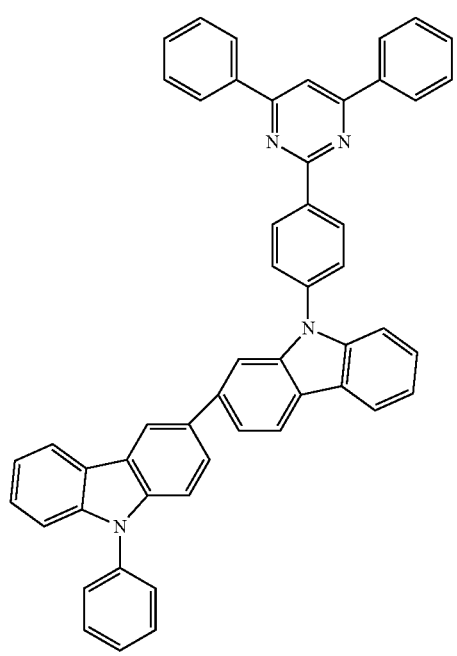
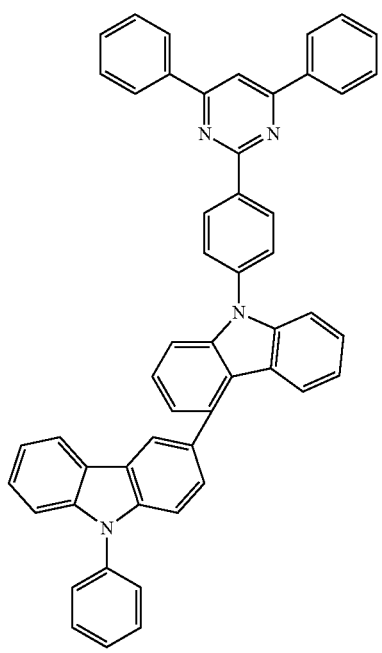

47
-continued
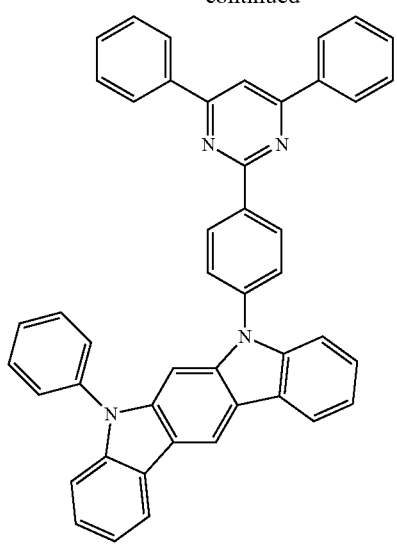
[Formula 39]
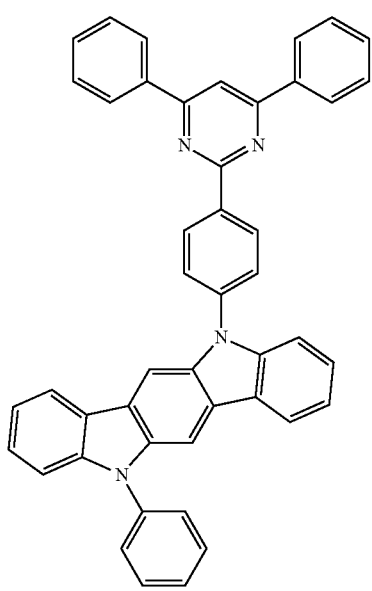
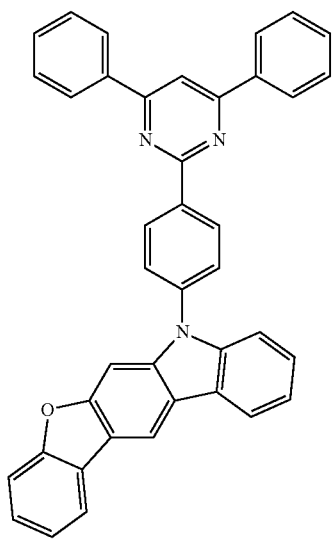
48
-continued
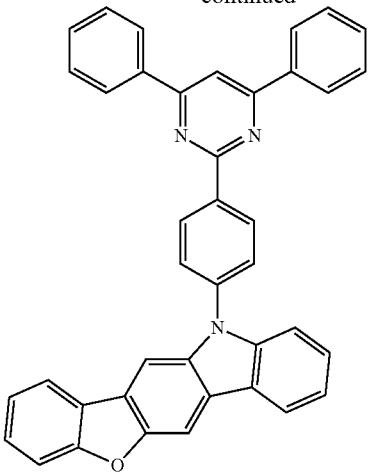
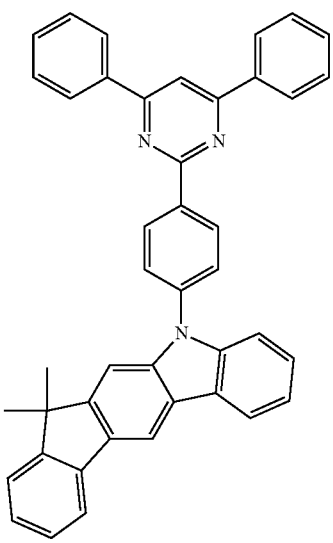
[Formula 40]
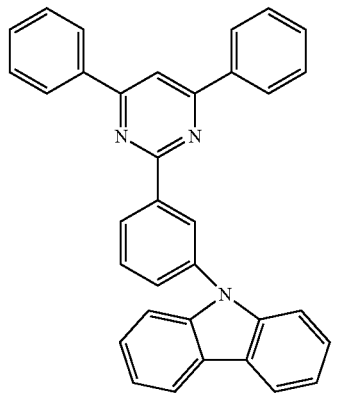

49
-continued
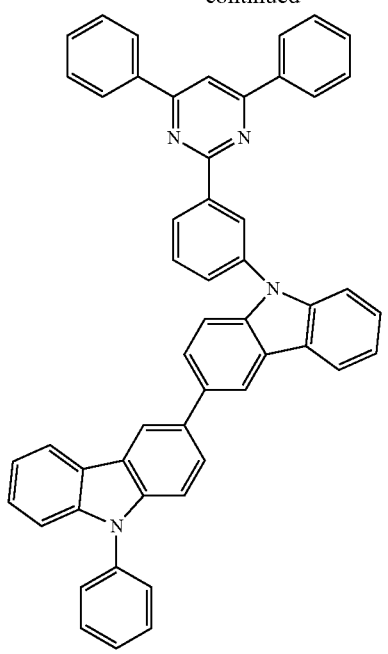
50
-continued
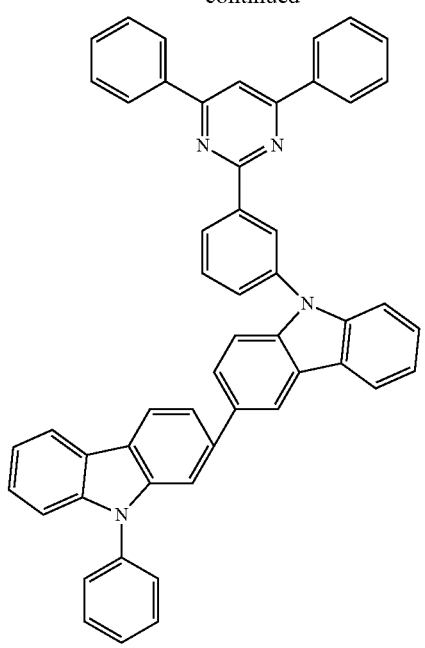
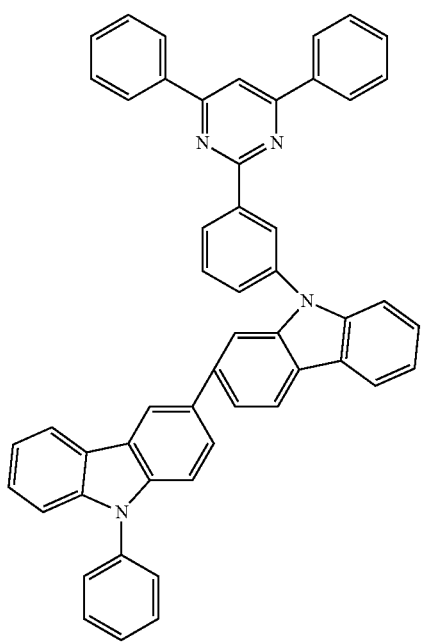
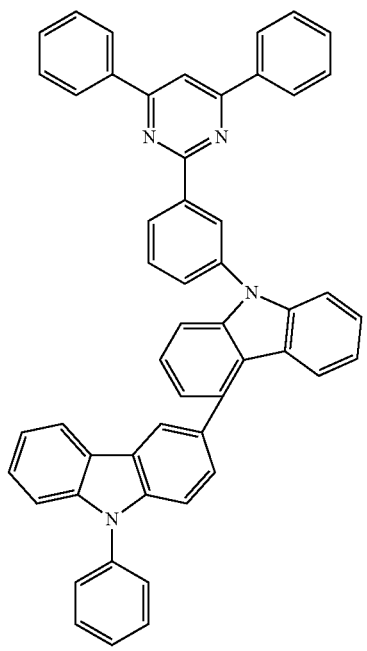

51
-continued
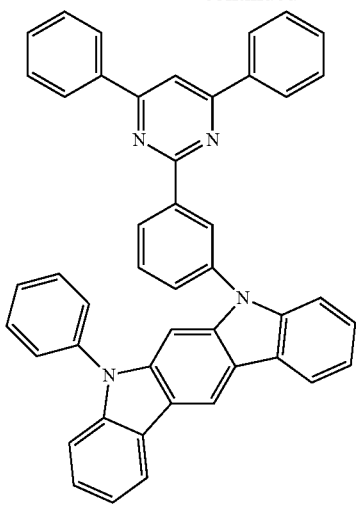
[Formula 41]
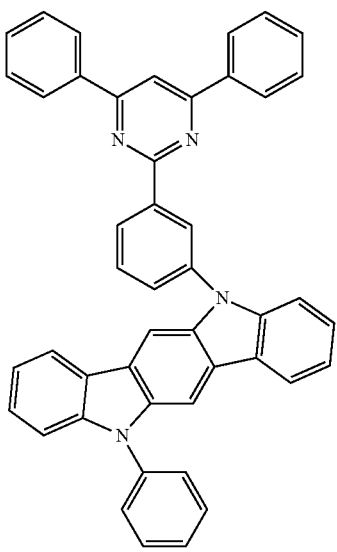
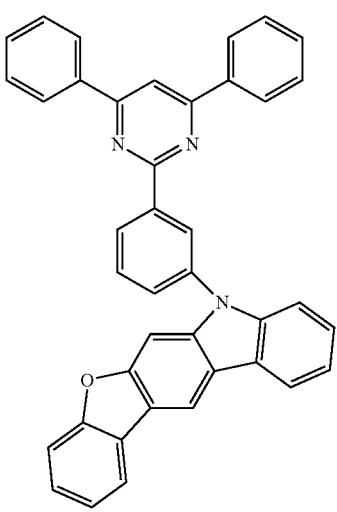
52
-continued
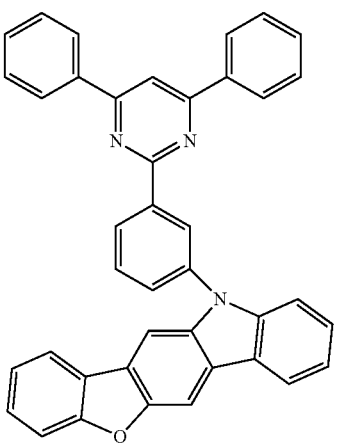
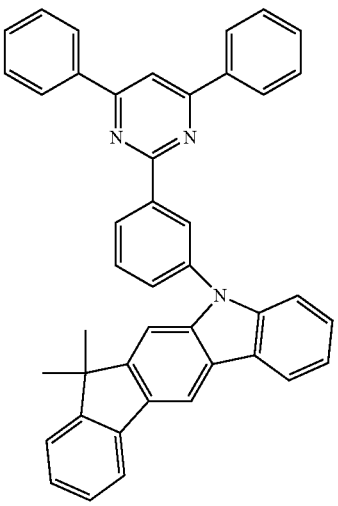
[Formula 42]
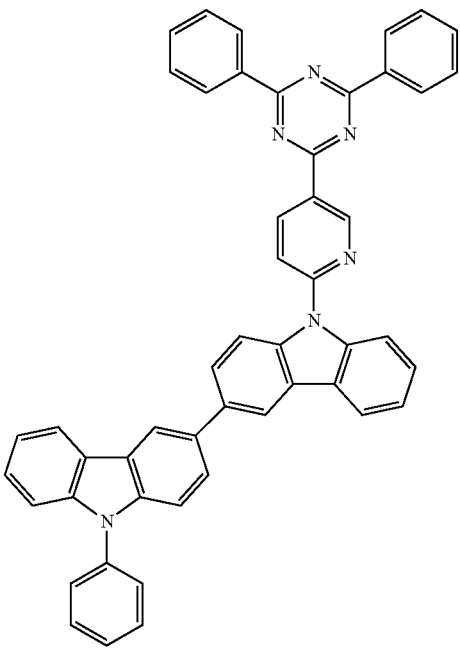

53
-continued
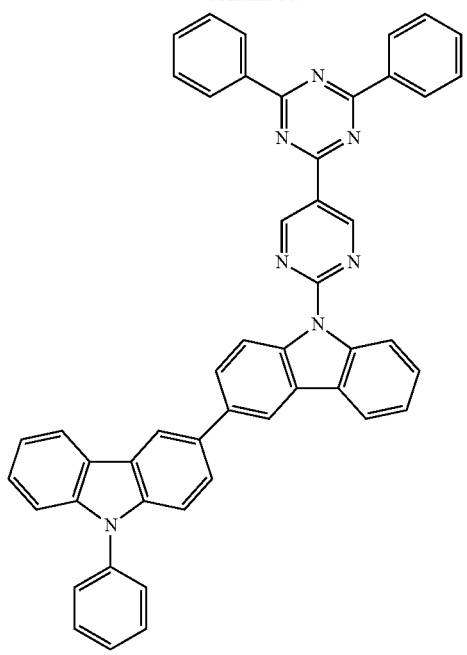
54
-continued
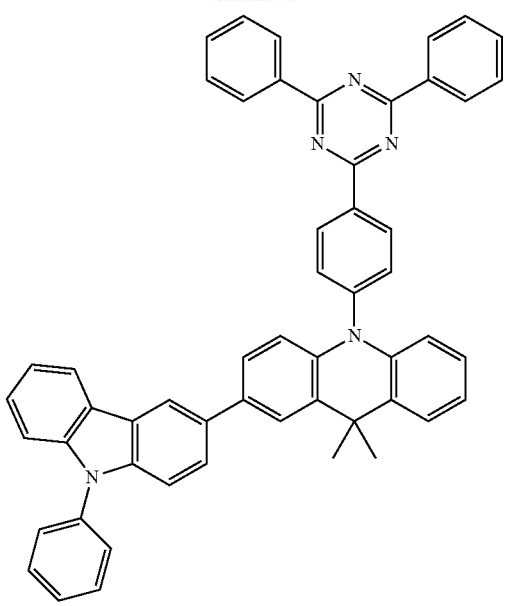
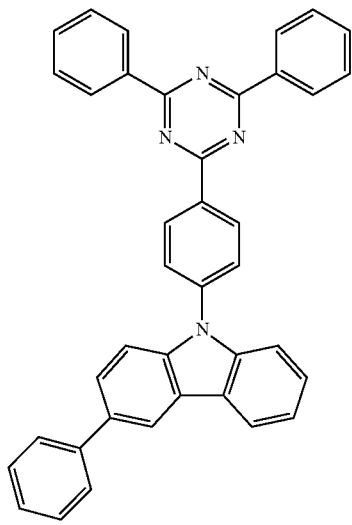
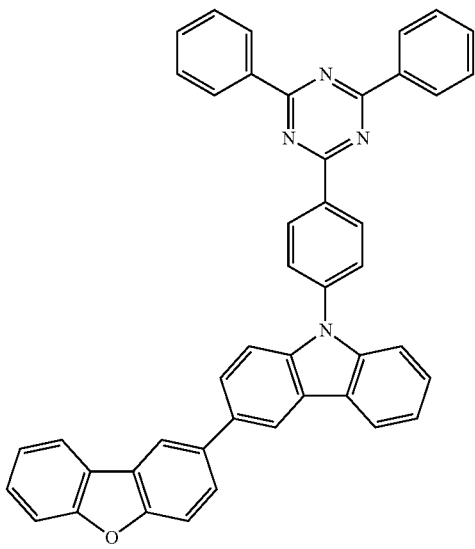

-continued
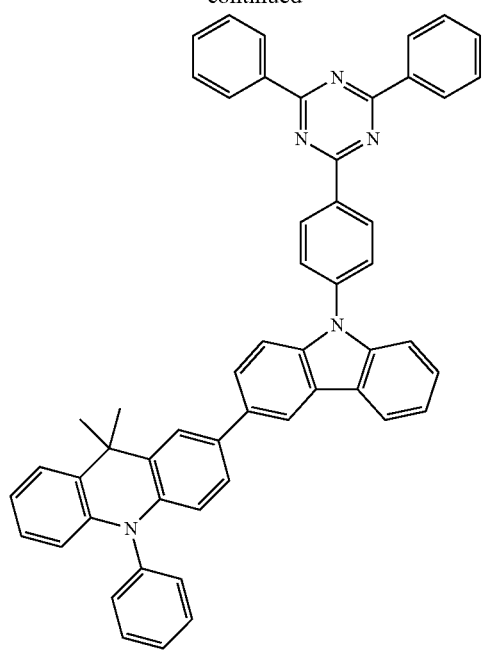
[Formula 43]
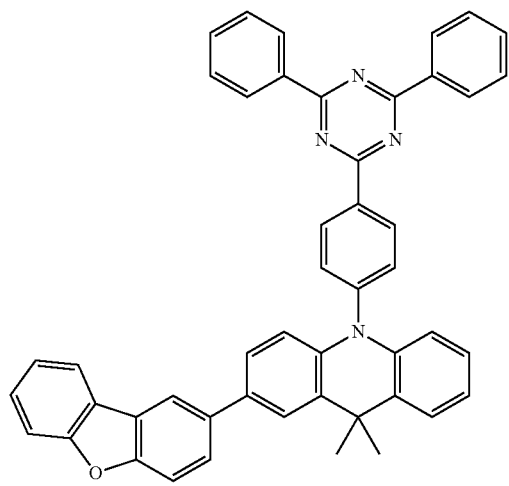
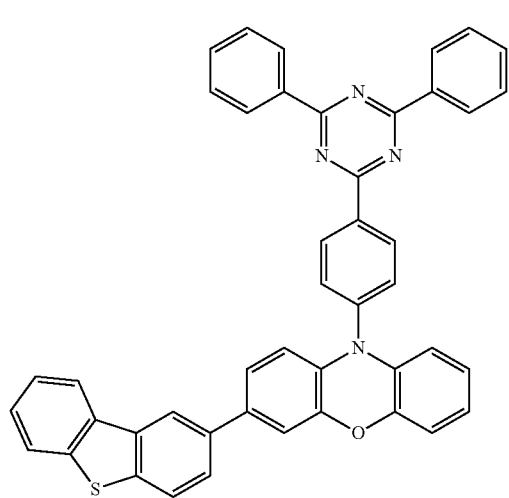
-continued
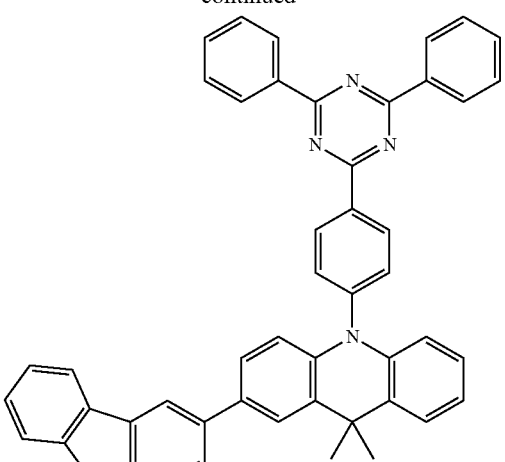
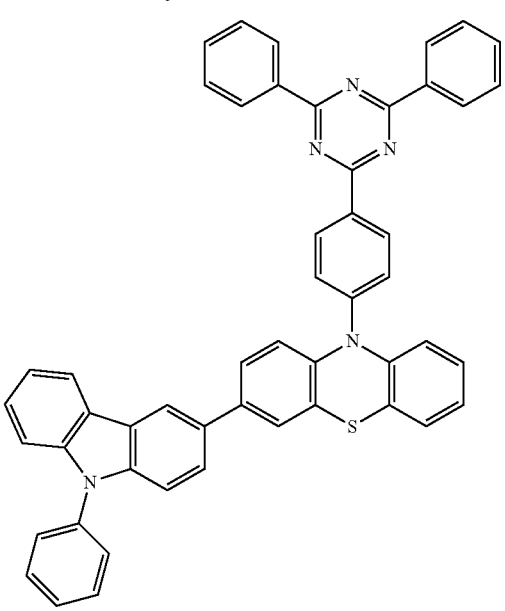
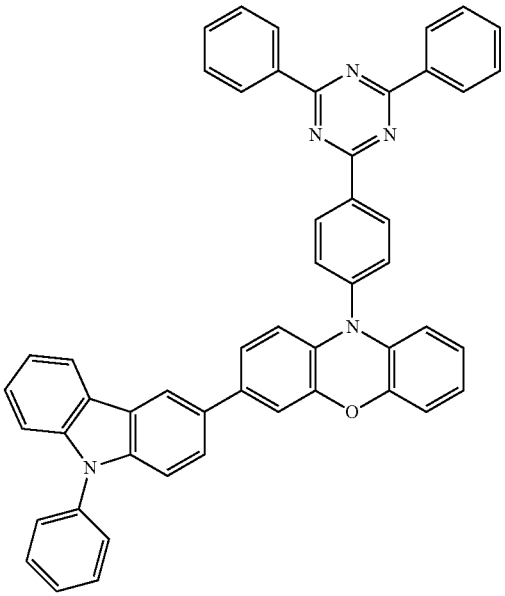

57
-continued
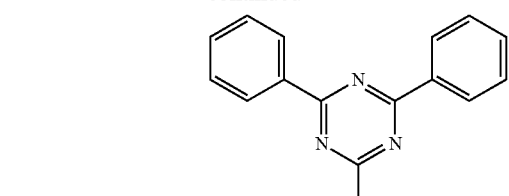
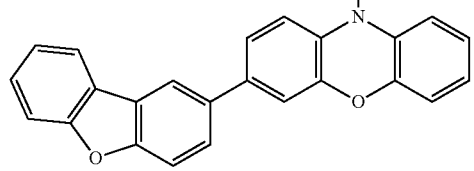
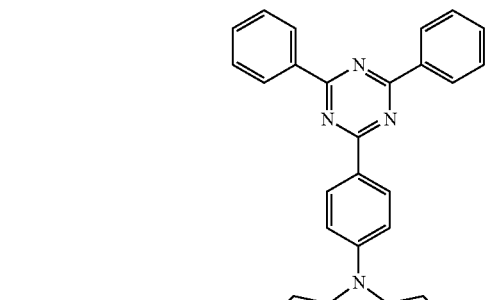
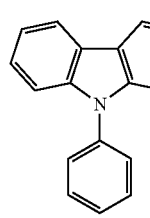
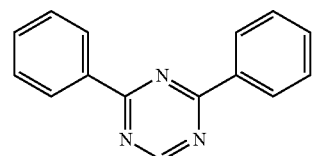
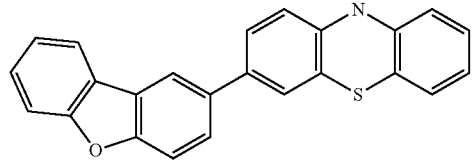
58
-continued
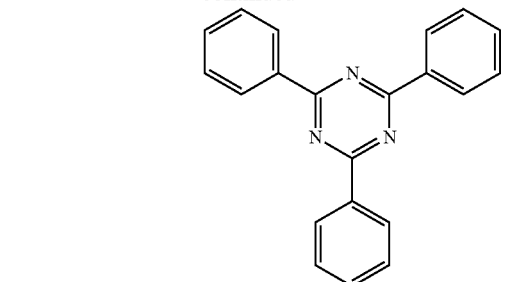
[Formula 44]
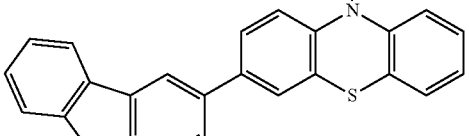
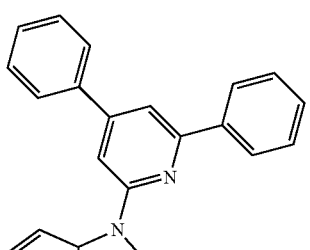
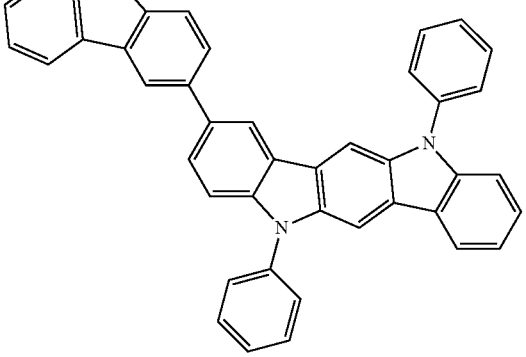
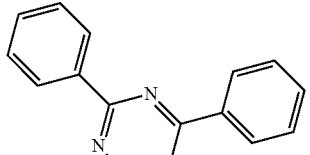
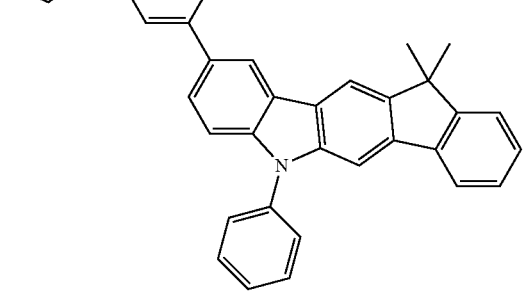

59
-continued
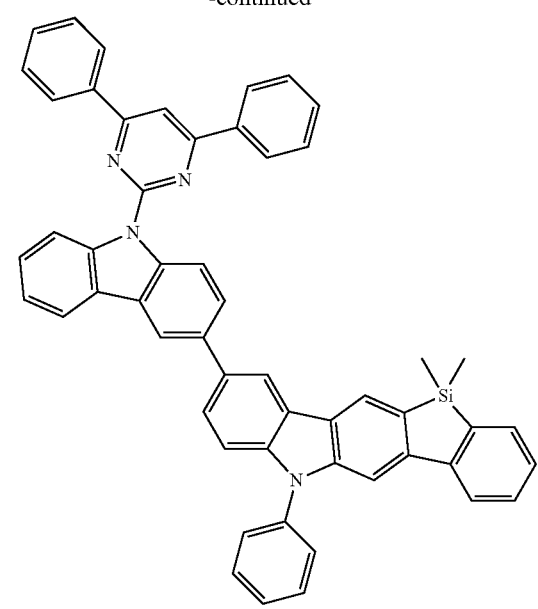
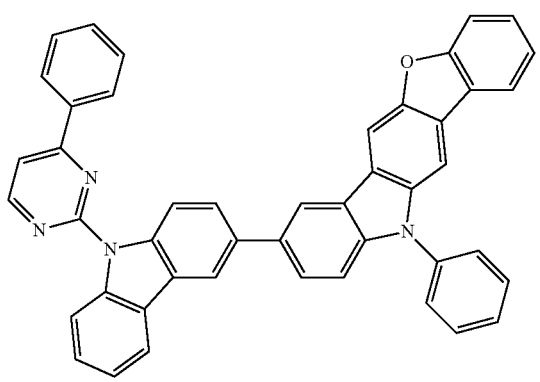
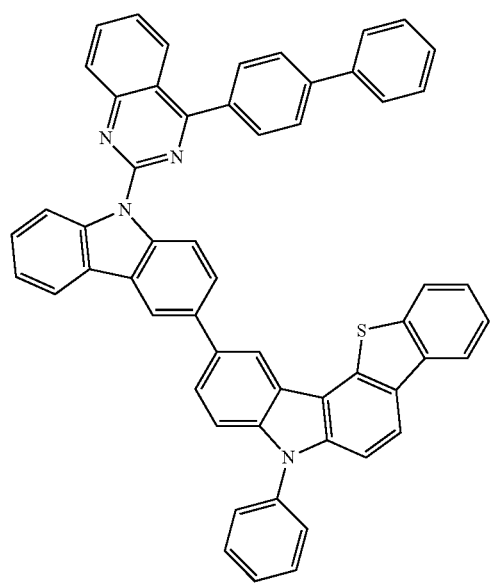
60
-continued
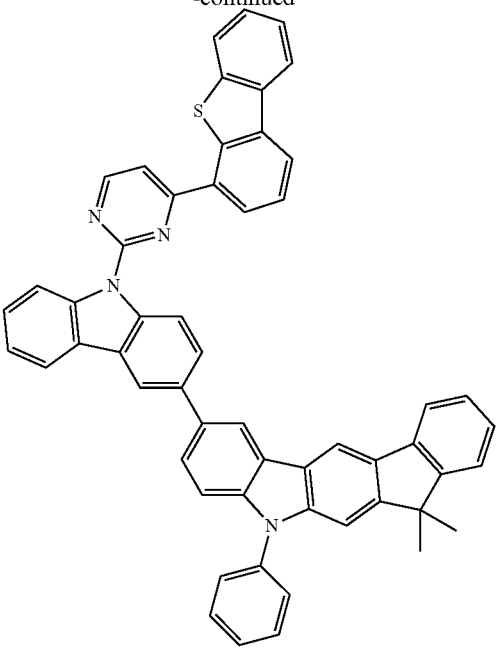
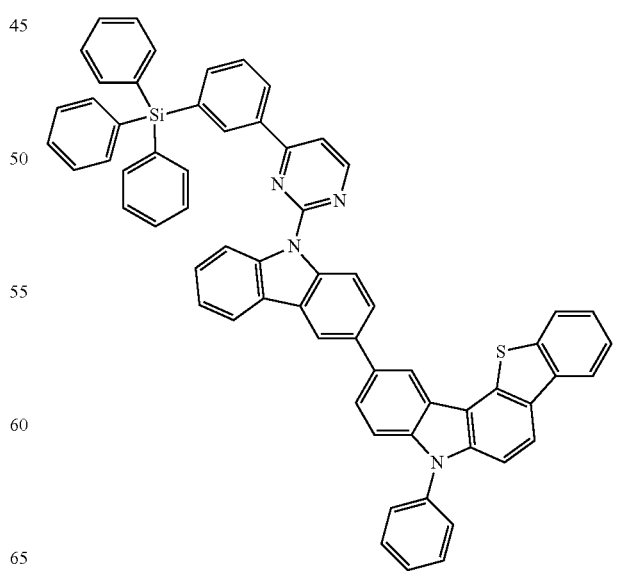

[Formula 45]
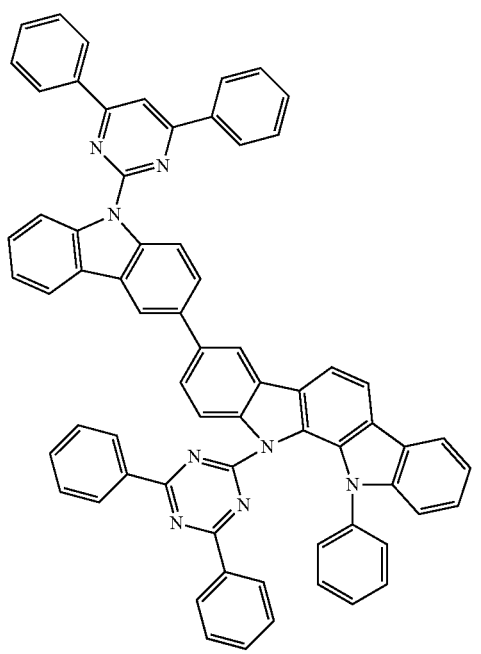
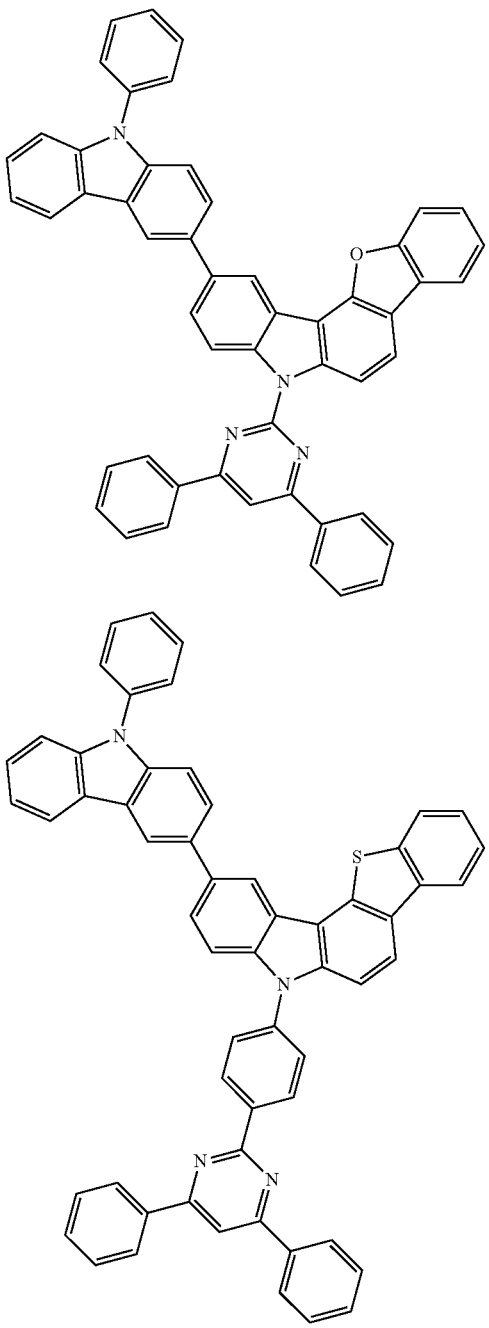
[Formula 46]
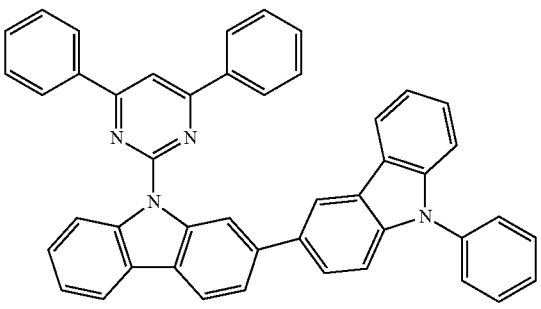

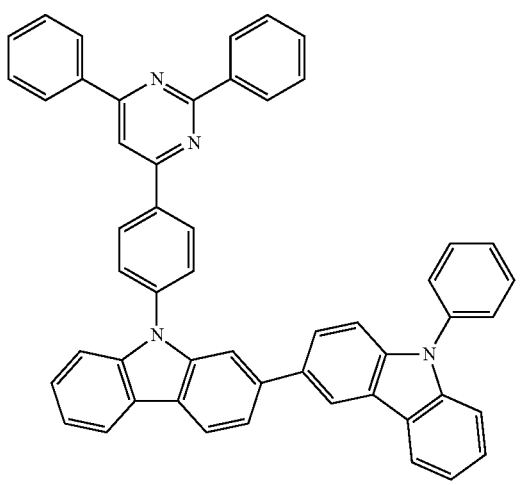
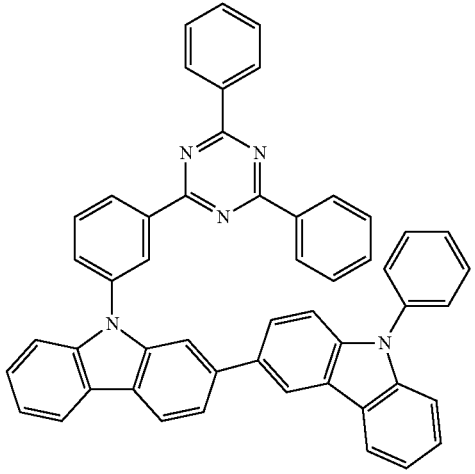
[Formula 47]
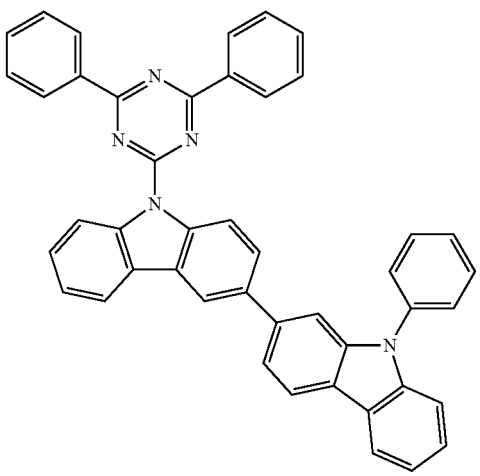
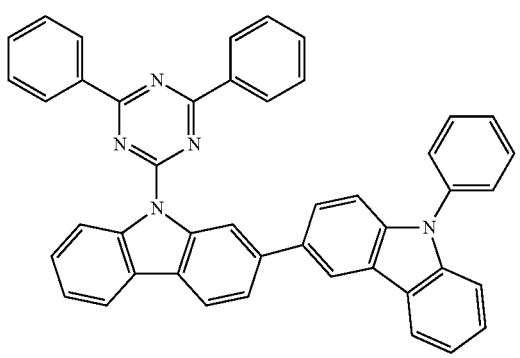
[Formula 48]
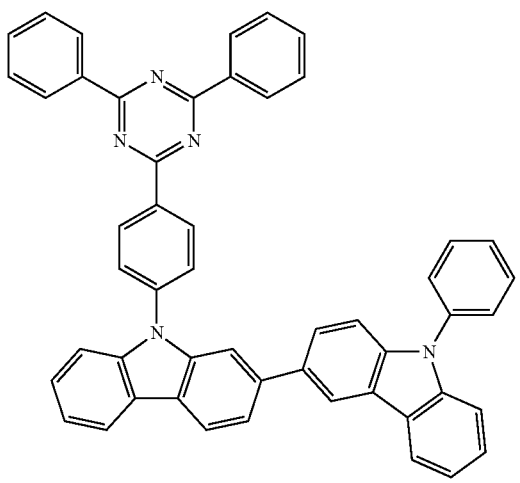
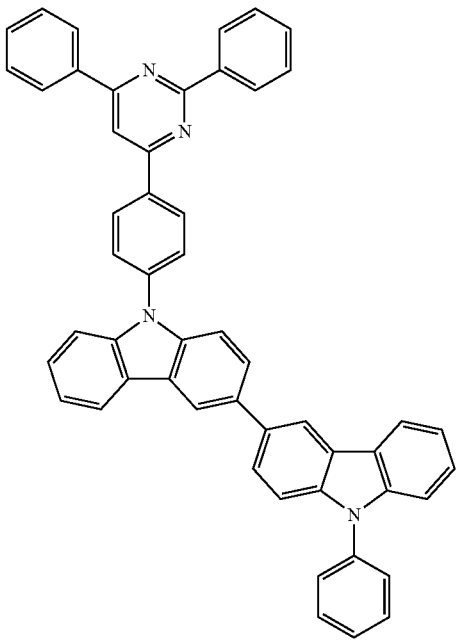

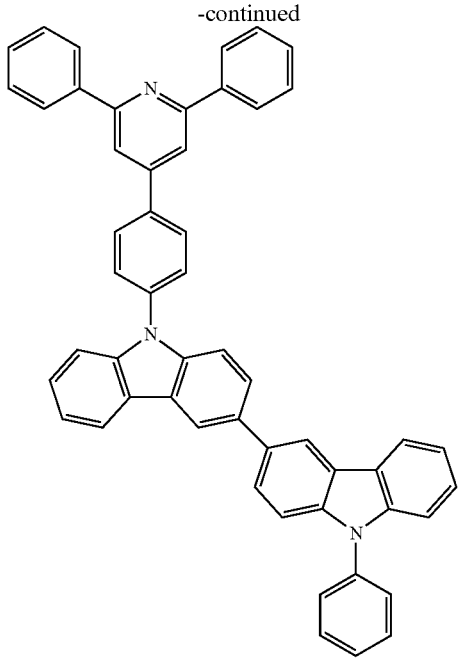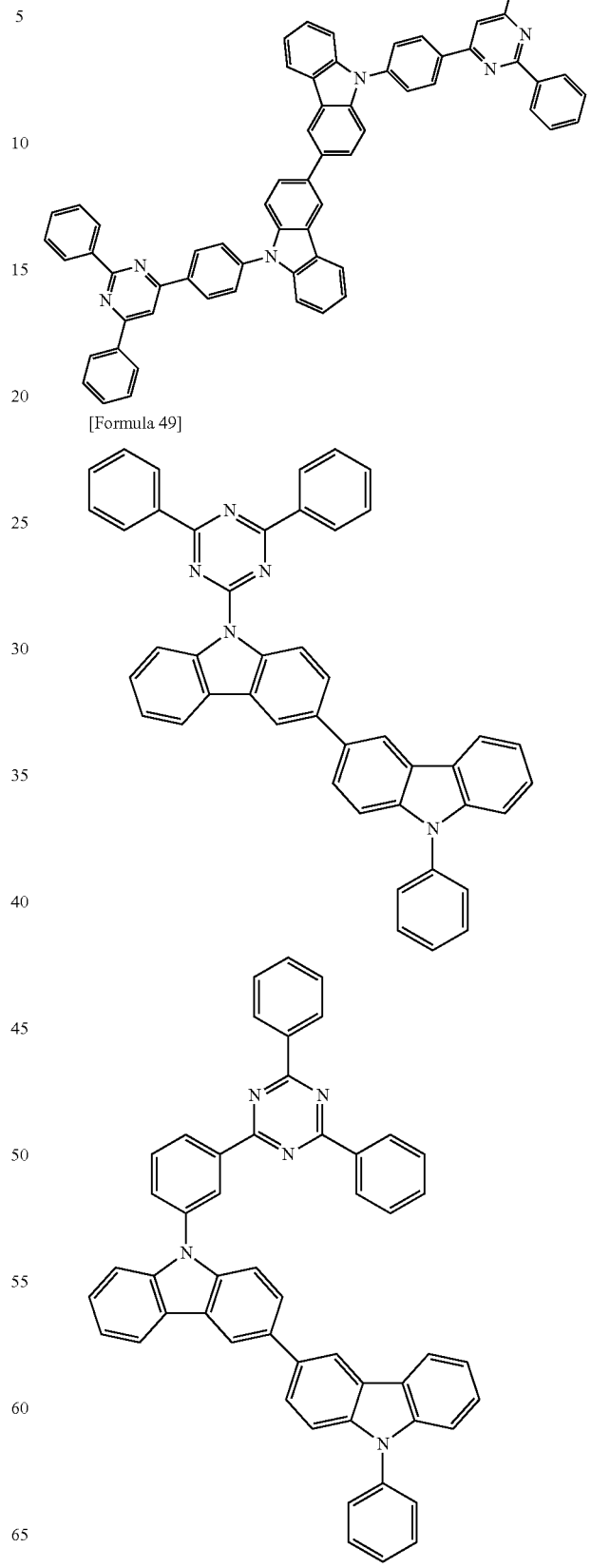
[Formula 49]

[Formula 50]
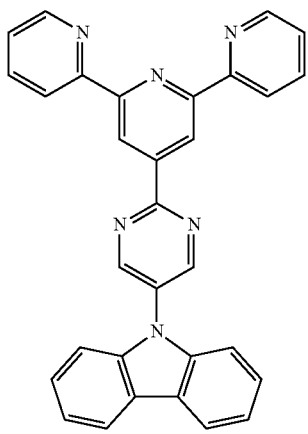
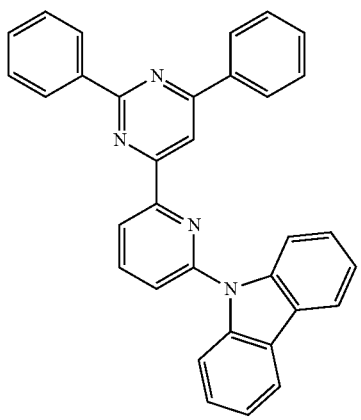
[Formula 51]
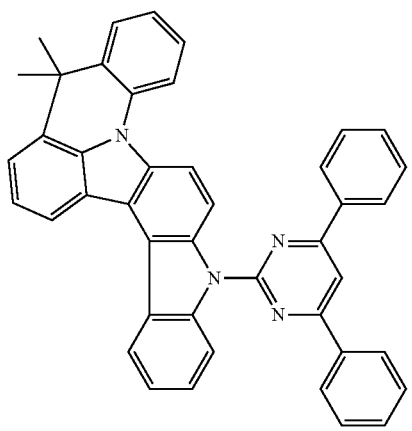
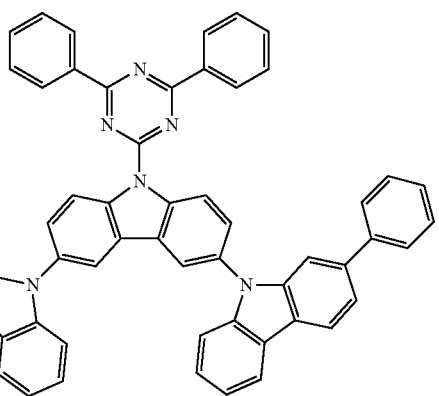
[Formula 52]
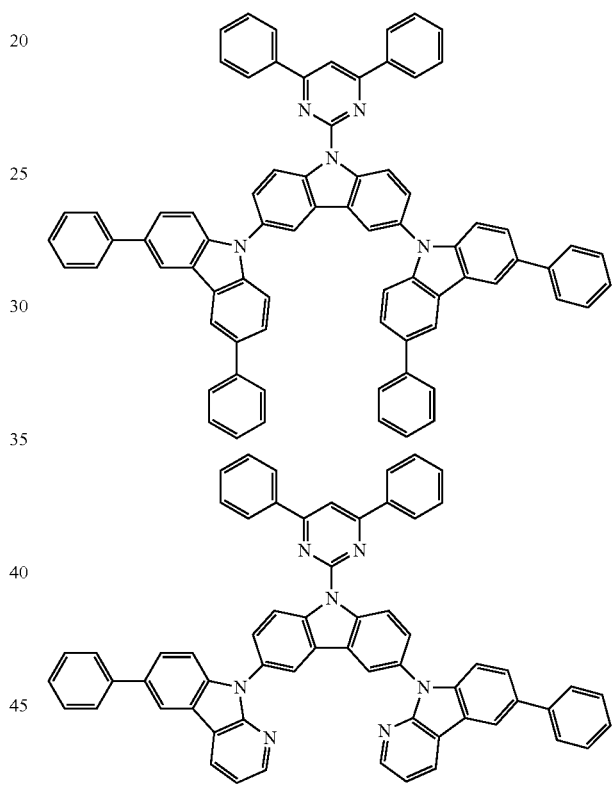
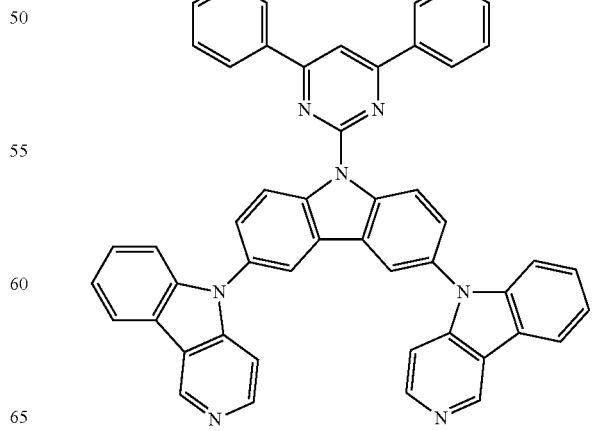

[Formula 53]
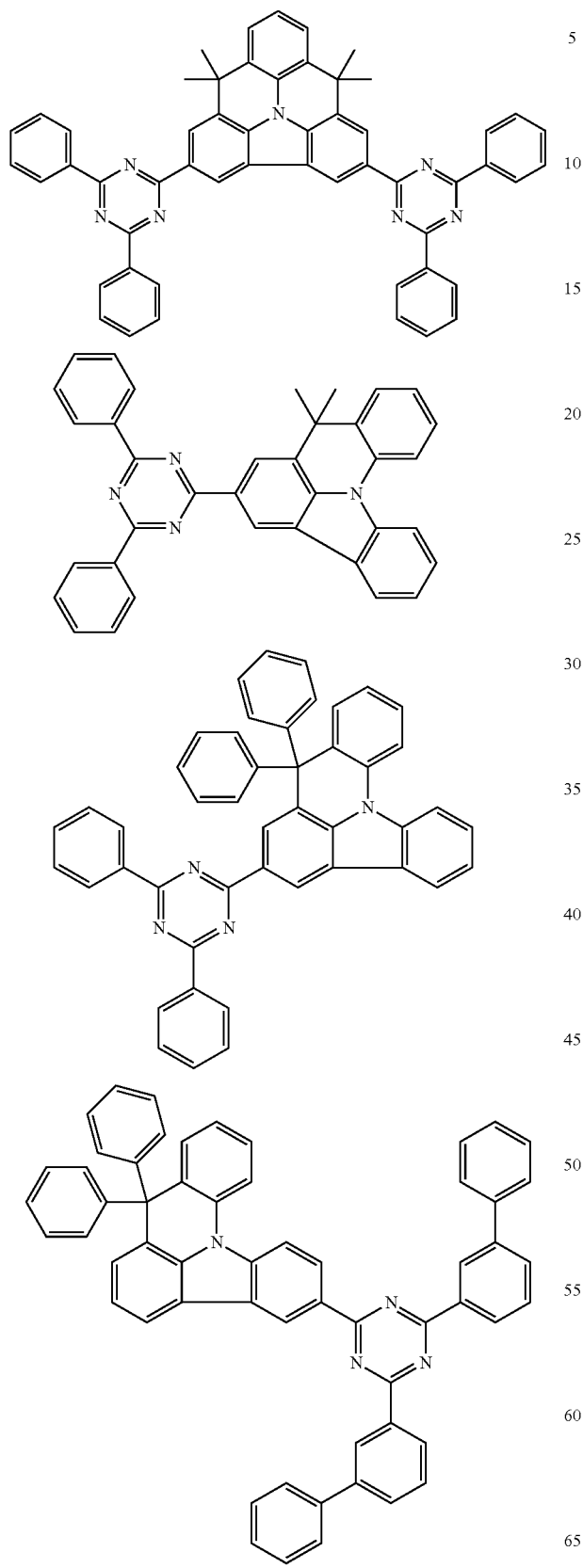
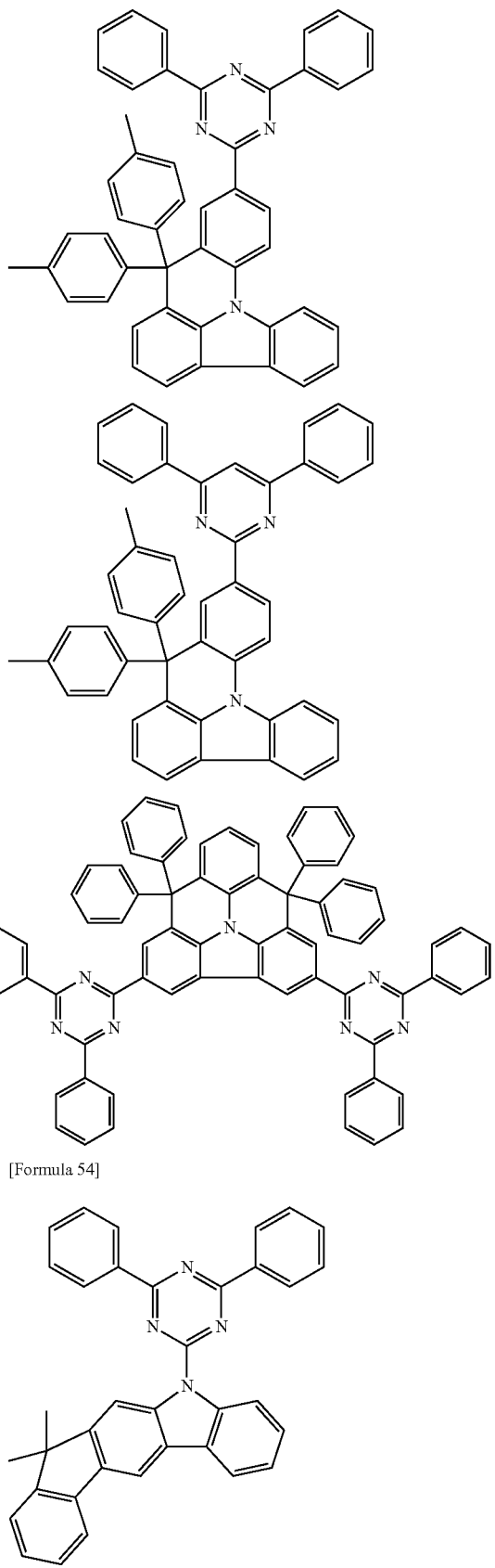
[Formula 54]

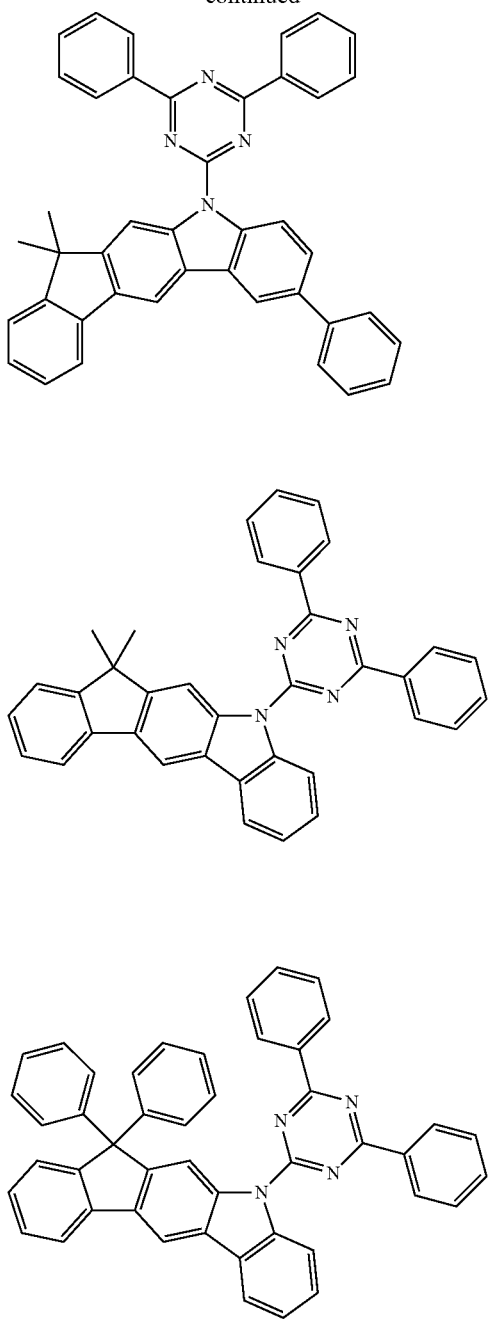
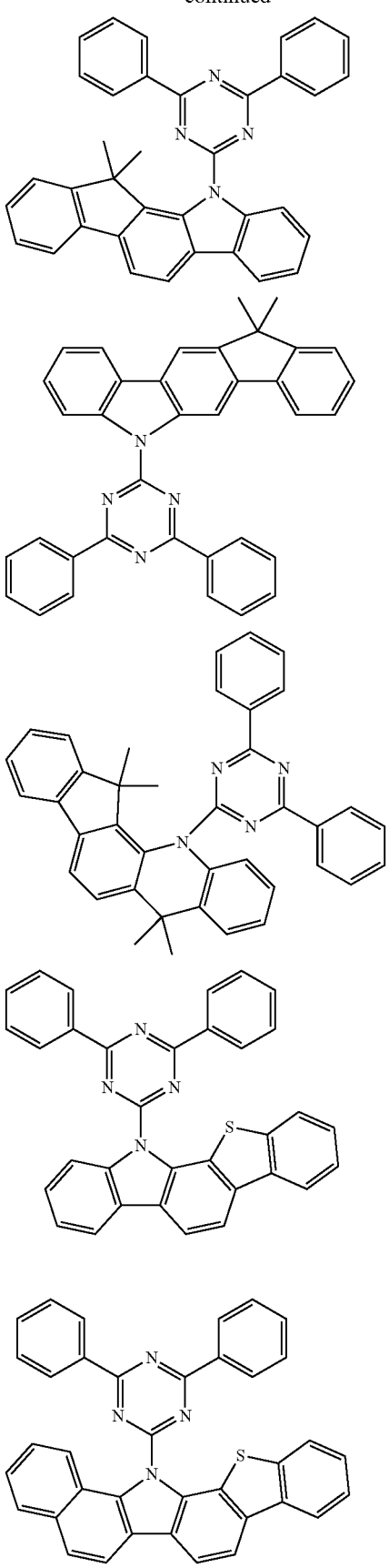
[Formula 55]

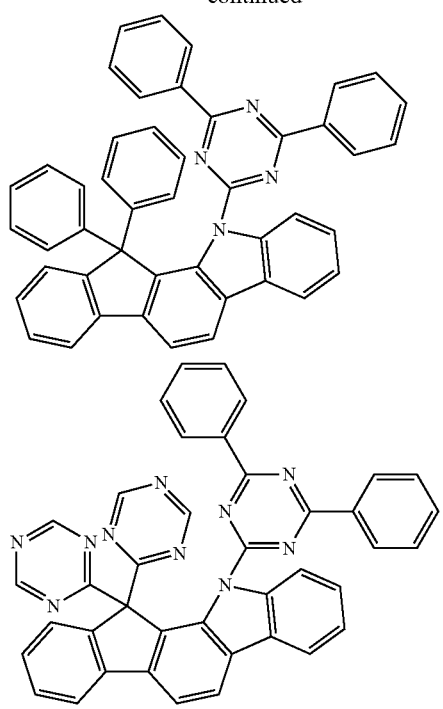
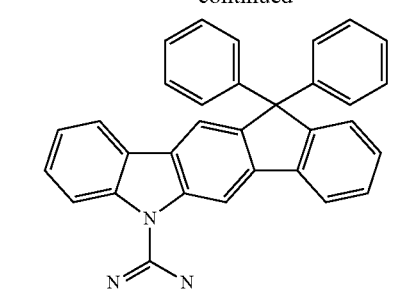
[Formula 56]
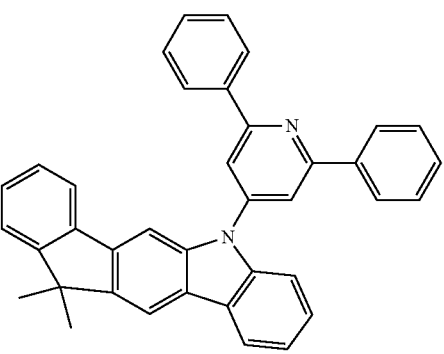
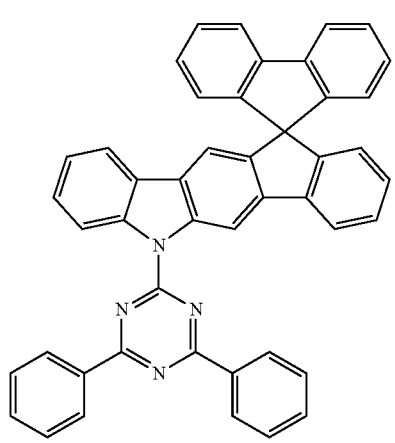
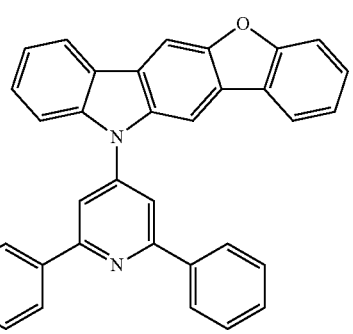
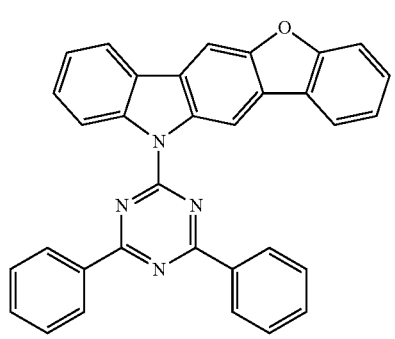
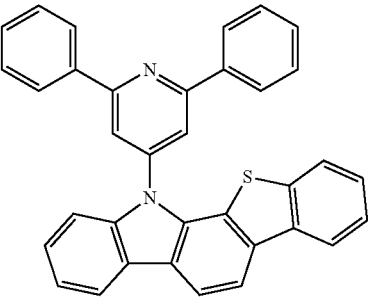

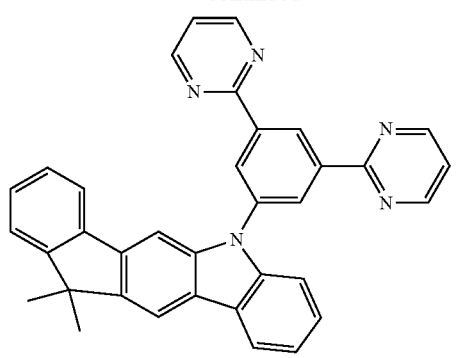
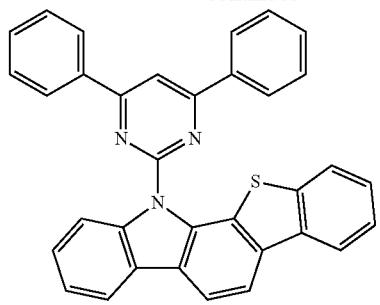
[Formula 57]
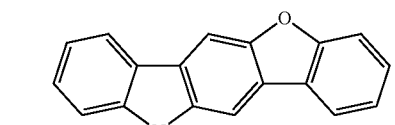
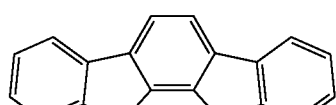
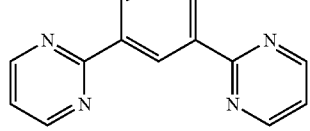
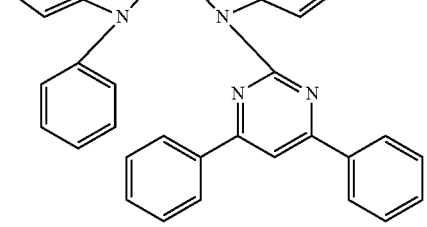
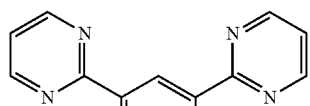
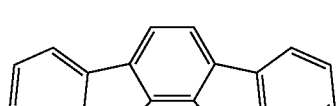
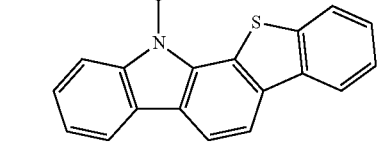
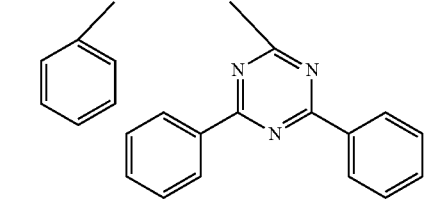
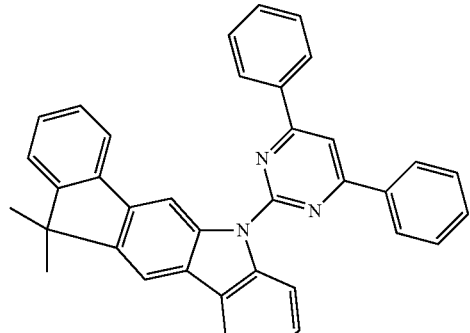
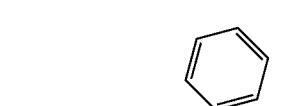
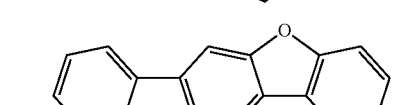
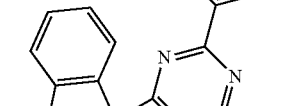
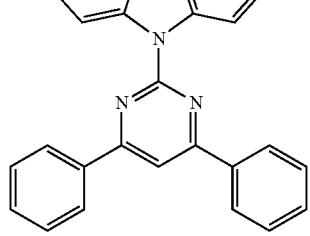
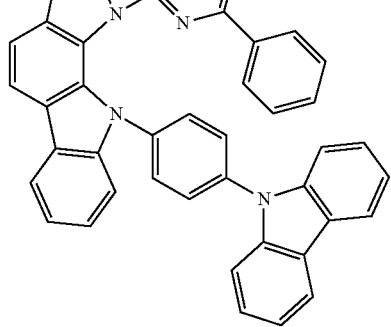

-continued
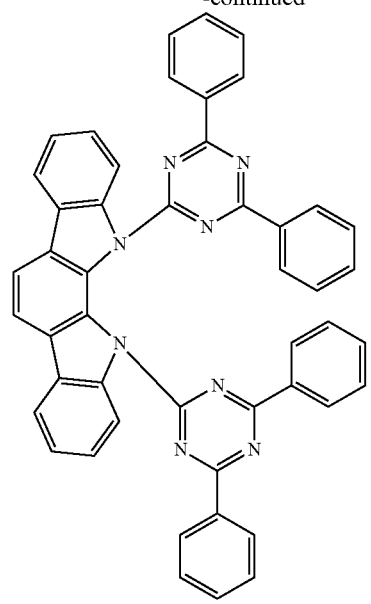
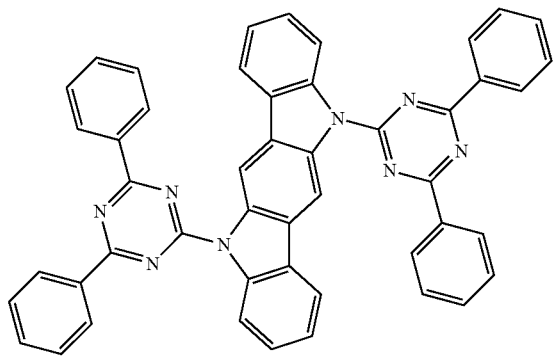
[Formula 58]
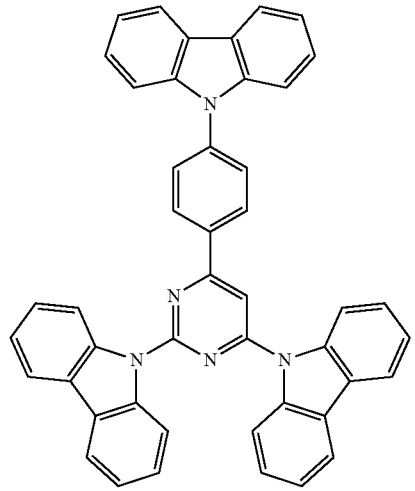
-continued
[Formula 59]
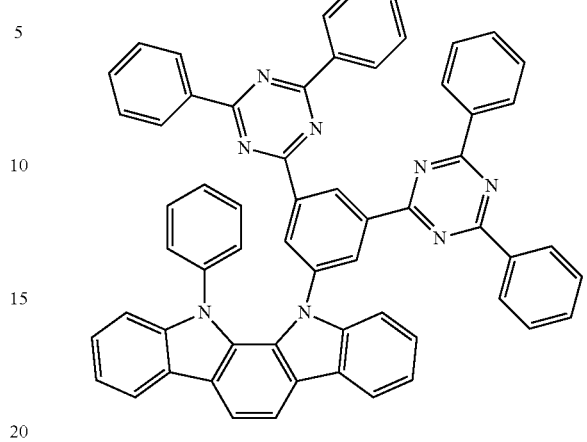
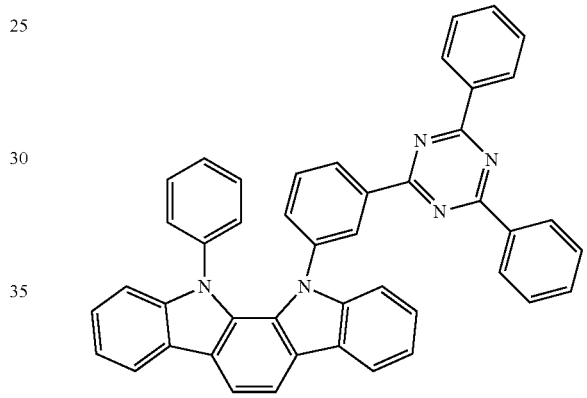
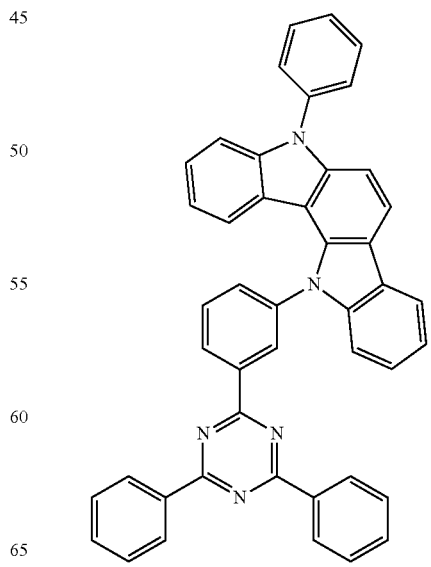

[Formula 60]
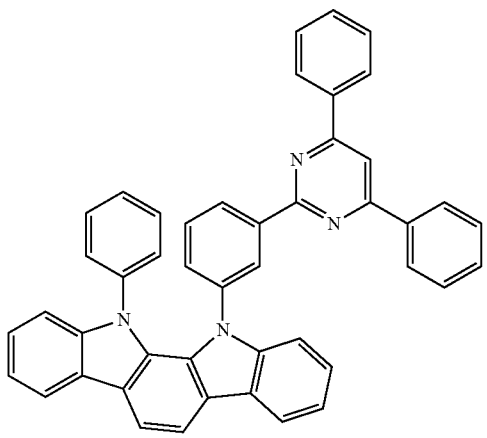
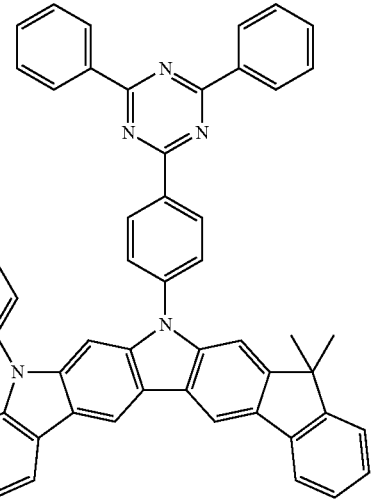
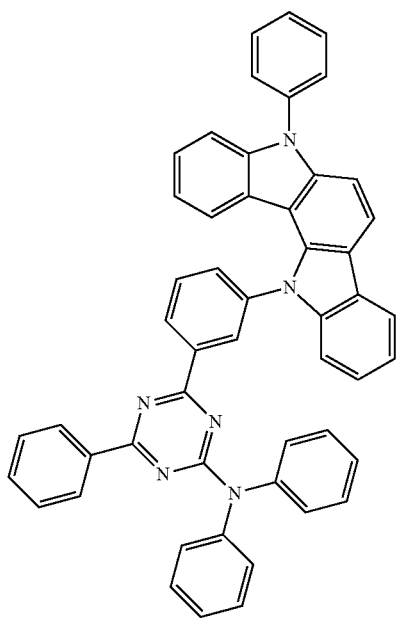
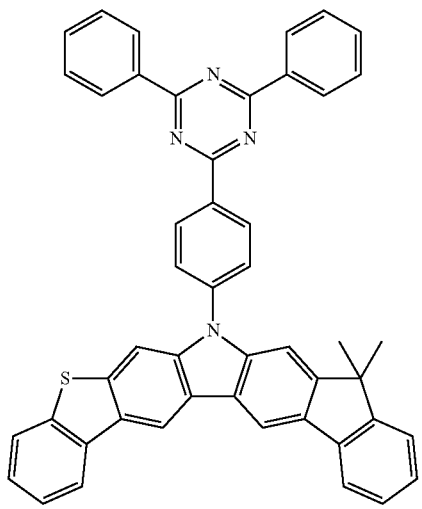
[Formula 61]
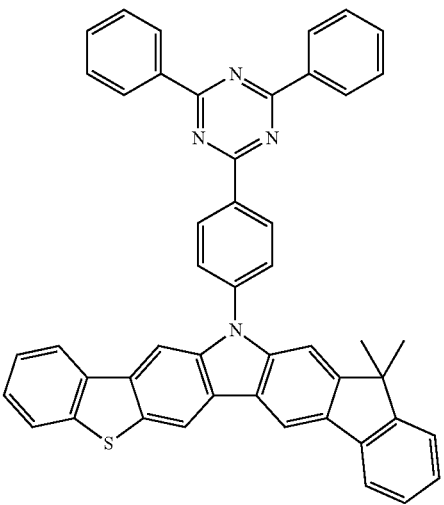

[Formula 62]
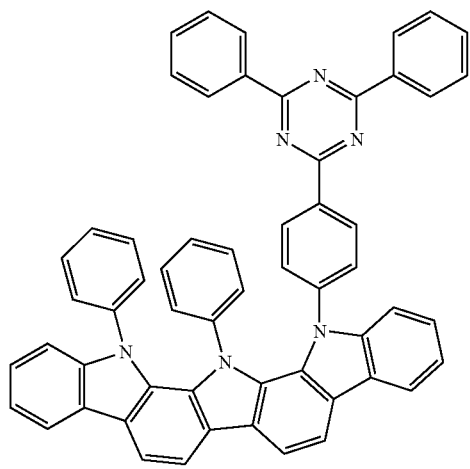
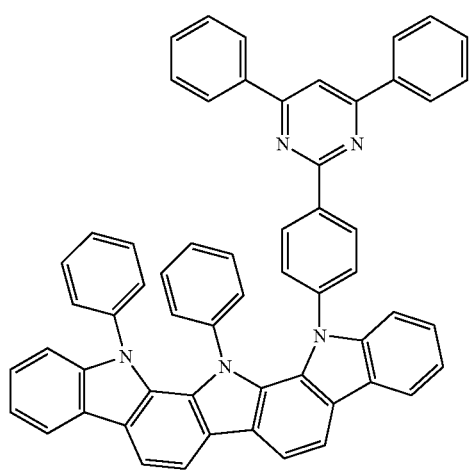
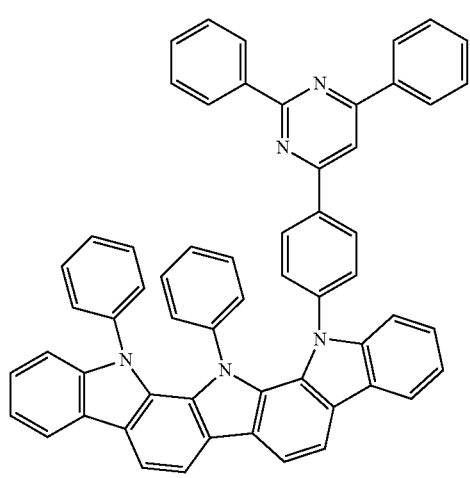
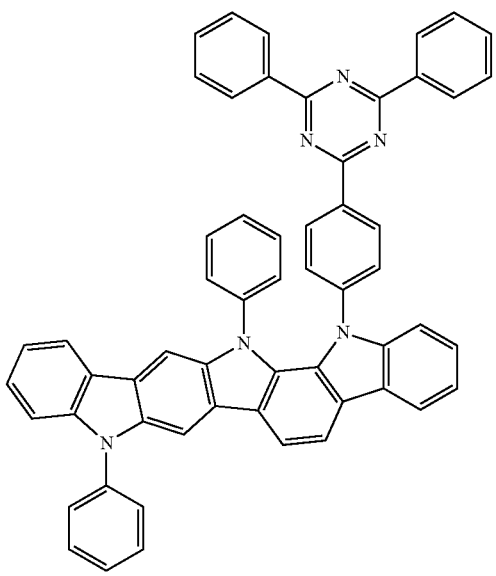
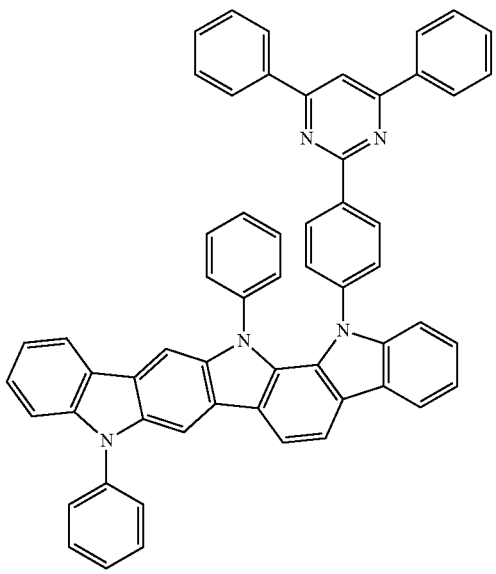
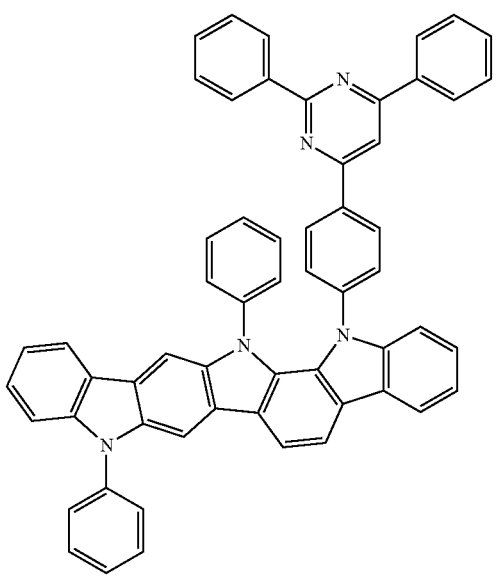

[Formula 63]
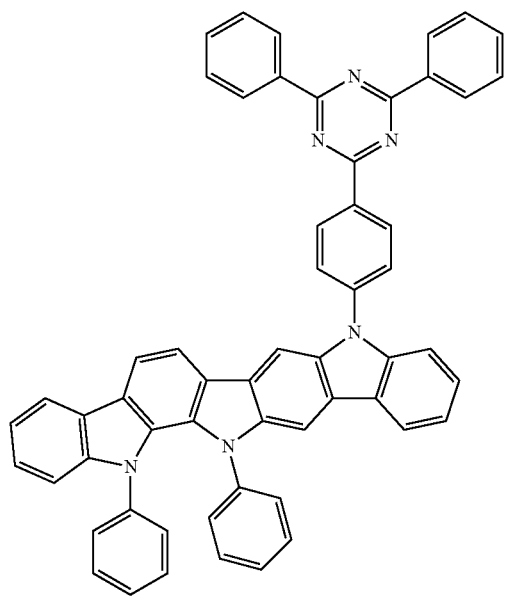
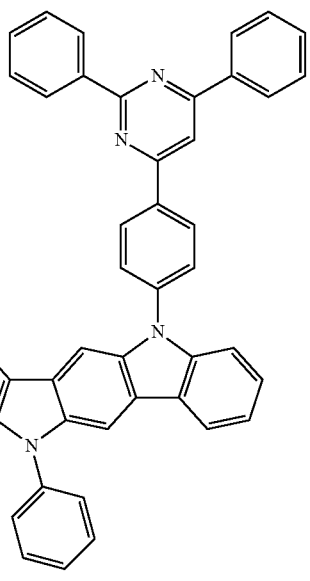
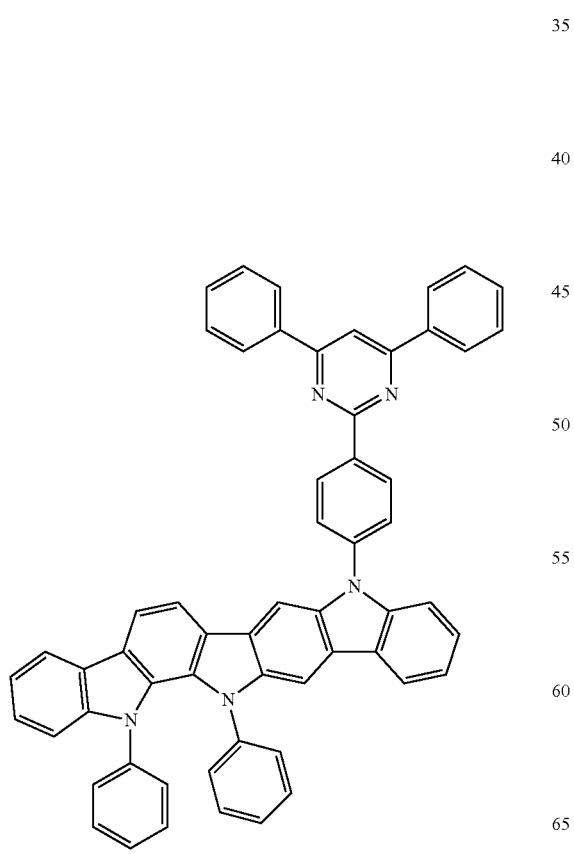
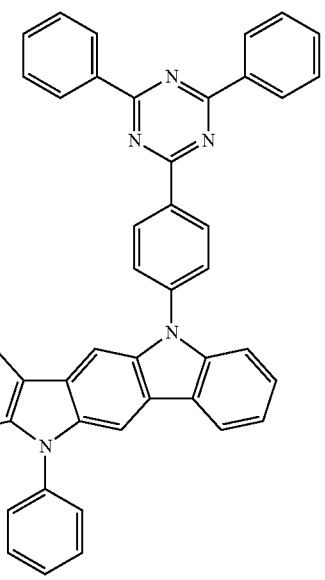

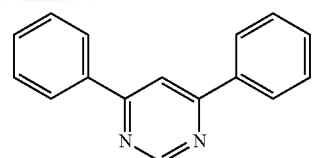
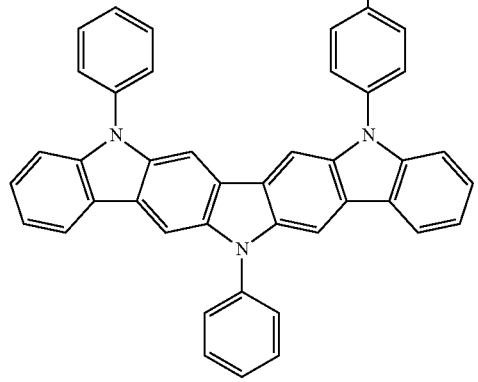
[Formula 64]
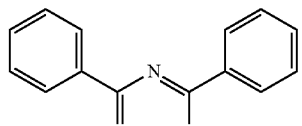
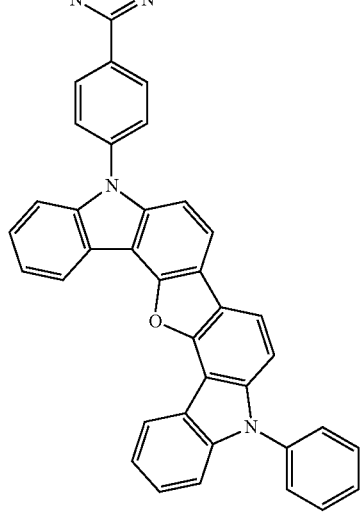
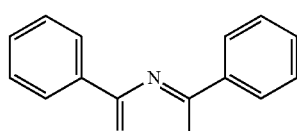
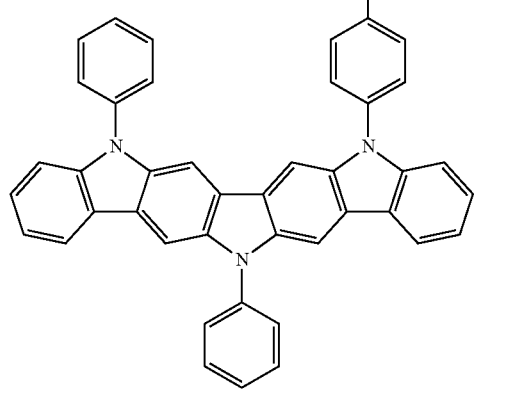
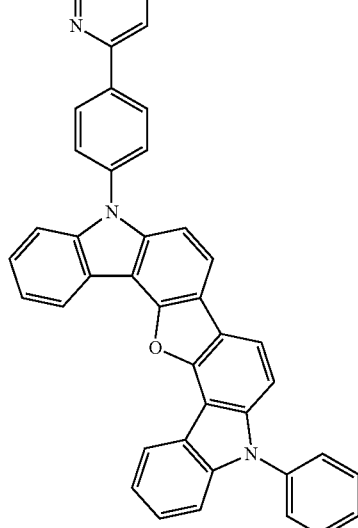

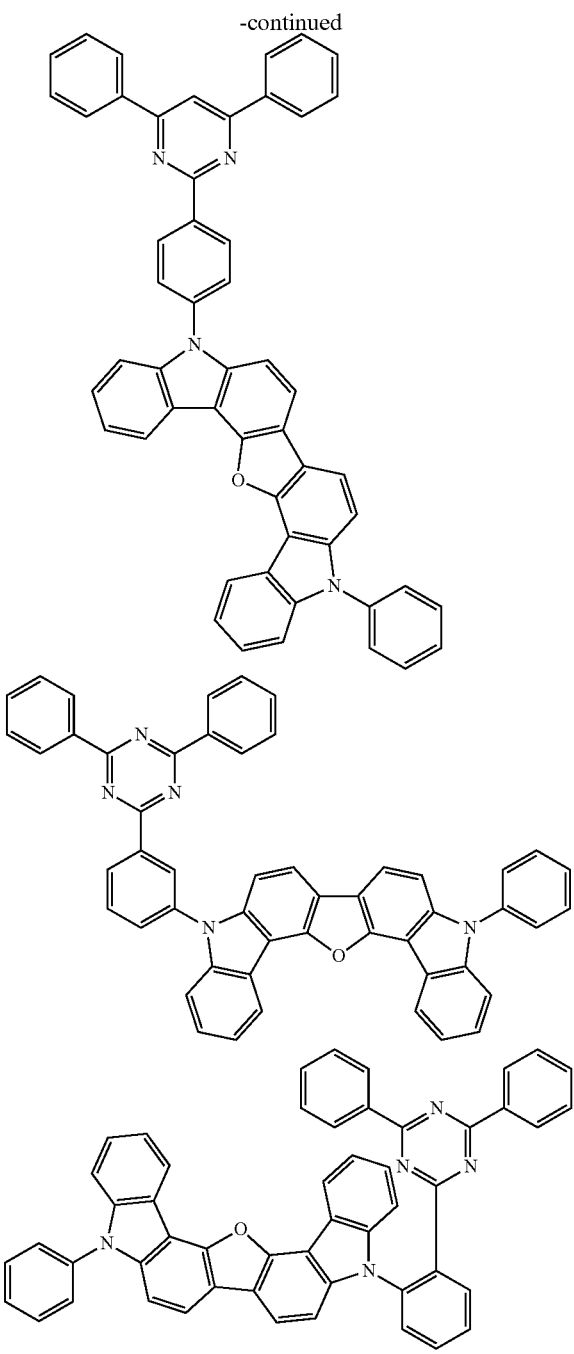

The compound represented by the formula (1) can be synthesized by a known synthetic method.

A film thickness of the emitting layer is preferably in a range of 5 nm to 50 nm, more preferably in a range of 7 nm to 50 nm and most preferably in a range of 10 nm to 50 nm. The thickness of less than 5 nm may cause difficulty in forming the emitting layer and in controlling chromaticity, while the thickness of more than 50 nm may raise drive voltage.

Substrate

The organic EL device according to the exemplary embodiment is formed on a light-transmissive substrate. The light-transmissive substrate, which supports the anode, the organic compound layer and the cathode forming the organic EL device, is preferably a smooth and flat substrate that transmits 50% or more of light in a visible region of 400 nm to 700 nm.

The light-transmissive plate is exemplarily a glass plate, a polymer plate or the like.

The glass plate is formed of soda-lime glass, barium/strontium-containing glass, lead glass, aluminosilicate glass, borosilicate glass, barium borosilicate glass, quartz and the like.

The polymer plate is formed of polycarbonate, acryl, polyethylene terephthalate, polyether sulfide and polysulfone.

Anode and Cathode

The anode of the organic EL device injects holes into the emitting layer, so that it is efficient that the anode has a work function of 4.5 eV or more.

Exemplary materials for the anode are indium-tin oxide (ITO), tin oxide (NESA), indium zinc oxide, gold, silver, platinum and copper.

When light from the emitting layer is to be emitted through the anode, the anode preferably transmits more than 10% of the light in the visible region. Sheet resistance of the anode is preferably several hundreds Q/sq. or lower. The thickness of the anode is typically in the range of 10 nm to 1 μm, and preferably in the range of 10 nm to 200 nm, though it depends on the material of the anode.

The cathode is preferably formed of a material with smaller work function in order to inject electrons into the emitting layer.

Although a material for the cathode is subject to no specific limitation, examples of the material are indium, aluminum, magnesium, alloy of magnesium and indium, alloy of magnesium and aluminum, alloy of aluminum and lithium, alloy of aluminum, scandium and lithium, and alloy of magnesium and silver.

Like the anode, the cathode may be made by forming a thin film on, for instance, the electron transporting layer and the electron injecting layer by a method such as vapor deposition. In addition, the light from the emitting layer may be emitted through the cathode. When light from the emitting layer is to be emitted through the cathode, the cathode preferably transmits more than 10% of the light in the visible region. Sheet resistance of the cathode is preferably several hundreds Q/sq. or lower. The thickness of the cathode is typically in the range of 10 nm to 1 μm, and preferably in the range of 50 nm to 200 nm, though it depends on the material of the cathode.

Hole Injecting•Transporting Layer

The hole injection/transport layer helps injection of holes to the emitting layer and transport the holes to an emitting region. A compound having a large hole mobility and a small ionization energy is used as the hole injection/transport layer.

A material for forming the hole injecting layer and the hole transporting layer is preferably a material for transporting the holes to the emitting layer at a lower electric field intensity. For instance, an aromatic amine compound is preferably used. A material for the hole injecting layer is preferably a porphyrin compound, an aromatic tertiary amine compound or a styryl amine compound, particularly preferably the aromatic tertiary amine compound such as hexacyanohexaazatriphenylene (HAT).

Electron Injecting•Transporting Layer

The electron injecting•transporting layer helps injection of the electrons into the emitting layer and transports the electrons to an emitting region. A compound having a large electron mobility is used as the electron injecting·transporting layer.

A preferable example of the compound used as the electron injecting·transporting layer is an aromatic heterocyclic compound having at least one heteroatom in a molecule. Particularly, a nitrogen-containing cyclic derivative is preferable. The nitrogen-containing cyclic derivative is preferably a heterocyclic compound having a nitrogen-containing six-membered or five-membered ring skeleton, or a fused aromatic cyclic compound having a nitrogen-containing six-membered or five-membered ring skeleton. Moreover, the electron injecting·transporting layer may contain an alkali metal and the like In the organic EL device in the exemplary embodiment, in addition to the aforementioned compounds, any compound selected from compounds to be used in a typical organic El device is usable as a compound for the organic compound layer other than the emitting layer.

Layer Formation Method(s)

A method for forming each layer of the organic EL device in the exemplary embodiment is subject to no limitation except for the above particular description. However, known methods of dry film-forming such as vacuum deposition, sputtering, plasma or ion plating and wet film-forming such as spin coating, dipping, flow coating or ink-jet are applicable.

Thickness

The thickness of each organic layer of the organic EL device in the exemplary embodiment is subject to no limitation except for the thickness particularly described above. However, the thickness is typically preferably in a range of several nanometers to 1 μm because an excessively thin film is likely to entail defects such as a pin hole while an excessively thick film requires high applied voltage and deteriorates efficiency.

Second Exemplary Embodiment

An organic EL device according to a second exemplary embodiment will be described below. In the description of the second exemplary embodiment, the same components as those in the first exemplary embodiment are denoted by the same reference signs and names to simplify or omit an explanation of the components. In the second exemplary embodiment, the same materials and compounds as described in the first exemplary embodiment are usable for a material and a compound which are not particularly described.

The organic EL device in the second exemplary embodiment has the same device arrangement as in the first exemplary embodiment, in which the compounds contained in the emitting layer are different. The organic EL device 1 in the second exemplary embodiment contains the first and second compounds according to the first exemplary embodiment and a third compound in the emitting layer. The third compound is also a compound emitting thermally activated delayed fluorescence. Also in the second exemplary embodiment, it is preferable to use the materials used in the above exemplary embodiment.

In the second exemplary embodiment, a concentration of the third compound in the emitting layer is preferably 20 mass % or more. It is preferable that the concentration of the first compound is 20 mass % or more, the concentration of the second compound is 20 mass % or more and the concentration of the third compound is 20 mass % or more in the emitting layer. A total concentration of the first compound, the second compound and the third compound in the emitting layer is 100 mass % or less.

In the second exemplary embodiment, it is preferable that a difference between the singlet energy EgS(M1) of the first compound and singlet energy EgS(M3) of the third compound is 0.2 eV or less and a difference between the singlet energy EgS(M2) of the second compound and the singlet energy EgS(M3) of the third compound is 0.2 eV or less. In other words, it is preferable to satisfy a relationship of |EgS(M1)−EgS(M3)|≤0.2 eV and a relationship of |EgS(M2)−EgS(M3)|≤0.2 eV.

Moreover, in the second exemplary embodiment, it is preferable that a difference between energy gap $Eg_{77K}(M1)$ at 77K of the first compound and energy gap $Eg_{77K}(M3)$ at 77K of the third compound is 0.2 eV or less and a difference between energy gap $Eg_{77K}(M2)$ at 77K of the second compound and the energy gap $Eg_{77K}(M3)$ at 77K of the third compound is 0.2 eV or less. In other words, it is preferable to satisfy a relationship of $|Eg_{77K}(M1)−Eg_{77K}(M3)|≤0.2$ eV and a relationship of $|Eg_{77K}(M2)−Eg_{77K}(M3)|≤0.2$ eV.

In the second exemplary embodiment, at least one of a plurality of the thermally activated delayed fluorescence compounds contained in the emitting layer is preferably a compound in which a difference ΔST between singlet energy EgS and energy gap $Eg_{77K}$ at 77K satisfies a relationship represented by a numerical formula (1) below.

$$\Delta ST = EgS - Eg_{77K} < 0.3 \text{ (eV)} \quad \text{(Numerical Formula 1)}$$

In the second exemplary embodiment, the first compound, the second compound and the third compound which are thermally activated delayed fluorescence compounds are contained in the emitting layer. Further alternatively, the first compound is preferably a compound satisfying the relationship represented by the numerical formula (1-1). Alternatively, the second compound is preferably a compound satisfying the relationship represented by the numerical formula (1-2). Still further alternatively, the third compound is preferably a compound in which a difference ΔST(M3) between the singlet energy EgS(M3) and the energy gap Eg77K(M3) at 77K satisfies a relationship represented by a numerical formula (1-3) below. The third compound is more preferably a compound in which ΔST(M3) is less than 0.2 eV.

$$\Delta ST(M3) = EgS(M3) - Eg_{77K}(M3) < 0.3 \text{ eV} \quad \text{(Numerical Formula 1-3)}$$

It is further preferable that the first compound satisfies the relationship of the numerical formula (1-1), the second compound satisfies the relationship of the numerical formula (1-2), and the third compound satisfies the relationship of the numerical formula (1-3).

The organic EL device of the second exemplary embodiment can also reduce the drive voltage and prolong the emission lifetime in the same manner as in the first exemplary embodiment.

Third Exemplary Embodiment

An organic EL device according to a third exemplary embodiment will be described below. In the description of the second exemplary embodiment, the same components as those in the first exemplary embodiment are denoted by the same reference signs and names to simplify or omit an explanation of the components. In the third exemplary embodiment, the same materials and compounds as described in the above exemplary embodiments are usable for a material and a compound which are not particularly described.

The thermally activated delayed fluorescence compound is exemplified by a compound represented by a formula (2) below. In the third exemplary embodiment, one of the thermally activated delayed fluorescence compounds contained in the emitting layer is represented by the formula (2) below. The compound represented by the formula (1) described in the above exemplary embodiments may also be used as the thermally activated delayed fluorescence compound.

[Formula 65]

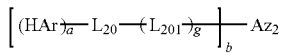
(2)

In the formula (2), $L_{20}$ represents a substituted or unsubstituted (a+g)-valent aromatic hydrocarbon group or a substituted or unsubstituted (a+g)-valent heterocyclic group.

In the formula (2), $L_{201}$ represents a substituted or unsubstituted divalent aromatic hydrocarbon group or a substituted or unsubstituted divalent heterocyclic group.

In the formula (2), a is an integer of 1 to 6 and b is an integer of 1 to 6. a and b are each independently preferably an integer of 1 to 3, more preferably 1 or 2. When a is 2 or more, HAr to be bonded to $L_{20}$ is 2 or more, in which HAr may be mutually the same or different.

In the formula (2), g is an integer of 0 to 2, in which g is preferably 0 or 1. When g is from 1 to 2, $L_{20}$ and $L_{201}$ may be mutually the same or different. When g is 2, two $L_{201}$ may be mutually the same or different.

In the formula (2), HAr is a group derived from a structure represented by a formula (20) below.

[Formula 66]

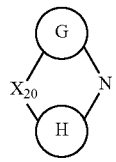
(20)

In the formula (20), $X_{20}$ represents a single bond, an oxygen atom, a sulfur atom, a carbonyl group, $NR_9$, $CR_{10}R_{11}$, $SiR_{12}R_{13}$ or $GeR_{14}R_{15}$. $R_9$ to $R_{15}$ each independently represent the same as $R_1$ to $R_7$ described above. In the formula (20), $X_{20}$ preferably represents an oxygen atom, a sulfur atom, a carbonyl group, $NR_9$, $CR_{10}R_{11}$, $SiR_{12}R_{13}$ or $GeR_{14}R_{15}$.

A cyclic structure represented by the formula (20) is selected from the group consisting of cyclic structures represented by formulae (20b) to (20i).

[Formula 67]

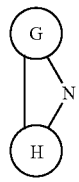
(20b)

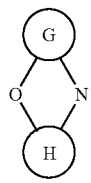
(20c)

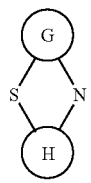
(20d)

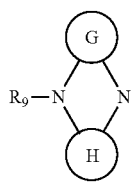
(20e)

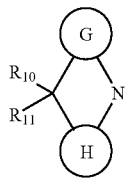
(20f)

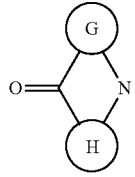
(20g)

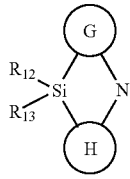
(20h)

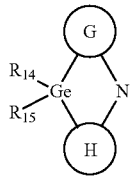
(20i)

In the formulae (20), (20b) to (20i), G and H each independently represent a substituted or unsubstituted cyclic structure. When at least one of the cyclic structure G and the cyclic structure H have a plurality of substituents, adjacent ones of the substituents may form a ring. The ring to be formed may be a saturated or unsaturated ring. The substituent at this time is preferably an electron donating substituent. Moreover, adjacent substituents preferably further form an electron donating ring. Among the cyclic structures, the cyclic structure selected from the group consisting of cyclic structures represented by the formulae (20c) to (20i) is preferable.

When at least one of the cyclic structure A and the cyclic structure B is a substituted or unsubstituted heterocyclic structure in the formulae (20) and (20b) to (20i), the heterocyclic structure has a partial structure represented by a formula (20-2) below.

[Formula 68]

(20-2)

The group derived from the structure represented by the formula (20) is preferably a group represented by formula (20-1) below.

[Formula 69]

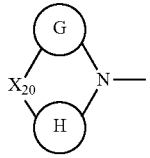
(20-1)

In the formula (20-1), $X_{20}$ represents the same as $X_{20}$ in the formula (20). In other words, the group represented by the formula (20-1) is a group selected from the group consisting of groups represented by formulae (20b-1) to (20i-1) below.

[Formula 70]

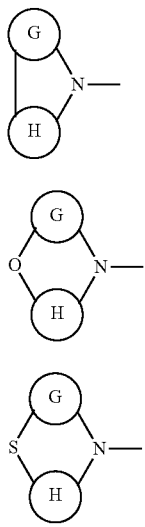

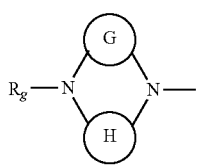

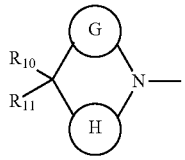
(20f-1)

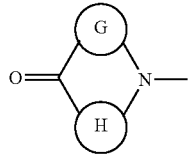
(20g-1)

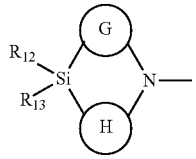
(20h-1)

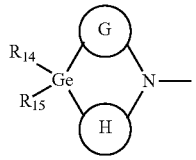
(20i-1)

In the formulae (20b-1) to (20i-1), the cyclic structure G and the cyclic structure H respectively represent the same as the cyclic structure G and the cyclic structure H in the formulae (20) and (20b) to (20i). Among the above groups, the group selected from the group consisting of the groups represented by the formulae (20c-1) to (20i-1) is preferable as HAr of the formula (2).

In the third exemplary embodiment, HAr of the formula (2) is preferably a group derived from a structure represented by a formula (2B) below.

[Formula 71]

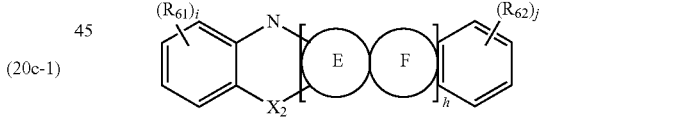
(2B)

In the formula (2B), $X_2$ represents the same as $X_2$ of the formula (20). $X_2$ is preferably an oxygen atom, a sulfur atom, a carbonyl group, $NR_9$, $CR_{10}R_{11}$, $SiR_{12}R_{13}$ or $GeR_{14}R_{15}$.

In the formula (2B), $R_{61}$ and $R_{62}$ each independently represent the same as $R_8$ described above. Adjacent ones of $R_{61}$ may form a ring. Adjacent ones of $R_{62}$ may form a ring.

In the formula (2B), i and j are 4.

In the formula (2B), E represents a cyclic structure represented by a formula (2h) below and F represents a cyclic structure represented by a formula (2i) or (2j) below. Each of the cyclic structure E and the cyclic structure F is fused to an adjacent cyclic structure at any position. In the formula (2B), h is an integer of 0 to 4. h is a repeating unit of a linking cyclic structure in which the cyclic structure E and the cyclic structure F are fused to each other. When h is 2 or more, a plurality of cyclic structures F may be the same or different.

[Formula 72]

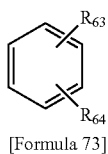
(2h)

[Formula 73]

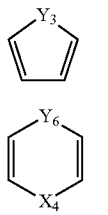
(2i)

(2j)

In the formula (2h), when $R_{63}$ and $R_{64}$ are substituents at adjacent positions, $R_{63}$ and $R_{64}$ may form a ring.

$Y_3$ in the formula (2i) represents $CR_{65}R_{66}$, $NR_{67}$, a sulfur atom, an oxygen atom or a nitrogen atom to be bonded to $L_{20}$. $Y_6$ in the formula (2j) represents $CR_{65}R_{66}$, $NR_{67}$, or a nitrogen atom to be bonded to $L_{20}$.

$X_4$ in the formula (2j) represents $NR_9$ or $CR_{10}R_{11}$ in which $R_9$ to $R_{11}$ each independently represent the same as $R_1$ to $R_7$ described above. $R_{63}$ and $R_{64}$ each independently represent the same as $R_8$ described above. $R_{65}$ to $R_{67}$ each independently represent the same as $R_1$ to $R_7$ described above.

In the exemplary embodiment, h in the formula (2B) is preferably 0 or 1.

In the formula (2B), when h is 0, HAr is preferably a group represented by a formula (2b) or (2bx) below.

[Formula 74]

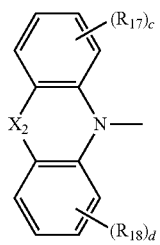
(2b)

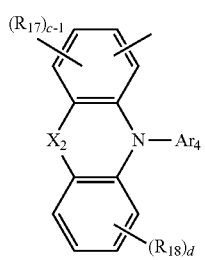
(2bx)

In the formulae (2b) and (2bx), $X_2$ represents a single bond, an oxygen atom, a sulfur atom, a carbonyl group, $NR_9$, $CR_{10}R_{11}$, $SiR_{12}R_{13}$ or $GeR_{14}R_{15}$. In other words, the group represented by the formula (2b) is a group selected from the group consisting of groups represented by formulae (2b-1) to (2b-8) below.

[Formula 75]

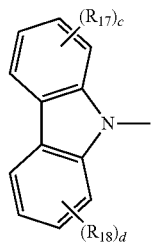
(2b-1)

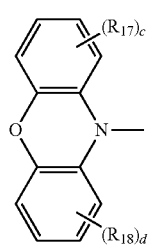
(2b-2)

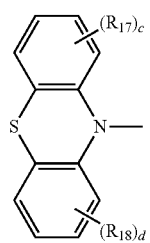
(2b-3)

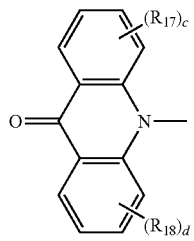
(2b-4)

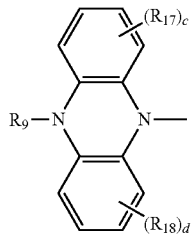
(2b-5)

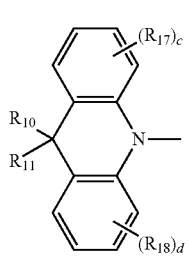
(2b-6)

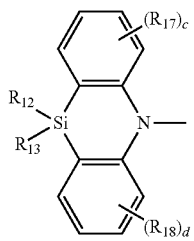

(2b-7)

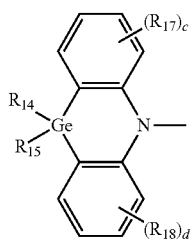

(2b-8)

In the formulae (2b), (2bx) and (2b-1) to (2b-8), c and d are 4. Among the above groups, the group selected from the group consisting of the groups represented by the formulae (2b-2) to (2b-8) is preferable as HAr of the formula (2).

In the formulae (2b), (2bx) and (2b-1) to (2b-8), $R_9$ to $R_{15}$ each independently represent the same as $R_1$ to $R_7$ described above. $R_{17}$ and $R_{18}$ each independently represent the same as $R_8$ described above. Adjacent ones of $R_{17}$ may form a ring. Adjacent ones of $R_{18}$ may form a ring.

In the formula (2bx), $Ar_4$ represents the same as $R_1$ to $R_8$ described above. $Ar_4$ is preferably a substituted or unsubstituted aryl group having 6 to 30 ring carbon atoms or a substituted or unsubstituted heterocyclic group having 5 to 30 ring atoms, more preferably a substituted or unsubstituted aryl group having 6 to 30 ring carbon atoms. $Ar_4$ is preferably a phenyl group, biphenyl group, terphenyl group, naphthyl group, phenanthryl group, triphenylyl group, dibenzofuranyl group, dibenzothiophenyl group, carbazolyl group and the like.

In the formula (2), $Az_2$ is represented by a formula (2d) below.

[Formula 76]

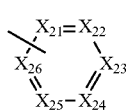

(2d)

In the formula (2d), $X_{21}$ to $X_{26}$ each independently represent $CR_{16}$ or a nitrogen atom. At least one of $X_{21}$ to $X_{26}$ is a nitrogen atom and b of $X_{21}$ to $X_{26}$ is a carbon atom to be bonded to $L_{20}$ or $L_{201}$. Since b is an integer of 1 to 3 as described above, one to three of $X_{21}$ to $X_{26}$ are carbon atom(s) to be bonded to $L_{20}$. $R_{16}$ represents the same as $R_8$ described above.

In the formula (21), one to three of $X_{21}$ to $X_{26}$ are preferably nitrogen atom(s). For instance, when $X_{26}$ is a carbon atom bonded to $L_{20}$ and one of $X_{21}$ to $X_{25}$ is a nitrogen atom, $X_{21}$ or $X_2$ is preferably a nitrogen atom. When two of $X_{21}$ to $X_{25}$ are nitrogen atoms, $X_{21}$ and $X_{25}$ are preferably nitrogen atoms. When three of $X_{21}$ to $X_{25}$ are nitrogen atoms, $X_{21}$, $X_{23}$ and $X_{25}$ are preferably nitrogen atoms. A triazine ring in which $X_{21}$, $X_{23}$ and $X_{25}$ are nitrogen atoms is preferable in the formula (2d).

In the exemplary embodiment, it is preferable that a and b are 1 and g is 0 in the formula (2) and $X_{26}$ is a carbon atom to be bonded to $L_{20}$ in formula (2d). In other words, the compound represented by the formula (2) is preferably a compound represented by a formula (21) below.

[Formula 77]

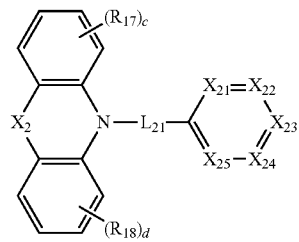

(21)

In the formula (21), $X_2$ represents the same as $X_2$ of the formula (2b).

In the formula (21), $L_{21}$ represents a substituted or unsubstituted divalent aromatic hydrocarbon group or a substituted or unsubstituted divalent heterocyclic group.

In the formula (21), $X_{21}$ to $X_{25}$ each independently represent $CR_{16}$ or a nitrogen atom and at least one of $X_{21}$ to $X_{25}$ is a nitrogen atom. When one of $X_{21}$ to $X_{25}$ is a nitrogen atom, $X_{21}$ or $X_{25}$ is preferably nitrogen atoms. When two of $X_{21}$ to $X_{25}$ are nitrogen atoms, $X_{21}$ and $X_{25}$ are preferably nitrogen atoms. When three of $X_{21}$ to $X_{25}$ are nitrogen atoms, $X_{21}$, $X_{23}$ and $X_{25}$ are preferably nitrogen atoms.

In the formula (21), c and d are 4 and $R_{17}$ and $R_{18}$ each independently represent the same as $R_8$ described above. A plurality of $R_{17}$ may be mutually the same or different. A plurality of $R_{18}$ may be mutually the same or different.

In the third exemplary embodiment, the compound represented by the formula (2) is preferably the compound represented by the formula (21), in which $X_2$ is preferably an oxygen atom.

In the third exemplary embodiment, it is preferable that a is 2 and b is 1 in the formula (2) and $X_{26}$ is a carbon atom to be bonded to $L_{20}$ in formula (2d). In other words, the compound represented by the formula (2) is preferably a compound represented by a formula (22) below.

[Formula 78]

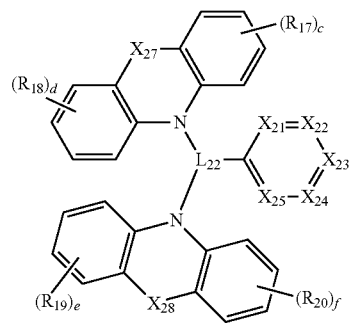

(22)

In the formula (22), $X_{27}$ and $X_{28}$ each independently represent the same as $X_2$ of the formula (2b), in which $X_{27}$ and $X_{28}$ may be mutually the same or different.

In the formula (22), $L_{22}$ is a substituted or unsubstituted trivalent aromatic hydrocarbon group or a substituted or unsubstituted trivalent heterocyclic group.

In the formula (22), $X_{21}$ to $X_{25}$ each independently represent $CR_{16}$ or a nitrogen atom and at least one of $X_{21}$ to $X_{25}$ is a nitrogen atom. When one of $X_{21}$ to $X_{25}$ is a nitrogen atom, $X_{21}$ or $X_{25}$ is preferably nitrogen atoms. When two of $X_{21}$ to $X_{25}$ are nitrogen atoms, $X_{21}$ and $X_{25}$ are preferably nitrogen atoms. When three of $X_{21}$ to $X_{25}$ are nitrogen atoms, $X_{21}$, $X_{23}$ and $X_{25}$ are preferably nitrogen atoms.

In the formula (22), c, d, e and f are each 4 and $R_{17}$ to $R_{20}$ each independently represent the same as $R_8$ described above. Adjacent ones of $R_{17}$ may form a ring. Adjacent ones of $R_{18}$ may form a ring.

In the third exemplary embodiment, the compound represented by the formula (2) is preferably the compound represented by the formula (22), in which $X_{27}$ and $X_{28}$ are preferably oxygen atoms.

In the third exemplary embodiment, it is preferable that a is 1, b is 2, and g is 0 in the formula (2) and $X_{24}$ and $X_{26}$ are carbon atoms to be bonded to $L_{20}$ and $X_{21}$, $X_{23}$ and $X_{25}$ are nitrogen atoms in formula (2d). In other words, the compound represented by the formula (2) is preferably a compound represented by a formula (23) below.

[Formula 79]

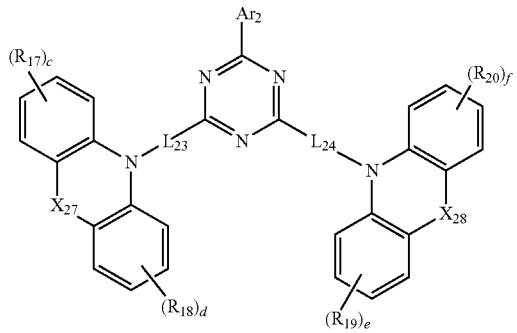

(23)

In the formula (23), $X_{27}$ and $X_{28}$ represent the same as $X_2$ of the formula (2b) and $X_{27}$ and $X_{28}$ may be mutually the same or different.

In the formula (23), $L_{23}$ and $L_{24}$ each independently represent a substituted or unsubstituted divalent aromatic hydrocarbon group or a substituted or unsubstituted divalent heterocyclic group.

In the formula (23), $Ar_2$ represents the same as $R_1$ to $R_8$ described above. $Ar_2$ is preferably a substituted or unsubstituted aryl group having 6 to 30 ring carbon atoms or a substituted or unsubstituted heterocyclic group having 5 to 30 ring atoms, more preferably a substituted or unsubstituted aryl group having 6 to 30 ring carbon atoms. $Ar_2$ is preferably a phenyl group, biphenyl group, terphenyl group, naphthyl group, phenanthryl group, triphenylyl group, dibenzofuranyl group, dibenzothiophenyl group, carbazolyl group and the like.

In the formula (23), c, d, e and f are each 4 and $R_{17}$ to $R_{20}$ each independently represent the same as $R_8$ described above. Adjacent ones of $R_{17}$ may form a ring. Adjacent ones of $R_{18}$ may form a ring.

In the third exemplary embodiment, the compound represented by the formula (2) is preferably the compound represented by the formula (23), in which $X_{27}$ and $X_{28}$ are preferably oxygen atoms.

In the third exemplary embodiment, in the compound represented by the formula (2), it is preferable that HAr is the group represented by the formula (2b), $L_{20}$ is a substituted or unsubstituted divalent heterocyclic group, and g is 1. In this arrangement, $L_{20}$ is more preferably a substituted or unsubstituted divalent carbazolyl group. Further, the compound represented by the formula (2) is preferably a compound represented by a formula (24) below.

[Formula 80]

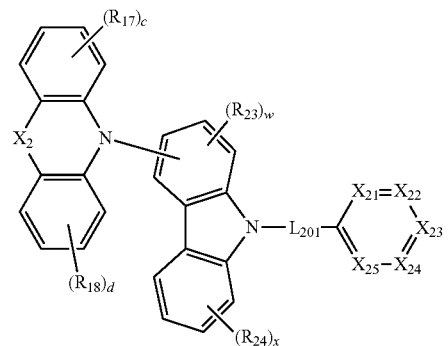

(24)

In the formula (24), $X_{21}$ to $X_{25}$ represent the same as $X_{21}$ to $X_{25}$ of the formula (21).

In the formula (24), $R_{17}$ to $R_{18}$ and $R_{23}$ to $R_{24}$ each independently represent the same as $R_8$ described above. Adjacent ones of $R_{17}$ may form a ring. Adjacent ones of $R_{18}$ may form a ring. Adjacent ones of $R_{23}$ may form a ring. Adjacent ones of $R_{24}$ may form a ring.

In the formula (24), $L_{201}$ represents the same as $L_{201}$ of the formula (2).

In the formula (24), c, d and x are 4 and w is 3.

In the formula (2B), when h is 1 and the cyclic structure F is represented by the formula (2i), the structure of the formula (2B) is represented by formulae (2B-1) to (2B-6) below.

[Formula 81]

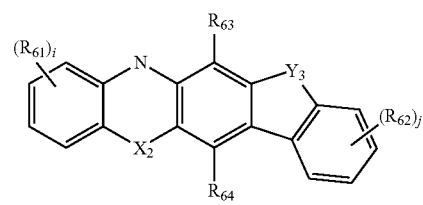

(2B-1)

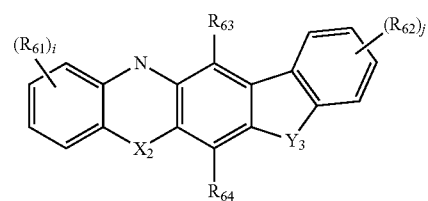

(2B-2)

-continued (2B-3)
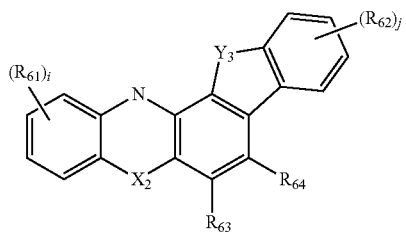

(2B-4)
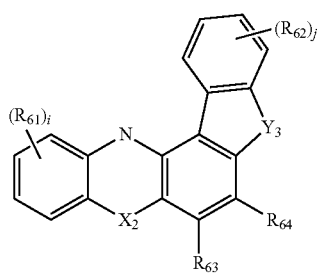

(2B-5)
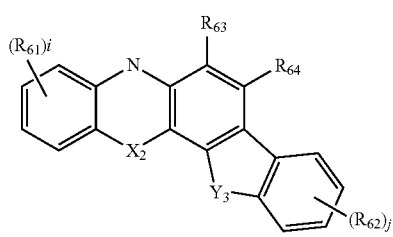

(2B-6)
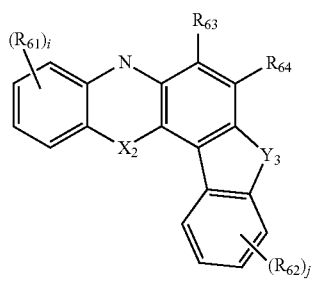

[Formula 82]

(2B-7)
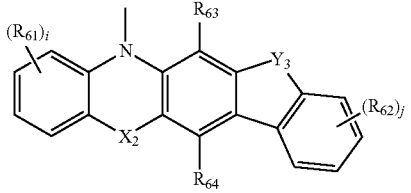

(2B-8)
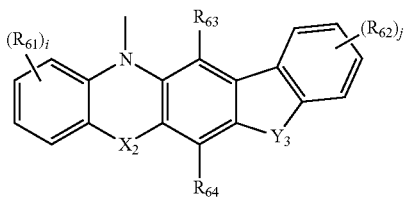

(2B-9)
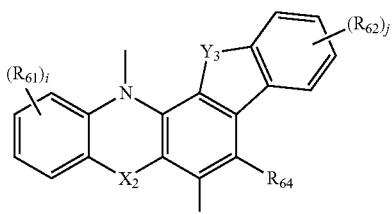

(2B-10)
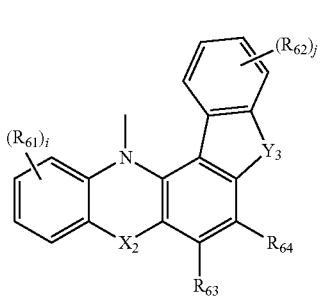

(2B-11)
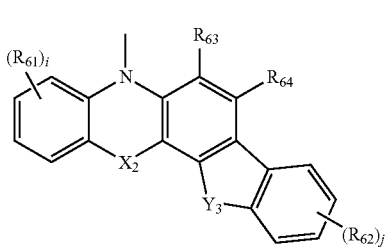

(2B-12)
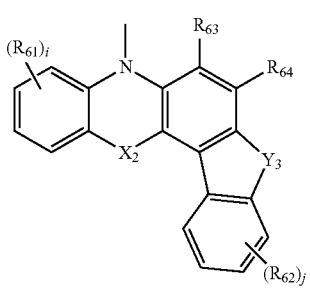

In the formulae (2B-1) to (2B-6), $X_2$ represents the same as $X_2$ of the formula (2b).

In the formulae (2B-1) to (2B-6), $R_{61}$ to $R_{64}$ each independently represent the same as $R_8$ described above. Adjacent ones of $R_{61}$ may form a ring. Adjacent ones of $R_{62}$ may form a ring. Adjacent $R_{63}$ and $R_{64}$ may form a ring.

In the formulae (2B-1) to (2B-6), $Y_3$ represents the same as $Y_3$ of the formula (2i).

In the formulae (2B-1) to (2B-6), i and j are 4.

Groups derived from the structure represented by the formulae (2B-1) to (2B-6) are preferably groups represented by formulae (2B-7) to (2B-18) below.

[Formula 83]

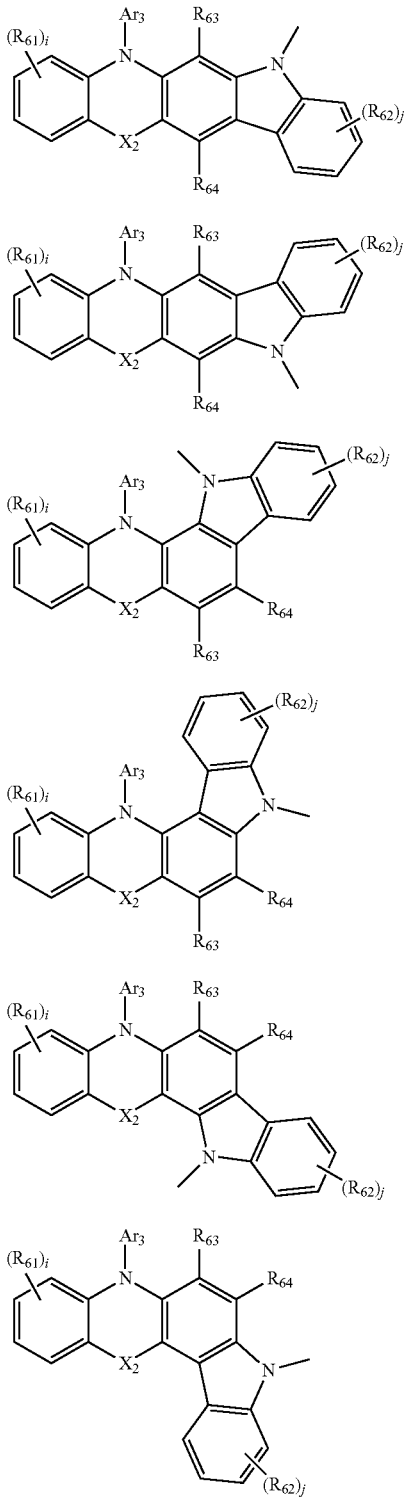

(2B-13)

(2B-14)

(2B-15)

(2B-16)

(2B-17)

(2B-18)

In the formulae (2B-7) to (2B-12), $X_2$ represents the same as $X_2$ of the formula (2b), in which $X_2$ is preferably an oxygen atom.

In the formulae (2B-7) to (2B-12), $R_{61}$ to $R_{64}$ each independently represent the same as $R_8$ described above. Adjacent ones of $R_{61}$ may form a ring. Adjacent ones of $R_{62}$ may form a ring. Adjacent $R_{63}$ and $R_{64}$ may form a ring.

In the formulae (2B-7) to (2B-12), $Y_3$ represents the same as $Y_3$ of the formula (2i), among which $Y_3$ is preferably $NR_{67}$. $R_{67}$ represents the same as $R_1$ to $R_7$ described above and is preferably a substituted or unsubstituted aryl group having 6 to 30 ring carbon atoms.

In the formulae (2B-7) to (2B-12), i and j are 4.

In the formulae (2B-13) to (2B-18), $X_2$ represents the same as $X_2$ of the formula (2b), in which $X_2$ is preferably an oxygen atom.

In the formulae (2B-13) to (2B-18), $R_{61}$ to $R_{64}$ each independently represent the same as $R_8$ described above. Adjacent ones of $R_{61}$ may form a ring. Adjacent ones of $R_{62}$ may form a ring. Adjacent $R_{63}$ and $R_{64}$ may form a ring.

In the formulae (2B-13) to (2B-18), $Ar_3$ represents the same as $R_1$ to $R_7$ described above. $Ar_3$ is preferably a substituted or unsubstituted aryl group having 6 to 30 ring carbon atoms or a substituted or unsubstituted heterocyclic group having 5 to 30 ring atoms, more preferably a substituted or unsubstituted aryl group having 6 to 30 ring carbon atoms. $Ar_3$ is preferably a phenyl group, biphenyl group, terphenyl group, naphthyl group, phenanthryl group, triphenylyl group, dibenzofuranyl group, dibenzothiophenyl group, carbazolyl group and the like.

In the formulae (2B-13) to (2B-18), i and j are 4.

In the formula (2B), when h is 1 and the cyclic structure F is represented by the formula (2i), the structure of the formula (2B) is represented by formulae (2B-19) to (2B-20) below.

[Formula 84]

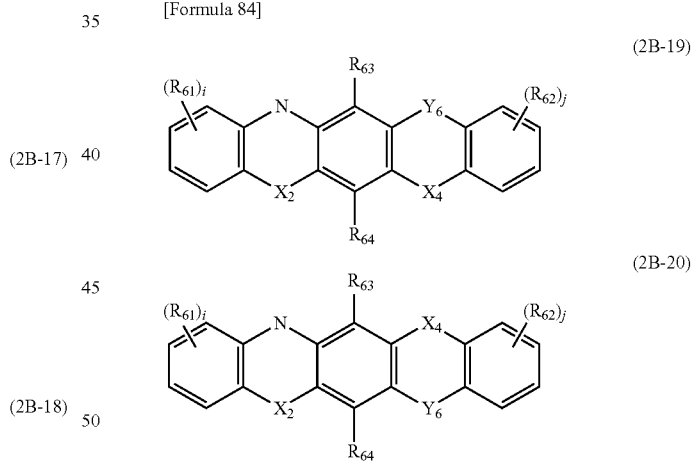

(2B-19)

(2B-20)

In the formulae (2B-19) to (2B-20), $X_2$ and $X_4$ represent the same as $X_2$ of the formula (2b) and $X_4$ represents the same as $X_4$ of the formula (2j).

In the formulae (2B-19) to (2B-20), $R_{61}$ to $R_{64}$ each independently represent the same as $R_8$ described above. Adjacent ones of $R_{61}$ may form a ring. Adjacent ones of $R_{62}$ may form a ring. Adjacent $R_{63}$ and $R_{64}$ may form a ring.

In the formulae (2B-19) to (2B-20), $Y_6$ represents the same as $Y_3$ of the formula (2i).

In the formulae (2B-19) to (2B-20), i and j are 4.

Groups derived from the structure represented by the formulae (2B-19) to (2B-20) are preferably groups represented by formulae (2B-21) to (2B-22) below.

[Formula 85]

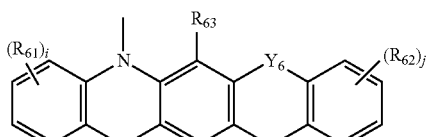
(2B-21)

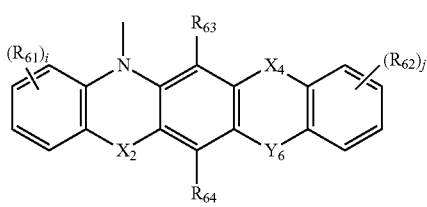
(2B-22)

In the formulae (2B-21) to (2B-22), $X_2$, $X_4$, $R_{61}$ to $R_{64}$, $Y_6$, i and j respectively represent the same as $X_2$, $X_4$, $R_{61}$ to $R_{64}$, $Y_6$, i and j of the formulae (2B-19) to (2B-20).

In the exemplary embodiment, when $L_{20}$ to $L_{24}$ and $L_{201}$ are divalent linking groups to be bonded to $Az_2$, $L_{20}$ to $L_{24}$ and $L_{201}$ are each preferably a substituted or unsubstituted divalent aromatic hydrocarbon group. When g is 1 or more in the formula (2), not $L_{20}$ but $L_{201}$ is a divalent linking group to be bonded to $Az_2$.

Moreover, in the exemplary embodiment, when $L_{20}$ to $L_{24}$ and $L_{201}$ are divalent linking groups to be bonded to $Az_2$, $L_{20}$ to $L_{24}$ and $L_{201}$ each preferably have a divalent six-membered ring structure, more preferably a divalent six-membered ring structure represented by a formula (2e), (2f) or (2g) below, further preferably a divalent six-membered ring structure represented by the formula (2e) below.

[Formula 86]

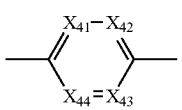
(2e)

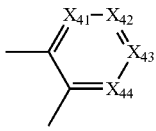
(2f)

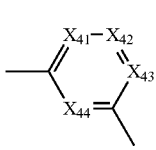
(2g)

In the formulae (2e) to (2g), $X_{41}$ to $X_{44}$ each independently represent $CR_{52}$ or a nitrogen atom, in which $R_{52}$ each independently represents the same as $R_8$ in the formula (1).

In the exemplary embodiment, $X_{41}$ to $X_{44}$ of the formulae (2e) to (2g) are each independently preferably $CR_{52}$, in which $R_{52}$ is more preferably a hydrogen atom, alkyl group, alkoxy group, aryloxy group, cyano group, halogen atom and silyl group.

When g is 1 in the formula (2), $L_{201}$ preferably has a divalent six-membered ring structure represented by the formula (2e) and $L_{20}$ is preferably a heterocyclic group having 5 to 30 ring atoms. In this arrangement, the heterocyclic group is preferably a carbazolyl group, in which a nitrogen atom at a position 9 of the carbazolyl group is preferably bonded to $L_{201}$. Further preferably, at least one of the structures represented by the formulae (2b) and (2bx) is bonded to the carbazolyl group.

Moreover, $L_{21}$ of the formula (21), $L_{22}$ of the formula (22), $L_{23}$ and $L_{24}$ of the formula (23) and $L_{201}$ of the formula (24) each preferably have a divalent six-membered ring structure represented by the formula (2e).

Specific examples of the compound represented by the formula (2) are shown below, but the invention is not limited thereto.

[Formula 87]

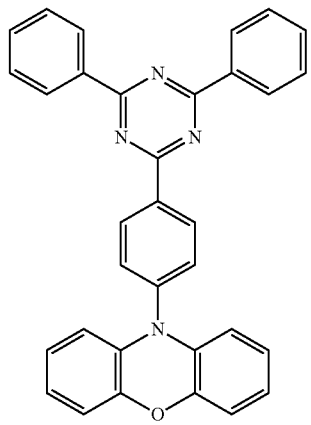

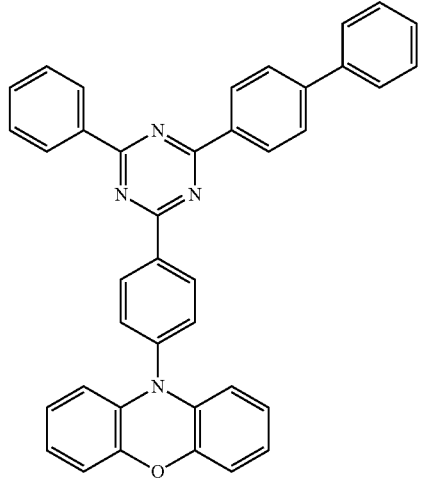

107
-continued
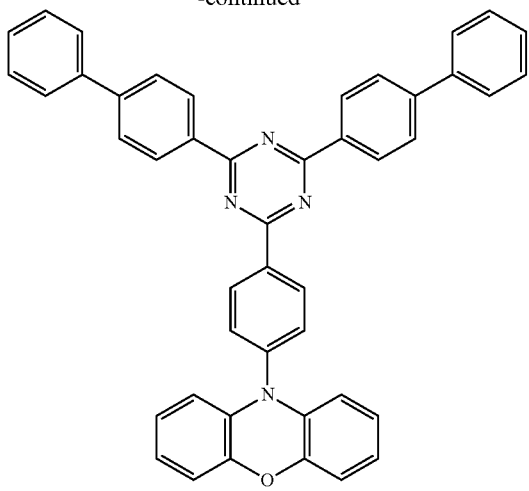
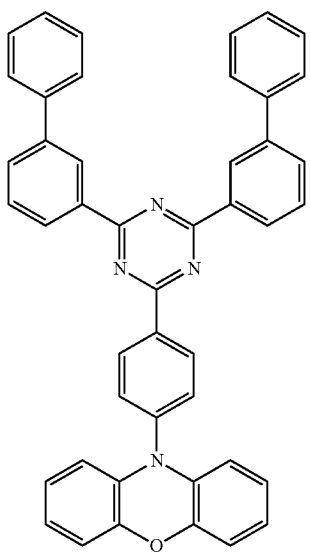
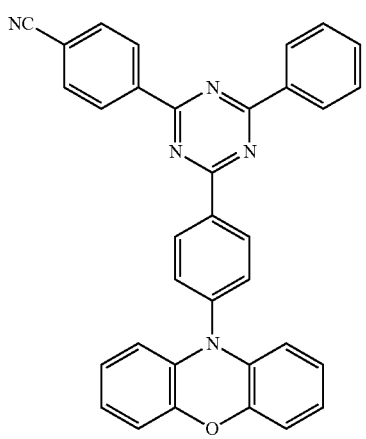
108
-continued
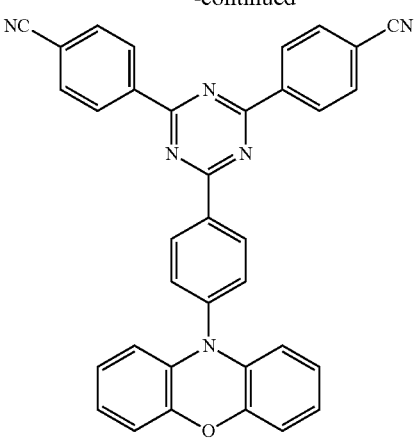
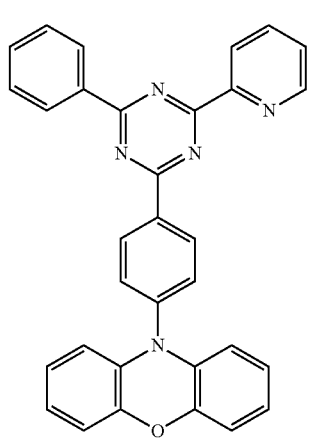
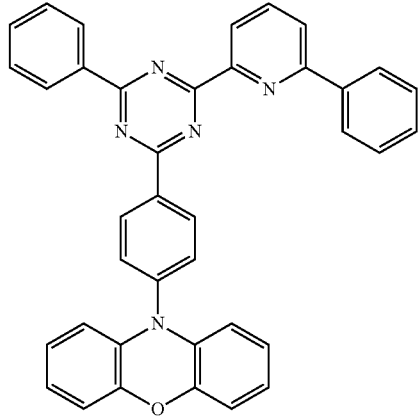

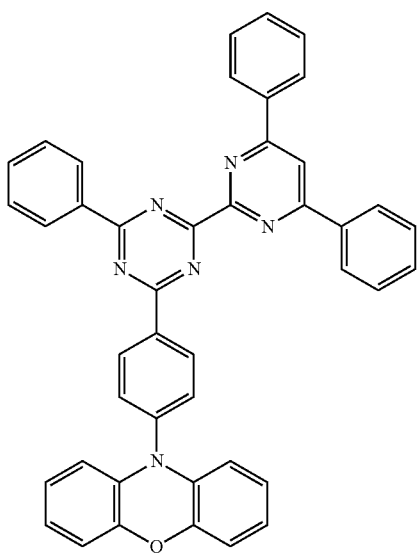
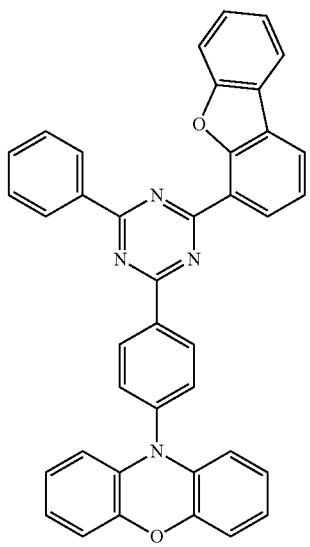
[Formula 88]
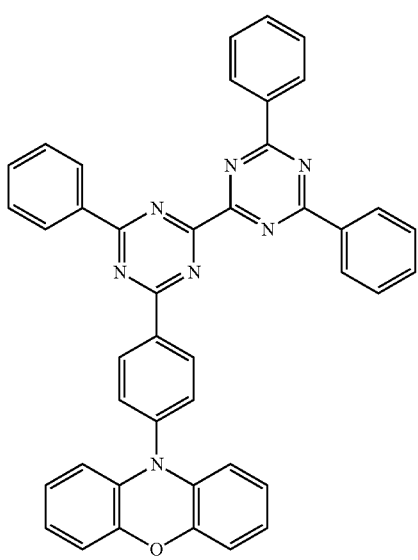
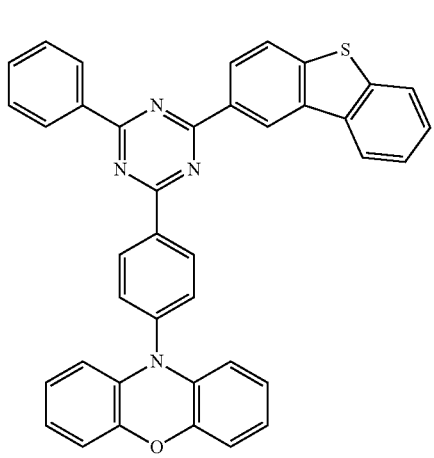
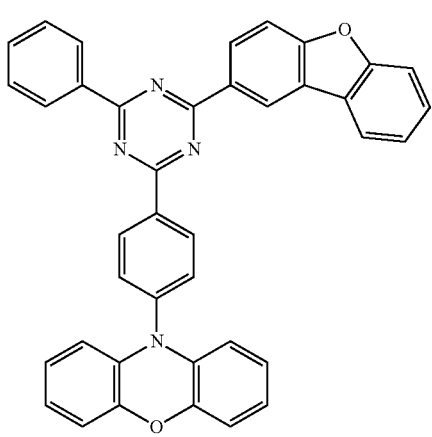
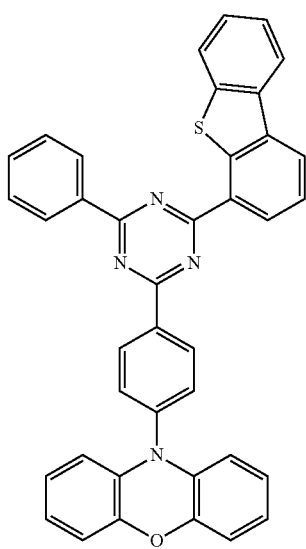

111
-continued
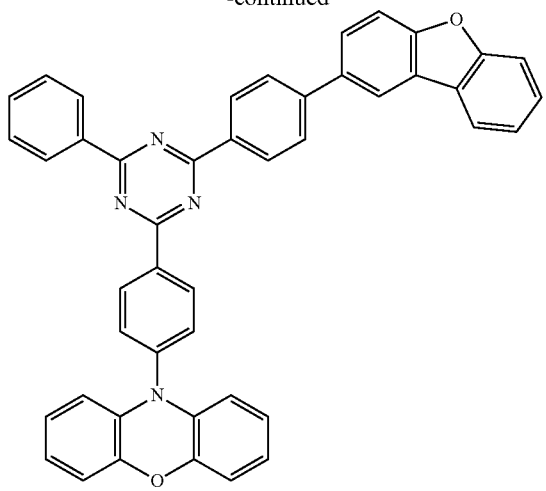
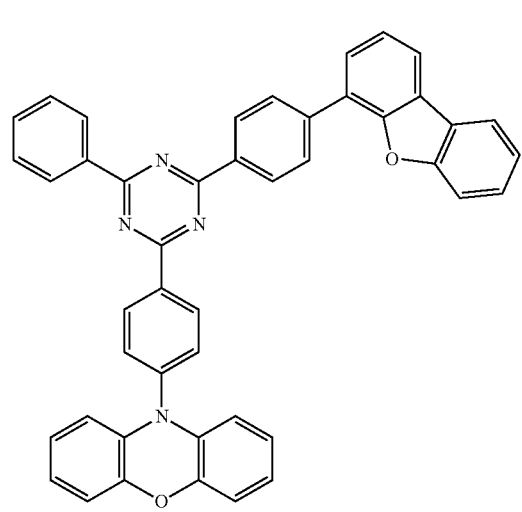
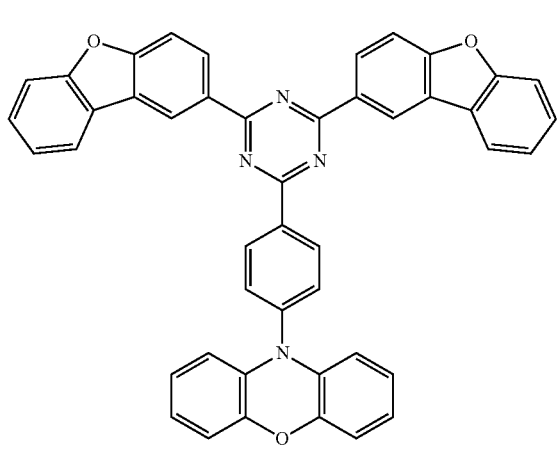
112
-continued
[Formula 89]
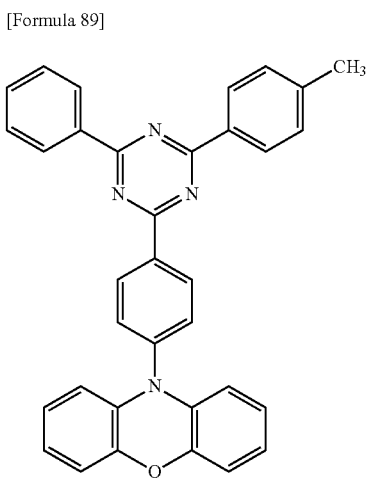
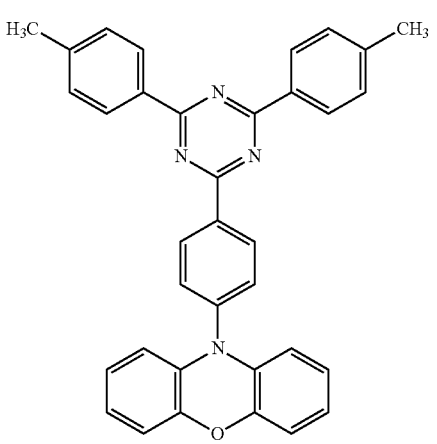
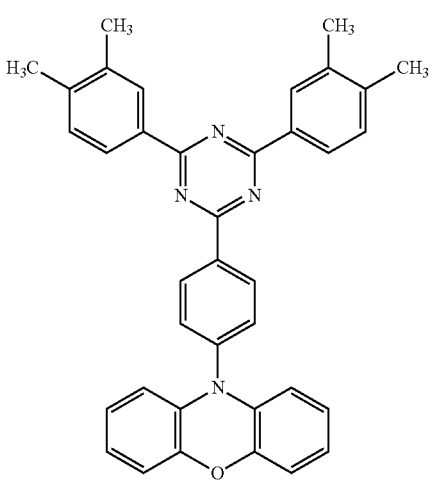

113
-continued
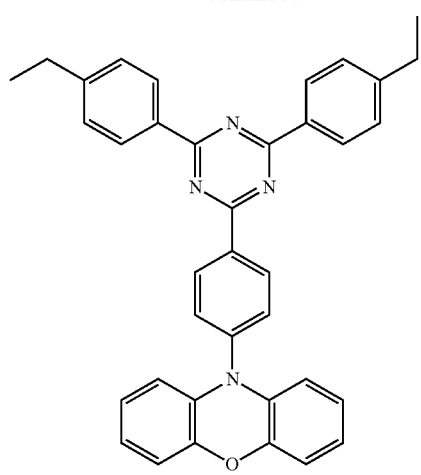
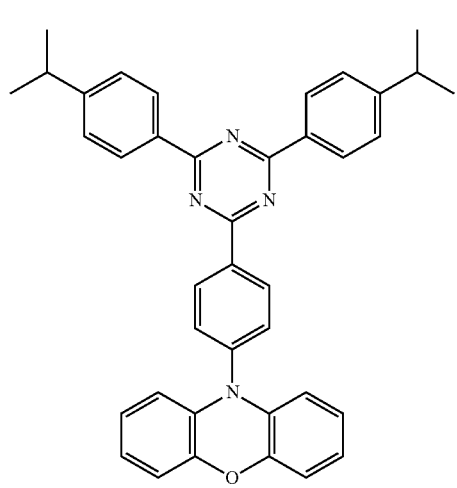
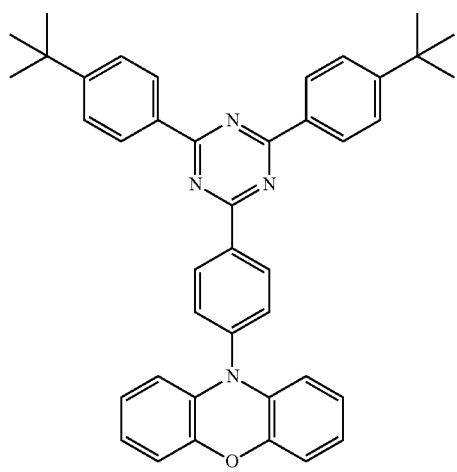
114
-continued
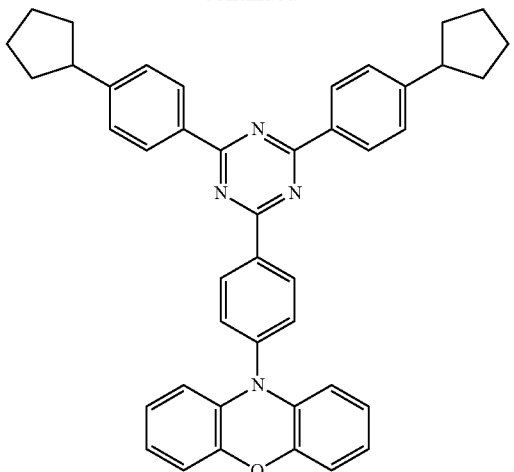
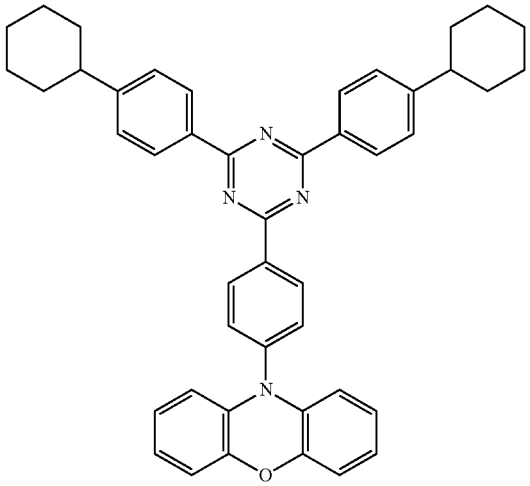

[Formula 90]
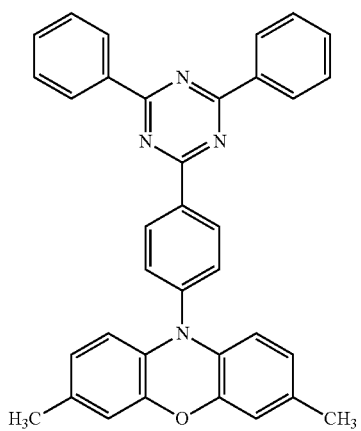
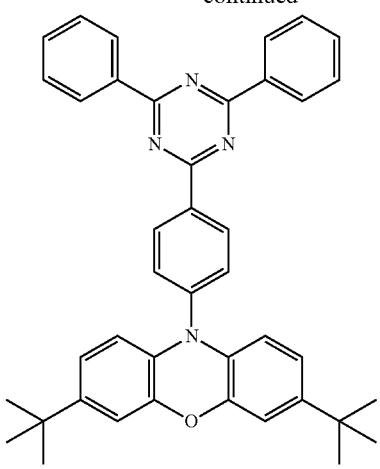
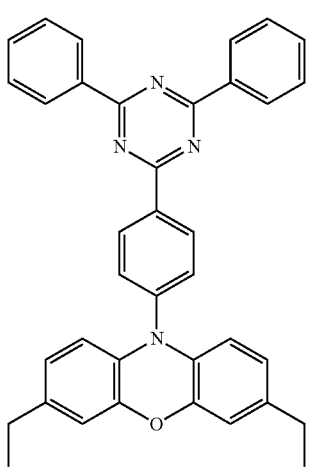
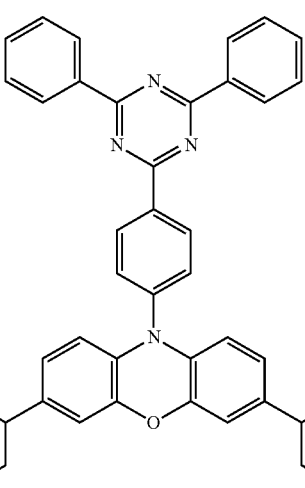
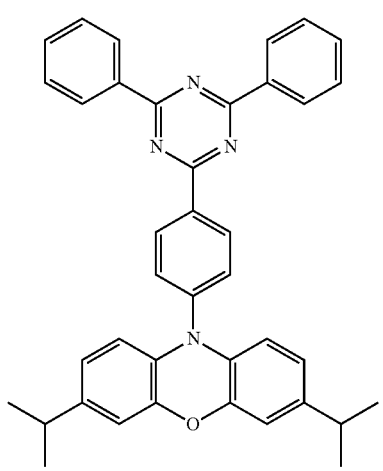
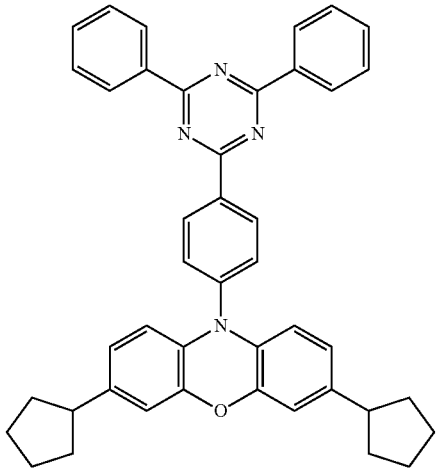

117
-continued
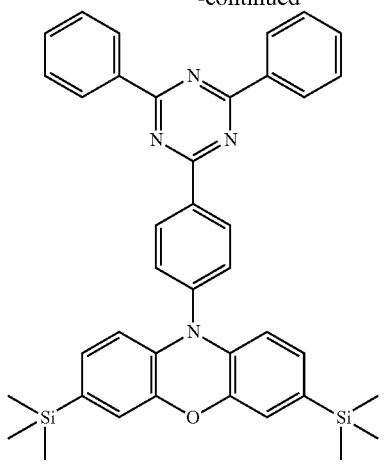
[Formula 91]
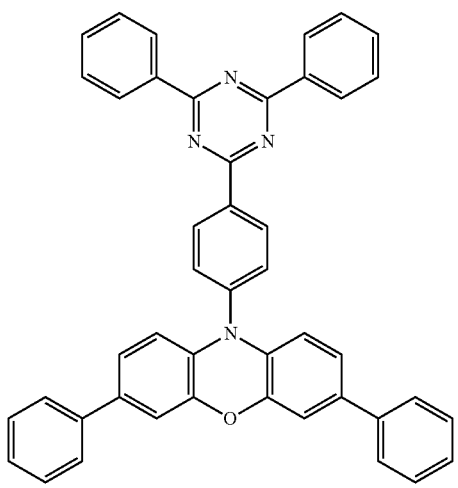
118
-continued
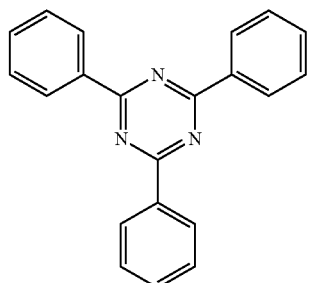
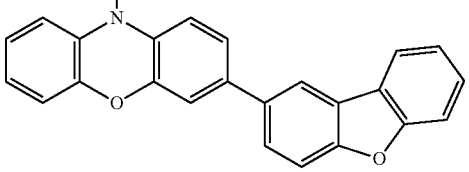
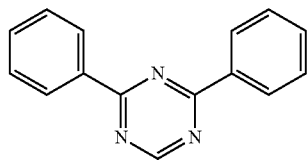
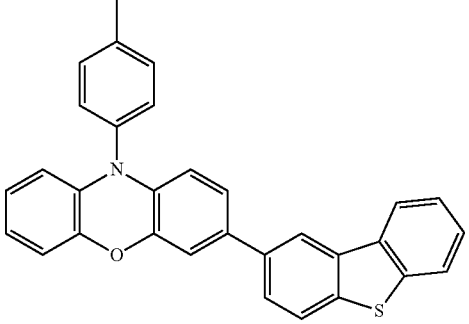
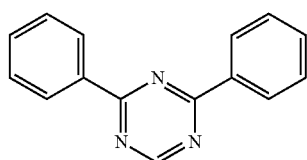
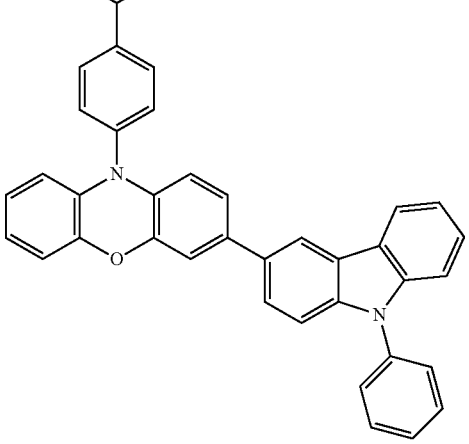

119
-continued
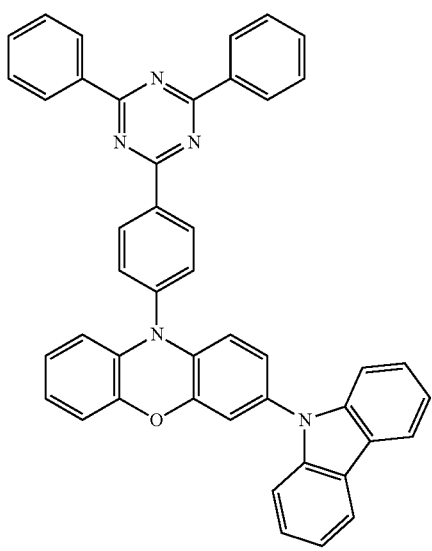
120
-continued
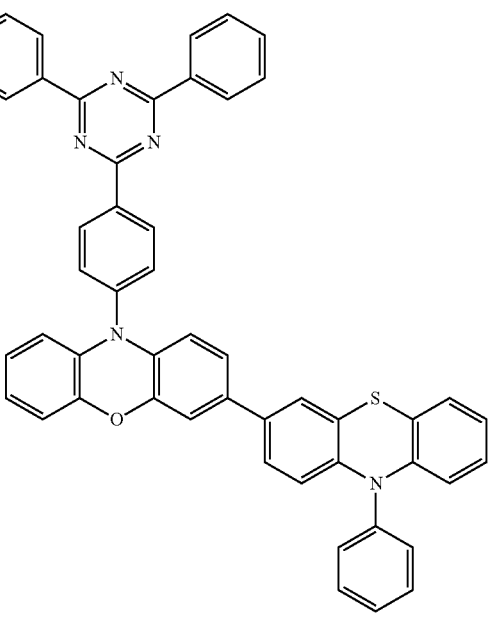
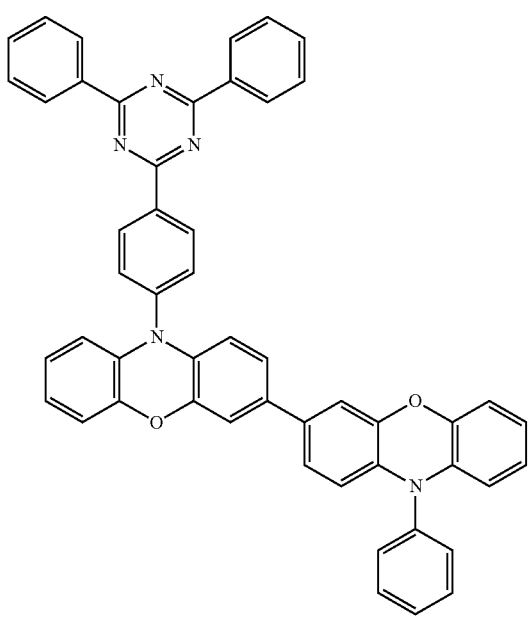
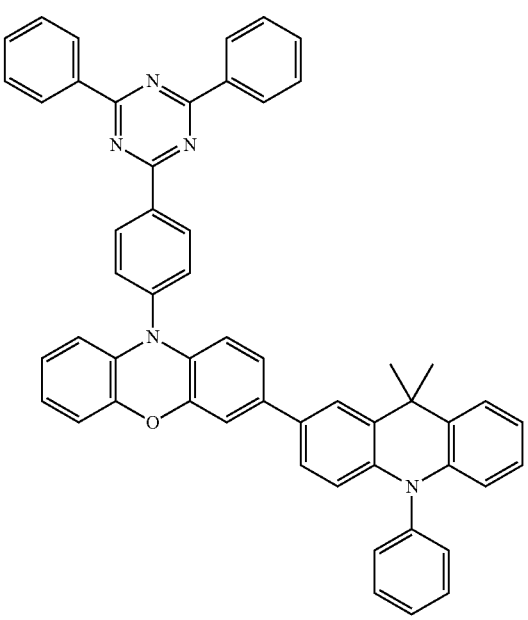

[Formula 92]
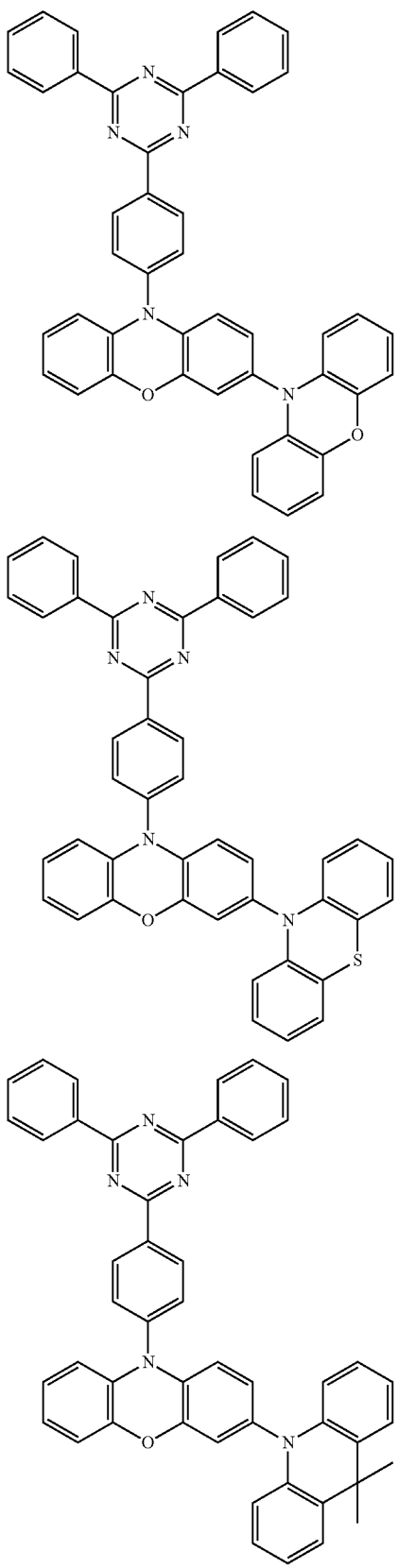
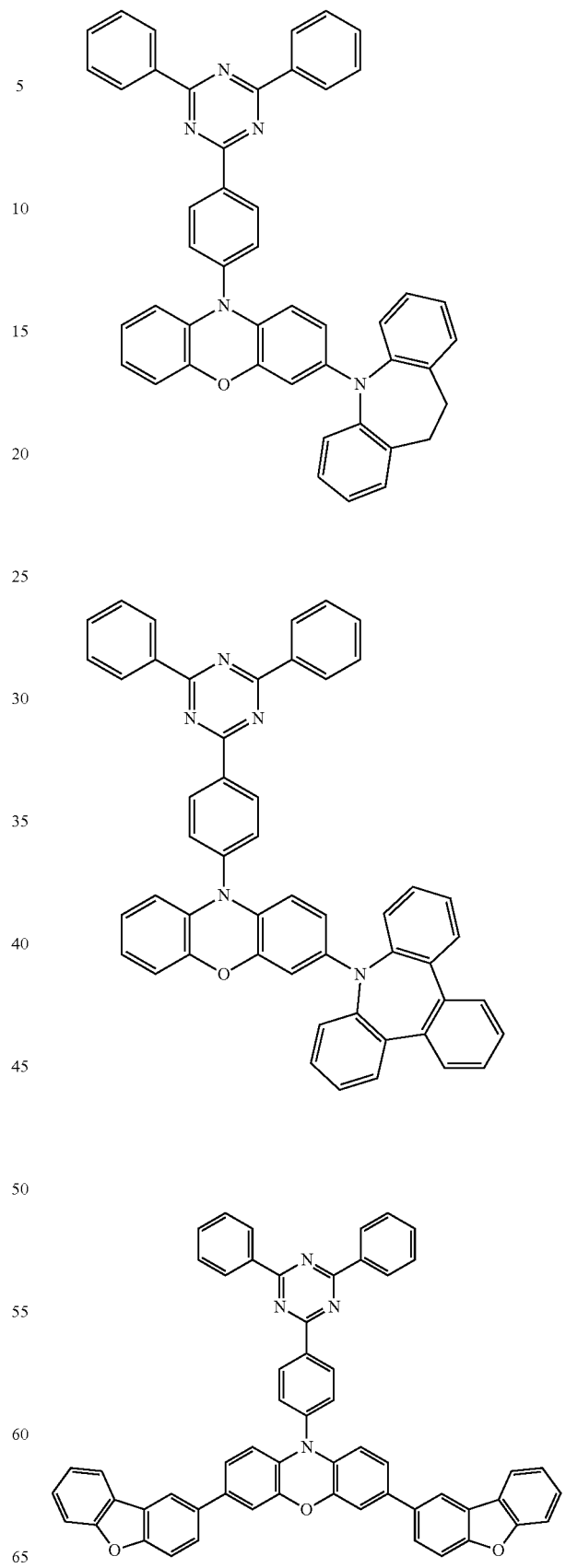

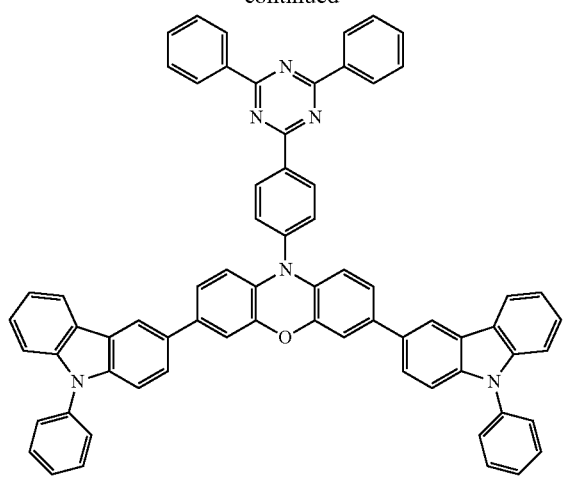
[Formula 93]
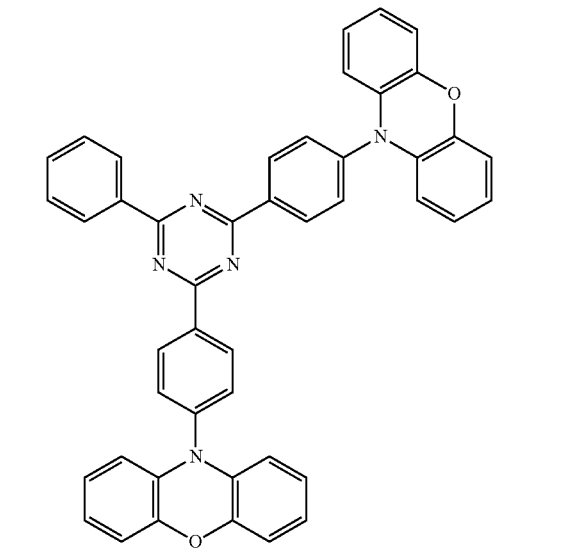
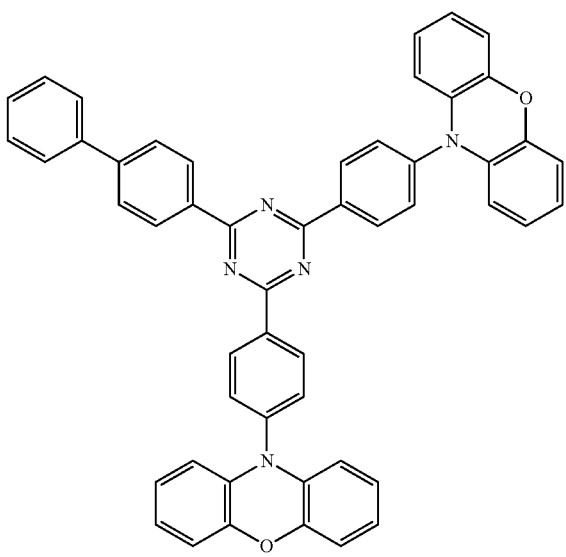
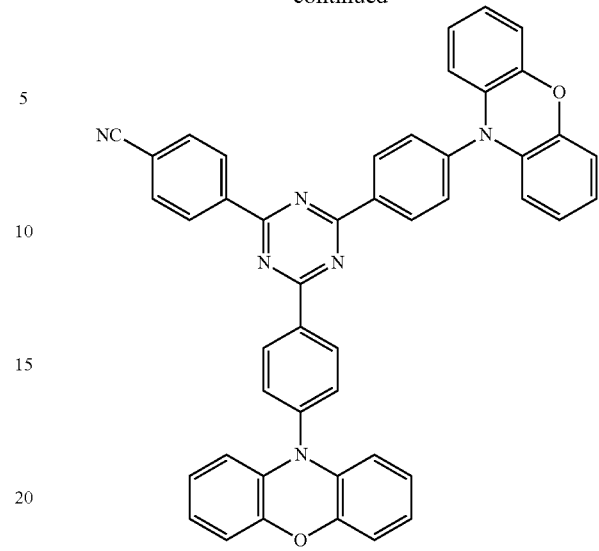
[Formula 94]
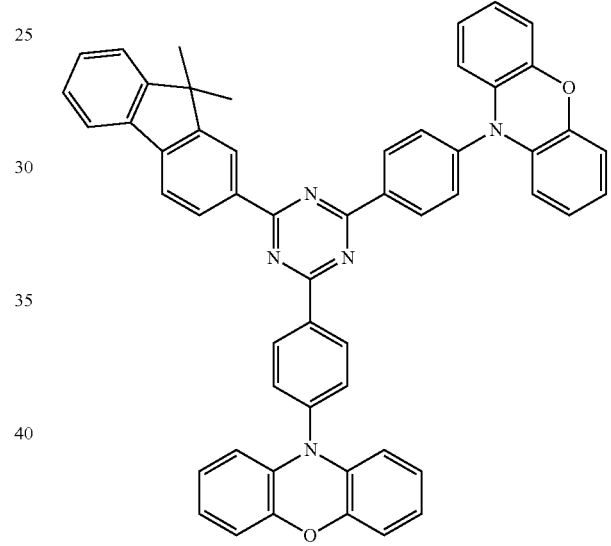
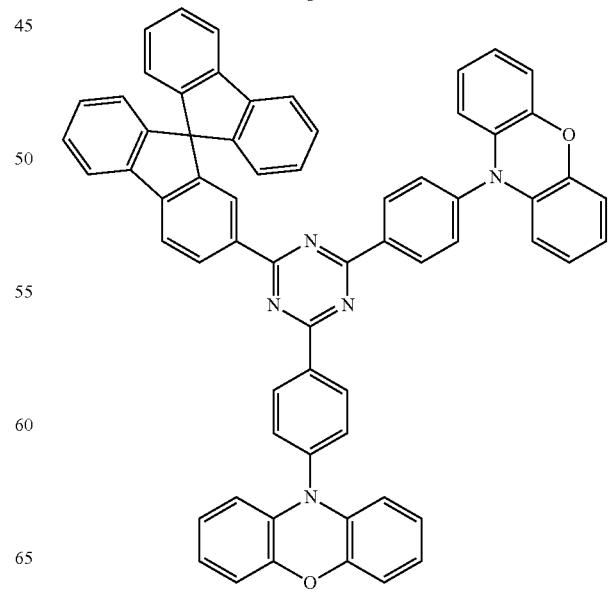

125
-continued
[Formula 95]
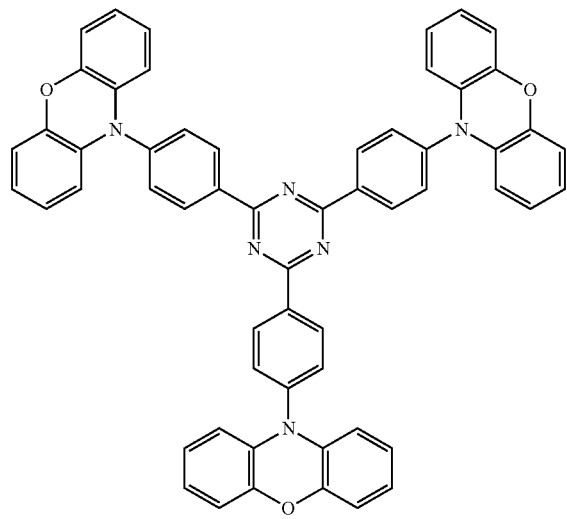
[Formula 96]
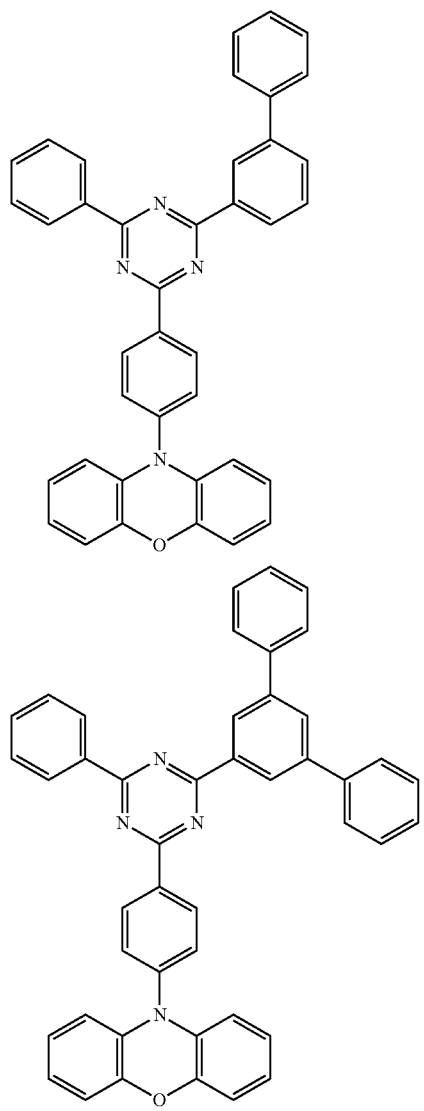
126
-continued
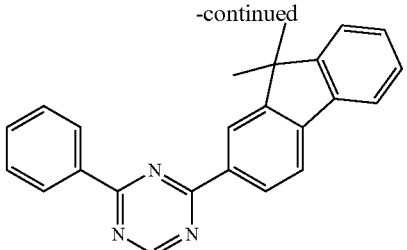

127
-continued
[Formula 97]
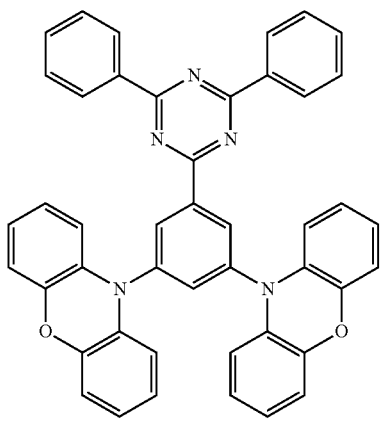
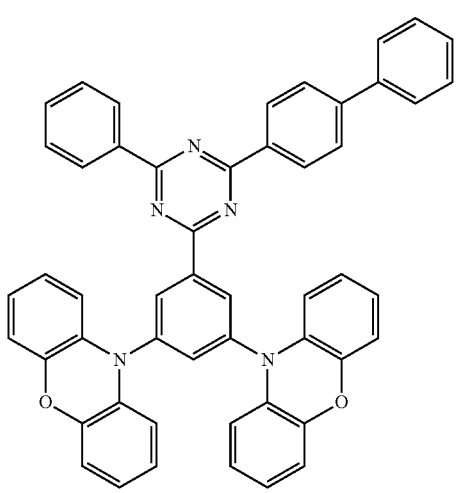
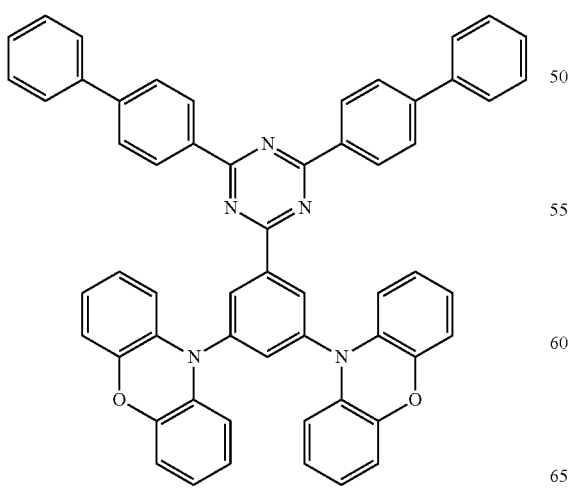
128
-continued
[Formula 98]
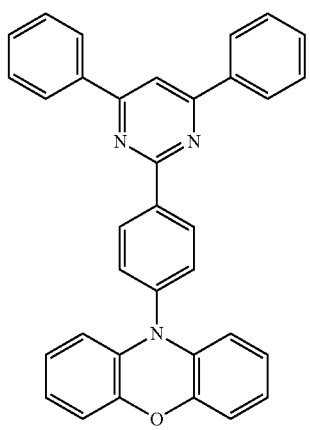
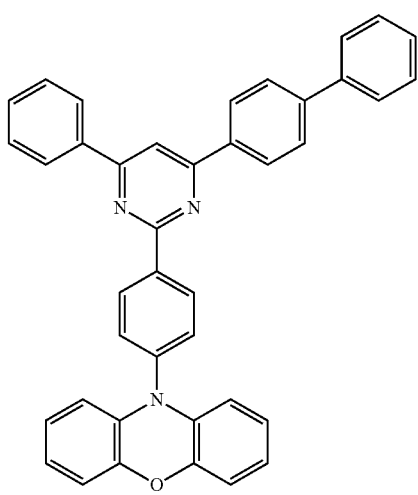
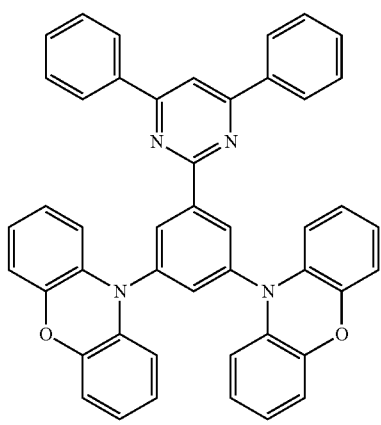

129
-continued
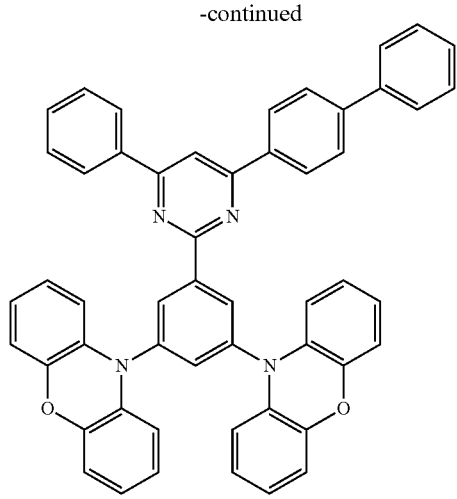
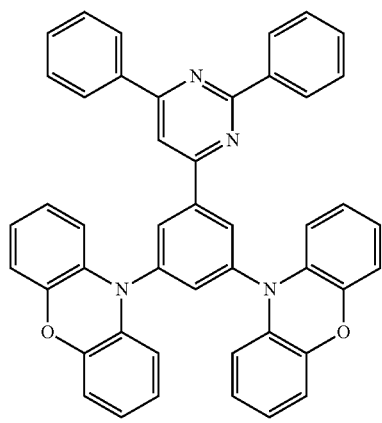
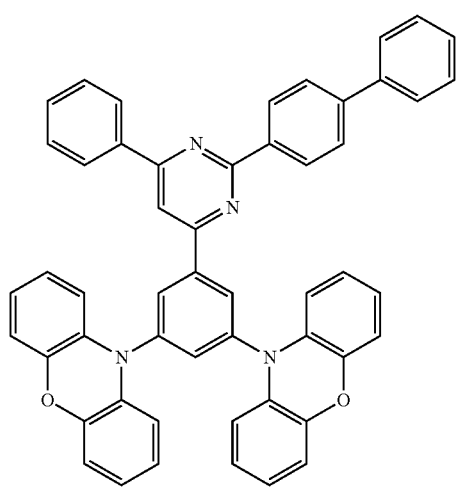
130
-continued
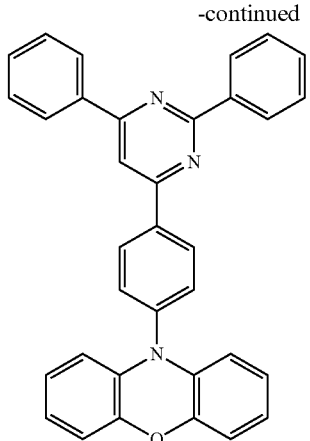
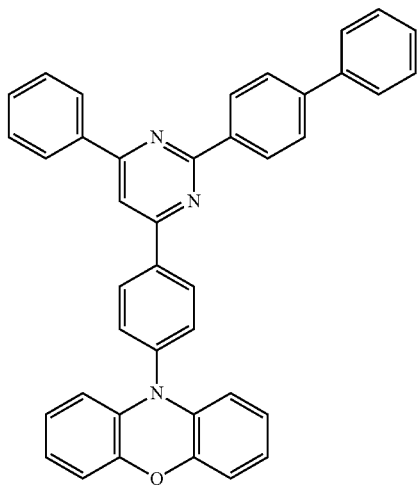
[Formula 99]
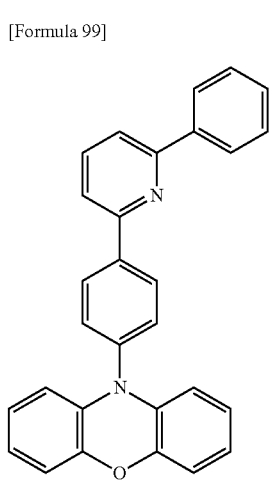

131
-continued
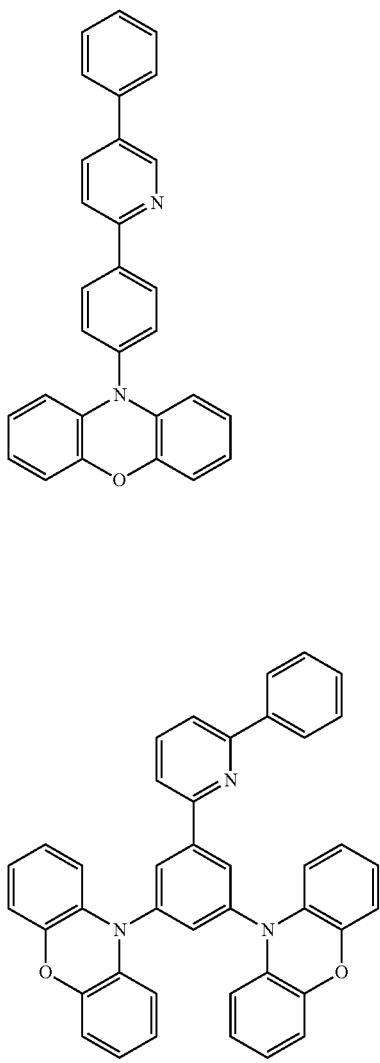
[Formula 100]
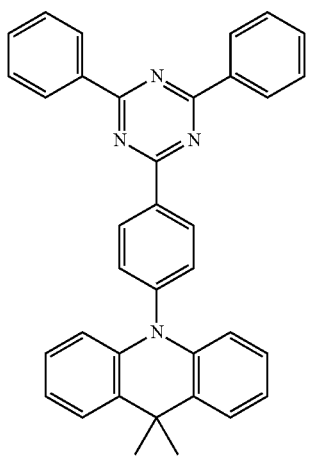
132
-continued
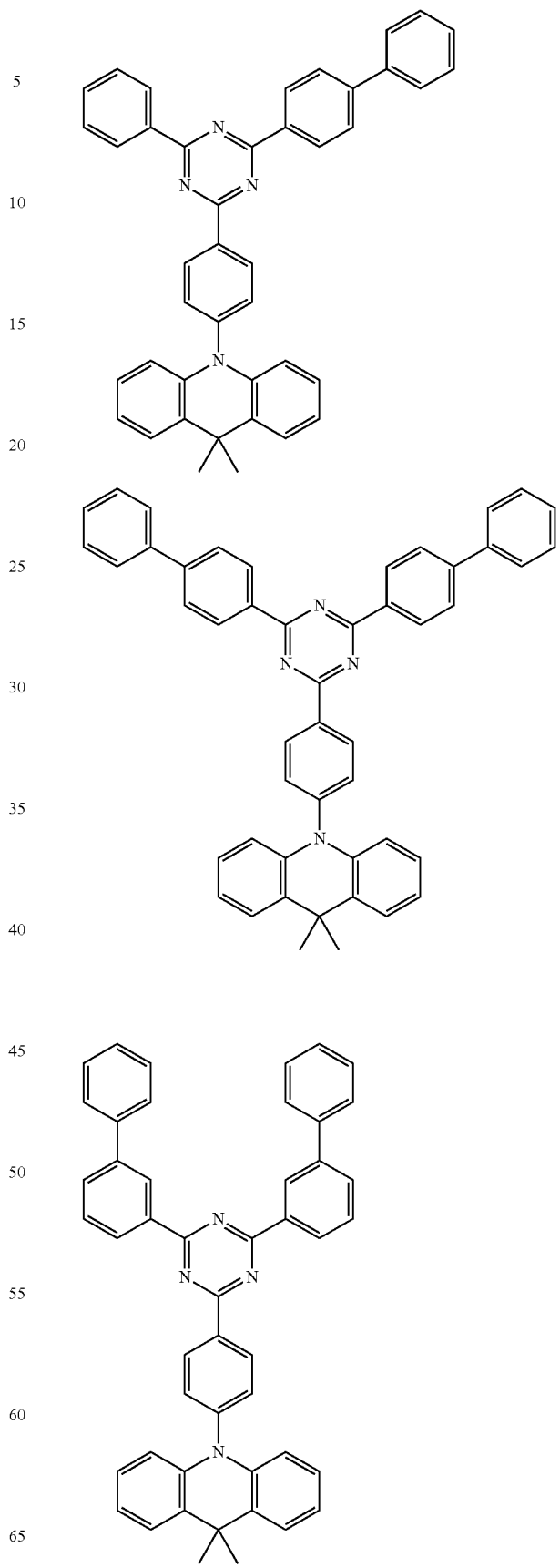

133
-continued
134
-continued
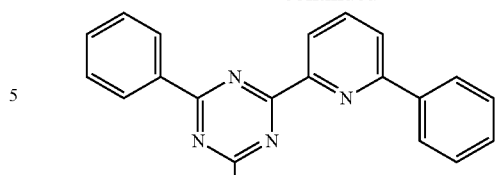
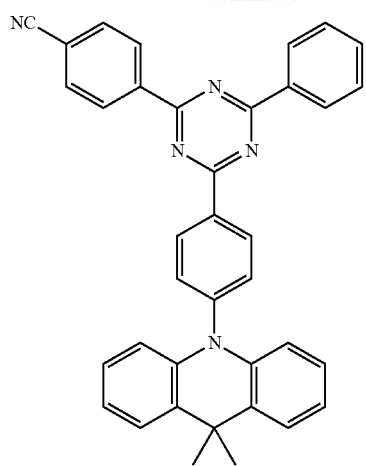
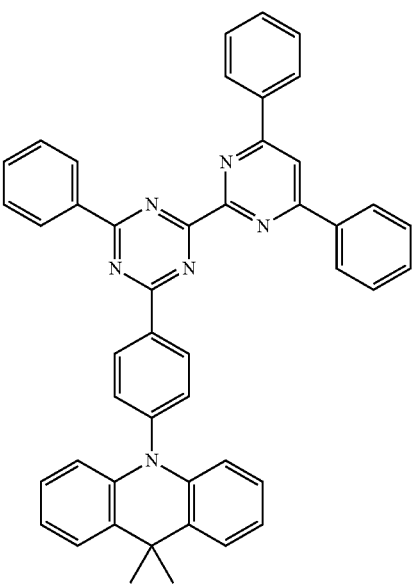
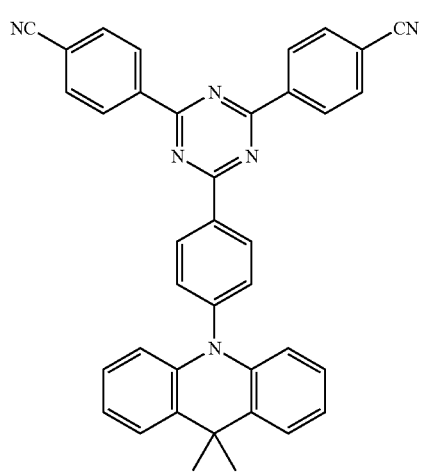
[Formula 101]
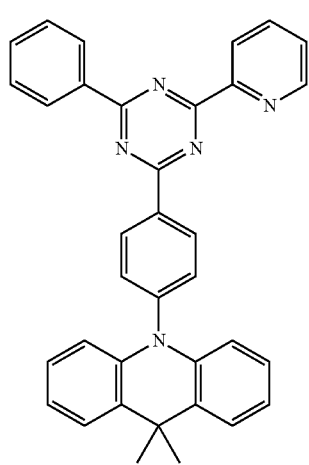

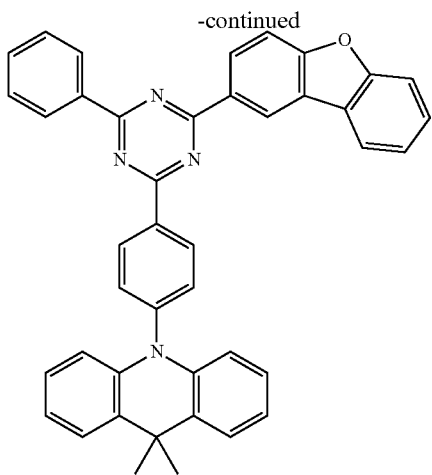
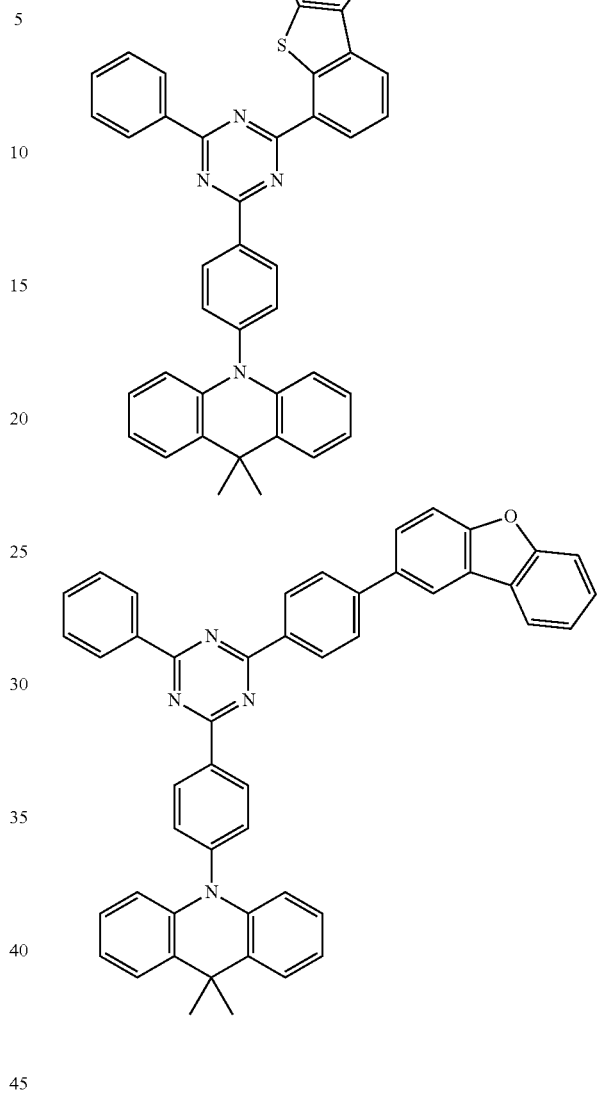
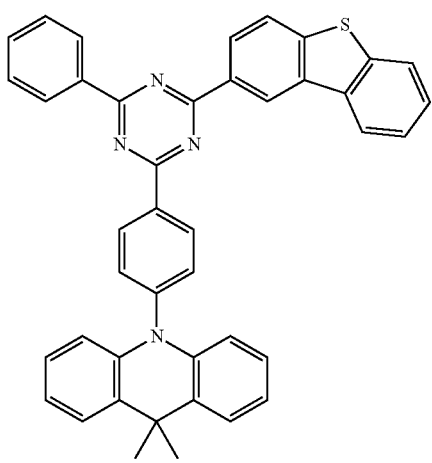

137
-continued
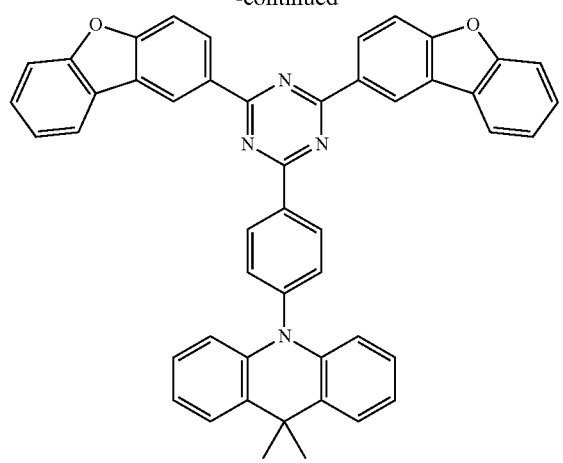
[Formula 102]
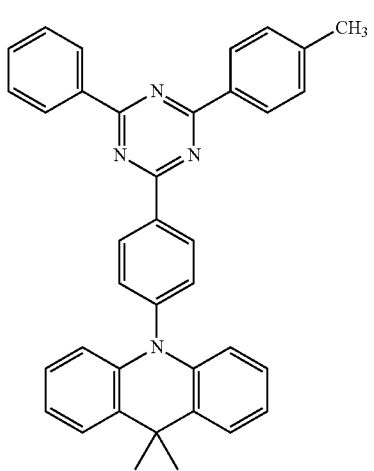
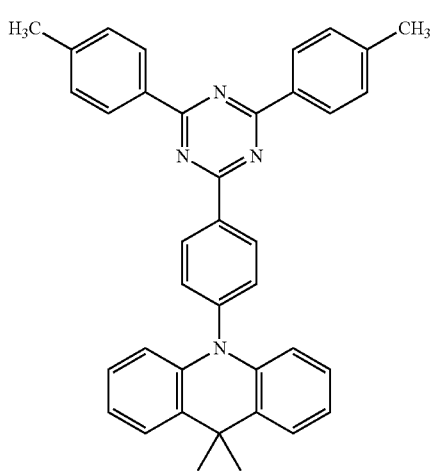
138
-continued
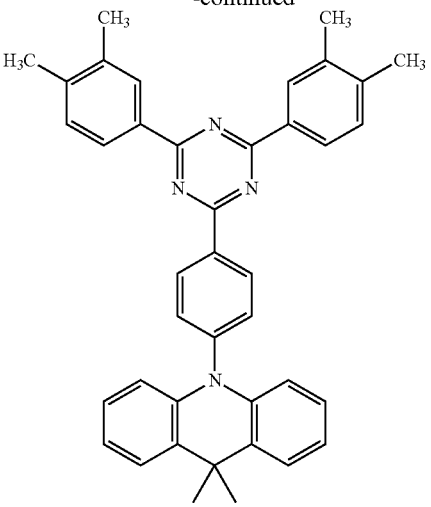
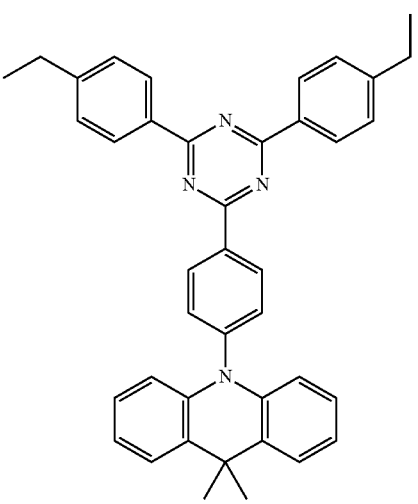
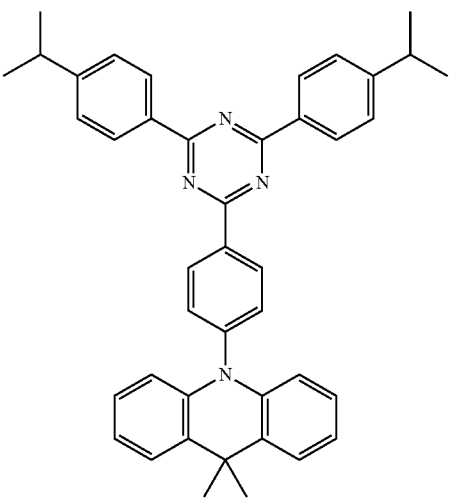

139
-continued
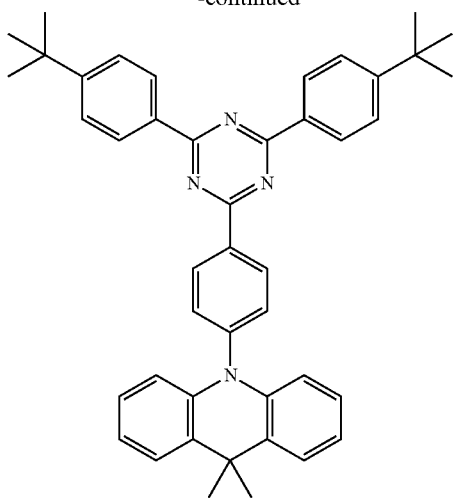
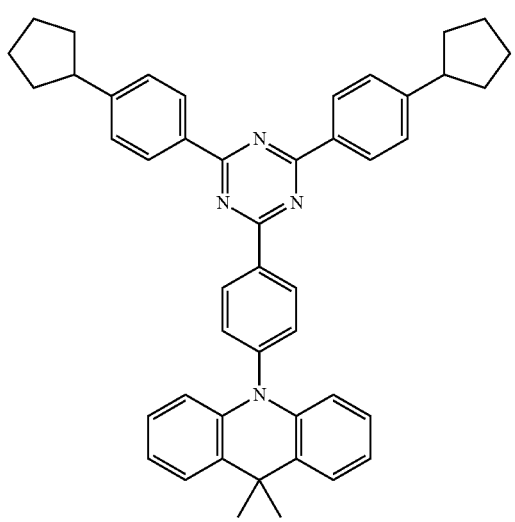
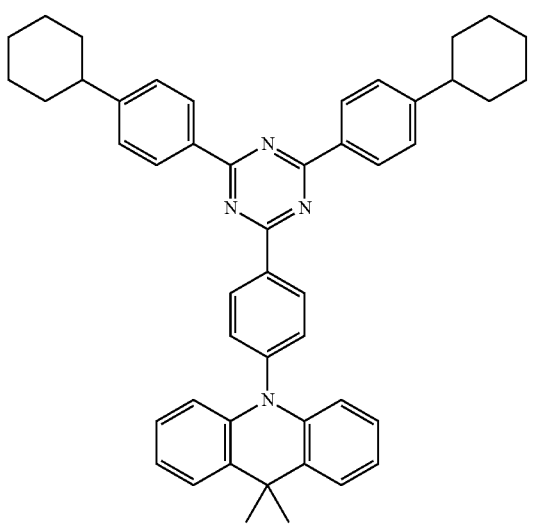
140
-continued
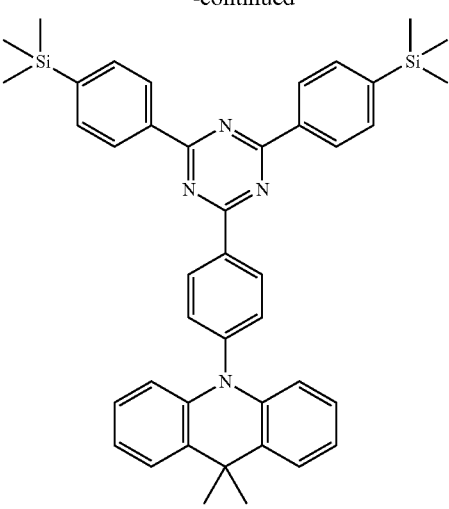
[Formula 103]
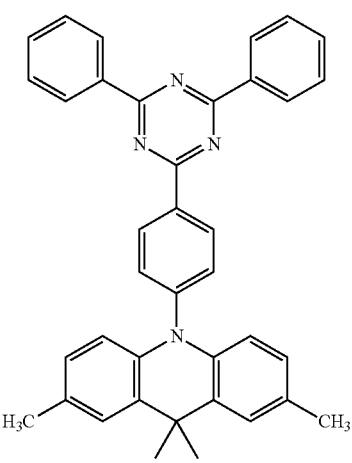
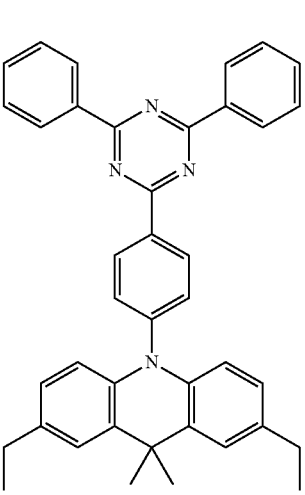

141
-continued
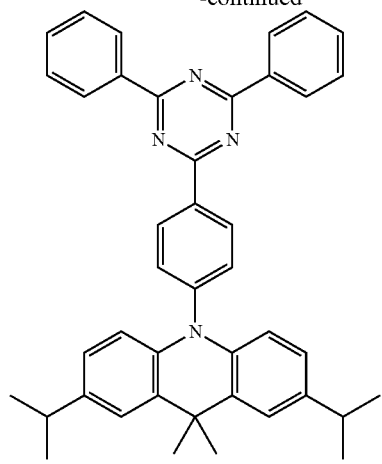
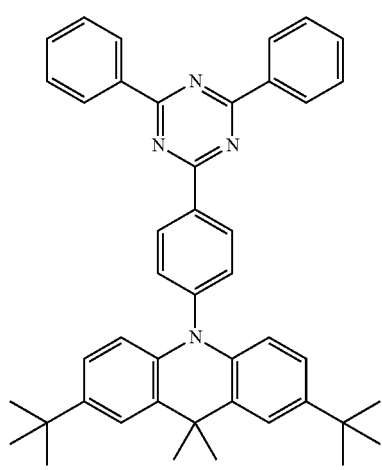
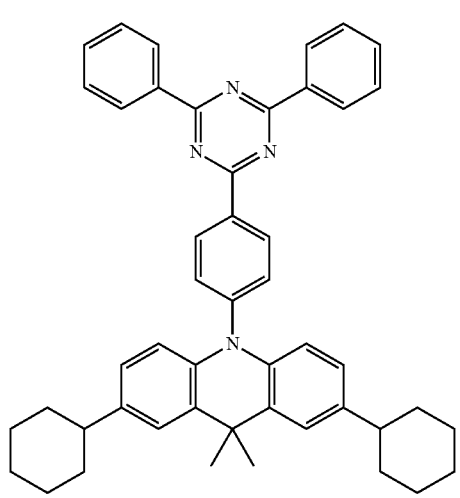
142
-continued
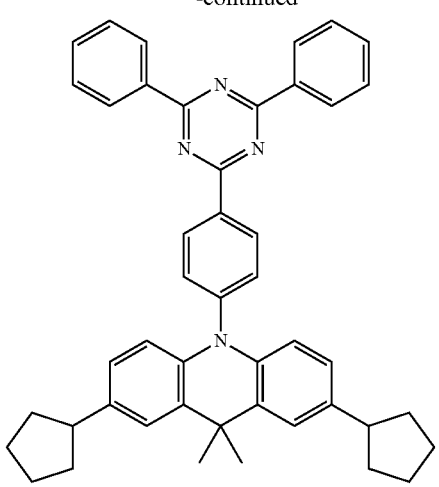
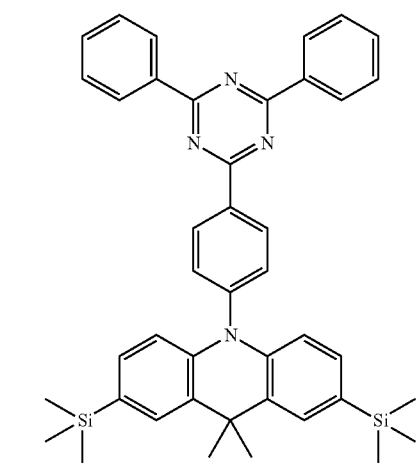
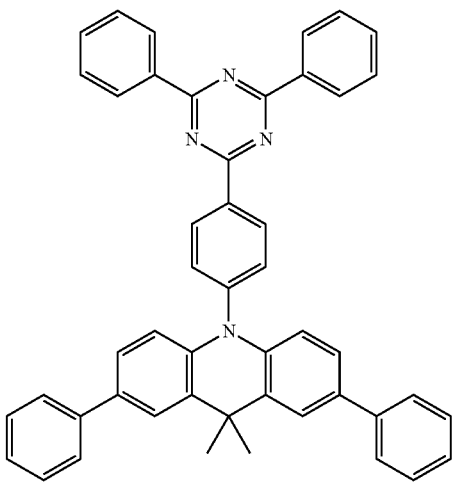

[Formula 104]
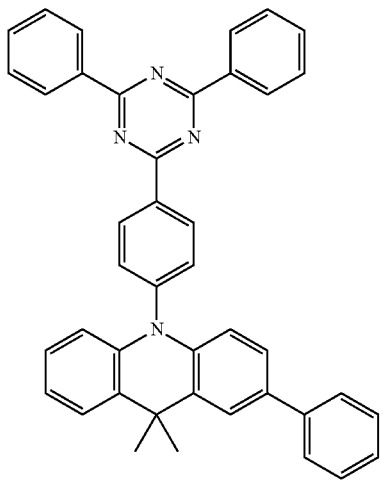
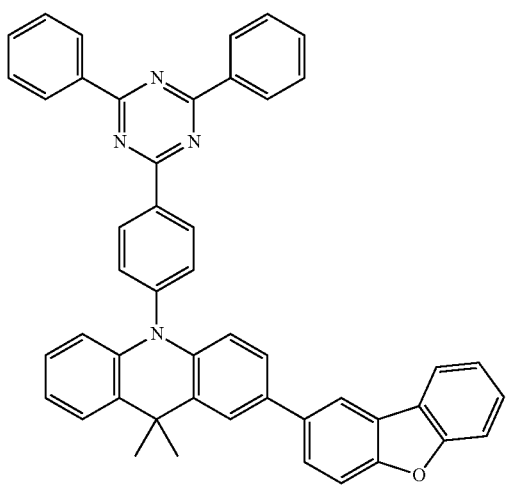
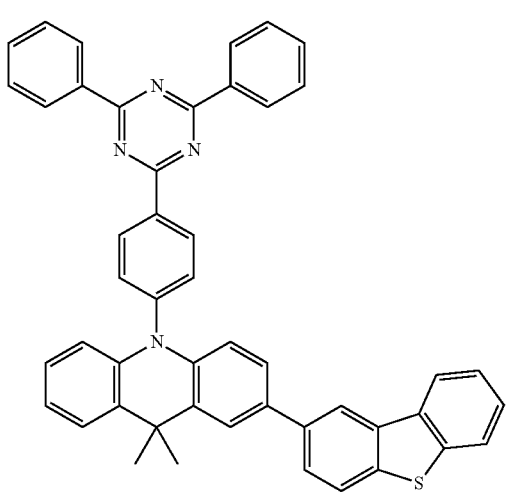
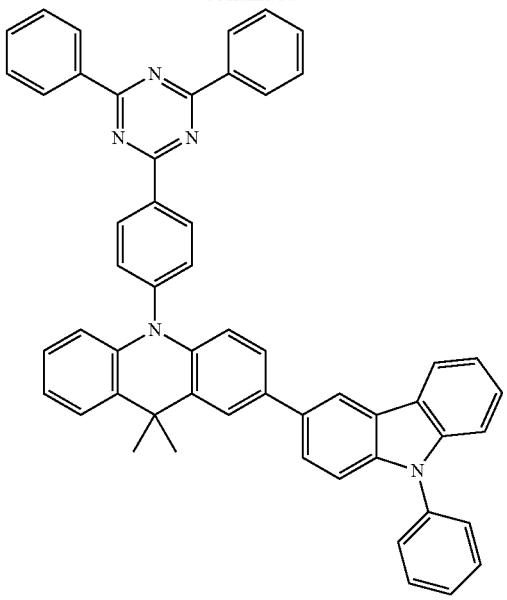
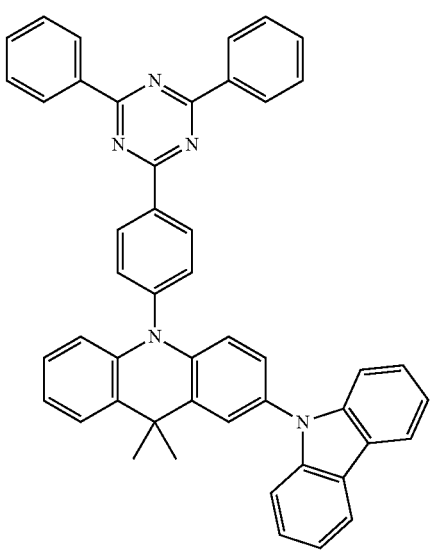

-continued
[Formula 105]
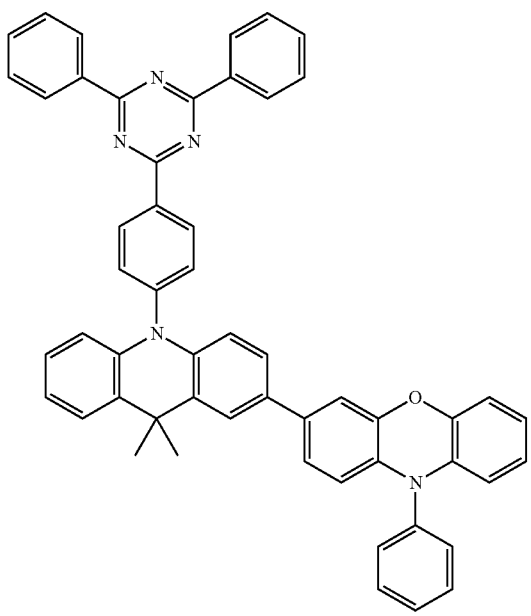
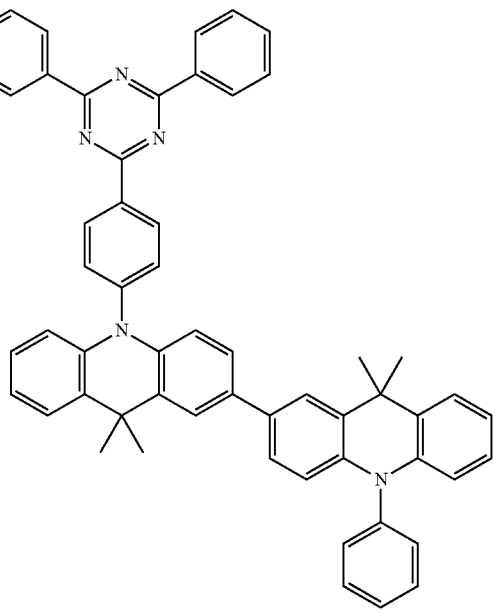
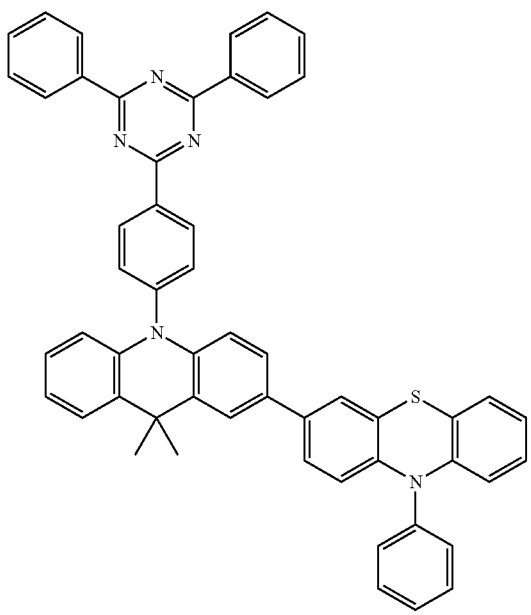
[Formula 106]
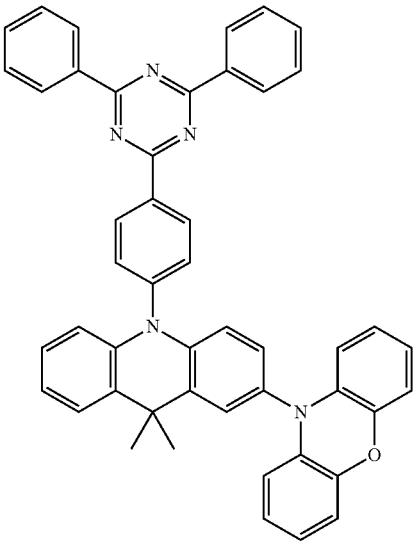

147
-continued
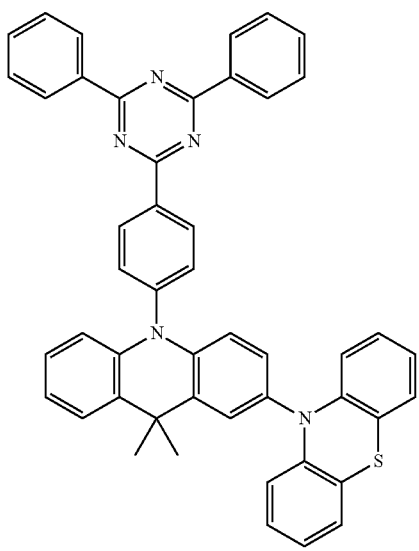
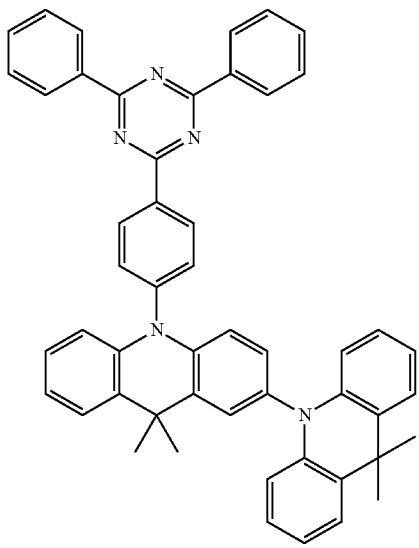
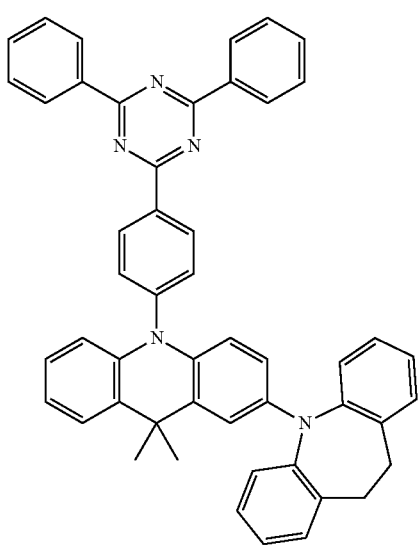
148
-continued
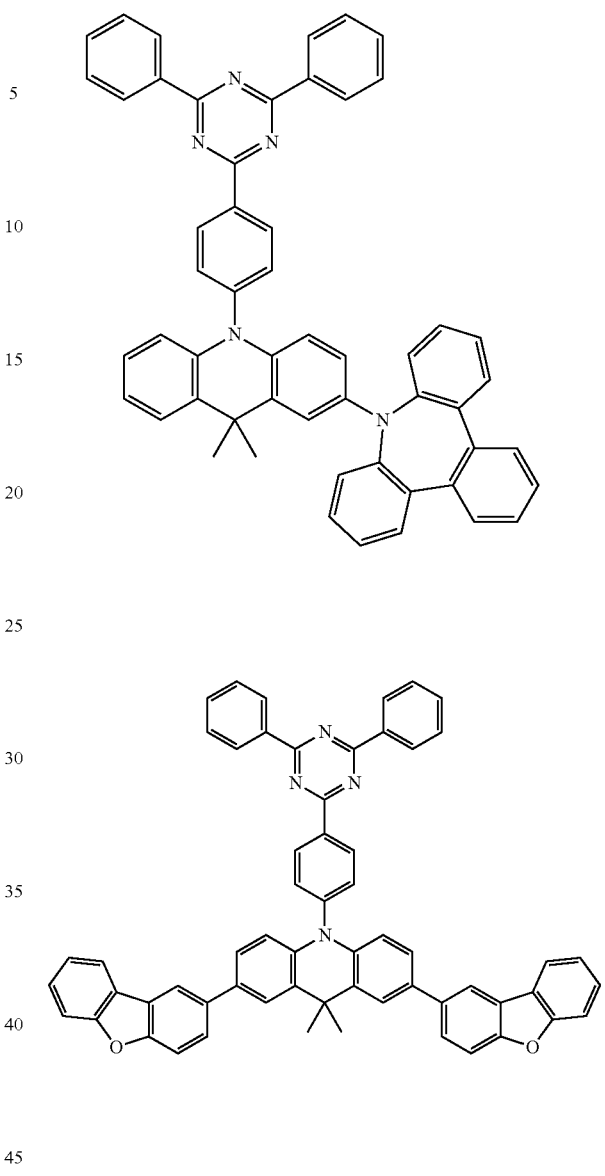
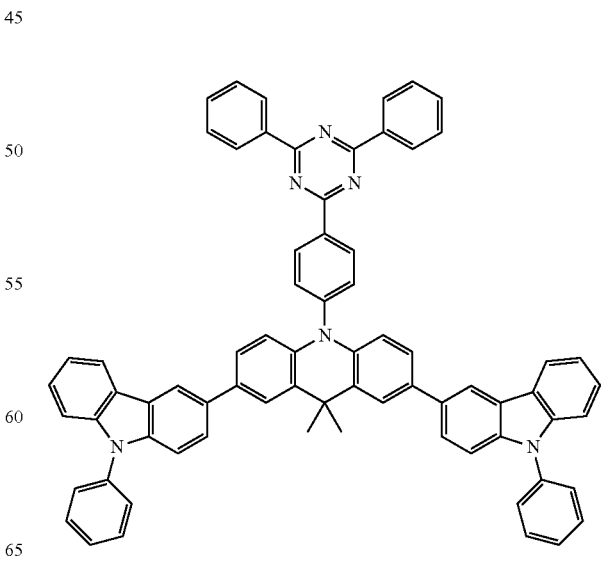

-continued
[Formula 107]
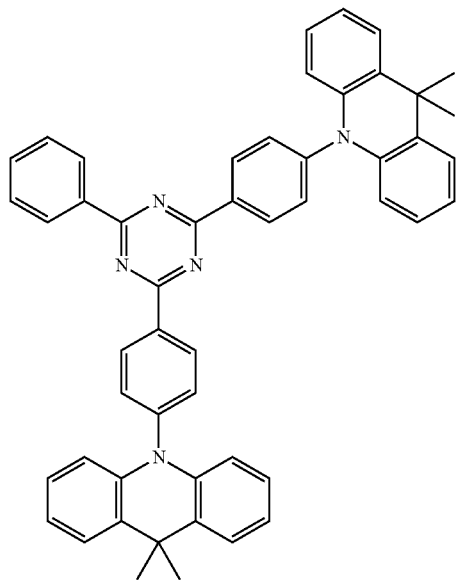
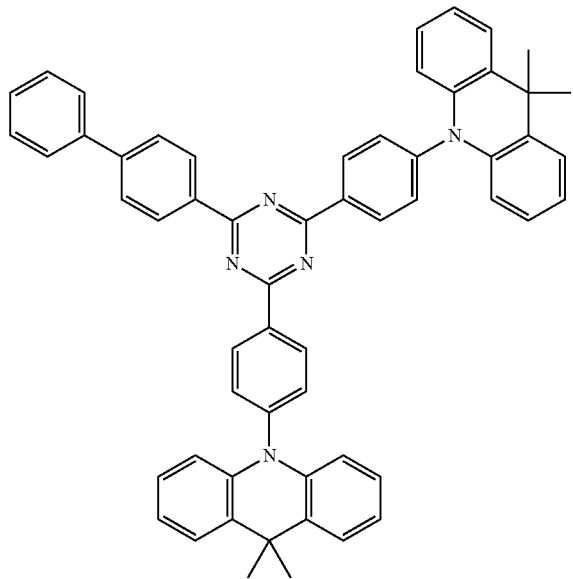
-continued
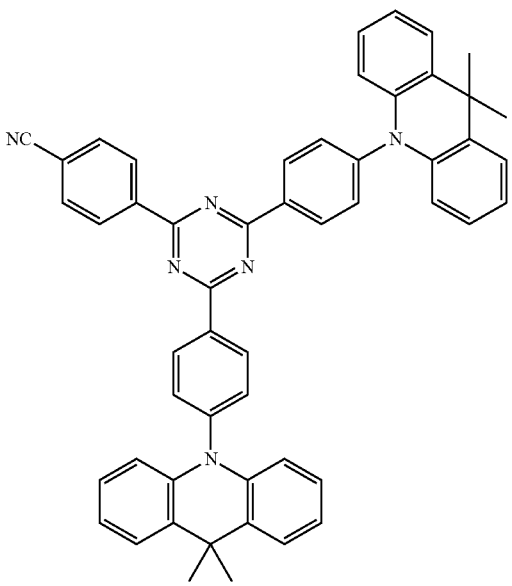
[Formula 108]
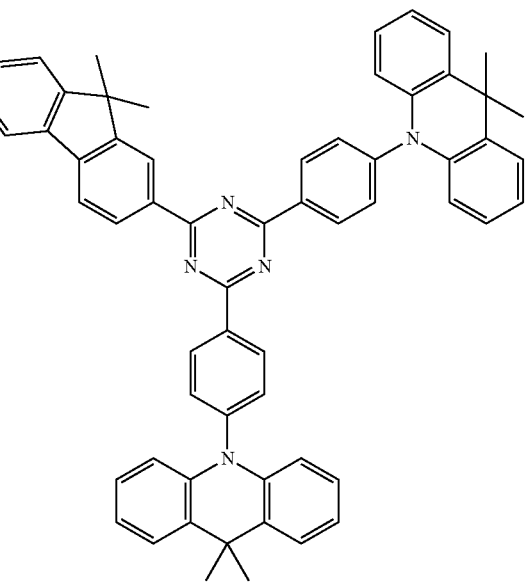

151
-continued
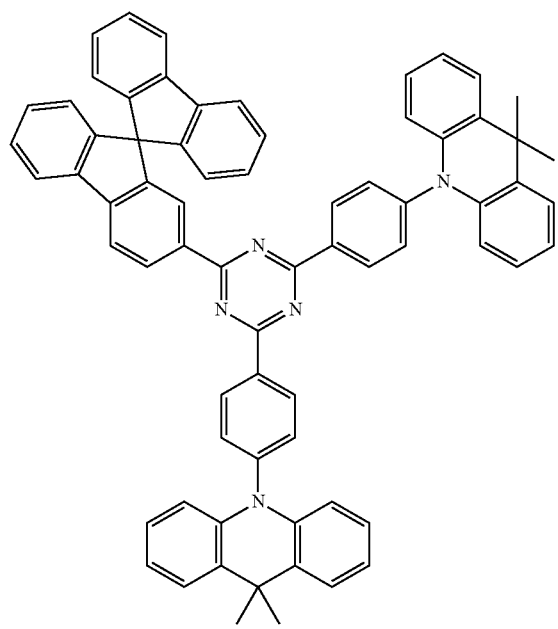
[Formula 109]
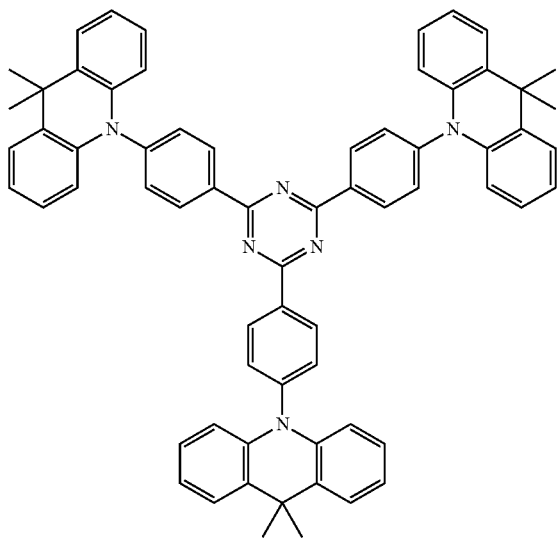
152
-continued
[Formula 110]
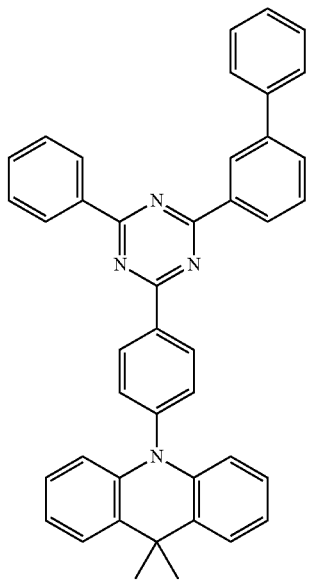
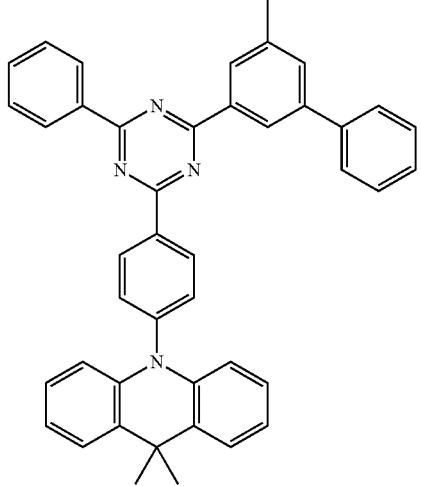
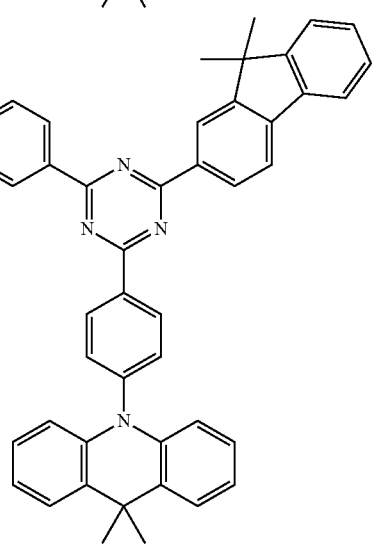

153
-continued
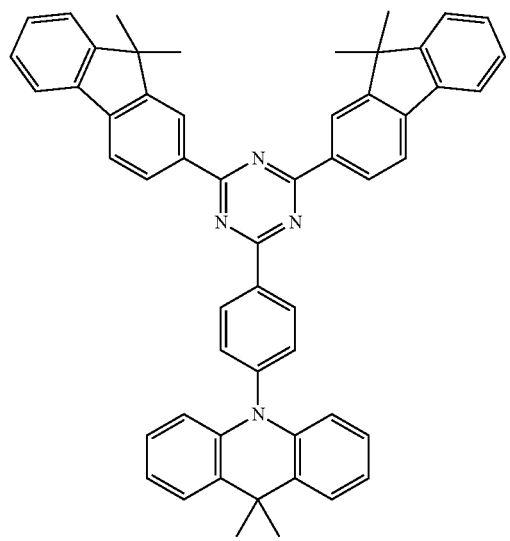
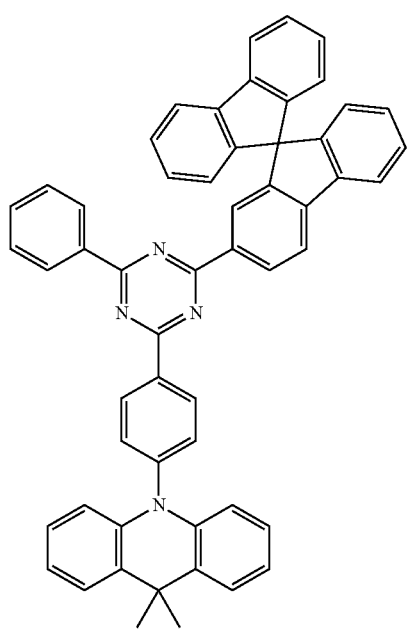
[Formula 111]
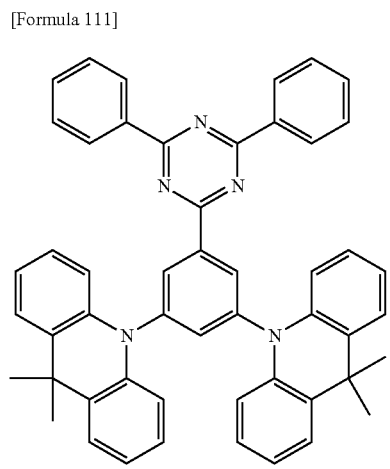
154
-continued
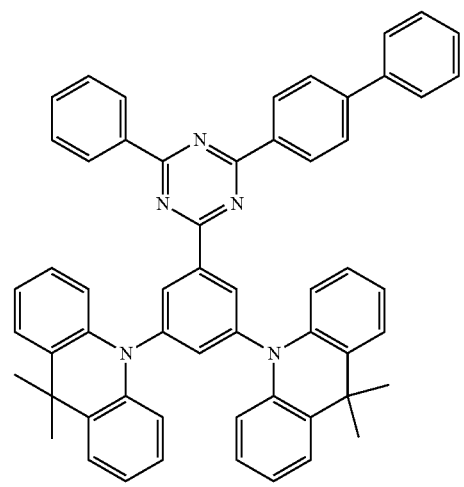
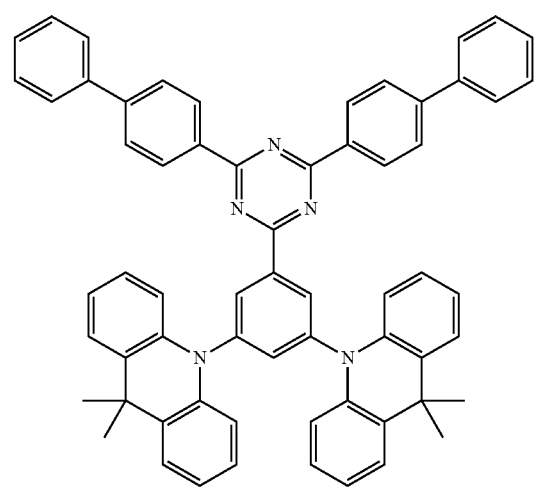
[Formula 112]
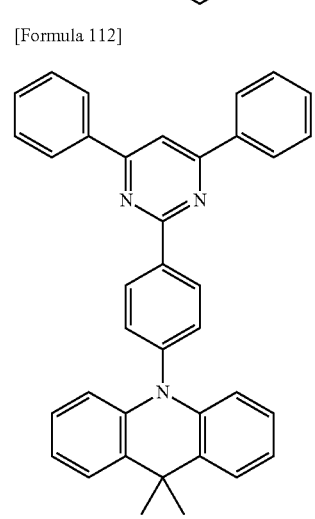

155
-continued
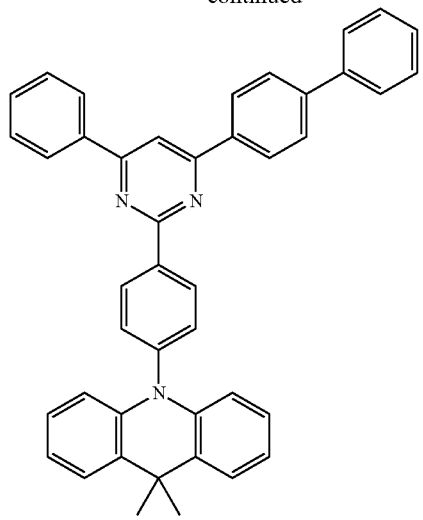
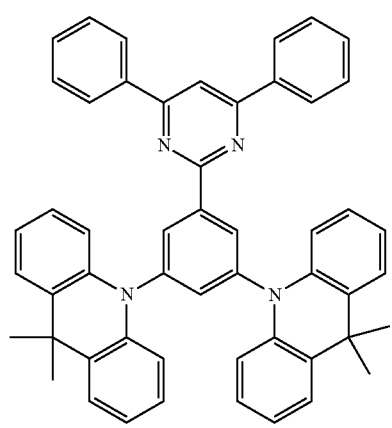
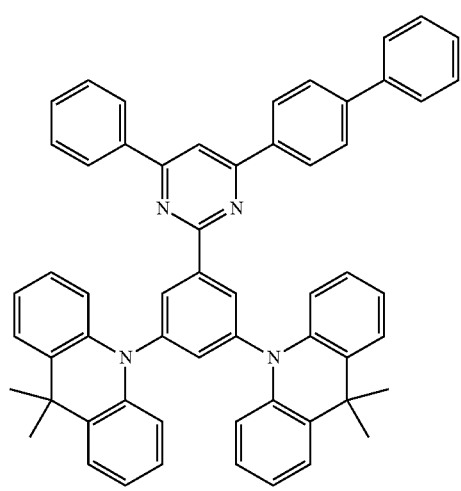
156
-continued
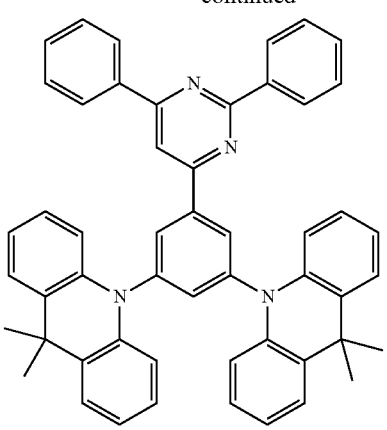
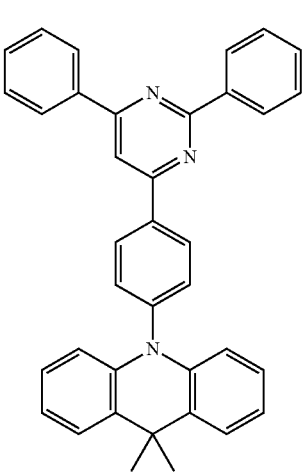

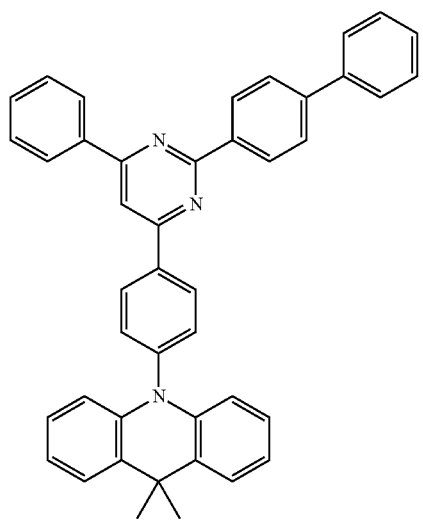
[Formula 113]
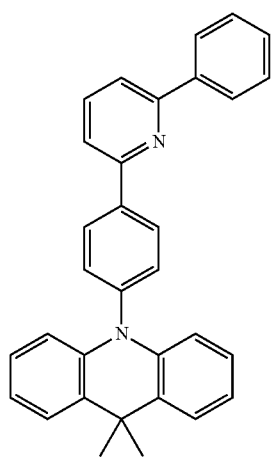
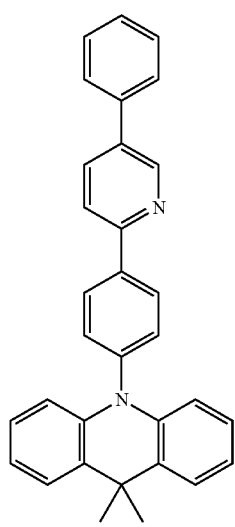
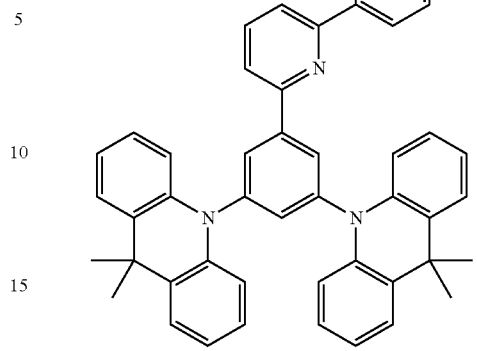
[Formula 114]
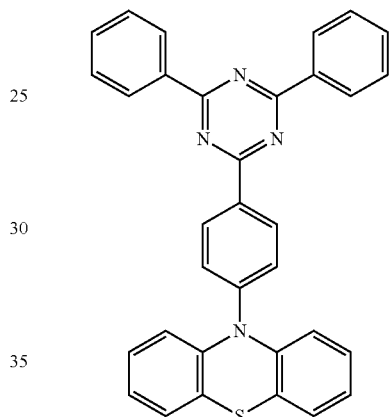
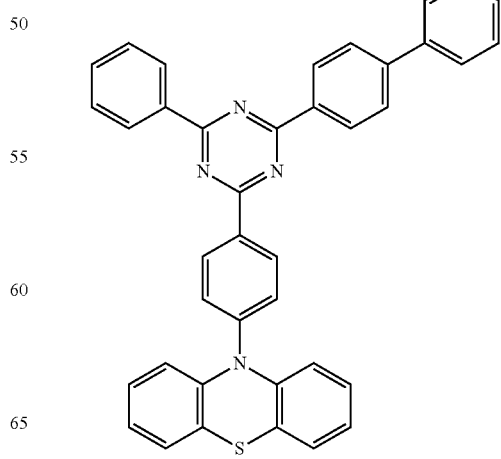

159
-continued
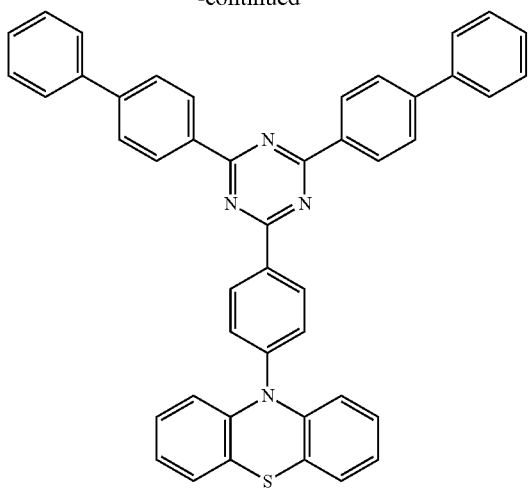
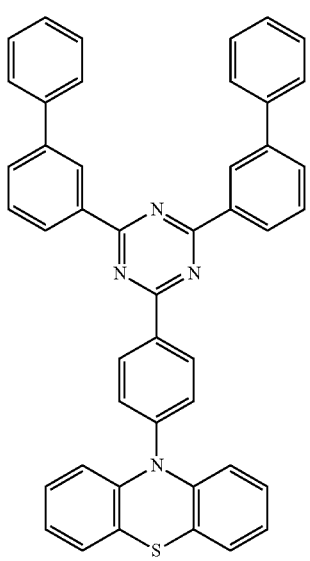
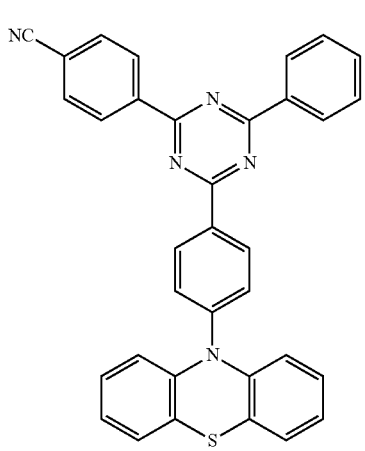
160
-continued
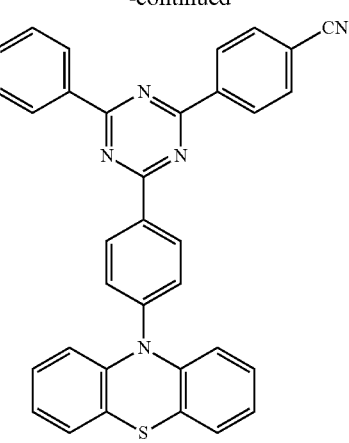
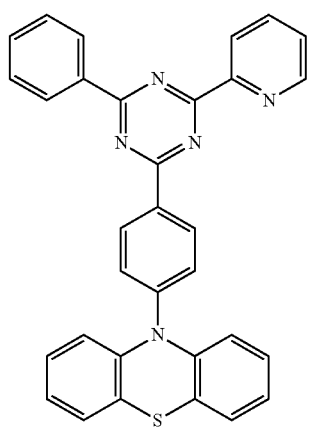
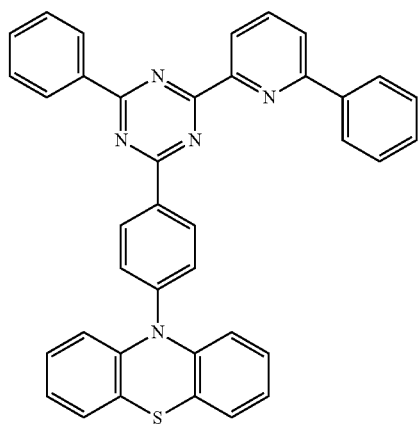

-continued
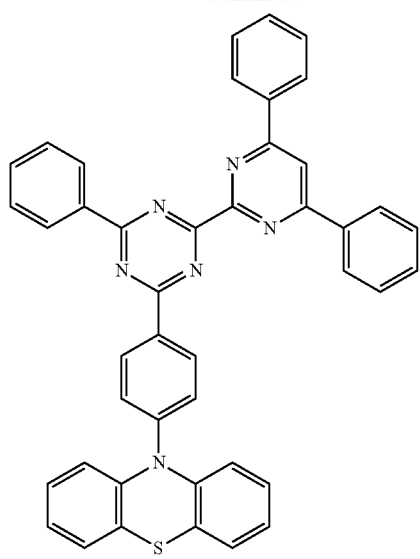
[Formula 115]
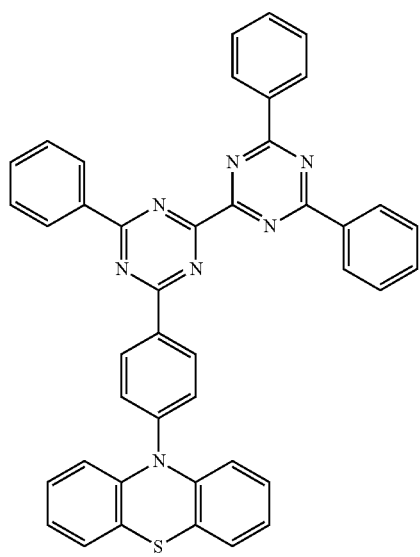
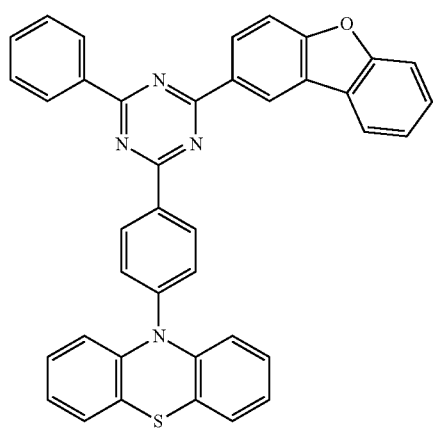
-continued
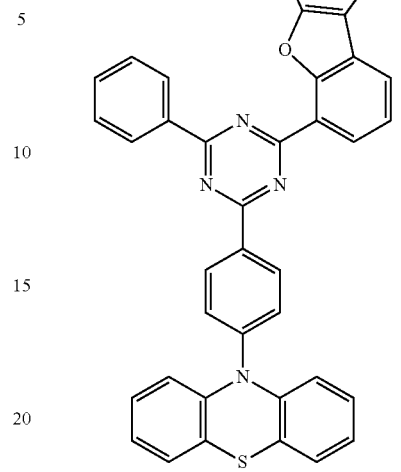
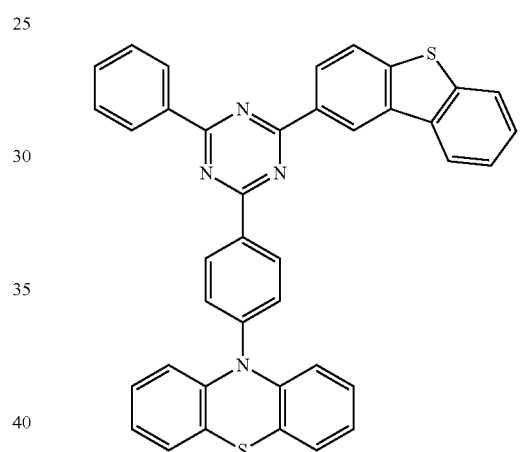
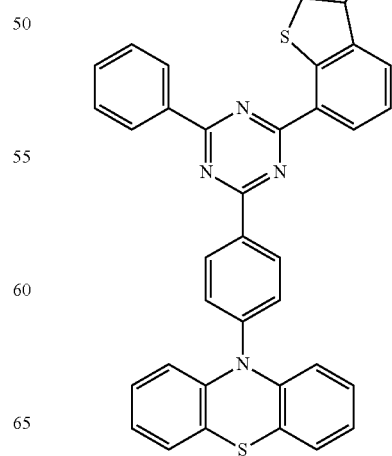

163
-continued
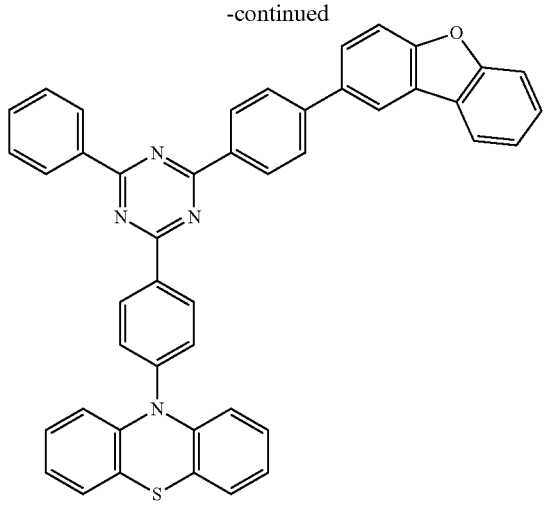
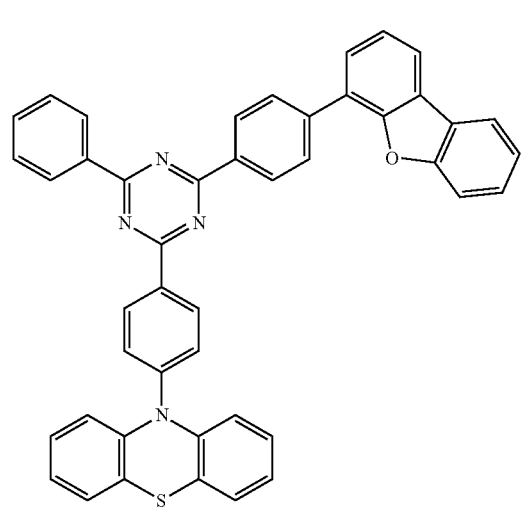
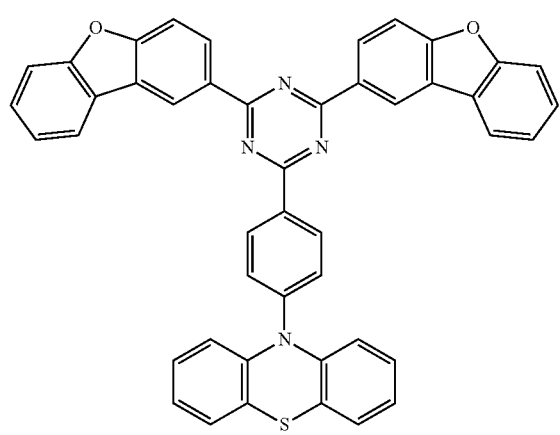
164
-continued
[Formula 116]
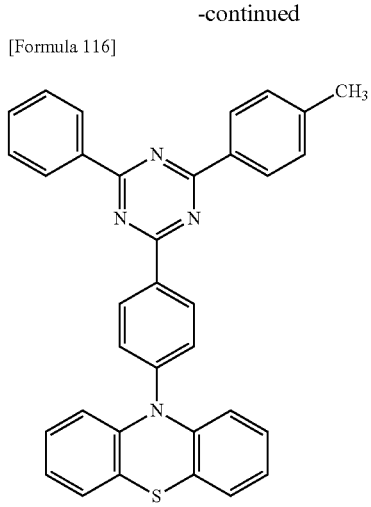
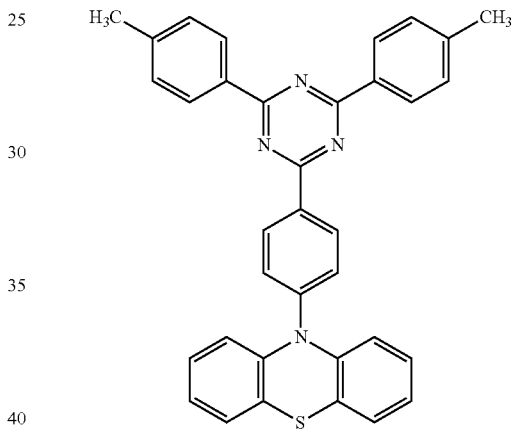
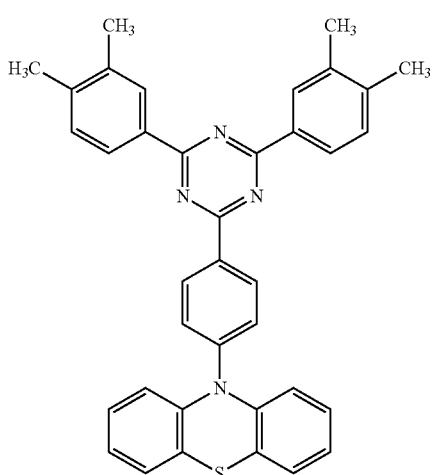

-continued
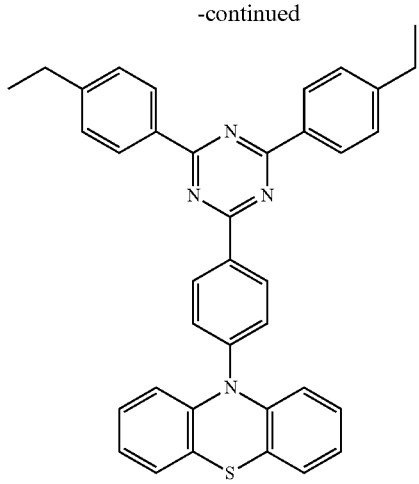
-continued
[Formula 117]
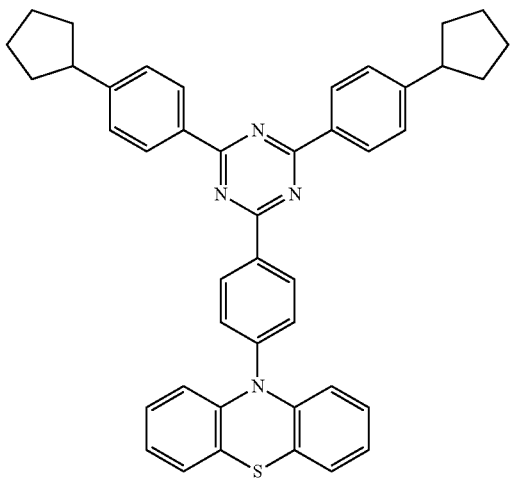
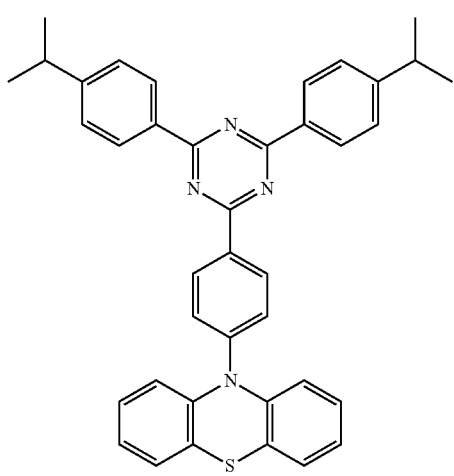
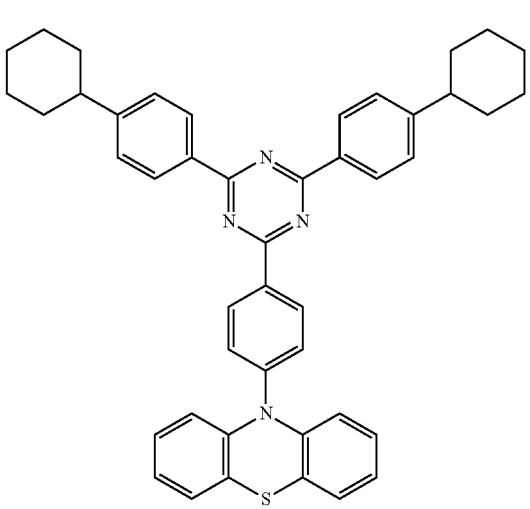
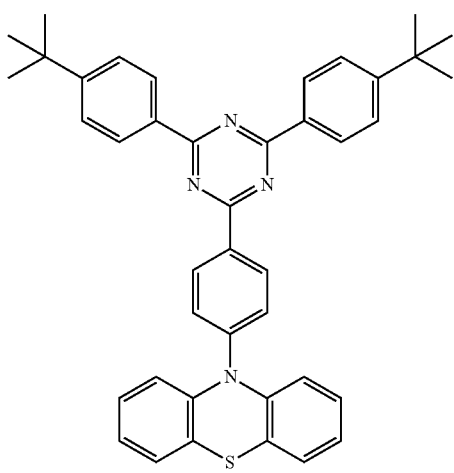
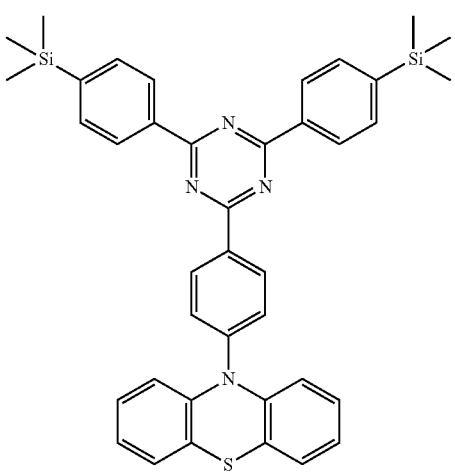

[Formula 118]
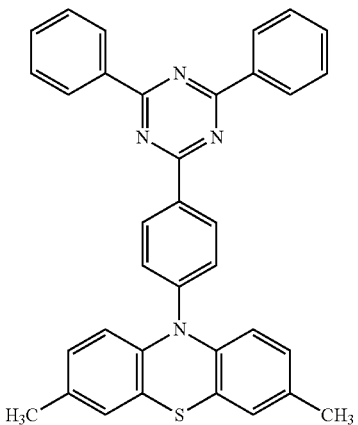
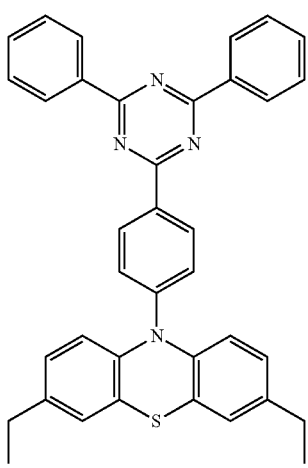
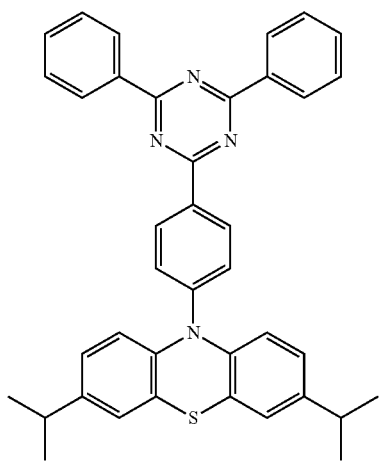
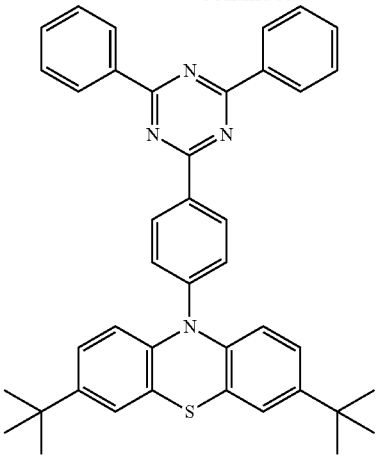
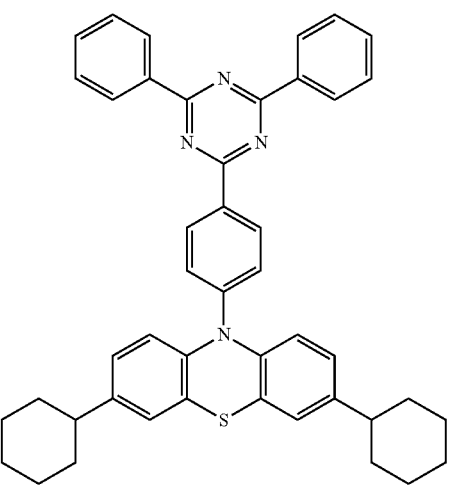
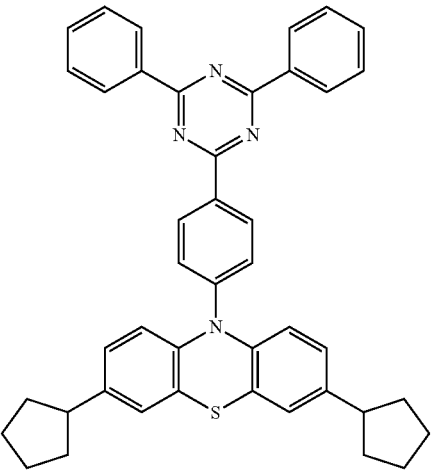

169
-continued
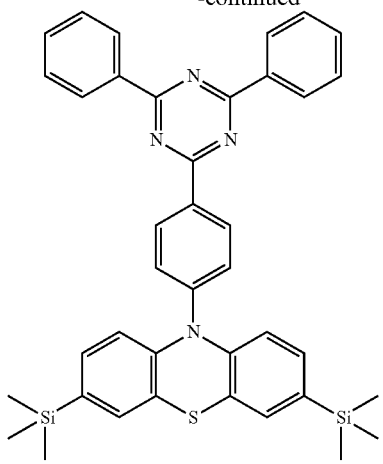
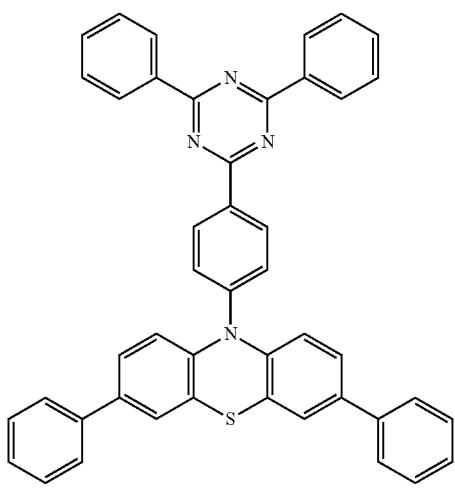
[Formula 119]
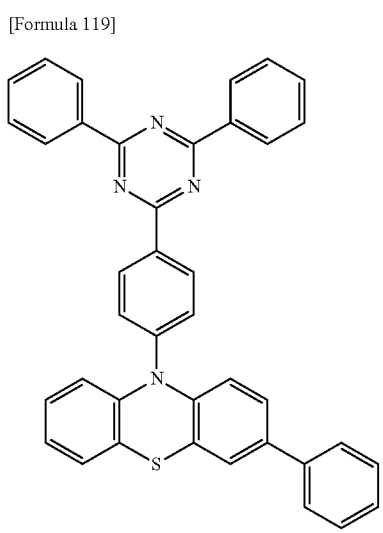
170
-continued
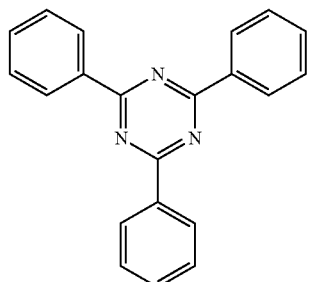
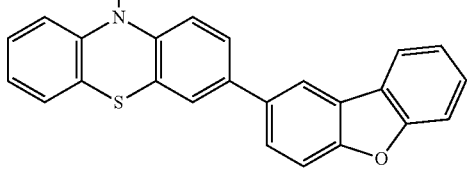
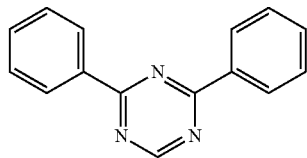
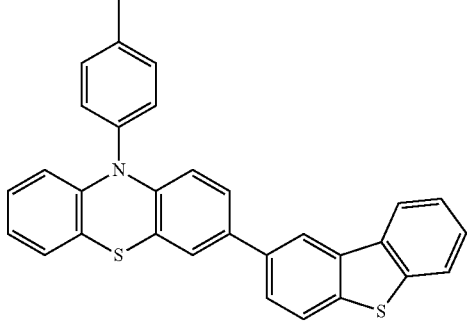
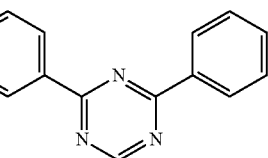
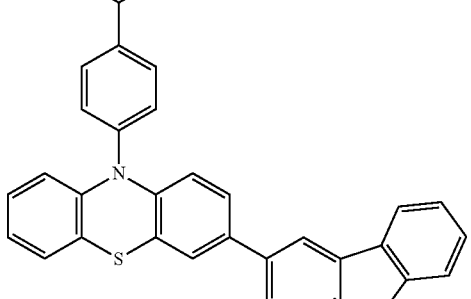
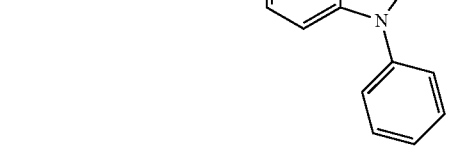

171
-continued
[Formula 120]
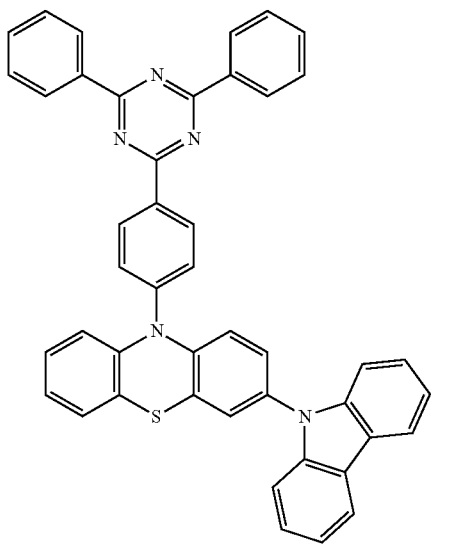
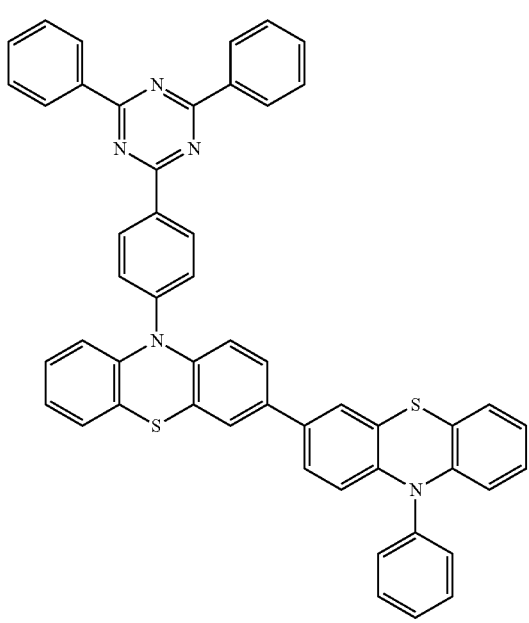
172
-continued
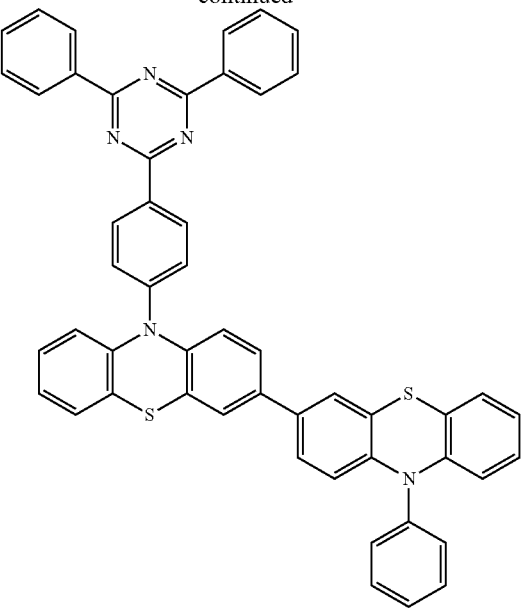
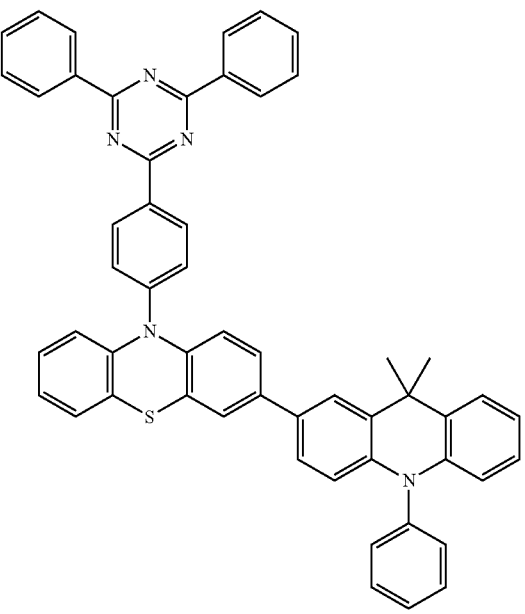

[Formula 121]
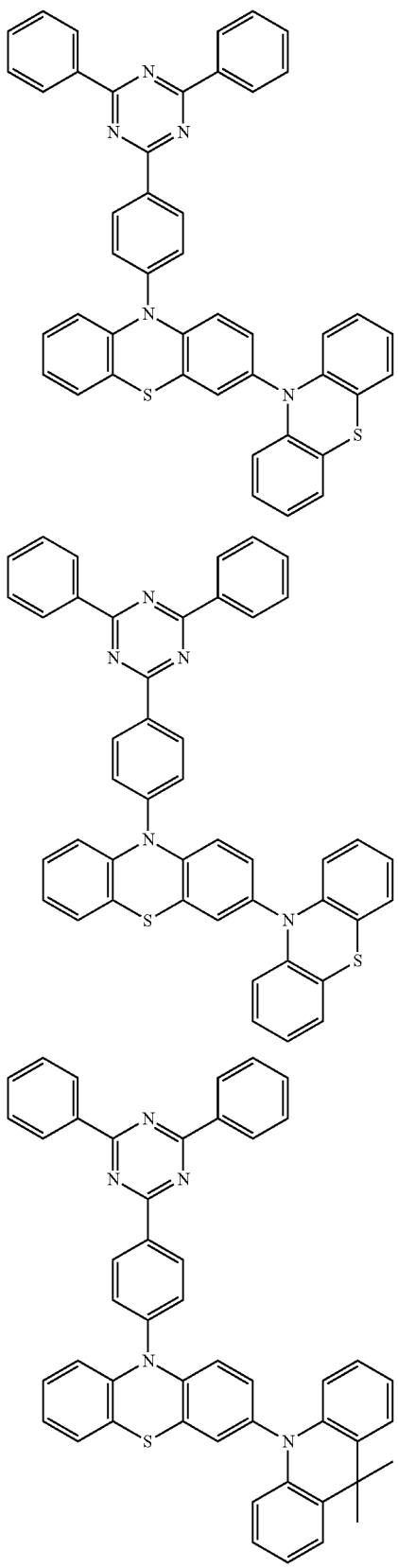
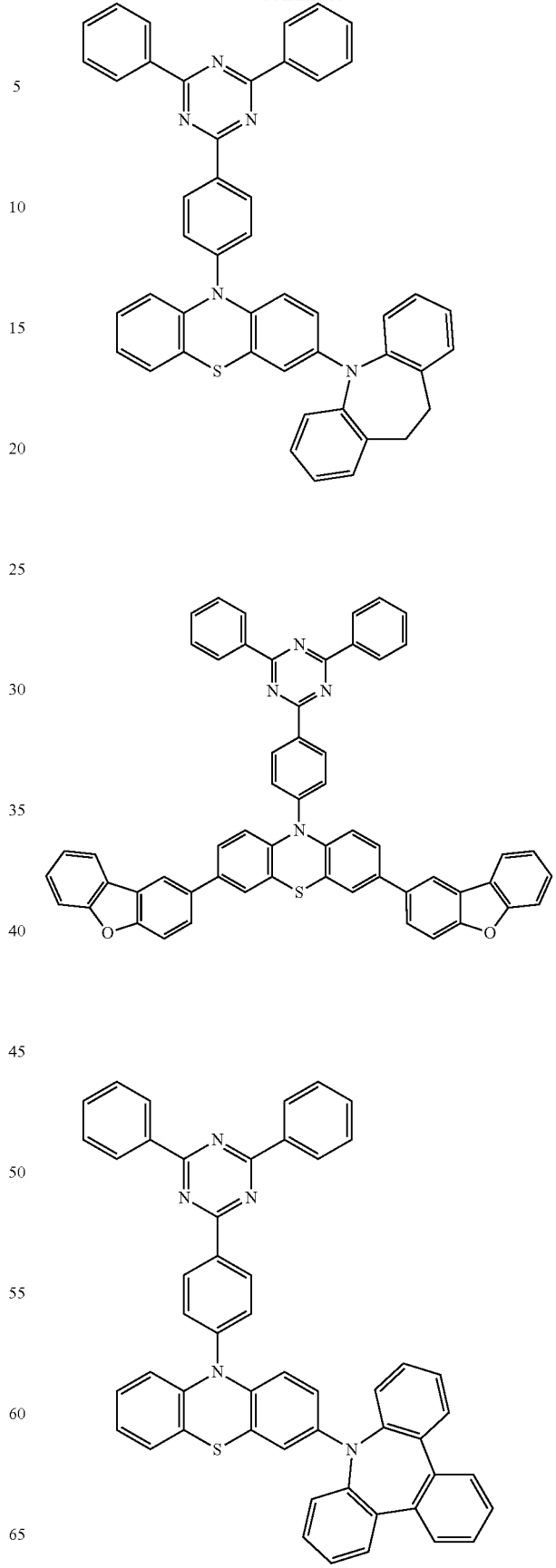

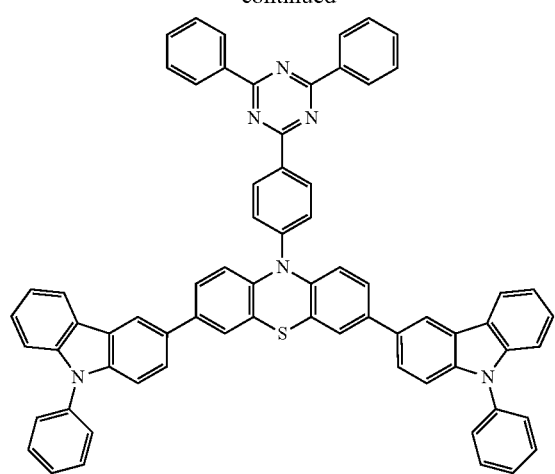
[Formula 122]
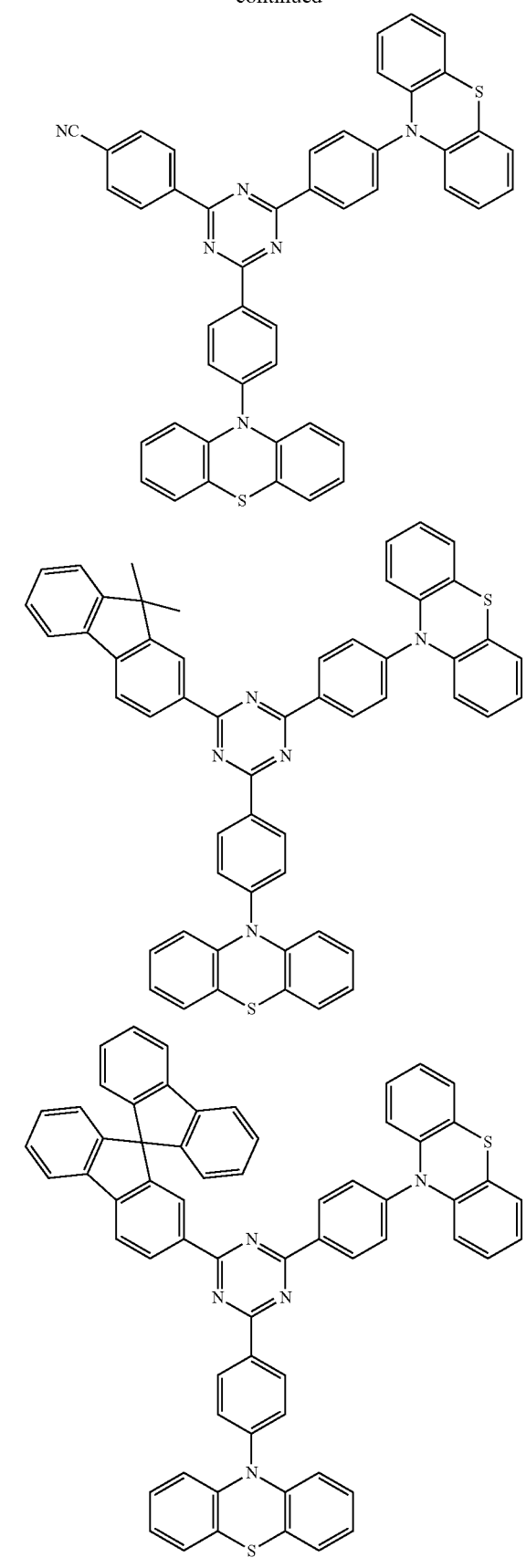

[Formula 123]
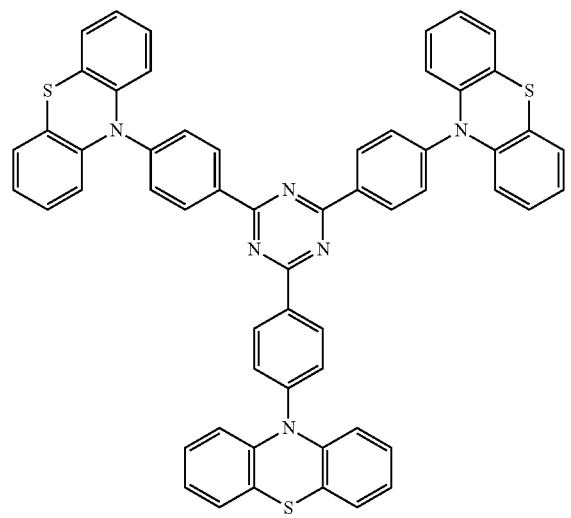
[Formula 124]
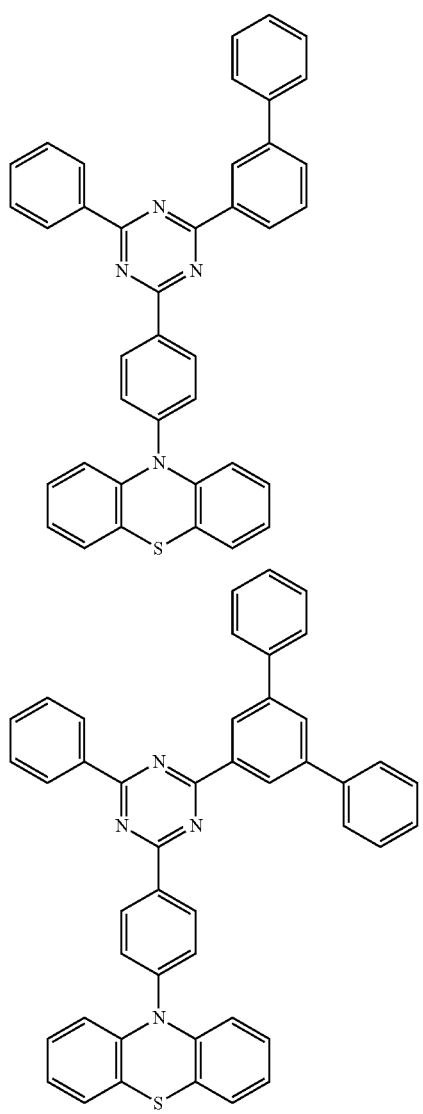
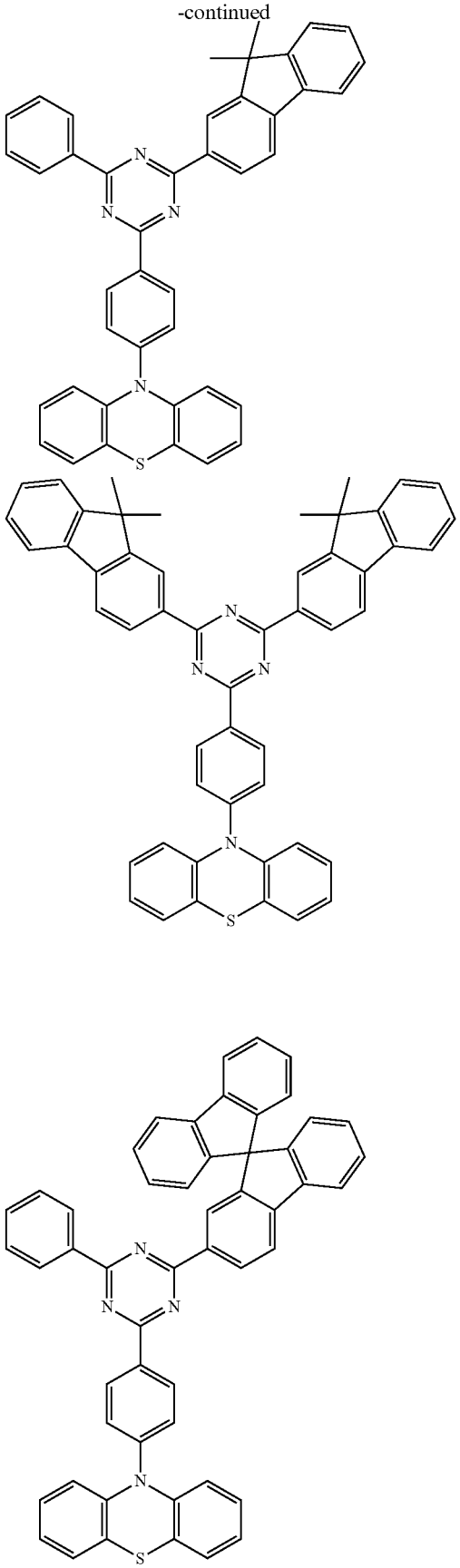

[Formula 125]
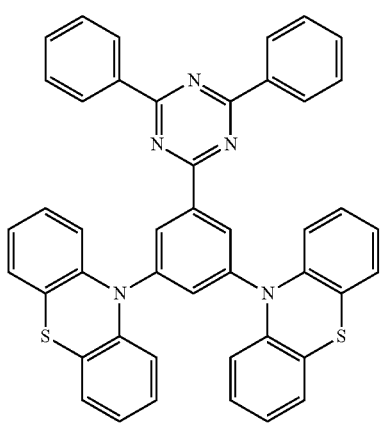
[Formula 126]
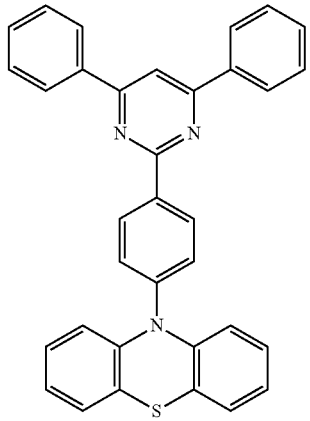
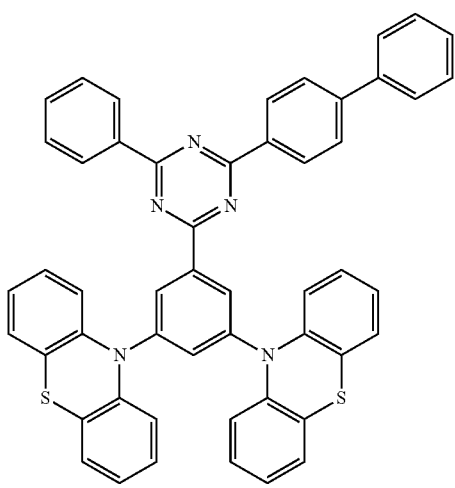
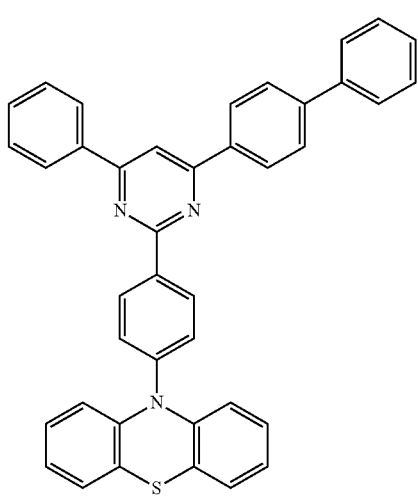
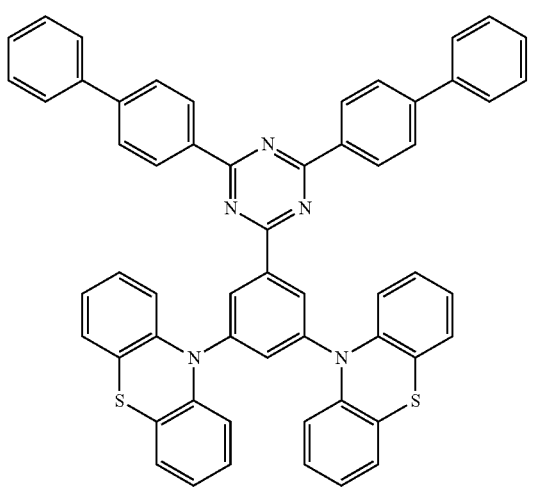
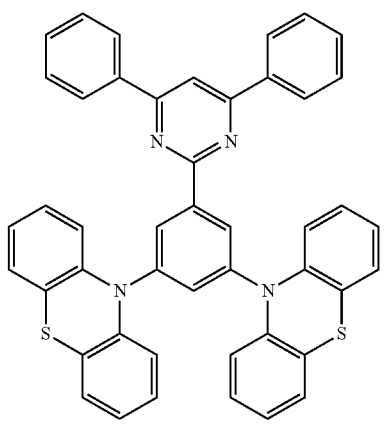

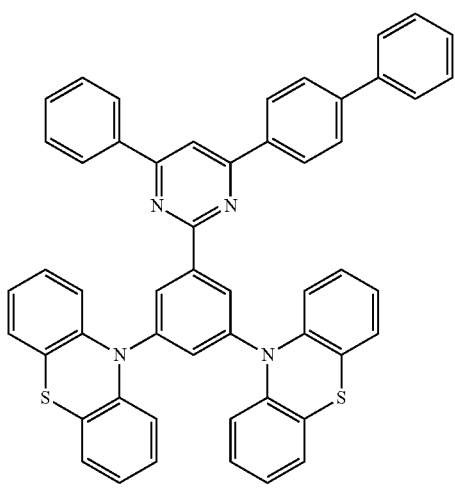
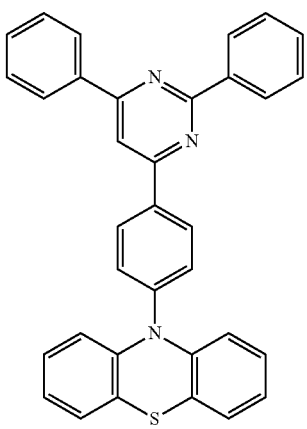
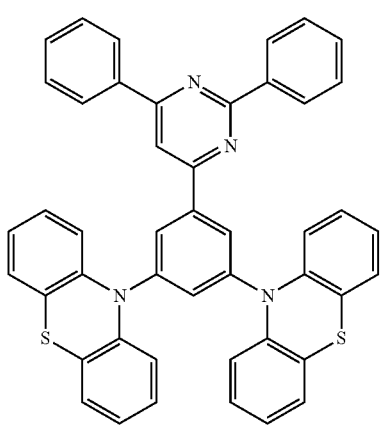
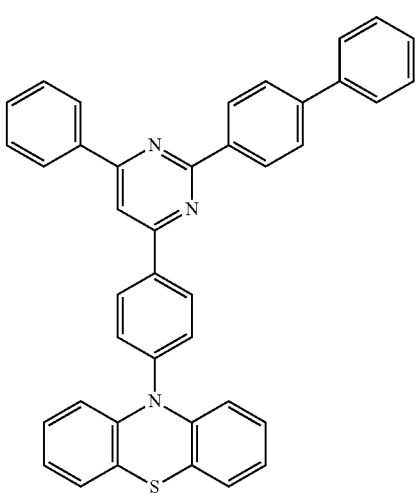
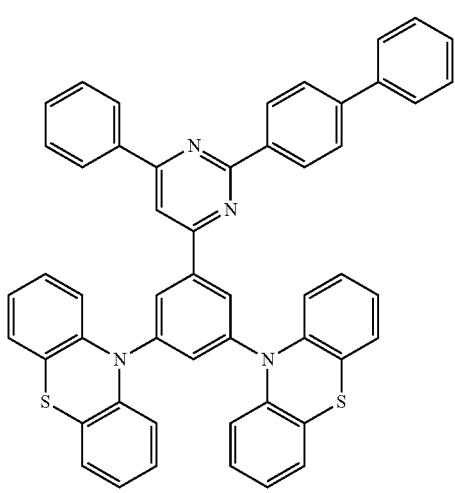
[Formula 127]
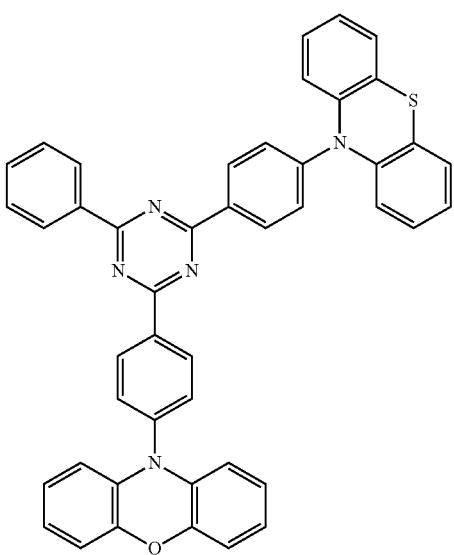

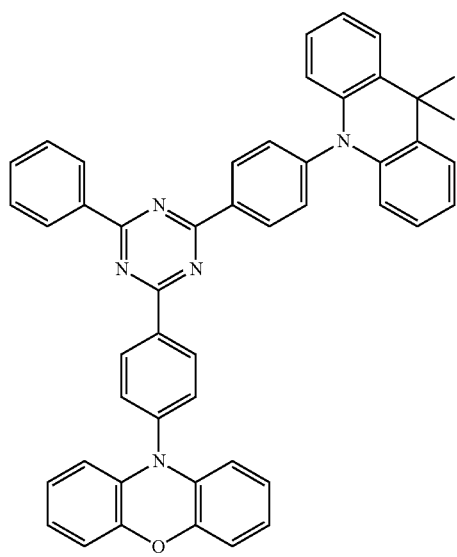
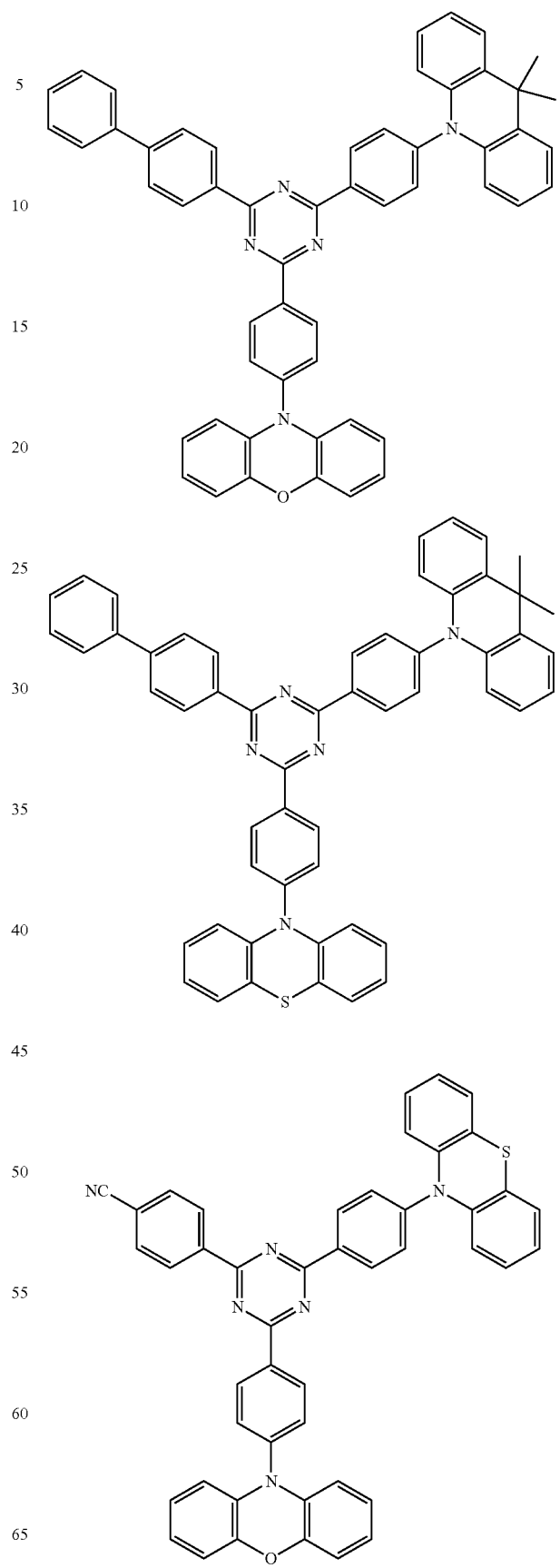

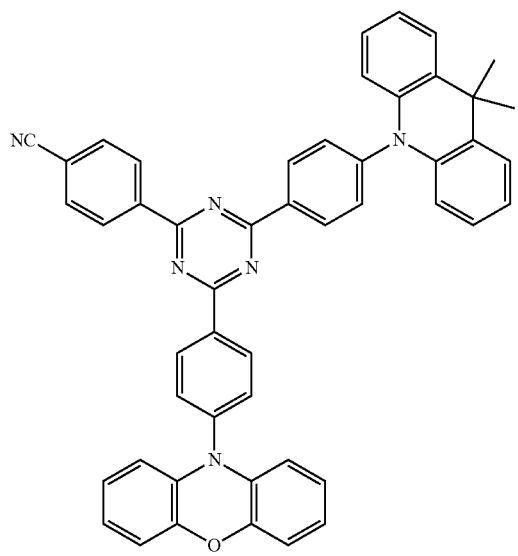
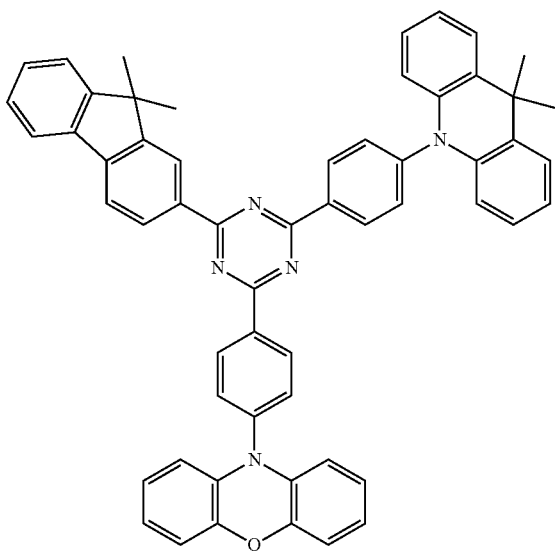
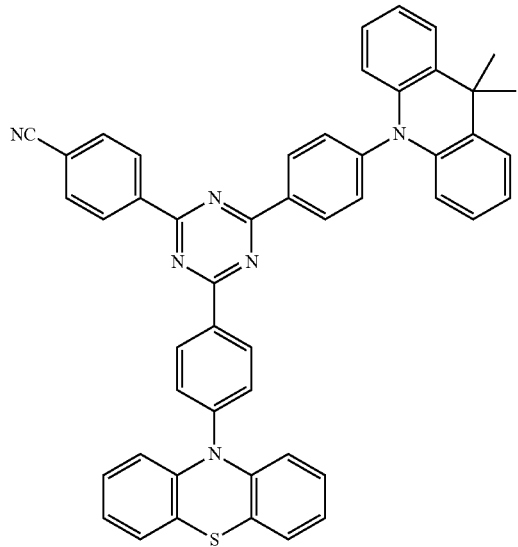
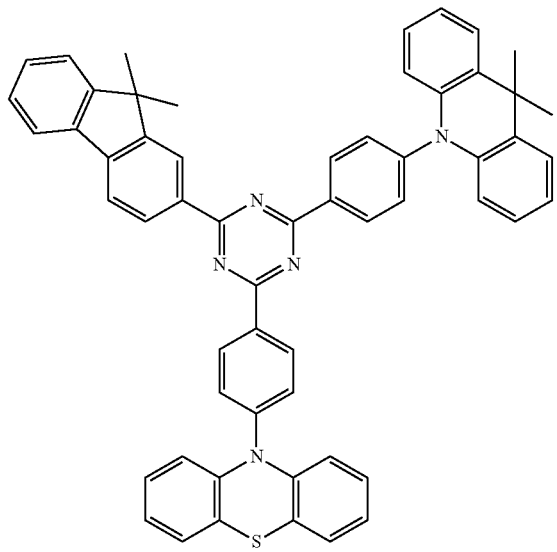
[Formula 128]
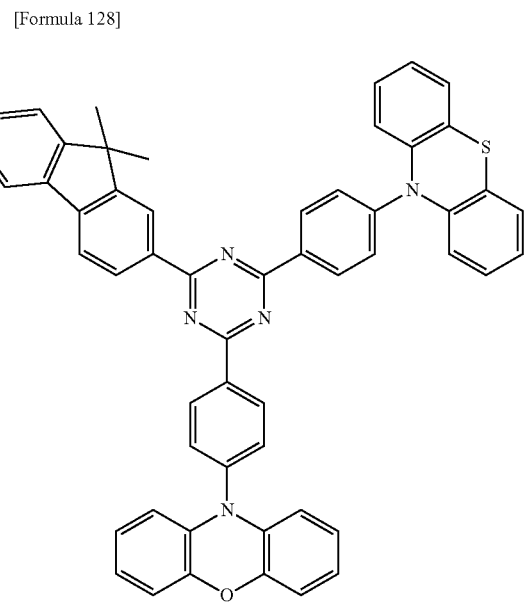
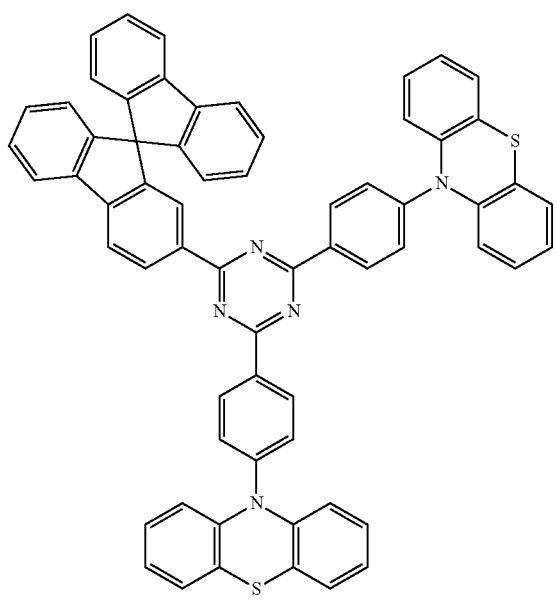

187
-continued
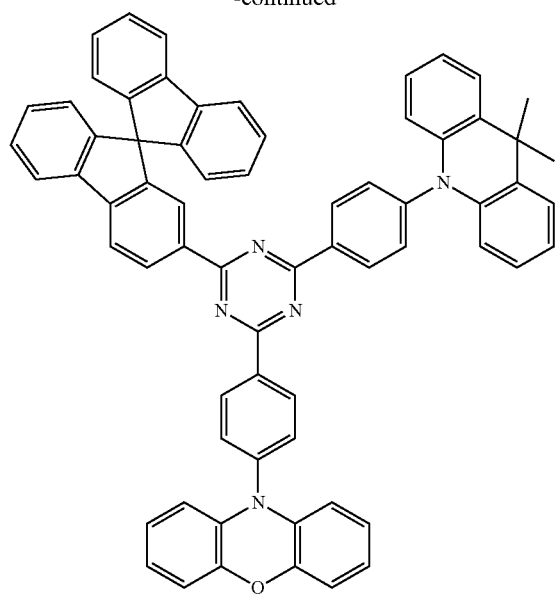
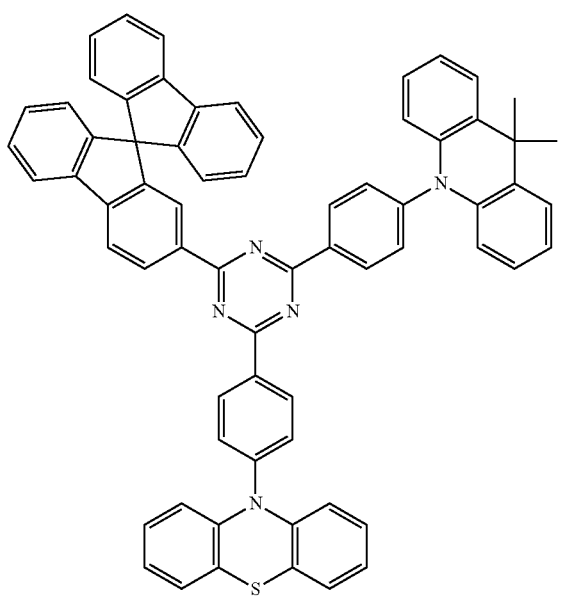
[Formula 129]
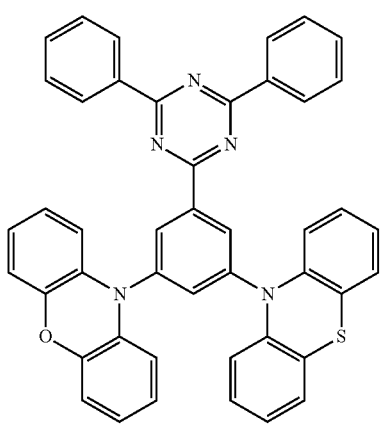
188
-continued
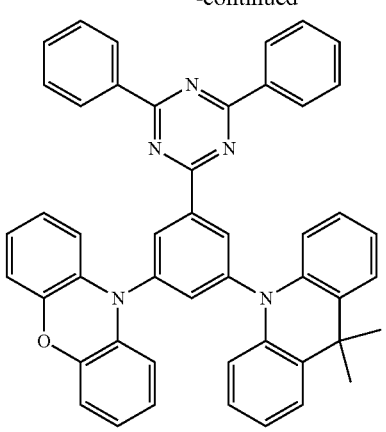
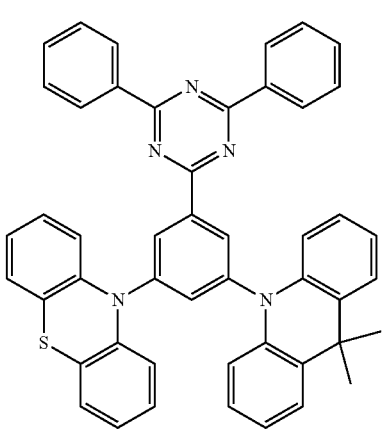
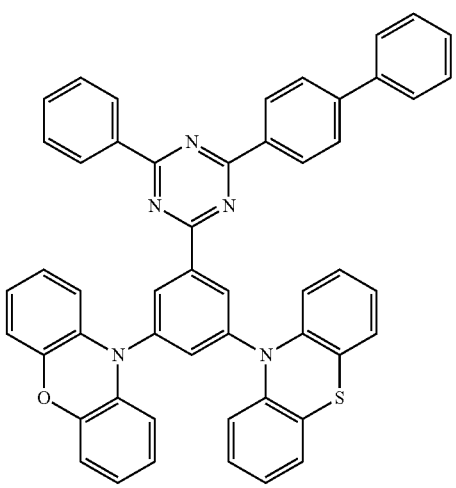

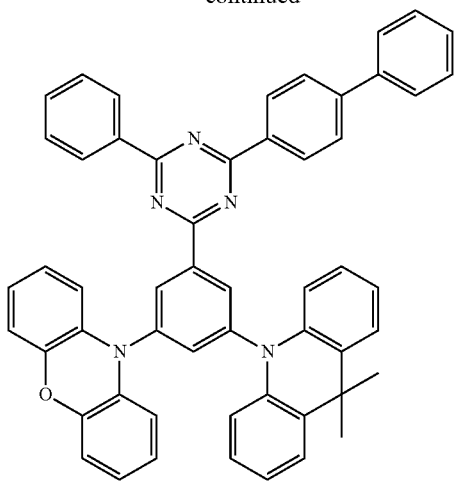
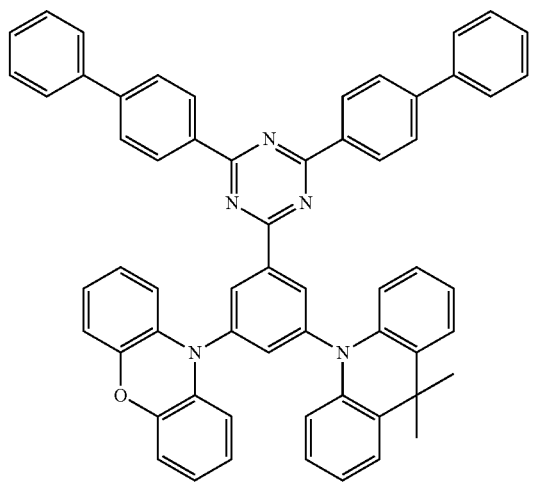
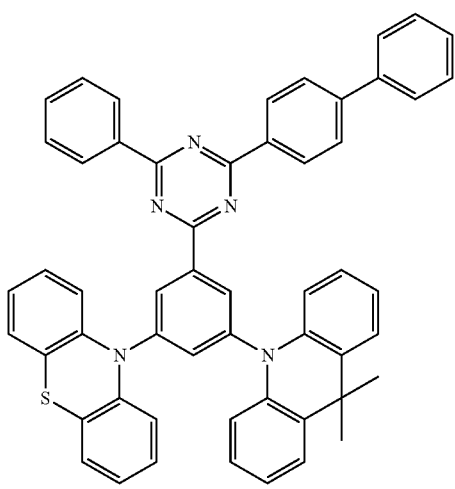
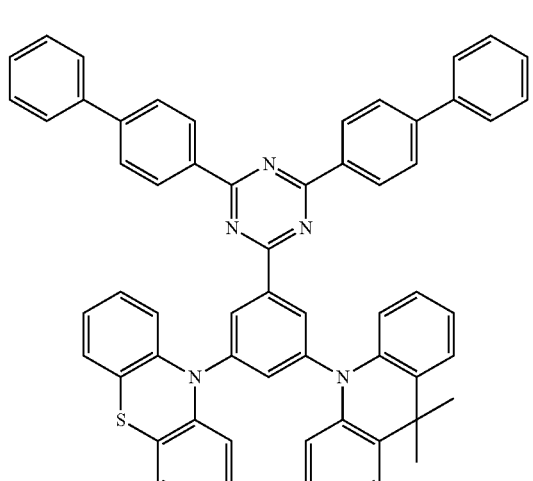
[Formula 130]
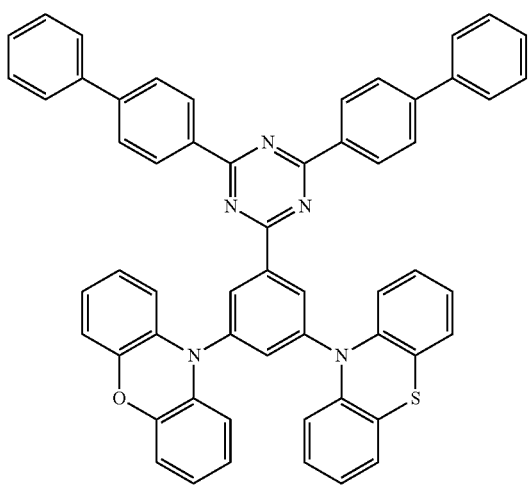
[Formula 131]
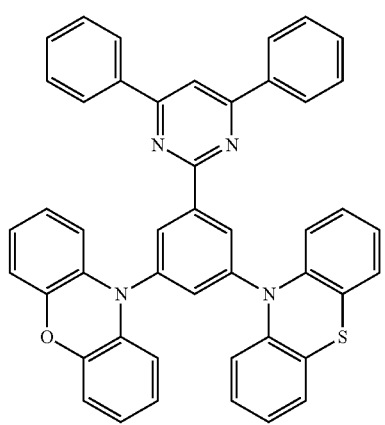

191
-continued
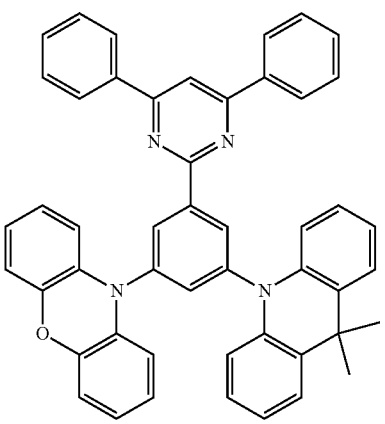
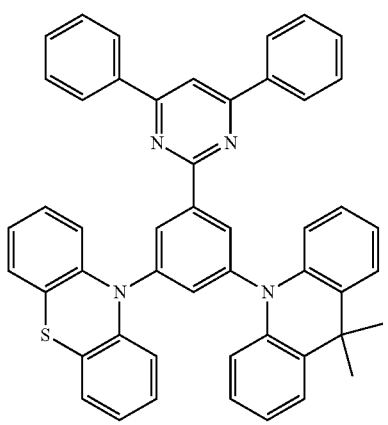
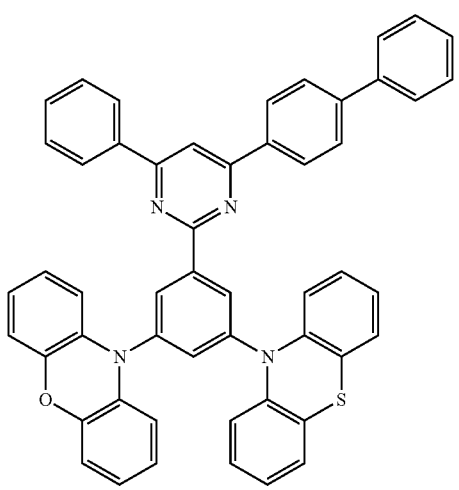
192
-continued
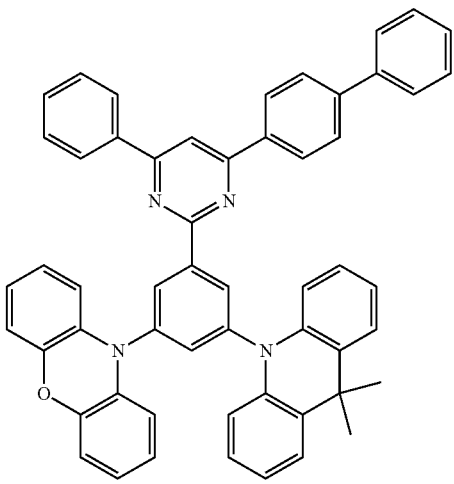
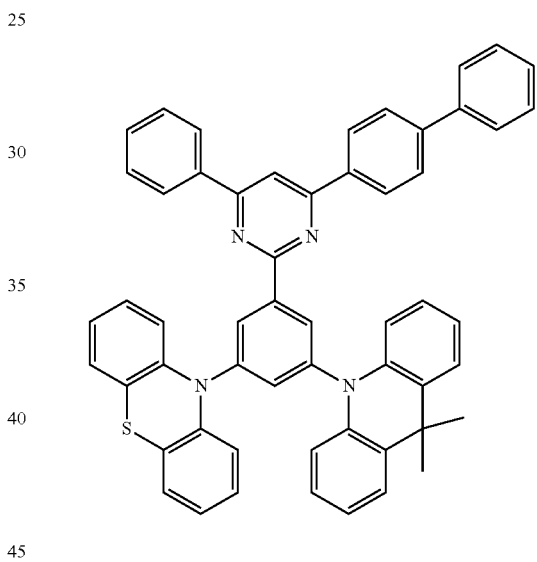
[Formula 132]
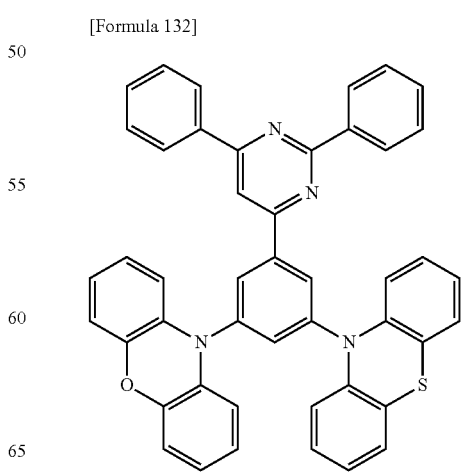

193
-continued
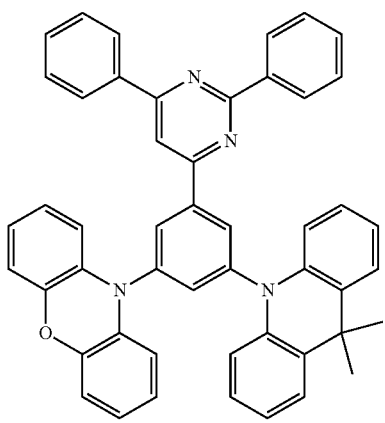
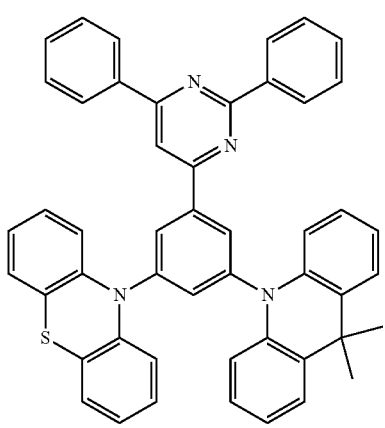
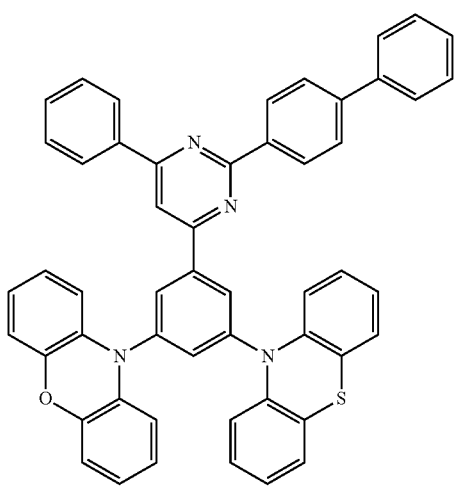
194
-continued
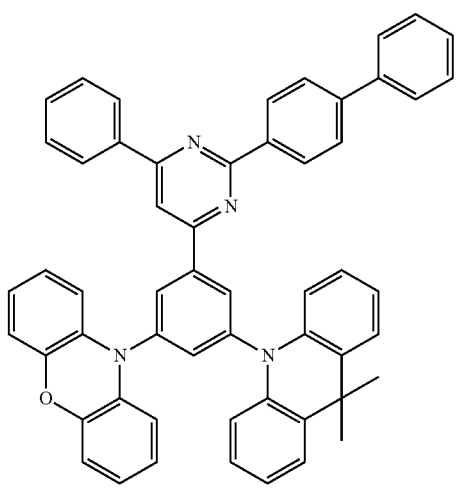
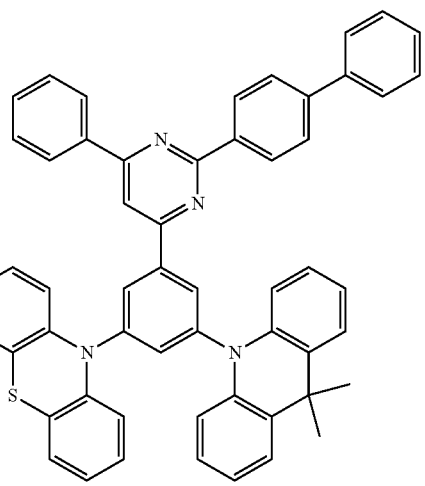
[Formula 133]
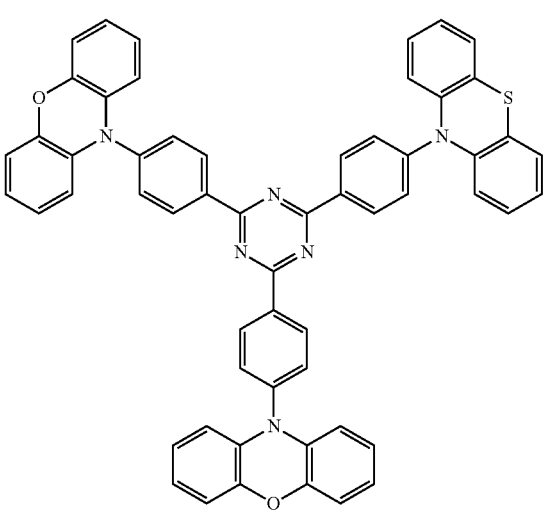

195
-continued
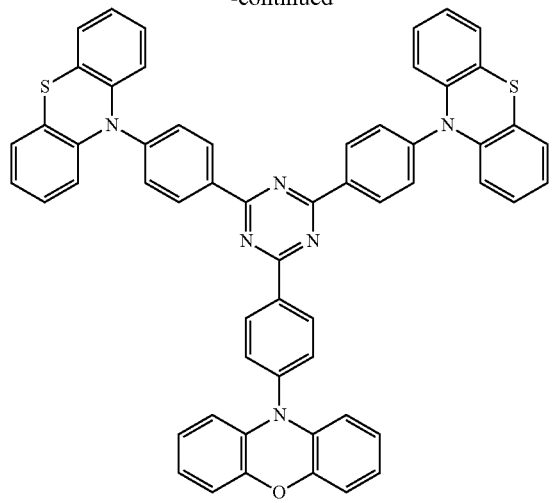
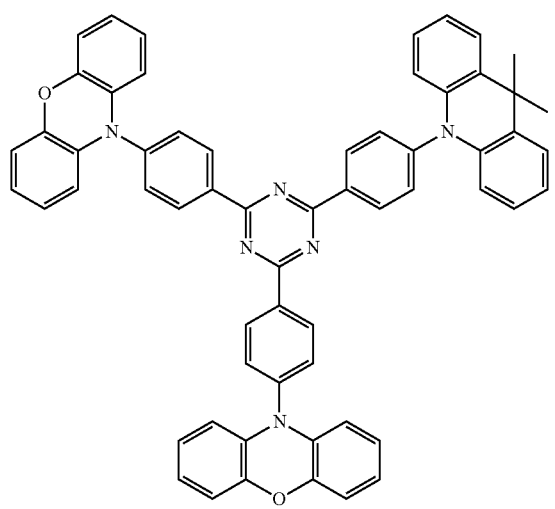
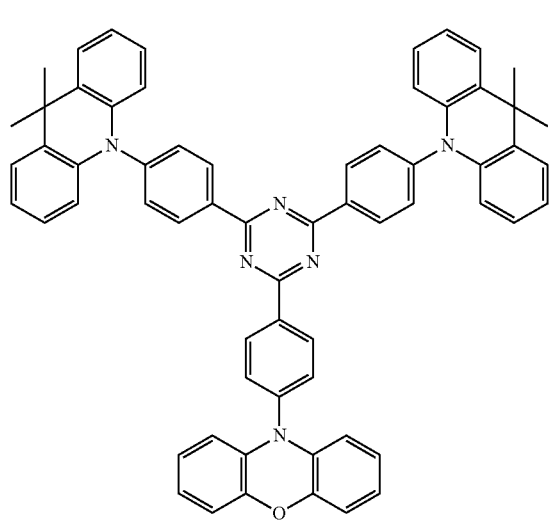
196
-continued
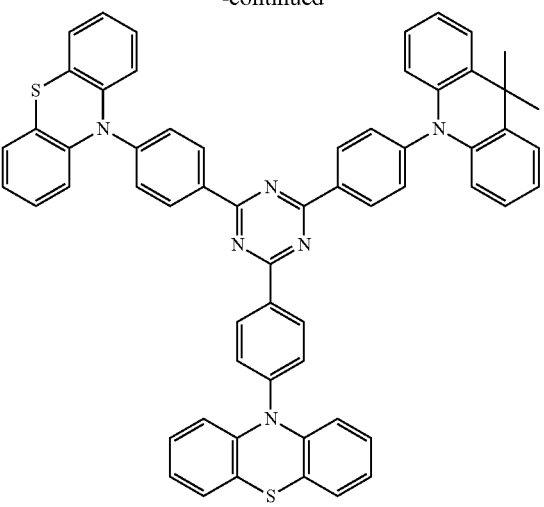
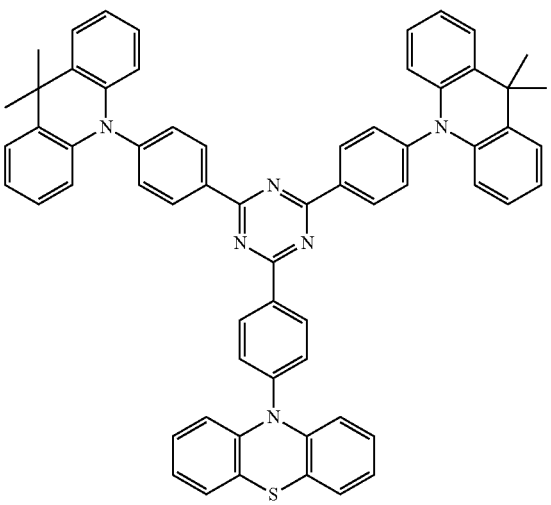
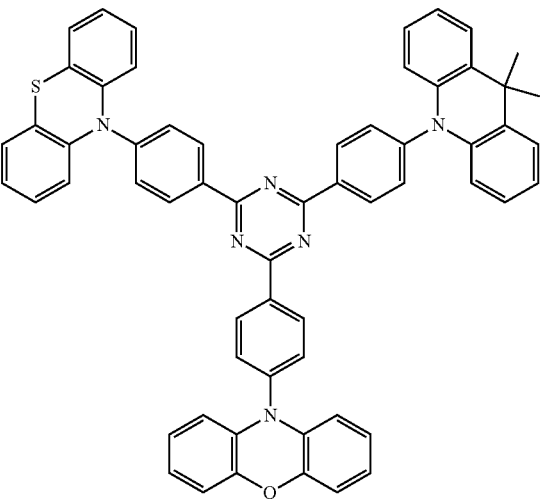

[Formula 134]
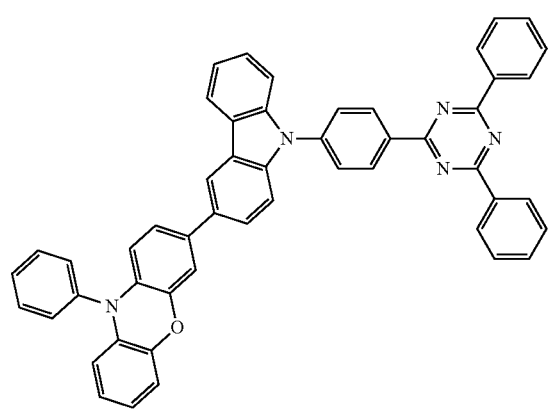
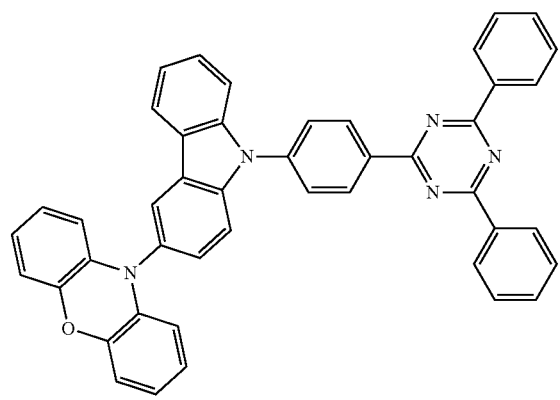
[Formula 135]
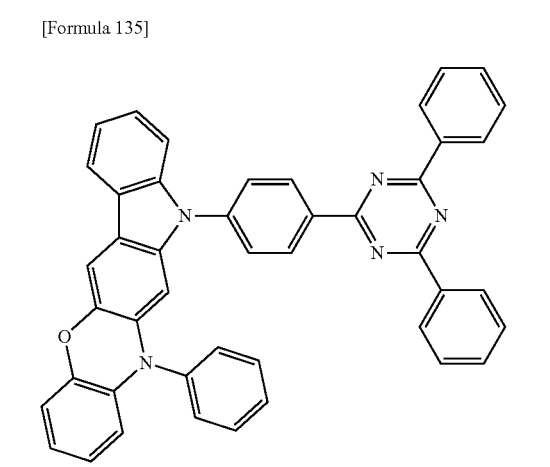
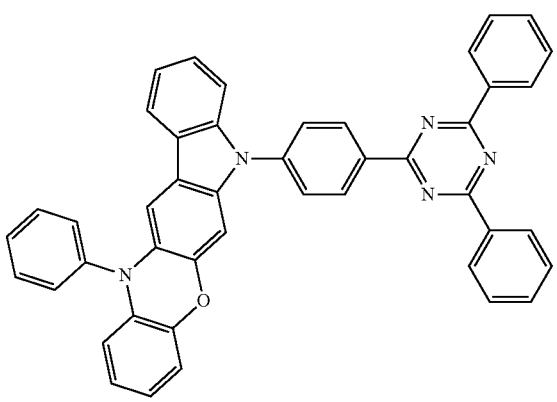
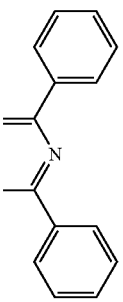
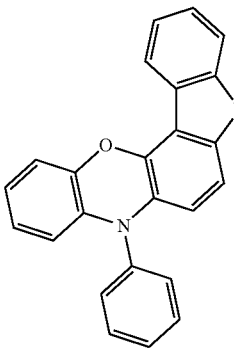
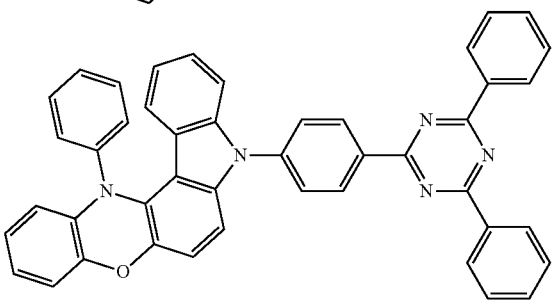
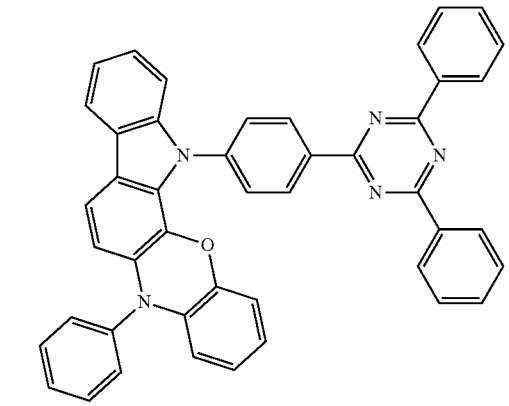
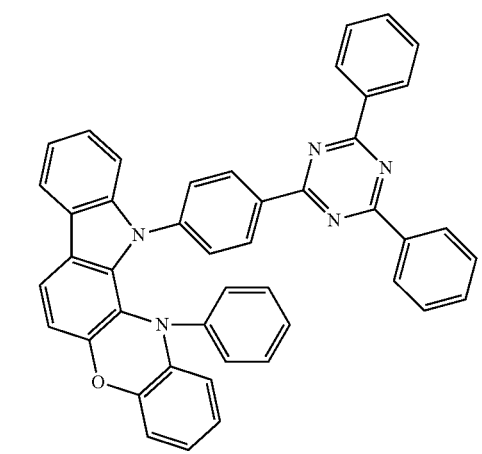

[Formula 136]

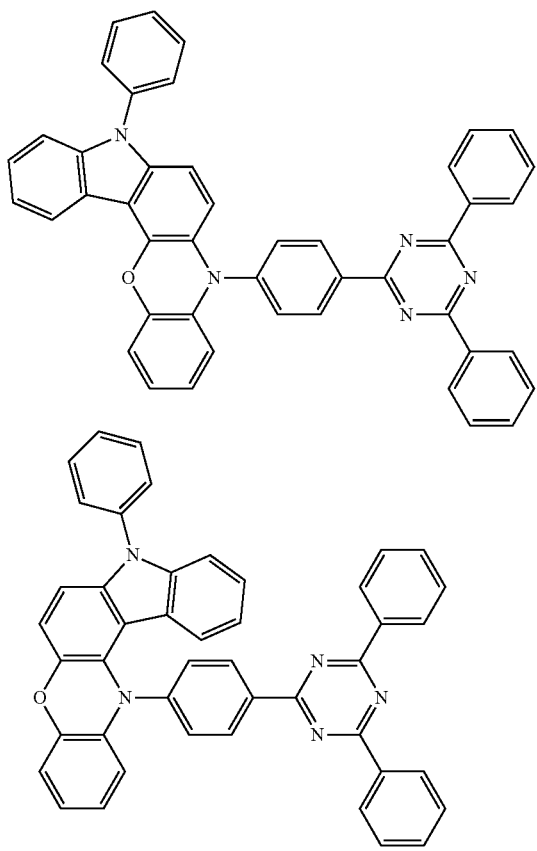

Also in the organic EL device of the third exemplary embodiment, the drive voltage can be reduced and the emission lifetime can be prolonged in the same manner as in the above exemplary embodiments.

Modifications of Embodiment(S)

It should be noted that the invention is not limited to the above exemplary embodiments but may include any modification and improvement as long as such modification and improvement are compatible with the invention.

The emitting layer is not limited to a single layer, but may be provided as laminate by a plurality of emitting layers. When the organic EL device includes the plurality of emitting layers, it is only required that at least one of the emitting layers includes the compound represented by the formula (1) and the compound represented by the formula (2). The rest of the emitting layers may be a fluorescent emitting layer or a phosphorescent emitting layer.

When the organic EL device includes the plurality of emitting layers, the plurality of emitting layers may be adjacent to each other, or may be laminated on each other via an intermediate layer, a so-called tandem organic EL device.

Figure 4:
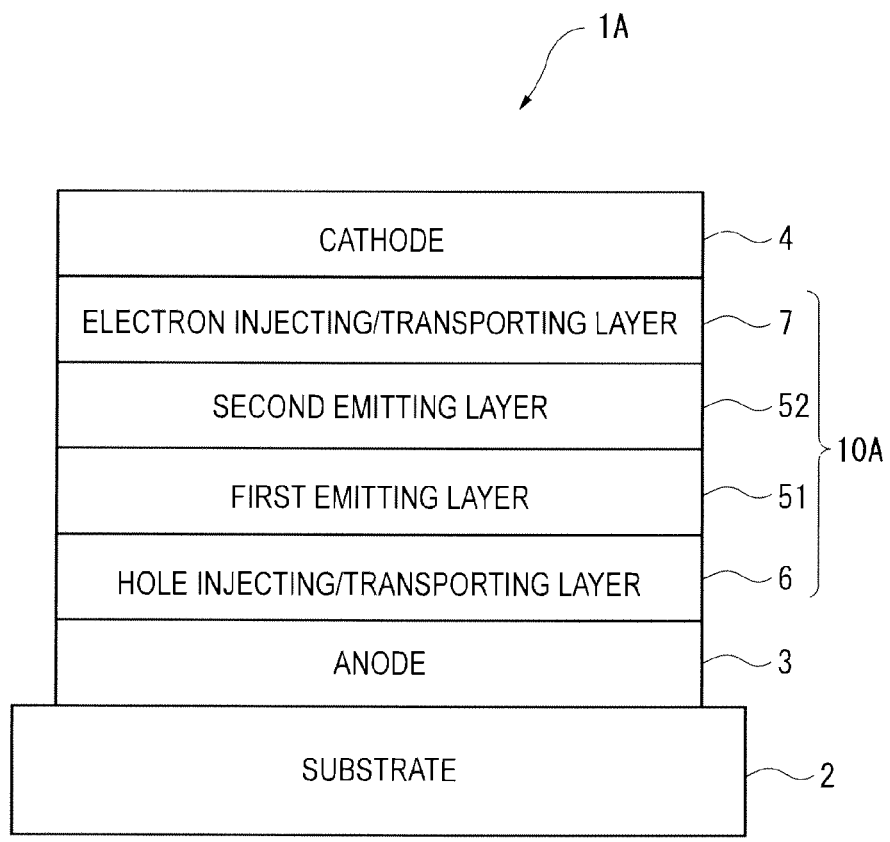
FIG. 4 schematically shows an exemplary arrangement of an organic EL device according to a modification of the invention.

When the plurality of emitting layers are laminated, an organic EL device 1A is exemplarily shown in FIG. 4. The organic EL device 1A includes an organic layer 10A. The organic EL device 1A is different from organic EL device 1 shown in FIG. 1 in that the organic layer 10A has a first emitting layer 51 and a second emitting layer 52 between the hole injecting/transporting layer 6 and the electron injecting/transporting layer 7. At least one of the first emitting layer 51 and the second emitting layer 52 contains the compound represented by the formula (1) and the compound represented by the formula (2). As for other points, the organic EL device 1A is formed in the same manner as the organic EL device 1.

The electron blocking layer may be provided to the emitting layer adjacent to the anode while the hole blocking layer may be provided adjacent to the emitting layer near the cathode. With this arrangement, the electrons and the holes can be trapped in the emitting layer, thereby enhancing probability of exciton generation in the emitting layer.

The organic EL device of the invention is suitably applicable to an electronic device such as: a display component of an organic EL panel module and the like, a display device of a television, a mobile phone, a personal computer and the like; and an emitting unit of an illuminator or a vehicle light.

Further, the specific arrangement and disposition for practicing the invention may be altered to other arrangements and treatments as long as such other arrangements and dispositions are compatible with the invention.

EXAMPLES

Examples of the invention will be described below. However, the invention is not limited by these Examples.

Compounds used in Examples for preparing the organic EL device will be shown as follows.

[Formula 137]

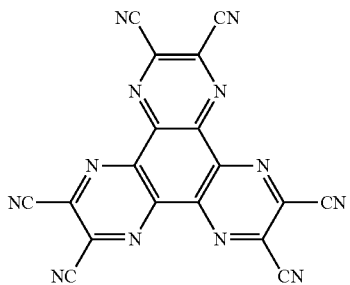

HI

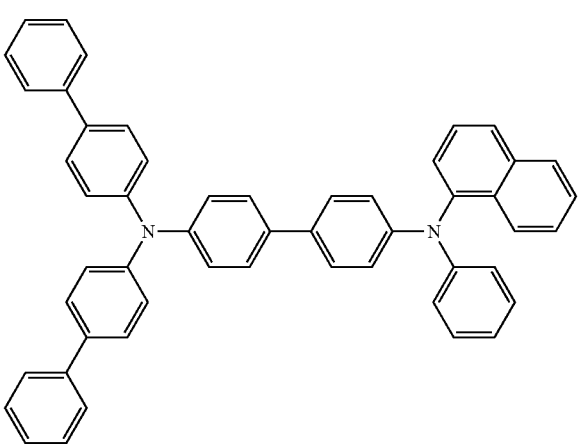

HT-1

HT-2
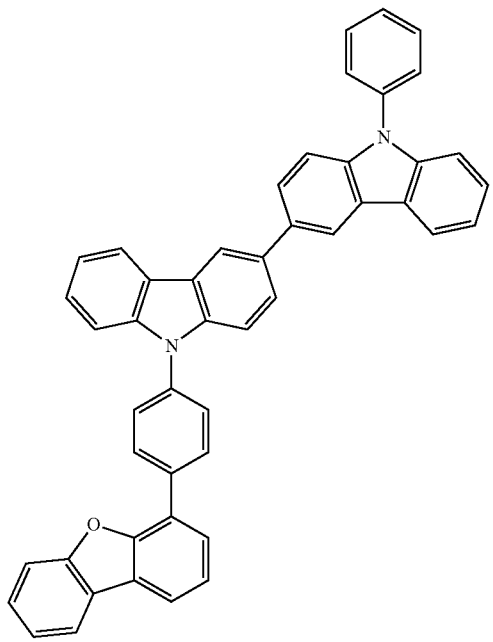
H2
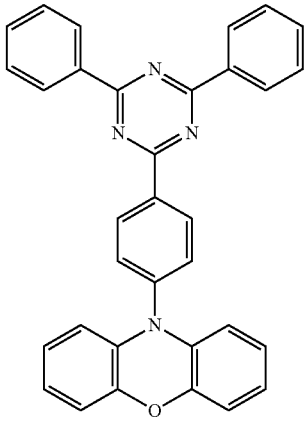
H3
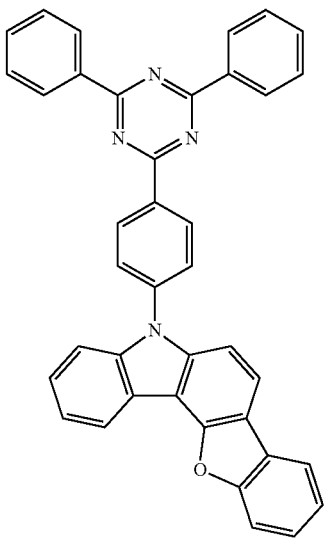
[Formula 138]
H1
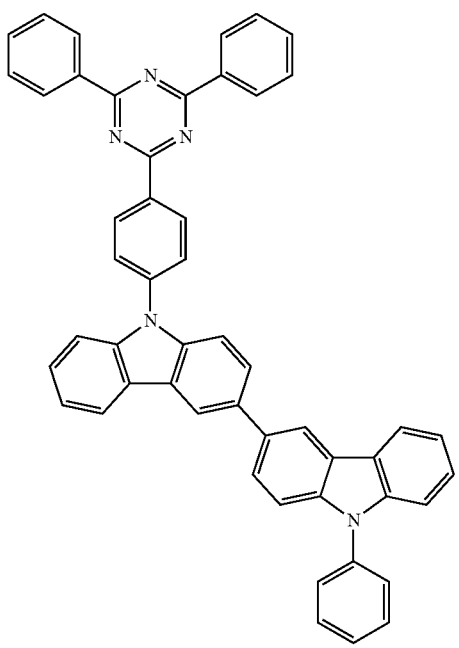
[Formula 139]
H4
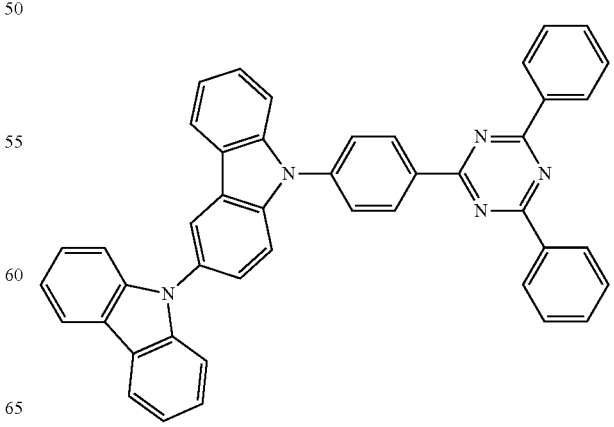

H5

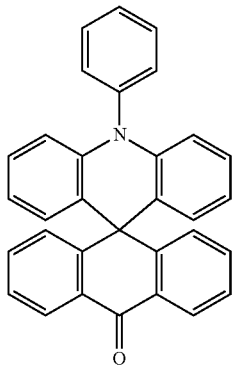

H6

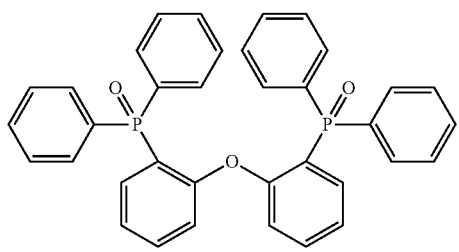

[Formula 140]

ET-1

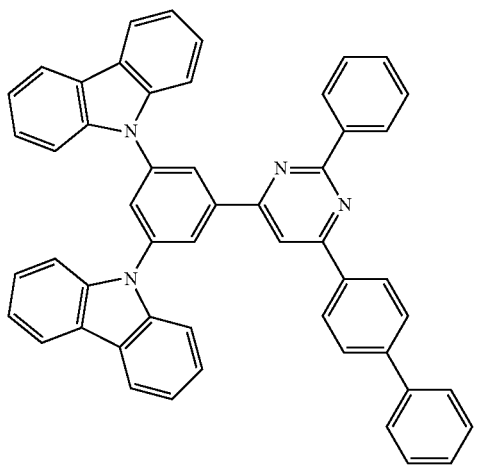

ET-2

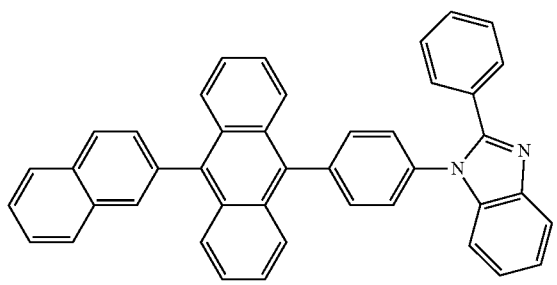

Evaluation of Compounds

Next, properties of the compounds used in Example were measured. The measurement target compounds are the compounds H1 to H6. A measurement method or a calculation method is described below. Measurement results or calculation results are shown in Table 1.

(Measurement 1) Singlet Energy EgS

Singlet Energy EgS was obtained by the following method.

A 100 nm thick film of each of the compounds was formed on a quartz substrate by vacuum deposition to provide a measurement sample. Emission spectrum of each sample was measured at a room temperature (300K). The emission spectrum was expressed in coordinates of which ordinate axis indicated the luminous intensity and of which abscissa axis indicated the wavelength. A tangent was drawn to the rise of the emission spectrum on the short-wavelength side, and a wavelength value λedge (nm) at an intersection of the tangent and the abscissa axis was obtained. The wavelength value was converted to an energy value by the following conversion equation. The energy value was defined as EgS.

$$EgS\ (eV)=1239.85/\lambda edge \qquad \text{Conversion Equation:}$$

For the emission spectrum measurement, a spectrophotofluorometer body F-7000 (manufactured by Hitachi High-Technologies Corporation) was used.

The tangent to the rise of the emission spectrum on the short-wavelength side was drawn as follows. While moving on a curve of the emission spectrum from the short-wavelength side to the maximum spectral value closest to the short-wavelength side among the maximum spectral values, a tangent is checked at each point on the curve toward the long-wavelength of the emission spectrum. An inclination of the tangent is increased as the curve rises (i.e., a value of the ordinate axis is increased). A tangent drawn at a point of the maximum inclination was defined as the tangent to the rise of the phosphorescence spectrum on the short-wavelength side.

The maximum with peak intensity being 10% or less of the maximum peak intensity of the spectrum is not included in the above-mentioned maximum closest to the short-wavelength side of the spectrum. The tangent drawn at a point of the maximum spectral value being closest to the short-wavelength side and having the maximum inclination is defined as a tangent to the rise of the emission spectrum on the short-wavelength side.

(Measurement 2) Energy Gap $Eg_{77K}$ $Eg_{77K}$ was obtained by the following method.

Energy gap $Eg_{77K}$ of each of the compounds H1 to H5 is measured as follows. Each of the measurement target compounds and a compound TH-2 below were co-deposited on a quartz substrate by vacuum deposition to prepare a sample encapsulated in an NMR tube. The samples were prepared under the following conditions.

quartz substrate/TH-2: measurement target compound (100 nm of thickness, 12 mass % of concentration of the measurement target compound)

The compound H6 was deposited on a quartz substrate by vacuum deposition to prepare a sample encapsulated in an NMR tube.

[Formula 141]

TH-2

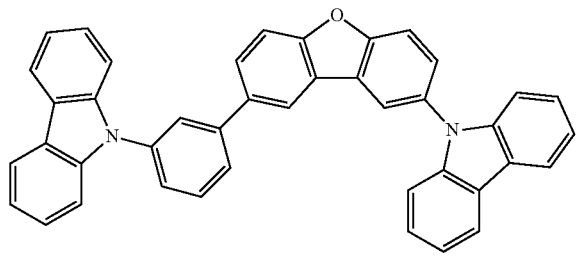

A phosphorescent spectrum (ordinate axis: phosphorescent luminous intensity, abscissa axis: wavelength) of each of the samples was measured at a low temperature (77K). A tangent was drawn to the rise of the phosphorescent spectrum on the short-wavelength side. An energy amount was calculated as the energy gap $Eg_{77K}$ at 77K according to a conversion equation 2 below based on a wavelength value $\lambda_{edge}$ (nm) at an intersection of the tangent and the abscissa axis.

$$Eg_{77K}(eV) = 1239.85/\lambda_{edge} \quad \text{Conversion Equation 2:}$$

For phosphorescence measurement, a spectrophotofluorometer body F-4500 (manufactured by Hitachi High-Technologies Corporation) was used.

The tangent to the rise of the phosphorescence spectrum on the short-wavelength side is drawn as follows. While moving on a curve of the phosphorescence spectrum from the short-wavelength side to the maximum spectral value closest to the short-wavelength side among the maximum spectral values, a tangent is checked at each point on the curve toward the long-wavelength of the phosphorescence spectrum. An inclination of the tangent is increased as the curve rises (i.e., a value of the ordinate axis is increased). A tangent drawn at a point of the maximum inclination (i.e., a tangent at an inflection point) is defined as the tangent to the rise of the phosphorescence spectrum on the short-wavelength side.

The maximum with peak intensity being 15% or less of the maximum peak intensity of the spectrum is not included in the above-mentioned maximum closest to the short-wavelength side of the spectrum. The tangent drawn at a point of the maximum spectral value being closest to the short-wavelength side and having the maximum inclination is defined as a tangent to the rise of the phosphorescence spectrum on the short-wavelength side.

The material used in the exemplary embodiment is preferably a compound having a small $\Delta ST$. When $\Delta ST$ is small, intersystem crossing and inverse intersystem crossing are likely to occur even at a low temperature (77K), so that the singlet state and the triplet state coexist. As a result, the spectrum to be measured in the same manner as the above includes emission from both the singlet state and the triplet state. Although it is difficult to distinguish the emission from the singlet state from the emission from the triplet state, the value of the triplet energy is basically considered dominant.

Accordingly, in the exemplary embodiment, the spectrum is measured by the same method as a typical triplet energy is measured, but an energy value of the spectrum measured in the aforementioned manner is referred to as an energy gap $Eg_{77K}$ in order to differentiate the measured energy from a typical triplet energy in a strict meaning.

(Measurement 3) $\Delta ST$ $\Delta ST$ was obtained as a difference between EgS and $Eg_{77K}$ respectively measured in the above (Measurement 1) and (Measurement 2) (see the above numerical formula (2)). The results are shown in Table 1.

(Measurement 4) Delayed Fluorescence

Delayed fluorescence was checked by measuring transitional PL using the device shown in FIG. 2. A measurement target compound and the compound TH-2 were co-deposited on a quartz substrate so that a ratio of the measurement target compound was 12 mass % to prepare a 100 nm thin-film sample. The measurement target compounds were the compounds H1 to H5.

Delayed fluorescence can be obtained using the device of FIG. 2. After the measurement target compounds are excited with pulse light (light irradiated from the pulse laser) having a wavelength to be absorbed in the measurement target compounds, Prompt Emission that is immediately observed in the excited state and Delay Emission that is not observed immediately after the excitation and is later observed are present. In the exemplary embodiments, delayed fluorescence means that an amount of Delay Emission is 5% or more based on an amount of Prompt Emission. It has been confirmed that the amount of Delay Emission is 5% or more based on the amount of Prompt Emission in the compounds H1 to H5 of the measurement target compounds.

The amount of Prompt Emission and the amount of Delay Emission can be obtained according to the method as a method described in "Nature 492, 234-238, 2012." A device used for calculating the amounts of Prompt Emission and Delay Emission is not limited to the device of FIG. 2 and a device described in the above document.

TABLE 1

| Compounds | EgS (eV) | $Eg_{77K}$ (eV) | $\Delta ST$ (eV) |
|---|---|---|---|
| H1 | 2.85 | 2.72 | 0.13 |
| H2 | 2.67 | 2.46 | 0.21 |
| H3 | 2.95 | 2.70 | 0.25 |
| H4 | 3.00 | 2.75 | 0.25 |
| H5 | 3.00 | 2.86 | 0.14 |
| H6 | 4.36 | 3.50 | 0.86 |

Preparation and Evaluation 1 of Organic EL Device

The organic EL device was prepared and evaluated as follows.

Example 1

A glass substrate (size: 25 mm×75 mm×1.1 mm thick, manufactured by Geomatec Co., Ltd.) having an ITO transparent electrode (anode) was ultrasonic-cleaned in isopropyl alcohol for five minutes, and then UV/ozone-cleaned for 30 minutes. A film of ITO was 130 nm thick.

After the glass substrate having the transparent electrode line was cleaned, the glass substrate was mounted on a substrate holder of a vacuum evaporation apparatus. Initially, a compound HI was evaporated on a surface of the glass substrate where the transparent electrode line was provided in a manner to cover the transparent electrode, thereby forming a 5 nm thick film of the compound HI. The HI film serves as a hole injecting layer.

After the film formation of the HI film, the compound HT-1 was deposited on the HI film to form a 160 nm thick HT-1 film. The HT-1 film serves as a first hole transporting layer.

The compound HT-2 was further deposited on the HT-1 film to form a 10 nm thick HT-2 film. The HT-2 film serves as a second hole transporting layer.

The compound H1 and the compound H2 were co-deposited on the HT-2 film to form a 35 nm thick emitting layer. The concentration of the compound H1 in the emitting layer was set at 94 mass % and the concentration of the compound H2 in the emitting layer was set at 6 mass %.

The compound ET-1 was deposited on the emitting layer to form a 5 nm thick ET-1 film. The ET-1 film serves as a first electron transporting layer.

The compound ET-2 was deposited on the ET-1 film to form a 25 nm thick ET-2 film. The ET-2 film serves as a second electron transporting layer.

LiF was deposited on the ET-2 film to form a 1 nm thick LiF film.

A metal Al was deposited on the LiF film to form an 80 nm thick metal cathode.

A device arrangement of the organic EL device in Example 1 is shown in symbols as follows.
   ITO(130)/HI(5)/HT-1(160)/HT-2(10)/H1:H2(35, 94%: 6%)/ET-1(5)/ET-2(25)/LiF(1)/Al(80)

Numerals in parentheses represent a film thickness (unit: nm). The numerals represented by percentage in parentheses indicate a ratio (mass percentage) of the compounds in the emitting layer. The same applies to Examples and Comparatives below.

Example 2

An organic EL device in Example 2 was manufactured in the same manner as in Example 1 except that the concentration of the compound H1 was changed to 88 mass % and the concentration of the compound H2 was changed to 12 mass % in the emitting layer of the organic EL device in Example 1.

A device arrangement of the organic EL device in Example 2 is shown in symbols as follows.
   ITO(130)/HI(5)/HT-1(160)/HT-2(10)/H1:H2(35, 88%: 12%)/ET-1(5)/ET-2(25)/LiF(1)/Al(80)

An organic EL device in Example 3 was manufactured in the same manner as in Example 1 except that the compound H1 was replaced by a compound H3 in the emitting layer of the organic EL device in Example 1.

A device arrangement of the organic EL device in Example 3 is shown in symbols as follows.
   ITO(130)/HI(5)/HT-1(160)/HT-2(10)/H3:H2(35, 94%: 6%)/ET-1(5)/ET-2(25)/LiF(1)/Al(80)

Numerals in parentheses represent a film thickness (unit: nm). Numerals represented by percentage in the same parentheses represent a ratio (mass %) of an added component such as the dopant material in the emitting layer.

Example 4

An organic EL device in Example 4 was manufactured in the same manner as in Example 1 except that the compound H1 was replaced by the compound H3 and the concentration of the compound H2 was changed to 12 mass % in the emitting layer of the organic EL device in Example 1.

A device arrangement of the organic EL device in Example 6 is shown in symbols as follows.
   ITO(130)/HI(5)/HT-1(160)/HT-2(10)/H3:H2(35, 88%: 12%)/ET-1(5)/ET-2(25)/LiF(1)/Al(80)

Numerals in parentheses represent a film thickness (unit: nm). Numerals represented by percentage in the same parentheses represent a ratio (mass %) of an added component such as the dopant material in the emitting layer.

Comparative 1

An organic EL device in Comparative 1 was manufactured in the same manner as in Example 1 except that a compound 1 was replaced by CBP in the emitting layer of the organic EL device in Example 1.

A device arrangement of the organic EL device in Comparative 1 is shown in symbols as follows.
   ITO(130)/HI(5)/HT-1(160)/HT-2(10)/CBP:H2(35, 94%: 6%)/ET-1(5)/ET-2(25)/LiF(1)/Al(80)

[Formula 142]

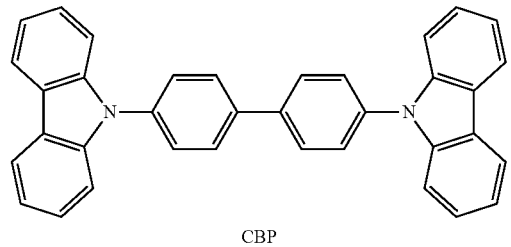

CBP

Comparative 2

An organic EL device in Comparative 2 was manufactured in the same manner as in Example 1 except that the compound 1 was replaced by CBP and the concentration of the compound H2 was changed to 12 mass % in the emitting layer of the organic EL device in Example 1.

A device arrangement of the organic EL device in Comparative 2 is shown in symbols as follows.
   ITO(130)/HI(5)/HT-1(160)/HT-2(10)/CBP:H2(35, 88%: 12%)/ET-1(5)/ET-2(25)/LiF(1)/Al(80)

Evaluation of Organic EL Devices

The prepared organic EL devices of Examples 1 to 4 and Comparatives 1 to 2 were evaluated as follows. The evaluation results are shown in Table 2.

Drive Voltage

Voltage was applied between ITO transparent electrode and Al metal cathode such that a current density was 10 mA/cm$^2$, where the voltage (unit: V) was measured.

Luminance and CIE1931 Chromaticity

Voltage was applied on each of the organic EL devices such that the current density was 10 mA/cm$^2$, where luminance and coordinates of CIE1931 chromaticity were measured by a spectroradiometer (CS-1000 manufactured by Konica Minolta, Inc.).

Current Efficiency L/J and Power Efficiency η

Voltage was applied on each of the organic EL devices such that the current density was 10.00 mA/cm$^2$, where spectral radiance spectra were measured by the aforementioned spectroradiometer. Based on the obtained spectral radiance spectra, the current efficiency (unit: cd/A) and the power efficiency η (unit: lm/W) were calculated.

Main Peak Wavelength $\lambda_p$

A main peak wavelength $\lambda_p$ was calculated based on the obtained spectral-radiance spectra.

External Quantum Efficiency EQE

Voltage was applied on each of the organic EL devices such that the current density was 10 mA/cm$^2$, where spectral radiance spectrum was measured by a spectroradiometer (CS-1000 manufactured by Konica Minolta, Inc.). The external quantum efficiency EQE (unit: %) was calculated based on the obtained spectral-radiance spectra, assuming that the spectra were provided under a Lambertian radiation.

TABLE 2

|  | Current Density [mA/cm$^2$] | Voltage [V] | Luminance [cd/m$^2$] | L/J [cd/A] | η [l/W] | Chromaticity x | Chromaticity y | λ$_p$ [nm] | EQE [%] |
|---|---|---|---|---|---|---|---|---|---|
| Example 1 | 10 | 3.73 | 5883.2 | 58.83 | 49.58 | 0.373 | 0.579 | 541 | 17.41 |
| Example 2 | 10 | 3.74 | 5981.7 | 59.82 | 50.21 | 0.384 | 0.579 | 545 | 17.59 |
| Example 3 | 10 | 3.93 | 4917.7 | 49.18 | 39.34 | 0.372 | 0.574 | 544 | 14.64 |
| Example 4 | 10 | 3.89 | 5163.1 | 51.63 | 41.68 | 0.384 | 0.575 | 545 | 15.36 |
| Comparative 1 | 10 | 6.70 | 4452.6 | 44.52 | 20.87 | 0.363 | 0.578 | 543 | 13.22 |
| Comparative 2 | 10 | 5.77 | 5067.6 | 50.68 | 27.61 | 0.381 | 0.577 | 544 | 15.07 |

As shown in Table 2, it was found that the organic EL devices of Examples 1 to 4 including the emitting layer containing the compounds H1 and H2 emitting thermally activated delayed fluorescence emitted light at a lower drive voltage with a higher efficiency than the drive voltage and the efficiency of the organic EL devices of Comparatives 1 to 2 containing CBP.

Preparation and Evaluation 2 of Organic EL Device

Example 5

An organic EL device in Example 5 was manufactured in the same manner as in Example 2 except that the compound H2 was replaced by the compound H4 and the thickness of the emitting layer was changed to 30 nm in the emitting layer of the organic EL device in Example 2.

A device arrangement of the organic EL device in Example 5 is shown in symbols as follows.
 ITO(130)/HI(5)/HT-1(160)/HT-2(10)/H1:H4(30, 88%:12%)/ET-1(5)/ET-2(25)/LiF(1)/Al(80)

Example 6

An organic EL device in Example 6 was manufactured in the same manner as in Example 5 except that the concentration of the compound H1 was changed to 76 mass % and the concentration of the compound H4 was changed to 24 mass % in the emitting layer of the organic EL device in Example 5.

A device arrangement of the organic EL device in Example 6 is shown in symbols as follows.
 ITO(130)/HI(5)/HT-1(160)/HT-2(10)/H1:H4(30, 76%:24%)/ET-1(5)/ET-2(25)/LiF(1)/Al(80)

Example 7

An organic EL device in Example 7 was manufactured in the same manner as in Example 1 except that the emitting layer of the organic EL device in Example 1 was formed as follows.

The compounds H1, H4 and H5 were co-deposited on the HT-2 film to form a 30 nm thick emitting layer. The concentration of the compound H1 was set at 33 mass %, the concentration of the compound H4 was set at 33 mass %, and the concentration of the compound H5 was set at 34 mass % in the emitting layer.

A device arrangement of the organic EL device in Example 7 is shown in symbols as follows.
 ITO(130)/HI(5)/HT-1(160)/HT-2(10)/H1:H4:H5 (30, 33%:33%:34%)/ET-1(5)/ET-2(25)/LiF(1)/Al(80)

Comparative 3

An organic EL device in Comparative 3 was manufactured in the same manner as in Example 1 except that the thickness of the emitting layer was changed to 30 nm, the concentration of the compound H1 was changed to 88 mass %, and the concentration of the compound H4 was changed to 12 mass % in the emitting layer of the organic EL device in Example 1.

A device arrangement of the organic EL device in Comparative 3 is shown in symbols as follows.
 ITO(130)/HI(5)/HT-1(160)/HT-2(10)/H1:H6(30, 12%:88%)/ET-1(5)/ET-2(25)/LiF(1)/Al(80)

Evaluation of Organic EL Devices

The prepared organic EL devices in Examples 5 to 7 and Comparative 3 were measured in terms of drive voltage, luminance, CIE1931 chromaticity, and main peak wavelength λ$_p$ according to the same method as the above, and further in terms of lifetime according to the following method.

Lifetime LT50 (Examples 5, 6 and Comparative 3)

Voltage was applied to the devices and a time until an initial luminance (1000 cd/m$^2$) was decreased in half was defined as the lifetime (unit: h).

Lifetime LT50 (Example 7)

Constant current of 50 mA/cm$^2$ was applied to the devices and a time until an initial luminance was decreased in half was defined as the lifetime (unit: h). Note that a time until an initial luminance (1000 cd/m$^2$) was decreased in half assuming that an acceleration factor is 1.8 was described in LT50 of Table 3.

TABLE 3

|  | Current Density [mA/cm$^2$] | Voltage [V] | Luminance [cd/m$^2$] | Chromaticity x | Chromaticity y | λ$_p$ [nm] | LT50 [h] |
|---|---|---|---|---|---|---|---|
| Example 5 | 10 | 3.85 | 1981.7 | 0.199 | 0.429 | 497 | 186 |
| Example 6 | 10 | 3.87 | 1834.4 | 0.194 | 0.414 | 495 | 176 |

TABLE 3-continued

| | Current Density [mA/cm$^2$] | Voltage [V] | Luminance [cd/m$^2$] | Chromaticity x | Chromaticity y | $\lambda_p$ [nm] | LT50 [h] |
|---|---|---|---|---|---|---|---|
| Example 7 | 10 | 3.60 | 1363.5 | 0.191 | 0.359 | 484 | 50 |
| Comparative 3 | 10 | 6.24 | 1761.4 | 0.196 | 0.411 | 494 | <1 |

As shown in Table 3, it was found that the organic EL devices of Examples 5 to 7 including the emitting layer containing the compounds H1 and H2 emitting thermally activated delayed fluorescence emitted light at a lower drive voltage with a longer lifetime than the drive voltage and the lifetime of the organic EL device of Comparative 3. It was found that, when the compound H6 was contained as a main component in the emitting layer instead of the compound H2 emitting thermally activated delayed fluorescence as in the organic EL device of Comparative 3, the drive voltage was high and the lifetime was short.

The invention claimed is:

1. An organic electroluminescence device, comprising:
   an anode;
   a cathode; and
   an emitting layer, wherein
   the emitting layer comprises a first compound and a second compound,
   each of the first compound and the second compound is a compound emitting thermally activated delayed fluorescence,
   a difference between singlet energy EgS(M1) of the first compound and energy gap Eg$_{77K}$(M1) at 77K of the first compound is 0.3 eV or less, and
   a difference between singlet energy EgS(M2) of the second compound and energy gap Eg$_{77K}$(M2) at 77K of the second compound is 0.3 eV or less.

2. The organic electroluminescence device according to claim 1, wherein
   a difference between the singlet energy EgS(M1) of the first compound and the singlet energy EgS(M2) of the second compound is 0.2 eV or less.

3. The organic electroluminescence device according to claim 1, wherein
   a difference between the energy gap Eg$_{77K}$(M1) at 77K of the first compound and the energy gap Eg$_{77K}$(M2) at 77K of the second compound is 0.2 eV or less.

4. The organic electroluminescence device according to claim 1, wherein
   at least one of the first compound and the second compound has a main peak wavelength of 500 nm or less.

5. The organic electroluminescence device according to claim 1, wherein
   at least one of the first compound and the second compound has a main peak wavelength of 480 nm or less.

6. The organic electroluminescence device according to claim 1, wherein
   the first compound has a concentration of 20 mass % or more in the emitting layer, and
   the second compound has a concentration of 20 mass % or more in the emitting layer.

7. The organic electroluminescence device according to claim 1, wherein
   the emitting layer further comprises a third compound, and
   the third compound is a compound emitting thermally activated delayed fluorescence.

8. The organic electroluminescence device according to claim 7, wherein
   a difference between singlet energy EgS(M3) of the third compound and energy gap Eg$_{77K}$(M3) at 77K of the third compound is 0.3 eV or less.

9. The organic electroluminescence device according to claim 7, wherein
   the third compound has a concentration of 20 mass % or more in the emitting layer.

10. The organic electroluminescence device according to claim 7, wherein
    a difference between the singlet energy EgS(M1) of the first compound and the singlet energy EgS(M3) of the third compound is 0.2 eV or less, and
    a difference between the singlet energy EgS(M2) of the second compound and the singlet energy EgS(M3) of the third compound is 0.2 eV or less.

11. The organic electroluminescence device according to claim 7, wherein
    a difference between the energy gap Eg$_{77K}$(M1) at 77K of the first compound and the energy gap Eg$_{77K}$(M3) at 77K of the third compound is 0.2 eV or less, and
    a difference between the energy gap Eg$_{77K}$(M2) at 77K of the second compound and the energy gap Eg$_{77K}$(M3) at 77K of the third compound is 0.2 eV or less.

12. The organic electroluminescence device according to claim 1, wherein
    the emitting layer does not comprise a metal complex.

13. An electronic device comprising the organic electroluminescence device according to claim 1.

14. The organic electroluminescence device according to claim 1, wherein
    a difference between singlet energy EgS(M1) of the first compound and energy gap Eg$_{77K}$(M1) at 77K of the first compound is less than 0.3 eV, and
    a difference between singlet energy EgS(M2) of the second compound and energy gap Eg$_{77K}$(M2) at 77K of the second compound is less than 0.3 eV.

15. The organic electroluminescence device according to claim 14, wherein
    a difference between singlet energy EgS and energy gap Eg$_{77K}$ at 77K of one of the first compound and the second compound is less than 0.2 eV.

16. The organic electroluminescence device according to claim 1, wherein
    a difference between singlet energy EgS(M1) of the first compound and energy gap Eg$_{77K}$(M1) at 77K of the first compound is less than 0.2 eV, and
    a difference between singlet energy EgS(M2) of the second compound and energy gap Eg$_{77K}$(M2) at 77K of the second compound is less than 0.2 eV.

17. The organic electroluminescence device according to claim 7, wherein
    a difference between singlet energy EgS(M1) of the first compound and energy gap Eg$_{77K}$(M1) at 77K of the first compound is less than 0.3 eV, a difference between singlet energy EgS(M2) of the second compound and energy gap $\mathrm{Eg}_{77K}$(M2) at 77K of the second compound is less than 0.3 eV, and a difference between singlet energy EgS(M3) of the third compound and energy gap $\mathrm{Eg}_{77K}$(M3) at 77K of the third compound is less than 0.3 eV.

18. The organic electroluminescence device according to claim 17, wherein a difference between singlet energy EgS and energy gap $\mathrm{Eg}_{77K}$ at 77K of one of the first, second and third compound is less than 0.2 eV.

19. The organic electroluminescence device according to claim 17, wherein a difference between singlet energy EgS and energy gap $\mathrm{Eg}_{77K}$ at 77K of two of the first, second and third compound is less than 0.2 eV.

20. The organic electroluminescence device according to claim 7, wherein a difference between singlet energy EgS(M1) of the first compound and energy gap $\mathrm{Eg}_{77K}$(M1) at 77K of the first compound is less than 0.2 eV, a difference between singlet energy EgS(M2) of the second compound and energy gap $\mathrm{Eg}_{77K}$(M2) at 77K of the second compound is less than 0.2 eV, and a difference between singlet energy EgS(M3) of the third compound and energy gap $\mathrm{Eg}_{77K}$(M3) at 77K of the third compound is less than 0.2 eV.

21. The organic electroluminescence device according to claim 1, wherein the emitting layer further comprises a third compound.

22. The organic electroluminescence device according to claim 21, wherein the third compound is a dopant.

23. The organic electroluminescence device according to claim 21, wherein the third compound does not emit thermally activated delayed fluorescence.

24. The organic electroluminescence device according to claim 2, wherein the emitting layer further comprises a third compound.

25. The organic electroluminescence device according to claim 24, wherein the third compound is a dopant.

26. The organic electroluminescence device according to claim 24, wherein the third compound does not emit thermally activated delayed fluorescence.

27. The organic electroluminescence device according to claim 12, wherein the emitting layer further comprises a third compound.

28. The organic electroluminescence device according to claim 27, wherein the third compound is a dopant.

29. The organic electroluminescence device according to claim 27, wherein the third compound does not emit thermally activated delayed fluorescence.

30. The organic electroluminescence device according to claim 22, wherein the third compound is a fluorescent dopant.

31. The organic electroluminescence device according to claim 25, wherein the third compound is a fluorescent dopant.

32. The organic electroluminescence device according to claim 28, wherein the third compound is a fluorescent dopant.

* * * * *